United States Patent
Tsvetkov et al.

(10) Patent No.: US 11,092,602 B2
(45) Date of Patent: Aug. 17, 2021

(54) METHODS AND COMPOSITIONS RELATING TO PROTEASOME INHIBITOR RESISTANCE

(71) Applicants: Whitehead Institute for Biomedical Research, Cambridge, MA (US); The Brigham and Women's Hospital, Inc., Boston, MA (US)

(72) Inventors: Peter Tsvetkov, Cambridge, MA (US); Sandro Santagata, West Roxbury, MA (US); Susan Lindquist, Chestnut Hill, MA (US)

(73) Assignees: Whitehead Institute for Biomedical Research, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/742,461

(22) PCT Filed: Jul. 6, 2016

(86) PCT No.: PCT/US2016/041207
§ 371 (c)(1),
(2) Date: Jan. 5, 2018

(87) PCT Pub. No.: WO2017/007858
PCT Pub. Date: Jan. 12, 2017

(65) Prior Publication Data
US 2018/0306796 A1 Oct. 25, 2018

Related U.S. Application Data

(60) Provisional application No. 62/189,173, filed on Jul. 6, 2015, provisional application No. 62/296,558, filed on Feb. 17, 2016, provisional application No. 62/336,198, filed on May 13, 2016.

(51) Int. Cl.
| | |
|---|---|
| G01N 33/574 | (2006.01) |
| G01N 33/68 | (2006.01) |
| G01N 33/50 | (2006.01) |
| A61K 31/713 | (2006.01) |
| C12N 15/113 | (2010.01) |
| A61P 35/02 | (2006.01) |
| A61K 31/69 | (2006.01) |
| A61K 31/325 | (2006.01) |

(52) U.S. Cl.
CPC ....... *G01N 33/57426* (2013.01); *A61K 31/69* (2013.01); *A61K 31/713* (2013.01); *A61P 35/02* (2018.01); *C12N 15/113* (2013.01); *G01N 33/5011* (2013.01); *G01N 33/6872* (2013.01); *A61K 31/325* (2013.01); *A61K 2300/00* (2013.01); *C12N 2310/14* (2013.01); *C12N 2310/141* (2013.01); *C12N 2310/531* (2013.01); *G01N 2333/4704* (2013.01)

(58) Field of Classification Search
CPC ...... G01N 33/574; A61P 35/00; A61K 31/713
See application file for complete search history.

(56) References Cited

U.S. PATENT DOCUMENTS

| | | | |
|---|---|---|---|
| 8,815,945 | B2 | 8/2014 | Nagai |
| 8,822,532 | B2 | 9/2014 | Nagai |
| 2010/0278921 | A1 | 11/2010 | Fischer et al. |
| 2013/0079370 | A1 | 3/2013 | Brnjic et al. |
| 2014/0288157 | A1 | 9/2014 | Shaul et al. |
| 2014/0370528 | A1 | 12/2014 | Brnjic et al. |

FOREIGN PATENT DOCUMENTS

| | | |
|---|---|---|
| WO | WO 2014/182744 A1 | 11/2014 |
| WO | WO 2017/007858 A1 | 1/2017 |

OTHER PUBLICATIONS

Yang et al. Am J Respir Cell Mol Biol 41, 14-23 (Year: 2009).*
Chiita et al. Blood 114, 22: 4919 (Year: 2009).*
Lu et al. Biomarker Resaerch Jan. 2013: 13, pp. 1-9 (Year: 2013).*
Green, Colin, et al. "Bortezomib for the treatment of multiple myeloma patients." Health Technology Assessment 13.1 (2009).
Richardson, Paul G., et al. "Bortezomib in the front-line treatment of multiple myeloma." Expert review of anticancer therapy 8.7 (2008): 1053-1072.
Synta and GlaxoSmithKline Announce Elesclomol Granted Orphan Drug Designation by the FDA Published Wednesday Jan. 30, 2008 Adapted Media Release.
Grosicki, Sebastian, et al. "Bortezomib for the treatment of multiple myeloma." Expert review of hematology 7.2 (2014): 173-185.
Non-Final Office Action in U.S. Appl. No. 15/870,747, dated Jun. 3, 2019.
Cai, Kai, et al. "Human mitochondrial ferredoxin 1 (FDX1) and ferredoxin 2 (FDX2) both bind cysteine desulfurase and donate electrons for iron-sulfur cluster biosynthesis." *Biochemistry* 56.3 (2017): 487-499.
Gohil, Vishal M., et al. "Discovery and therapeutic potential of drugs that shift energy metabolism from mitochondrial respiration to glycolysis." *Nature Biotechnology* 28.3 (2010): 249-255.

(Continued)

*Primary Examiner* — Brian Whiteman
(74) *Attorney, Agent, or Firm* — Morse, Barnes-Brown & Pendleton, P.C.; Lisa M. Warren, Esq.

(57) ABSTRACT

In some aspects, the disclosure provides methods of modulating the level of proteasome inhibitor resistance of a cell, the methods comprising manipulating the level of expression or activity of a subunit of the 19S proteasome in the cell. In some aspects, cells in which the level of a 19S subunit is modulated, e.g., reduced, are provided. In some aspects, methods of identifying agents that reduce proteasome inhibitor resistance are provided. In some aspects, methods of classifying cancers according to predicted proteasome inhibitor resistance are provided. In some aspects, methods of killing or inhibiting proliferation of cancer cells, e.g., proteasome inhibitor resistant cancer cells, are provided. In some aspects, methods of treating cancer, e.g., proteasome inhibitor resistant cancer, are provided.

12 Claims, 55 Drawing Sheets
Specification includes a Sequence Listing.

(56) References Cited

OTHER PUBLICATIONS

Maio, Nunziata, and Rouault, Tracey A., "Iron-sulfur cluster biogenesis in mammalian cells: new insights into the molecular mechanisms of cluster delivery." *Biochimica et Biophysica Acta (BBA)—Molecular Cell Research* 1853.6 (2015): 1493-1512.

Sheftel, Alex D., et al. "Humans possess two mitochondrial ferredoxins, Fdx1 and Fdx2, with distinct roles in steroidogenesis, heme, and Fe/S cluster biosynthesis." *Proceedings of the National Academy of Sciences* 107.26 (2010): 11775-11780.

Tsvetkov, Peter, et al. "Suppression of 19S proteasome subunits marks emergence of an altered cell state in diverse cancers." *Proceedings of the National Academy of Sciences* 114.2 (2017): 382-387.

Kale, Andrew J., and Moore, Bradley S., "Molecular mechanisms of acquired proteasome inhibitor resistance." *Journal of Medicinal Chemistry* 55.23 (2012): 10317-10327.

Mulligan, George, et al, "Gene expression profiling and correlation with outcome in clinical trials of the proteasome inhibitor bortezomib," *Blood* 109.8 (2007): 3177-3188.

Tomko Jr, Robert J., and Hochstrasser, Mark, "Molecular architecture and assembly of the eukaryotic proteasome." *Annual Review of Biochemistry* 82 (2013): 415-445.

Fuchs, et al., "Increased expression and altered subunit composition of proteasomes induced by continuous proteasome inhibition establish apoptosis resistance and hyperproliferation of Burkitt lymphoma cells," J Cell Biochem, Jan. 1, 2008 (Jan. 1, 2008), vol. 103, pp. 270-283.

Lee, et al., "Enhancement of Proteasome Activity by a Small-Molecule Inhibitor of Usp14," Nature, Sep. 9, 2010 (Sep. 9, 2010), vol. 467, pp. 179-184.

Su, et al., "p62 Stages an Interplay between the Ubiquitin-Proteasome System and Autophagy in the Heart of Defense against Proteotoxic Stress," Trends Cardiovasc Med, Nov. 1, 2011 (Nov. 1, 2011), vol. 21, pp. 224-228.

Arlt, et al., "Increased proteasome subunit protein expression and proteasome activity in colon cancer relate to an enhanced activation of nuclear factor E2-related factor 2 (Nrf2)," Oncogene, Sep. 7, 2009 (Sep. 7, 2009), vol. 28, pp. 3983-3996.

Kwak, et al., "Antioxidants Enhance Mammalian Proteasome Expression through the Keap 1-Nrf2 Signaling Pathway," Molecular and Cellular Biology, Dec. 1, 2003 (Dec. 1, 2003), vol. 23, pp. 8786-8794.

Acosta-Alvear, et al., "Paradoxical resistance of multiple myeloma to proteasome inhibitors by decreased levels of 19S proteasomal subunits," eLife, Sep. 1, 2015 (Sep. 1, 2015), vol. 4, e08153, pp. 1-19.

Asano, S., Fukuda, Y., Beck, F., Aufderheide, A., Forster, F., Danev, R., and Baumeister, W. (2015). Proteasomes. A molecular census of 26S proteasomes in intact neurons. Science 347, 439-442.

Tsvetkov, P., Myers, N., Eliav, R., Adamovich, Y., Nagai, T., Adler, J., Navon, A., and Shaul, Y. (2014). NADH binds and stabilizes the 26S proteasomes independent of ATP. J Biol Chem 289, 11272-11281.

Vilchez, D., Boyer, L., Morantte, I., Lutz, M., Merkwirth, C., Joyce, D., Spencer, B., Page, L., Masliah, E., Berggren, W.T., et al. (2012). Increased proteasome activity in human embryonic stem cells is regulated by PSMD11. Nature 489, 304-308.

Breslow, D.K., Cameron, D.M., Collins, S.R., Schuldiner, M., Stewart-Ornstein, J., Newman, H.W., Braun, S., Madhani, H.D., Krogan, N.J., and Weissman, J.S. (2008). A comprehensive strategy enabling high-resolution functional analysis of the yeast genome. Nature methods 5, 711-718.

International Search Report in International Application No. PCT/US2016/041207, dated Oct. 28, 2016.

Kirshner, Jessica R., et al. "Elesclomol induces cancer cell apoptosis through oxidative stress." Molecular cancer therapeutics 7.8 (2008): 2319-2327.

Non-Final Office Action in U.S. Appl. No. 15/870,747, dated Dec. 5, 2019.

* cited by examiner

1A

1B

| Gene | # Inserts | P-value |
|---|---|---|
| PSMD12 | 35 | 2.94E-83 |
| PSMC5 | 31 | 6.86E-76 |
| PSMD7 | 26 | 4.10E-63 |
| PSMC3 | 21 | 4.09E-47 |
| PSMD2 | 21 | 2.44E-50 |
| PSMC6 | 18 | 8.26E-43 |
| PSMC4 | 7 | 1.49E-15 |
| PSMC2 | 4 | 1.66E-07 |
| PSMD6 | 4 | 1.66E-07 |
| ZNF366 | 3 | 0.00025 |
| EXOSC10 | 3 | 0.00029 |

▒ 19S regulatory complex

3 sigma cells are highly resistant to proteasome inhibitors

3-Sigma cells are defined as cells that have a 3 std. decrease in the expression of at least one subunit of 19S proteasome complex

9A

Bortezomib

9B

Bortezomib n=31/351

9C

MG132

9D

MG132 n= 31/353

PSMD5 expression is frequently reduced in cancer cell lines

| | Observed | P-Value |
|---|---|---|
| PSMD5 | 30 | 1E-16 |
| PSMD1 | 6 | 0.000811097 |
| PSMC6 | 5 | 0.004723917 |
| PSMD10 | 5 | 0.004723917 |
| PSMD14 | 5 | 0.004723917 |
| PSMD6 | 5 | 0.004723917 |
| PSMD13 | 3 | 0.09254329 |
| PSMD7 | 3 | 0.09254329 |
| PSMC1 | 2 | 0.2882082 |
| PSMC5 | 2 | 0.2882082 |
| PSMD12 | 2 | 0.2882082 |
| PSMC3 | 1 | 0.6555718 |
| PSMC4 | 1 | 0.6555718 |
| PSMD4 | 1 | 0.6555718 |
| PSMD8 | 1 | 0.6555718 |
| ADRM1 | 0 | 1 |
| PSMC2 | 0 | 1 |
| PSMD11 | 0 | 1 |
| PSMD3 | 0 | 1 |
| PSMD9 | 0 | 1 |

FIG. 11A

Reduced 19S subunit expression in multiple models of acquired and natural resistance to proteasome inhibitors

14A Acquired resistance to Bortezomib in adenocarcinoma cells HT-29

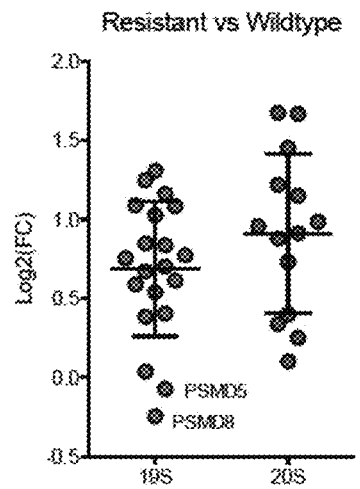

(GSE29713 Keats et al., Suzuki et al., Plos one, 2011)

14B Natural resistance to Bortezomib in mantle cell lymphoma (MCL)

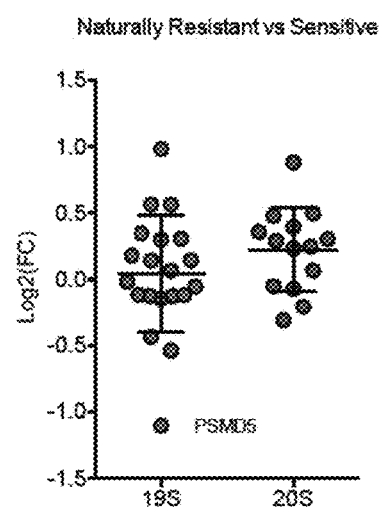

(Patricia Pérez-Galán et al., Blood 2011)

14C Acquired resistance to Carfilzomib in multiple myeloma cells

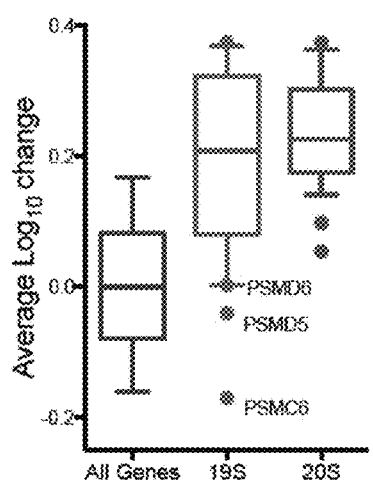

(Riz et al., Oncotarget 2015)

14D

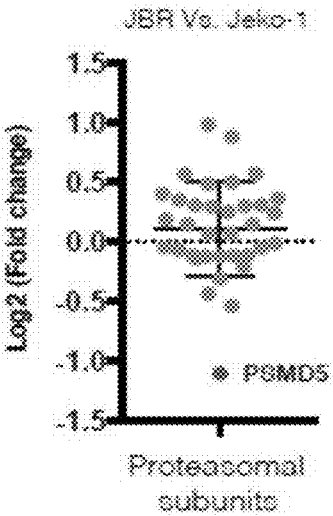

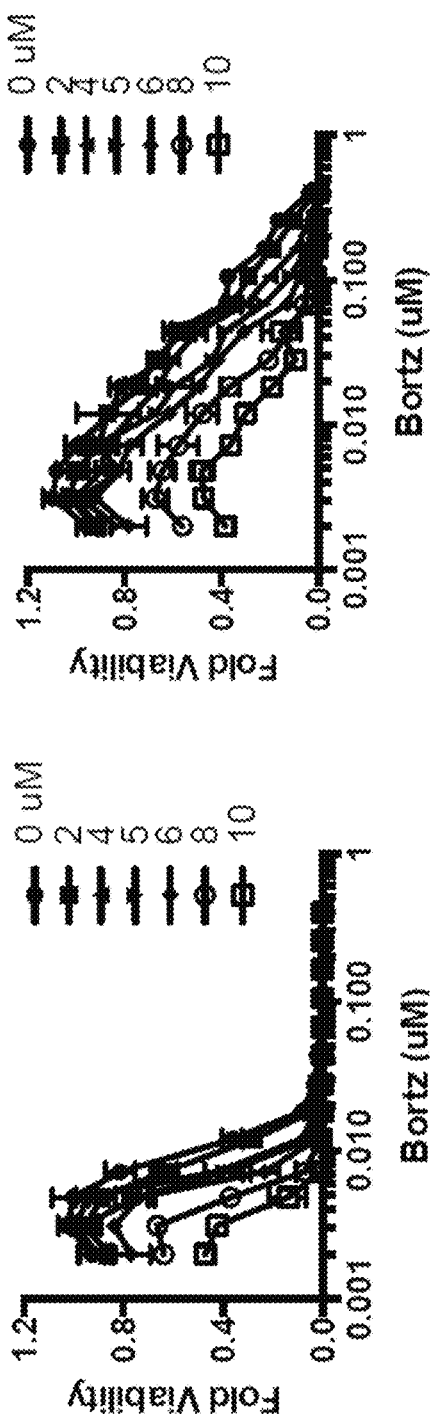
FIG. 20

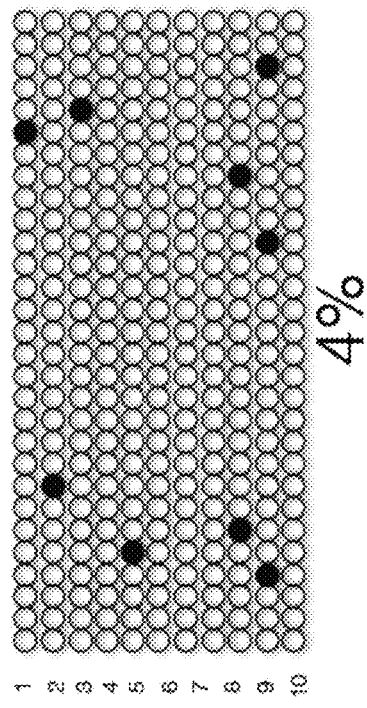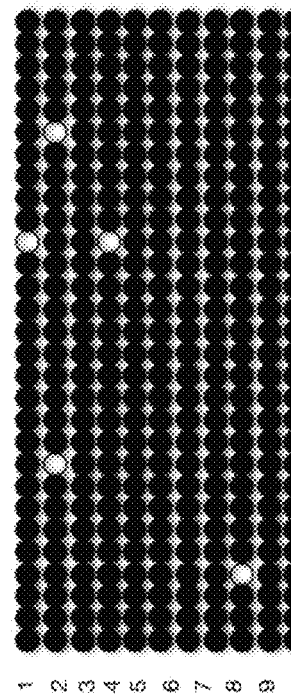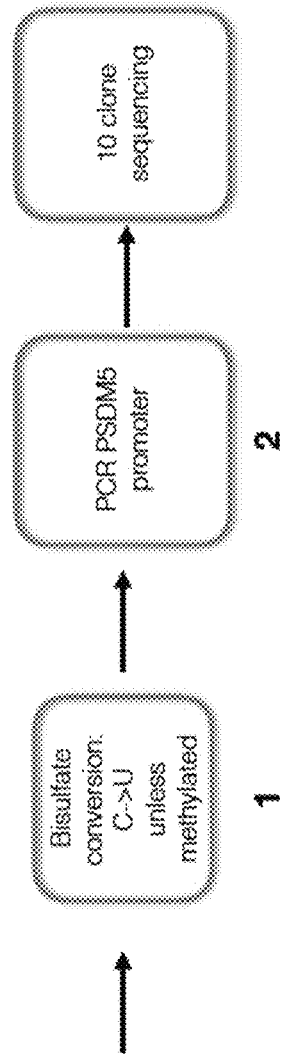
FIGS. 23A-23B

25A

25B

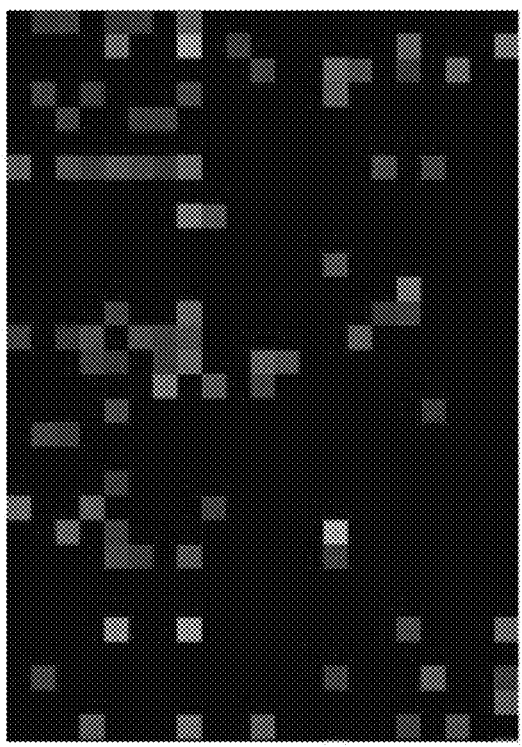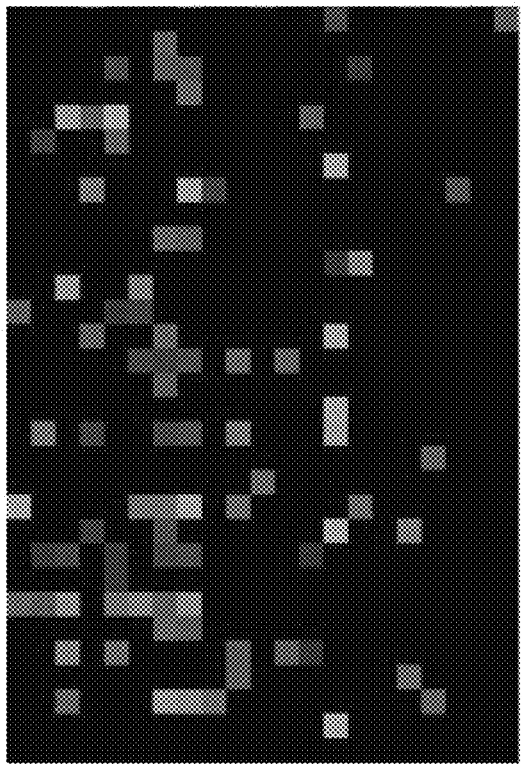
FIG. 35

SEQUENCE LISTING

<160> NUMBER OF SEQ ID NOS: 110

<210> SEQ ID NO 1
<211> LENGTH: 21
<212> TYPE: DNA
<213> ORGANISM: Unknown
<220> FEATURE:
<223> OTHER INFORMATION: shRNA

<400> SEQUENCE: 1
ccacatttgt agcgaacact t                                              21

<210> SEQ ID NO 2
<211> LENGTH: 21
<212> TYPE: DNA
<213> ORGANISM: Unknown
<220> FEATURE:
<223> OTHER INFORMATION: shRNA

<400> SEQUENCE: 2
gctggctcaa atcgtgaaga t                                              21

<210> SEQ ID NO 3
<211> LENGTH: 21
<212> TYPE: DNA
<213> ORGANISM: Unknown
<220> FEATURE:
<223> OTHER INFORMATION: shRNA

<400> SEQUENCE: 3
ccctataaca tggcccacaa t                                              21

<210> SEQ ID NO 4
<211> LENGTH: 21
<212> TYPE: DNA
<213> ORGANISM: Unknown
<220> FEATURE:
<223> OTHER INFORMATION: shRNA

<400> SEQUENCE: 4
cgaaacatta ttctaggcaa a                                              21

<210> SEQ ID NO 5
<211> LENGTH: 21
<212> TYPE: DNA
<213> ORGANISM: Unknown
<220> FEATURE:
<223> OTHER INFORMATION: shRNA

<400> SEQUENCE: 5
gaggataaac agcttcaaga t                                              21

<210> SEQ ID NO 6
<211> LENGTH: 21
<212> TYPE: DNA
<213> ORGANISM: Unknown
<220> FEATURE:
<223> OTHER INFORMATION: shRNA

<400> SEQUENCE: 6
gcacagagga acgaactaaa t                                              21

<210> SEQ ID NO 7
<211> LENGTH: 21
<212> TYPE: DNA
<213> ORGANISM: Unknown

```
<220> FEATURE:
<223> OTHER INFORMATION: shRNA

<400> SEQUENCE: 7
gaagattcat tctcggaaga t                                              21

<210> SEQ ID NO 8
<211> LENGTH: 21
<212> TYPE: DNA
<213> ORGANISM: Unknown
<220> FEATURE:
<223> OTHER INFORMATION: shRNA

<400> SEQUENCE: 8
caaggttatc atggctacta a                                              21

<210> SEQ ID NO 9
<211> LENGTH: 21
<212> TYPE: DNA
<213> ORGANISM: Unknown
<220> FEATURE:
<223> OTHER INFORMATION: shRNA

<400> SEQUENCE: 9
tgctccatct atcatcttca t                                              21

<210> SEQ ID NO 10
<211> LENGTH: 38
<212> TYPE: DNA
<213> ORGANISM: Unknown
<220> FEATURE:
<223> OTHER INFORMATION: primer

<400> SEQUENCE: 10
aaaaaaccgg tcgccaccat ggtgagcaag ggcgagga                            38

<210> SEQ ID NO 11
<211> LENGTH: 36
<212> TYPE: DNA
<213> ORGANISM: Unknown
<220> FEATURE:
<223> OTHER INFORMATION: primer

<400> SEQUENCE: 11
tttttatcga ttacttgtac agctcgtcca tgccga                              36

<210> SEQ ID NO 12
<211> LENGTH: 23
<212> TYPE: DNA
<213> ORGANISM: Unknown
<220> FEATURE:
<223> OTHER INFORMATION: primer

<400> SEQUENCE: 12
tcgacctcga gtaccaccac act                                            23

<210> SEQ ID NO 13
<211> LENGTH: 23
<212> TYPE: DNA
<213> ORGANISM: Unknown
<220> FEATURE:
<223> OTHER INFORMATION: primer

<400> SEQUENCE: 13
aaacgacggg atccgccatg tca                                            23
```

```
<210> SEQ ID NO 14
<211> LENGTH: 23
<212> TYPE: DNA
<213> ORGANISM: Unknown
<220> FEATURE:
<223> OTHER INFORMATION: primer

<400> SEQUENCE: 14
tatccagccc tcactccttc tct                                              23

<210> SEQ ID NO 15
<211> LENGTH: 20
<212> TYPE: DNA
<213> ORGANISM: Unknown
<220> FEATURE:
<223> OTHER INFORMATION: primer

<400> SEQUENCE: 15
ctgtggatga gtcagaggct                                                  20

<210> SEQ ID NO 16
<211> LENGTH: 20
<212> TYPE: DNA
<213> ORGANISM: Unknown
<220> FEATURE:
<223> OTHER INFORMATION: primer

<400> SEQUENCE: 16
ttggctatga ggtgtgtcgt                                                  20

<210> SEQ ID NO 17
<211> LENGTH: 20
<212> TYPE: DNA
<213> ORGANISM: Unknown
<220> FEATURE:
<223> OTHER INFORMATION: primer

<400> SEQUENCE: 17
acagccatta caggtggcaa                                                  20

<210> SEQ ID NO 18
<211> LENGTH: 20
<212> TYPE: DNA
<213> ORGANISM: Unknown
<220> FEATURE:
<223> OTHER INFORMATION: primer

<400> SEQUENCE: 18
gtccacaccg actctcatcc                                                  20

<210> SEQ ID NO 19
<211> LENGTH: 25
<212> TYPE: DNA
<213> ORGANISM: Unknown
<220> FEATURE:
<223> OTHER INFORMATION: primer

<400> SEQUENCE: 19
ggttggttta gcggtttagt tttcg                                            25

<210> SEQ ID NO 20
<211> LENGTH: 27
<212> TYPE: DNA
<213> ORGANISM: Unknown
<220> FEATURE:
<223> OTHER INFORMATION: primer
```

```
<400> SEQUENCE: 20
catccaatct tccaaaaaca taacgct                                          27

<210> SEQ ID NO 21
<211> LENGTH: 21
<212> TYPE: DNA
<213> ORGANISM: Unknown
<220> FEATURE:
<223> OTHER INFORMATION: shRNA

<400> SEQUENCE: 21
ccatgaggtt tcctcccaaa t                                                21

<210> SEQ ID NO 22
<211> LENGTH: 21
<212> TYPE: DNA
<213> ORGANISM: Unknown
<220> FEATURE:
<223> OTHER INFORMATION: shRNA

<400> SEQUENCE: 22
gcagggcttc ttcacttcaa a                                                21

<210> SEQ ID NO 23
<211> LENGTH: 21
<212> TYPE: DNA
<213> ORGANISM: Unknown
<220> FEATURE:
<223> OTHER INFORMATION: shRNA

<400> SEQUENCE: 23
tttcccacac acagctcata t                                                21

<210> SEQ ID NO 24
<211> LENGTH: 21
<212> TYPE: DNA
<213> ORGANISM: Unknown
<220> FEATURE:
<223> OTHER INFORMATION: shRNA

<400> SEQUENCE: 24
gccgcaaagt gttactatta t                                                21

<210> SEQ ID NO 25
<211> LENGTH: 21
<212> TYPE: DNA
<213> ORGANISM: Unknown
<220> FEATURE:
<223> OTHER INFORMATION: shRNA

<400> SEQUENCE: 25
acgctgagta cttcgaaatg t                                                21

<210> SEQ ID NO 26
<211> LENGTH: 21
<212> TYPE: DNA
<213> ORGANISM: Unknown
<220> FEATURE:
<223> OTHER INFORMATION: shRNA

<400> SEQUENCE: 26
ctatgatctc tccagtaaat a                                                21

<210> SEQ ID NO 27
```

```
<211> LENGTH: 24
<212> TYPE: DNA
<213> ORGANISM: Unknown
<220> FEATURE:
<223> OTHER INFORMATION: shRNA

<400> SEQUENCE: 27
cdsgacactt caggtgcttg attt                                              24

<210> SEQ ID NO 28
<211> LENGTH: 21
<212> TYPE: DNA
<213> ORGANISM: Unknown
<220> FEATURE:
<223> OTHER INFORMATION: shRNA

<400> SEQUENCE: 28
agatggtctc attaagcttt a                                                 21

<210> SEQ ID NO 29
<211> LENGTH: 21
<212> TYPE: DNA
<213> ORGANISM: Unknown
<220> FEATURE:
<223> OTHER INFORMATION: shRNA

<400> SEQUENCE: 29
cagacggtcg acattgaatt t                                                 21

<210> SEQ ID NO 30
<211> LENGTH: 21
<212> TYPE: DNA
<213> ORGANISM: Unknown
<220> FEATURE:
<223> OTHER INFORMATION: shRNA

<400> SEQUENCE: 30
agaatcgtcg tatgcagtga a                                                 21

<210> SEQ ID NO 31
<211> LENGTH: 21
<212> TYPE: DNA
<213> ORGANISM: Unknown
<220> FEATURE:
<223> OTHER INFORMATION: shRNA

<400> SEQUENCE: 31
tgaccctgaa gttcatctgc a                                                 21

<210> SEQ ID NO 32
<211> LENGTH: 21
<212> TYPE: DNA
<213> ORGANISM: Unknown
<220> FEATURE:
<223> OTHER INFORMATION: shRNA

<400> SEQUENCE: 32
gctcagtgtg gtggatcatt t                                                 21

<210> SEQ ID NO 33
<211> LENGTH: 21
<212> TYPE: DNA
<213> ORGANISM: Unknown
<220> FEATURE:
<223> OTHER INFORMATION: shRNA

<400> SEQUENCE: 33
```

-continued

```
gccatcaacg aactcatgaa a                                              21

<210> SEQ ID NO 34
<211> LENGTH: 21
<212> TYPE: DNA
<213> ORGANISM: Unknown
<220> FEATURE:
<223> OTHER INFORMATION: shRNA

<400> SEQUENCE: 34
gctgaggaag ttggagttga a                                              21

<210> SEQ ID NO 35
<211> LENGTH: 21
<212> TYPE: DNA
<213> ORGANISM: Unknown
<220> FEATURE:
<223> OTHER INFORMATION: shRNA

<400> SEQUENCE: 35
gtcggcttac ggcggtgatt t                                              21

<210> SEQ ID NO 36
<211> LENGTH: 21
<212> TYPE: DNA
<213> ORGANISM: Unknown
<220> FEATURE:
<223> OTHER INFORMATION: shRNA

<400> SEQUENCE: 36
attccgtatt ggtcatcatt g                                              21

<210> SEQ ID NO 37
<211> LENGTH: 21
<212> TYPE: DNA
<213> ORGANISM: Unknown
<220> FEATURE:
<223> OTHER INFORMATION: shRNA

<400> SEQUENCE: 37
ccgacgtgga aaggaaatta t                                              21

<210> SEQ ID NO 38
<211> LENGTH: 21
<212> TYPE: DNA
<213> ORGANISM: Unknown
<220> FEATURE:
<223> OTHER INFORMATION: shRNA

<400> SEQUENCE: 38
ggacatgcag tcgggtatta t                                              21

<210> SEQ ID NO 39
<211> LENGTH: 21
<212> TYPE: DNA
<213> ORGANISM: Unknown
<220> FEATURE:
<223> OTHER INFORMATION: shRNA

<400> SEQUENCE: 39
ctggtgtctt tgtactttga t                                              21

<210> SEQ ID NO 40
<211> LENGTH: 21
<212> TYPE: DNA
```

```
<213> ORGANISM: Unknown
<220> FEATURE:
<223> OTHER INFORMATION: shRNA

<400> SEQUENCE: 40
cctcatttgg tgcatctgta t                                              21

<210> SEQ ID NO 41
<211> LENGTH: 21
<212> TYPE: DNA
<213> ORGANISM: Unknown
<220> FEATURE:
<223> OTHER INFORMATION: shRNA

<400> SEQUENCE: 41
agtcaacgag tatctgaaca a                                              21

<210> SEQ ID NO 42
<211> LENGTH: 21
<212> TYPE: DNA
<213> ORGANISM: Unknown
<220> FEATURE:
<223> OTHER INFORMATION: shRNA

<400> SEQUENCE: 42
cagacggacg actcgcttat t                                              21

<210> SEQ ID NO 43
<211> LENGTH: 21
<212> TYPE: DNA
<213> ORGANISM: Unknown
<220> FEATURE:
<223> OTHER INFORMATION: shRNA

<400> SEQUENCE: 43
ccctgacgac tgtgagttca a                                              21

<210> SEQ ID NO 44
<211> LENGTH: 21
<212> TYPE: DNA
<213> ORGANISM: Unknown
<220> FEATURE:
<223> OTHER INFORMATION: shRNA

<400> SEQUENCE: 44
tgccggaaag tcaacgagta t                                              21

<210> SEQ ID NO 45
<211> LENGTH: 21
<212> TYPE: DNA
<213> ORGANISM: Unknown
<220> FEATURE:
<223> OTHER INFORMATION: shRNA

<400> SEQUENCE: 45
gacagccttt cgcaagacat a                                              21

<210> SEQ ID NO 46
<211> LENGTH: 21
<212> TYPE: DNA
<213> ORGANISM: Unknown
<220> FEATURE:
<223> OTHER INFORMATION: shRNA

<400> SEQUENCE: 46
caggaactgt ccaggtttat t                                              21
```

<210> SEQ ID NO 47
<211> LENGTH: 21
<212> TYPE: DNA
<213> ORGANISM: Unknown
<220> FEATURE:
<223> OTHER INFORMATION: shRNA

<400> SEQUENCE: 47
cttgaagtgt tgcacagtct t                                              21

<210> SEQ ID NO 48
<211> LENGTH: 21
<212> TYPE: DNA
<213> ORGANISM: Unknown
<220> FEATURE:
<223> OTHER INFORMATION: shRNA

<400> SEQUENCE: 48
gcagtaccaa gaaactatca a                                              21

<210> SEQ ID NO 49
<211> LENGTH: 21
<212> TYPE: DNA
<213> ORGANISM: Unknown
<220> FEATURE:
<223> OTHER INFORMATION: shRNA

<400> SEQUENCE: 49
tatcgacatc ccgtatctta g                                              21

<210> SEQ ID NO 50
<211> LENGTH: 21
<212> TYPE: DNA
<213> ORGANISM: Unknown
<220> FEATURE:
<223> OTHER INFORMATION: shRNA

<400> SEQUENCE: 50
gtagacagat tagcaggaat t                                              21

<210> SEQ ID NO 51
<211> LENGTH: 21
<212> TYPE: DNA
<213> ORGANISM: Unknown
<220> FEATURE:
<223> OTHER INFORMATION: shRNA

<400> SEQUENCE: 51
gactgttata atggtgtata t                                              21

<210> SEQ ID NO 52
<211> LENGTH: 21
<212> TYPE: DNA
<213> ORGANISM: Unknown
<220> FEATURE:
<223> OTHER INFORMATION: shRNA

<400> SEQUENCE: 52
ccttcctatc aaacttcgat t                                              21

<210> SEQ ID NO 53
<211> LENGTH: 21
<212> TYPE: DNA
<213> ORGANISM: Unknown
<220> FEATURE:

```
<223> OTHER INFORMATION: shRNA

<400> SEQUENCE: 53
gccaaacagg tcatcgagta t                                              21

<210> SEQ ID NO 54
<211> LENGTH: 21
<212> TYPE: DNA
<213> ORGANISM: Unknown
<220> FEATURE:
<223> OTHER INFORMATION: shRNA

<400> SEQUENCE: 54
gctgaccaaa cagcagctaa t                                              21

<210> SEQ ID NO 55
<211> LENGTH: 21
<212> TYPE: DNA
<213> ORGANISM: Unknown
<220> FEATURE:
<223> OTHER INFORMATION: shRNA

<400> SEQUENCE: 55
gatgacagac tacgccaaga a                                              21

<210> SEQ ID NO 56
<211> LENGTH: 21
<212> TYPE: DNA
<213> ORGANISM: Unknown
<220> FEATURE:
<223> OTHER INFORMATION: shRNA

<400> SEQUENCE: 56
cccagctcaa atgctactac t                                              21

<210> SEQ ID NO 57
<211> LENGTH: 21
<212> TYPE: DNA
<213> ORGANISM: Unknown
<220> FEATURE:
<223> OTHER INFORMATION: shRNA

<400> SEQUENCE: 57
gctggagtct aaattggact a                                              21

<210> SEQ ID NO 58
<211> LENGTH: 21
<212> TYPE: DNA
<213> ORGANISM: Unknown
<220> FEATURE:
<223> OTHER INFORMATION: shRNA

<400> SEQUENCE: 58
cattggtgaa agtgctcgtt t                                              21

<210> SEQ ID NO 59
<211> LENGTH: 21
<212> TYPE: DNA
<213> ORGANISM: Unknown
<220> FEATURE:
<223> OTHER INFORMATION: shRNA

<400> SEQUENCE: 59
cctcttacaa acccagagtt a                                              21
```

```
<210> SEQ ID NO 60
<211> LENGTH: 21
<212> TYPE: DNA
<213> ORGANISM: Unknown
<220> FEATURE:
<223> OTHER INFORMATION: shRNA

<400> SEQUENCE: 60
cccattacaa agcatggtga a                                         21

<210> SEQ ID NO 61
<211> LENGTH: 21
<212> TYPE: DNA
<213> ORGANISM: Unknown
<220> FEATURE:
<223> OTHER INFORMATION: shRNA

<400> SEQUENCE: 61
ccagacggtg aagaaggtga t                                         21

<210> SEQ ID NO 62
<211> LENGTH: 21
<212> TYPE: DNA
<213> ORGANISM: Unknown
<220> FEATURE:
<223> OTHER INFORMATION: shRNA

<400> SEQUENCE: 62
tctggctctg tgtatgcata t                                         21

<210> SEQ ID NO 63
<211> LENGTH: 21
<212> TYPE: DNA
<213> ORGANISM: Unknown
<220> FEATURE:
<223> OTHER INFORMATION: shRNA

<400> SEQUENCE: 63
cgaaataagg aacgcatctc t                                         21

<210> SEQ ID NO 64
<211> LENGTH: 21
<212> TYPE: DNA
<213> ORGANISM: Unknown
<220> FEATURE:
<223> OTHER INFORMATION: shRNA

<400> SEQUENCE: 64
caatgtcgaa tctatgagct t                                         21

<210> SEQ ID NO 65
<211> LENGTH: 21
<212> TYPE: DNA
<213> ORGANISM: Unknown
<220> FEATURE:
<223> OTHER INFORMATION: shRNA

<400> SEQUENCE: 65
caagctgcaa agacggaaat a                                         21

<210> SEQ ID NO 66
<211> LENGTH: 21
<212> TYPE: DNA
<213> ORGANISM: Unknown
<220> FEATURE:
<223> OTHER INFORMATION: shRNA
```

```
<400> SEQUENCE: 66
agaaatgacc tgccgtgata t                                              21

<210> SEQ ID NO 67
<211> LENGTH: 21
<212> TYPE: DNA
<213> ORGANISM: Unknown
<220> FEATURE:
<223> OTHER INFORMATION: shRNA

<400> SEQUENCE: 67
catcaggtgt ttcatacggt t                                              21

<210> SEQ ID NO 68
<211> LENGTH: 21
<212> TYPE: DNA
<213> ORGANISM: Unknown
<220> FEATURE:
<223> OTHER INFORMATION: shRNA

<400> SEQUENCE: 68
gtacatgacg aagttaagga t                                              21

<210> SEQ ID NO 69
<211> LENGTH: 21
<212> TYPE: DNA
<213> ORGANISM: Unknown
<220> FEATURE:
<223> OTHER INFORMATION: shRNA

<400> SEQUENCE: 69
ccacatgaag cagcacgact t                                              21

<210> SEQ ID NO 70
<211> LENGTH: 21
<212> TYPE: DNA
<213> ORGANISM: Unknown
<220> FEATURE:
<223> OTHER INFORMATION: shRNA

<400> SEQUENCE: 70
gctgtcatgg atagtcctca a                                              21

<210> SEQ ID NO 71
<211> LENGTH: 21
<212> TYPE: DNA
<213> ORGANISM: Unknown
<220> FEATURE:
<223> OTHER INFORMATION: shRNA

<400> SEQUENCE: 71
ccatactatg tgaaacctgt t                                              21

<210> SEQ ID NO 72
<211> LENGTH: 21
<212> TYPE: DNA
<213> ORGANISM: Unknown
<220> FEATURE:
<223> OTHER INFORMATION: shRNA

<400> SEQUENCE: 72
ccctgcttaa cgagaaccat a                                              21

<210> SEQ ID NO 73
<211> LENGTH: 21
```

```
<212> TYPE: DNA
<213> ORGANISM: Unknown
<220> FEATURE:
<223> OTHER INFORMATION: shRNA

<400> SEQUENCE: 73
ccctgtcaag aatatcacta a                                            21

<210> SEQ ID NO 74
<211> LENGTH: 21
<212> TYPE: DNA
<213> ORGANISM: Unknown
<220> FEATURE:
<223> OTHER INFORMATION: shRNA

<400> SEQUENCE: 74
acaacagcca caacgtctat a                                            21

<210> SEQ ID NO 75
<211> LENGTH: 21
<212> TYPE: DNA
<213> ORGANISM: Unknown
<220> FEATURE:
<223> OTHER INFORMATION: shRNA

<400> SEQUENCE: 75
cagattgatc aatgctaata t                                            21

<210> SEQ ID NO 76
<211> LENGTH: 21
<212> TYPE: DNA
<213> ORGANISM: Unknown
<220> FEATURE:
<223> OTHER INFORMATION: shRNA

<400> SEQUENCE: 76
acagcagaac aagtctatat c                                            21

<210> SEQ ID NO 77
<211> LENGTH: 21
<212> TYPE: DNA
<213> ORGANISM: Unknown
<220> FEATURE:
<223> OTHER INFORMATION: shRNA

<400> SEQUENCE: 77
catggactaa acagacatta t                                            21

<210> SEQ ID NO 78
<211> LENGTH: 21
<212> TYPE: DNA
<213> ORGANISM: Unknown
<220> FEATURE:
<223> OTHER INFORMATION: shRNA

<400> SEQUENCE: 78
caagccatct atccaggcat t                                            21

<210> SEQ ID NO 79
<211> LENGTH: 21
<212> TYPE: DNA
<213> ORGANISM: Unknown
<220> FEATURE:
<223> OTHER INFORMATION: shRNA

<400> SEQUENCE: 79
```
gcgggtctgc aagtggatga t                                              21

<210> SEQ ID NO 80
<211> LENGTH: 21
<212> TYPE: DNA
<213> ORGANISM: Unknown
<220> FEATURE:
<223> OTHER INFORMATION: shRNA

<400> SEQUENCE: 80
gcgcagatca aggccaacta t                                              21

<210> SEQ ID NO 81
<211> LENGTH: 21
<212> TYPE: DNA
<213> ORGANISM: Unknown
<220> FEATURE:
<223> OTHER INFORMATION: shRNA

<400> SEQUENCE: 81
aggtactggt gtgattatta t                                              21

<210> SEQ ID NO 82
<211> LENGTH: 21
<212> TYPE: DNA
<213> ORGANISM: Unknown
<220> FEATURE:
<223> OTHER INFORMATION: shRNA

<400> SEQUENCE: 82
accagcttag acttgttcca a                                              21

<210> SEQ ID NO 83
<211> LENGTH: 21
<212> TYPE: DNA
<213> ORGANISM: Unknown
<220> FEATURE:
<223> OTHER INFORMATION: shRNA

<400> SEQUENCE: 83
gaggataaac agcttcaaga t                                              21

<210> SEQ ID NO 84
<211> LENGTH: 21
<212> TYPE: DNA
<213> ORGANISM: Unknown
<220> FEATURE:
<223> OTHER INFORMATION: shRNA

<400> SEQUENCE: 84
ccacatttgt agcgaacact t                                              21

<210> SEQ ID NO 85
<211> LENGTH: 21
<212> TYPE: DNA
<213> ORGANISM: Unknown
<220> FEATURE:
<223> OTHER INFORMATION: shRNA

<400> SEQUENCE: 85
gctggctcaa atcgtgaaga t                                              21

<210> SEQ ID NO 86
<211> LENGTH: 21
<212> TYPE: DNA
<213> ORGANISM: Unknown

```
<220> FEATURE:
<223> OTHER INFORMATION: shRNA

<400> SEQUENCE: 86
cgaaacatta ttctaggcaa a                                              21

<210> SEQ ID NO 87
<211> LENGTH: 21
<212> TYPE: DNA
<213> ORGANISM: Unknown
<220> FEATURE:
<223> OTHER INFORMATION: shRNA

<400> SEQUENCE: 87
cacggagcaa tacagtgaca t                                              21

<210> SEQ ID NO 88
<211> LENGTH: 21
<212> TYPE: DNA
<213> ORGANISM: Unknown
<220> FEATURE:
<223> OTHER INFORMATION: shRNA

<400> SEQUENCE: 88
gtgcagatgt tcattggaga t                                              21

<210> SEQ ID NO 89
<211> LENGTH: 21
<212> TYPE: DNA
<213> ORGANISM: Unknown
<220> FEATURE:
<223> OTHER INFORMATION: shRNA

<400> SEQUENCE: 89
ccagcccaac acccaagtta a                                              21

<210> SEQ ID NO 90
<211> LENGTH: 21
<212> TYPE: DNA
<213> ORGANISM: Unknown
<220> FEATURE:
<223> OTHER INFORMATION: shRNA

<400> SEQUENCE: 90
ctcagttcca gtacggctcc a                                              21

<210> SEQ ID NO 91
<211> LENGTH: 21
<212> TYPE: DNA
<213> ORGANISM: Unknown
<220> FEATURE:
<223> OTHER INFORMATION: shRNA

<400> SEQUENCE: 91
gctcctggat gttgatccta a                                              21

<210> SEQ ID NO 92
<211> LENGTH: 21
<212> TYPE: DNA
<213> ORGANISM: Unknown
<220> FEATURE:
<223> OTHER INFORMATION: shRNA

<400> SEQUENCE: 92
gcacagagga acgaactaaa t                                              21
```

```
<210> SEQ ID NO 93
<211> LENGTH: 21
<212> TYPE: DNA
<213> ORGANISM: Unknown
<220> FEATURE:
<223> OTHER INFORMATION: shRNA

<400> SEQUENCE: 93
tcgtattaca acgtcgtgac t                                              21

<210> SEQ ID NO 94
<211> LENGTH: 21
<212> TYPE: DNA
<213> ORGANISM: Unknown
<220> FEATURE:
<223> OTHER INFORMATION: shRNA

<400> SEQUENCE: 94
gaagattcat tctcggaaga t                                              21

<210> SEQ ID NO 95
<211> LENGTH: 21
<212> TYPE: DNA
<213> ORGANISM: Unknown
<220> FEATURE:
<223> OTHER INFORMATION: shRNA

<400> SEQUENCE: 95
caaggttatc atggctacta a                                              21

<210> SEQ ID NO 96
<211> LENGTH: 21
<212> TYPE: DNA
<213> ORGANISM: Unknown
<220> FEATURE:
<223> OTHER INFORMATION: shRNA

<400> SEQUENCE: 96
ccaacgtgac ctatcccatt a                                              21

<210> SEQ ID NO 97
<211> LENGTH: 21
<212> TYPE: DNA
<213> ORGANISM: Unknown
<220> FEATURE:
<223> OTHER INFORMATION: shRNA

<400> SEQUENCE: 97
tgctccatct atcatcttca t                                              21

<210> SEQ ID NO 98
<211> LENGTH: 21
<212> TYPE: DNA
<213> ORGANISM: Unknown
<220> FEATURE:
<223> OTHER INFORMATION: shRNA

<400> SEQUENCE: 98
gagcattgag gcccagtaag a                                              21

<210> SEQ ID NO 99
<211> LENGTH: 21
<212> TYPE: DNA
<213> ORGANISM: Unknown
<220> FEATURE:
<223> OTHER INFORMATION: shRNA
```

```
<400> SEQUENCE: 99
acattggtgc agccctagtt t                                              21

<210> SEQ ID NO 100
<211> LENGTH: 21
<212> TYPE: DNA
<213> ORGANISM: Unknown
<220> FEATURE:
<223> OTHER INFORMATION: shRNA

<400> SEQUENCE: 100
gagattgagg tgctggaaga a                                              21

<210> SEQ ID NO 101
<211> LENGTH: 21
<212> TYPE: DNA
<213> ORGANISM: Unknown
<220> FEATURE:
<223> OTHER INFORMATION: shRNA

<400> SEQUENCE: 101
tgccgtcttg gaagccgatt t                                              21

<210> SEQ ID NO 102
<211> LENGTH: 21
<212> TYPE: DNA
<213> ORGANISM: Unknown
<220> FEATURE:
<223> OTHER INFORMATION: shRNA

<400> SEQUENCE: 102
gcacggaata tagggttaga t                                              21

<210> SEQ ID NO 103
<211> LENGTH: 21
<212> TYPE: DNA
<213> ORGANISM: Unknown
<220> FEATURE:
<223> OTHER INFORMATION: shRNA

<400> SEQUENCE: 103
acaatgaagc cattcgaaat g                                              21

<210> SEQ ID NO 104
<211> LENGTH: 21
<212> TYPE: DNA
<213> ORGANISM: Unknown
<220> FEATURE:
<223> OTHER INFORMATION: shRNA

<400> SEQUENCE: 104
ctctcatcag ttctccgatt t                                              21

<210> SEQ ID NO 105
<211> LENGTH: 21
<212> TYPE: DNA
<213> ORGANISM: Unknown
<220> FEATURE:
<223> OTHER INFORMATION: shRNA

<400> SEQUENCE: 105
gtggacaaca gtgagtatat g                                              21

<210> SEQ ID NO 106
```

```
<211> LENGTH: 21
<212> TYPE: DNA
<213> ORGANISM: Unknown
<220> FEATURE:
<223> OTHER INFORMATION: shRNA

<400> SEQUENCE: 106
gttctactgt tgtcgtatat t                                           21

<210> SEQ ID NO 107
<211> LENGTH: 21
<212> TYPE: DNA
<213> ORGANISM: Unknown
<220> FEATURE:
<223> OTHER INFORMATION: shRNA

<400> SEQUENCE: 107
gaagagttga aggagagtat t                                           21

<210> SEQ ID NO 108
<211> LENGTH: 21
<212> TYPE: DNA
<213> ORGANISM: Unknown
<220> FEATURE:
<223> OTHER INFORMATION: shRNA

<400> SEQUENCE: 108
cactcggata tttgatatgt g                                           21

<210> SEQ ID NO 109
<211> LENGTH: 21
<212> TYPE: DNA
<213> ORGANISM: Unknown
<220> FEATURE:
<223> OTHER INFORMATION: shRNA

<400> SEQUENCE: 109
gctcaagtga atgctgtcaa t                                           21

<210> SEQ ID NO 110
<211> LENGTH: 21
<212> TYPE: DNA
<213> ORGANISM: Unknown
<220> FEATURE:
<223> OTHER INFORMATION: shRNA

<400> SEQUENCE: 110
caagggtaac ttgaagatga t                                           21
```

METHODS AND COMPOSITIONS RELATING TO PROTEASOME INHIBITOR RESISTANCE

RELATED APPLICATIONS

This application is a national stage filing under 35 U.S.C. 371 of International Application No.: PCT/US2016/041207, filed Jul. 6, 2016, which claims the benefit of U.S. Provisional Application No. 62/189,173 filed on Jul. 6, 2015, U.S. Provisional Application No. 62/296,558, filed on Feb. 17, 2016, and U.S. Provisional Application No. 62/336,198, filed on May 13, 2016. The entire teachings of the above applications are incorporated herein by reference. International Application No.: PCT/US2016/041207 was published under PCT Article 21(2) in English.

BACKGROUND

Maintaining the integrity of the proteome is a basic function of cells. Protein chaperone systems and the ubiquitin-proteasome pathway are components of the global architecture that sustains protein homeostasis. The ubiquitin-proteasome system (UPS) is responsible for most regulatory and quality-control protein degradation in eukaryotic cells. The 26S proteasome is a multi-subunit protein complex that is present in all eukaryotes. This complex is comprised of a 20S catalytic core (also referred to as a 20S proteasome complex or 20S proteasome) that orchestrates peptide bond cleavage and a 19S regulatory complex on one or both ends of the 20S core. Proteins are targeted for degradation by the proteasome by the covalent attachment of the protein ubiquitin (Ub) to one or more lysines within the protein via the concerted action of three enzymes: E1, E2, and E3. The 19S proteasome complex recognizes ubiquitin-tagged substrates, cleaves ubiquitin chains, unfolds substrates, and translocates the unfolded proteins into the catalytic chamber of the 20S core.

Proteasome inhibition is a useful therapeutic approach for the treatment of cancer. Bortezomib (VELCADE®, PS-341), the first proteasome inhibitor to be approved by the US Food & Drug Administration, is particularly effective in certain hematopoietic tumors such as myeloma and mantle cell lymphoma. Despite intense study of proteasome function, and of the mechanism of action of proteasome inhibitors, understanding of the molecular mechanisms that cells deploy to resist the cytotoxic effects of reduced flux through the proteasome is limited. Such an understanding is of great importance in the treatment of cancer, in which pre-existing intrinsic resistance and acquired resistance following drug exposure have limited the effectiveness of bortezomib as a therapeutic. Although bortezomib can improve clinical outcomes, many patients do not respond to the drug, and patients that initially respond frequently relapse due to the development of bortezemib resistance.

SUMMARY

In some aspects, the present disclosure relates to the discovery of a mechanism by which cancer cells can be resistant to or acquire resistance to proteasome inhibitors. As described herein, a modest reduction in the level of expression or activity of one or more subunits of the 19S proteasome results in increased resistance (decreased sensitivity) of a cancer cell to exposure to a proteasome inhibitor.

In some aspects, described herein are methods of modulating the level of proteasome inhibitor resistance of a cell, the methods comprising manipulating the level of expression or activity of a subunit of the 19S proteasome in the cell. In some embodiments, a method comprises decreasing the level of expression of a subunit of the 19S proteasome, thereby increasing the level of proteasome resistance of the cell. In some embodiments, a method comprises increasing the level of expression of a subunit of the 19S proteasome, thereby decreasing the level of proteasome resistance of the cell. In some embodiments the cell is a cancer cell.

Cells in which the level of expression or activity of a 19S subunit is modulated (e.g., reduced) may be used, e.g., in screens to identify agents that inhibit the survival or proliferation of proteasome inhibitor resistant cancer cells and/or reduce proteasome inhibitor resistance. In some aspects, methods of identifying inhibitors of proteasome inhibitor resistance, e.g., using cells that have a reduced level of expression or activity of a 19S subunit, are provided. For example, agents that are selectively toxic to proteasome inhibitor resistant cells may be identified. Agents that increase proteasome inhibitor sensitivity may be identified.

In some aspects, described herein are agents that inhibit expression or activity of a 19S subunit. In some embodiments, such agents may be contacted with cells, e.g., cells that are sensitive to a proteasome inhibitor, in order to generate cells that have increased proteasome inhibitor resistance, which cells may be used, e.g., in screens as described herein.

In some aspects, described herein are agents that increase expression or activity of a 19S subunit. In some embodiments, such agents may be contacted with cells, e.g., cancer cells that are resistant to a proteasome inhibitor, in order to increase the sensitivity of such cells to a proteasome inhibitor. In some embodiments, such agents may be used to treat a subject in need of treatment for a proteasome inhibitor resistant cancer. In some embodiments, such agents may be administered in combination with a proteasome inhibitor.

Also described herein are methods of inhibiting cell survival or proliferation comprising contacting a cell, e.g., a cancer cell, with a 19S subunit inhibitor in an amount and for a time effective to inhibit survival or proliferation of the cell, e.g., in an amount effective to kill the cell or cause the cell to cease proliferating. Also described herein are methods of treating cancer comprising administering a 19S subunit inhibitor to a subject in an amount and for a time effective to inhibit survival or proliferation of cancer cells in the subject. The agent may be, e.g., an RNAi agent, antisense nucleic acid, small molecule, or polypeptide. In some embodiments, the agent may reduce the level of expression or activity of a 19S subunit to no more than 1%, or in some embodiments no more than 5%, of its level in the absence of the agent.

In some aspects, described herein are newly identified vulnerabilities in cancer cells that have reduced expression or activity of one or more 19S subunits. Also described herein are methods of inhibiting cancer cell growth to take advantage of such vulnerabilities. In some aspects, the methods comprise contacting cancer cells that have reduced expression or activity of one or more 19S subunits with a BCL2 family inhibitor, an ALDH inhibitor (e.g., disulfiram), or a bis(thio-hydrazide amide) (e.g., elesclomol). Also described herein are methods of treating cancer that take advantage of such vulnerabilities. In some aspects, the methods comprise administering a BCL2 family inhibitor (e.g., ABT-263), an ALDH inhibitor (e.g., disulfiram), a bis(thio-hydrazide amide) (e.g., elesclomol) to a subject in need of treatment for a cancer that has reduced expression or activity of one or more 19S subunits relative to a reference level.

In some aspects, described herein are methods of classifying a subject according to predicted likelihood that a subject in need of treatment for cancer will benefit from treatment with an agent that selectively inhibits growth of cancer cells that have reduced expression or activity of one or more 19S subunits. In some embodiments the agent comprises a BCL2 family inhibitor (e.g., ABT-263), an ALDH inhibitor (e.g., disulfiram), or a bis(thio-hydrazide amide) (e.g., elesclomol). In some embodiments the method comprises measuring expression of one or more 19S subunits in a sample obtained from cancer, wherein a reduced level of expression of one or more 19S subunits as compared to a reference value indicates that a subject has an increased likelihood of benefiting from treatment with the agent as compared to a subject with a cancer in which the level of expression of said one or more 19S subunits is not reduced. In some embodiments the method comprises measuring methylation of at least a portion of a promoter region of a gene that encodes a 19S subunit in a sample obtained from the cancer, wherein hypermethylation of at least a portion of a promoter region of a gene that encodes a 19S subunit indicates that subject has an increased likelihood of benefiting from treatment with the agent as compared to a subject with a cancer in which said portion of a promoter region of a gene that encodes a 19S subunit is not hypermethylated. In some embodiments the method comprises measuring expression of a miRNA that has a target site in an mRNA transcript that encodes a 19S subunit in a sample obtained from the cancer, wherein increased expression of the miRNA relative to a reference level indicates that a subject has an increased likelihood of benefiting from treatment with the agent as compared to a subject with a cancer in which expression of said miRNA is not increased. In some embodiments the method comprises treating the subject with the agent based on predicted likelihood that the subject will benefit. In some embodiments the method comprises treating the subject with the agent based on predicted likelihood that the subject will benefit.

In some aspects, described herein are methods of selecting a subject in need of treatment for cancer who is a suitable candidate for treatment with an agent that selectively inhibits growth of cancer cells that have reduced expression or activity of one or more 19S subunits. In some embodiments the agent comprises a BCL2 family inhibitor (e.g., ABT-263), an ALDH inhibitor (e.g., disulfiram), or a bis(thio-hydrazide amide) (e.g., elesclomol). In some embodiments the method comprises measuring expression of one or more 19S subunits in a sample obtained from cancer, wherein the subject is a suitable candidate for treatment with the agent if the level of expression of one or more 19S subunits is reduced. In some embodiments the method comprises measuring methylation of at least a portion of a promoter region of a gene that encodes a 19S subunit in a sample obtained from the cancer, wherein the subject is a suitable candidate for treatment with the agent if at least a portion of a promoter region of a gene that encodes a 19S subunit is hypermethylated. In some embodiments the method comprises measuring expression of a miRNA that has a target site in an mRNA transcript that encodes a 19S subunit in a sample obtained from the cancer, wherein the subject is a suitable candidate for treatment with the agent if expression of the miRNA is increased relative to a reference level. In some embodiments the method comprises treating the subject with the agent.

In some aspects, described herein are methods comprising measuring expression or activity of one or more 19S subunits in a sample obtained from a cancer. In some embodiments the 19S subunit is PSMD5, PSMD1, PSMC6, PSMD10, PSMD14 or PSMD6 (or any combination thereof). In some embodiments described herein are methods comprising making a clinical decision based on results of such a measurement. In some embodiments the clinical decision comprises whether or not to treat a subject from whom the sample was obtained with a proteasome inhibitor. In some embodiments the clinical decision comprises whether or not to treat a subject from whom the sample was obtained with a BCL2 family inhibitor. In some embodiments the methods further comprise administering a BCL2 family inhibitor, e.g., ABT-263, to a subject in need of treatment for the cancer if expression of a 19S subunit is reduced, e.g., if the cancer is a 2.5 sigma cancer or a 3-sigma cancer.

In some aspects, described herein are methods comprising measuring promoter methylation of one or more genes encoding a 19S subunits in a sample obtained from cancer. In some embodiments the 19S subunit is PSMD5, PSMD1, PSMC6, PSMD10, PSMD14 or PSMD6. In some embodiments described herein are methods comprising making a clinical decision based on results of such a measurement. In some embodiments the clinical decision comprises whether or not to treat a subject from whom the sample was obtained with a proteasome inhibitor. In some embodiments the clinical decision comprises whether or not to treat a subject from whom the sample was obtained with a BCL2 family inhibitor. In some embodiments the methods further comprise administering a BCL2 family inhibitor, e.g., ABT-263, to a subject in need of treatment for the cancer if expression of a 19S subunit is reduced, e.g., if the cancer is a 3-sigma cancer. In some embodiments the methods further comprise administering a BCL2 family inhibitor, e.g., ABT-263, to a subject in need of treatment for the cancer if such promoter is hypermethylated.

In some aspects, a method of inhibiting growth of a cancer cell that has reduced expression of one or more 19S subunits (e.g., PSMD5, PSMD1, PSMC6, PSMD10, PSMD14 or PSMD6) comprises dual targeting of BCL2 and BCL-XL. In some embodiments, such dual targeting is achieved by contacting the cell with a BCL2 family inhibitor that inhibits both BCL2 and BCL-XL, such as ABT-263. In some embodiments, such dual targeting is achieved by contacting the cell with a first BCL2 family inhibitor that is selective for BCL2 (e.g., ABT-199 or a BCL2-selective analog thereof) and a second BCL2 family inhibitor that is selective for BCL-XL (e.g., WEHI-539 or a BCL-XL-selective analog thereof).

In some aspects, a method of treating cancer that has reduced expression of one or more 19S subunits (e.g., PSMD5, PSMD1, PSMC6, PSMD10, PSMD14, or PSMD6) comprises dual targeting of BCL2 and BCL-XL. In some embodiments, such dual targeting is achieved by administration of a BCL2 family inhibitor that inhibits both BCL2 and BCL-XL, such as ABT-263. In some embodiments, such dual targeting is achieved by administration of a first BCL2 family inhibitor that is selective for BCL2 (e.g., ABT-199 or a BCL2-selective analog thereof) and a second BCL2 family inhibitor that is selective for BCL-XL (e.g., WEHI-539 or a BCL-XL-selective analog thereof).

In certain embodiments of any method or composition described herein relating to a cancer or cancer cell, the cancer or cancer cell type is a carcinoma. In certain embodiments of any method or composition described herein relating to a cancer or cancer cell, the cancer or cancer cell type is a hematologic malignancy. In certain embodiments of any method or composition described herein relating to a cancer or cancer cell, the cancer or cancer cell type is a low grade glioma, pheochromocytoma, paraganglioma, acute myeloid leukemia, renal cell carcinoma, cutaneous melanoma, kidney cancer (e.g., kidney chromophobe cancer, renal papillary cell carcinoma, renal clear cell carcinoma), glioblastoma multiforme, uterine cancer, thyroid carcinoma, hepatocellular carcinoma, colon adenocarcinoma, rectal adenocarcinoma, thymoma, stomach adenocarcinoma, prostate adenocarcinoma, lung squamous cell carcinoma, mesothelioma, lung adenocarcinoma, ovarian cancer, diffuse large B-cell lymphoma, bladder carcinoma, or neuroblastoma.

Certain conventional techniques and concepts of cell biology, cell culture, molecular biology, microbiology, recombinant nucleic acid (e.g., DNA) technology, immunology, etc., which are within the skill and knowledge of those of ordinary skill in the art, may be of use in aspects of the invention. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., editions as of 2008; Sambrook, Russell, and Sambrook, *Molecular Cloning: A Laboratory Manual*, 3$^{rd}$ ed., Cold Spring Harbor Laboratory Press, Cold Spring Harbor, 2001; Harlow, E. and Lane, D., *Antibodies—A Laboratory Manual*, Cold Spring Harbor Laboratory Press, Cold Spring Harbor, 1988; Burns, R., *Immunochemical Protocols* (Methods in Molecular Biology) Humana Press; 3rd ed., 2005; Buchwalow, I. and Böcker, W. (2010) *Immunohistochemistry: Basics and Methods*, Methods in Molecular Medicine, Springer) Lodish H, et al. (2007). Molecular cell biology (6th ed.). New York: W.H. Freeman and CO. Further information on cancer and treatment thereof may be found in *Cancer: Principles and Practice of Oncology* (V. T. De Vita et al., eds., J.B. Lippincott Company, 8$^{th}$ ed., 2008 or 9$^{th}$ ed., 2011) and Weinberg, R A, *The Biology of Cancer*, Garland Science, 2$^{nd}$ ed. 2013. All patents, patent applications, books, journal articles, databases, websites, and other publications mentioned herein are incorporated herein by reference in their entirety. In the event of a conflict or inconsistency with the specification (including any amendments thereof, which may be based on an incorporated reference), the specification shall control. Applicants reserve the right to amend the specification based on any of the incorporated references and/or to correct obvious errors. None of the content of the incorporated references shall limit the invention. Standard art-accepted meanings of terms are used herein unless indicated otherwise. Standard abbreviations for various terms are used herein.

BRIEF DESCRIPTION OF THE DRAWINGS

FIGS. 1A-1C: The 19S regulatory subunits of the proteasome are the most significant mediators of resistance to proteasome inhibitor toxicity. (FIG. 1A) Schematic representation of the screen. One hundred million KBM7 cells subjected to random gene deletion using retroviral gene-trap insertions were exposed to either MG132 (700 nM) or bortezomib (18 nM) for 4 weeks. Surviving cells were expanded and insertions identified by sequencing. (FIG. 1B) The p-values of the recovered insertions from the MG132 screen are plotted (log 2). Bubble sizes represent the number of insertions. (FIG. 1C) Compilation of the most significant gene deletions conferring resistance to MG132 with the gene name, number of inserts and p-value. The subunits of the 19S regulatory complex are highlighted with orange.

(FIG. 2A) HepG2 cells were infected with 80 shRNAs targeting 20 different subunits of the proteasome and 10 control shRNAs. Infected cells were then exposed to 12 nM bortezomib and cell number was examined 4 days later. The plot represents the average (+/−SEM) of four different hairpins targeting the indicated proteasome subunits and their relative cell number following bortezomib treatment. 19S subunits are depicted with orange bars, the control with a blue bar and 20S subunits with green bars. (FIG. 2B) HepG2 Cells harboring either a control shGFP or shRNAs targeting two proteasome subunits (shPSMC5, shPSMD2) displayed significant growth differences in the presence of 12 nM bortezomib. (FIG. 2C) The relative cell number of cells harboring a control shLacZ or each of 4 individual shRNAs targeting shPSMD2 was analyzed 4 days after addition of the indicated concentrations of bortezomib. (FIG. 2D) HepG2 cells stably expressing four different shRNAs targeting the PSMD2 subunit and a control shRNA (lacZ) were analyzed by western blot for the indicated proteins 24 hours with or without bortezomib treatment. (FIG. 2E) Proteasome complex content in the shGFP-, shPSMC5- and shPSMD2-expressing cells was analyzed by native gel electrophoresis after 24 hours of treatment with or without 12 nM bortezomib revealing an increase in 20S proteasome levels and activity in cells knocked down for PSMC5 or PSMD2. (FIG. 2F) Proteasome complex levels and activity in a control HepG2 cells and 4 cell lines with reduced PSMD2 levels with and without a 24 hour incubation with bortezomib (12 nM). Proteasome complex levels were detected by immunoblot analysis and 20S proteasome activity by measuring the hydrolysis of Suc-LLVY-AMC by substrate overlay assays. * p<0.05 **p<0.01. Bortz-Bortezomib (FIGS. 3A-3B) Heat-shock-(black), oxidative stress-(blue) and ER stress-(green) related gene expression were all lower in the PSMD2 knockdown cells versus control cells under both basal conditions (FIG. 3A) and upon introduction of 12 nM bortezomib for 24 hours (FIG. 3B). (FIG. 3C) Gene set enrichment analysis of genes upregulated in control but not in PSMD2 shRNA cells following bortezomib treatment. Enrichment was calculated for the indicated gene sets and is presented as a normalized enrichment score (NES). Statistically significant enrichment (false discovery rate [FDR] q-value <0.05) is shown in red; nonsignificant enrichment is shown in gray. (FIG. 3D) Expression levels of genes previously characterized as suppressors of bortezomib-induced toxicity (Chen et al., 2010) are downregulated in the PSMD2 knockdown cells following the addition of bortezomib. (FIG. 3E) Heat map depicting fold change in mRNA levels of genes differentially expressed in cells harboring control shRNA or PSMD2 shRNAs in the presence or absence of 12 nM bortezomib. Gene Ontology (GO) enrichment is shown to the right of the panel.

(FIG. 4A) Schematic representation of the experimental design. (FIG. 4B) T47D cells harboring a doxycycline-inducible PSMD2 shRNA were grown in the presence of 1 µg/ml doxycycline for 48 hours. Cells were then collected, washed and plated in the absence of doxycycline for 24 hours prior to exposure to increasing concentrations of bortezomib. Relative cell numbers were measured 3 days later. (FIG. 4C) Native gel analysis of proteasome complexes in cells pre-treated for 48 hours with doxycycline (Dox), followed by a recovery of 24 hours and then incubation with 10 nM bortezomib for an additional 24 hours. The proteasome complex levels and activity of the 20S proteasome were assessed by native gel electrophoresis. Loading controls were analyzed by immunoblot for PSMD2 and tubulin following SDS-PAGE. (FIG. 4D) Protein content analysis by immunoblot for the indicated proteins on lysates from cells treated as in (FIG. 4C). (FIG. 4E) The rate of degradation was analyzed in cells with reduced levels of PSMD2 (green bars) versus control (red bars) in the presence or absence of 10 nM bortezomib (treatment for 20 hours) by monitoring the release of H3-Phe in pre-labeled cells. (FIG. 4F) Rate of total protein synthesis was determined in cells with reduced levels of PSMD2 (green bars) versus control (red bars) in the presence or absence of 10 nM bortezomib (treatment for 20 hours) by measuring the rate of incorporation of 3H-phenylalanine for 1 hour. $p<0.01$ *$p<0.001$ (FIGS. 5A and 5B) Analysis of expression data from 315 cell lines in the Genomics of Drug Sensitivity in Cancer (GDSC) database (Garnett et al., 2012). The levels of 20S proteasome subunit (PSMAs and PSMBs) gene expression (FIGS. 5A and 5B left panels) and 19S subunit (PSMCs and PSMDs) gene expression (FIGS. 5A and 5B right panels) were analyzed in the cell lines that are the 10% most sensitive or the 10% most resistant to either MG132 (FIG. 5A) or bortezomib (FIG. 5B). (FIG. 5C) The relative expression level of each 19S complex subunit was analyzed in the bortezomib resistant and sensitive groups. Expression levels with deviation of more than 2-fold from the average were color-coded (red—up green—down). The p-values were obtained by conducting a two-tailed unpaired t-test.  $p<0.01$, * $p<0.001$ (FIGS. 6A-6B) T47D cells that harbor a doxycycline inducible control shRNA (GFP) or a doxycycline-inducible PSMD2 shRNA (TurboRFP) were incubated with doxycycline for 48 hours. Cells were collected, counted and plated at the indicated ratios of TurboRFP-expressing PSMD2 shRNAs/GFP expression control shRNAs (1:1, 1:2, 1:5 and 1:10). 24 hours later bortezomib was added at the specified concentrations and incubation continued for 48 hours. Cells were allowed to recover in the absence of bortezomib for another 48 hours and then visualized by microscopy (FIG. 6B) or analyzed by FACS after 6 days of recovery (FIG. 6A, and pie charts in FIG. 6B). The green and red images were overlaid using ImageJ.

(FIG. 8A) T47D cells harboring a doxycycline inducible PSMD2 shRNA (TurboRFP) were incubated with or without (control) doxycycline for 3 days. Cells were then split and grown in the absence of Dox for 24 hours and the indicated proteasome inhibitors were then added at the specified concentrations. After a 96 hour culture period, cell viability was determined. (FIG. 8B) T47D cells harboring a doxycycline inducible control shRNA (GFP) or a doxycycline-inducible PSMD2 shRNA (TurboRFP) were incubated with doxycycline for 3 days. Cells were collected, counted, and plated at a 1:10 ratio of TurboRFP-expressing PSMD2 shRNA cells/GFP expression control shRNA cells in the absence of Dox. 24 hours later proteasome inhibitors were added at the specified concentrations and incubation continued for 48 hours. Cells were allowed to recover in the absence of the proteasome inhibitor for another 48 hours and then analyzed by FACS (top) or visualized by microscopy (bottom). The green and red images were overlaid using ImageJ. (FIG. 8C) Schematic of PSMD2 knockdown and control constructs (FIG. 9A) Plot of the relationship between sigma score and $\ln(IC_{50})$ values for bortezomib in panel of cancer cell lines (the 345 cancer cell lines for which bortezomib sensitivity data were available in the GDSC database); (FIG. 9B) Box plots of $\ln(IC_{50})$ values for bortezomib in 3-Sigma cell lines (red, left) and all other cell lines (blue, right). (FIG. 9C) Plot of the relationship between sigma score and $\ln(IC_{50})$ values for MG132 in panel of cancer cell lines (the 347 cancer cell lines for which MG132 sensitivity data were available in the GDSC database). (FIG. 9D) Box plots of $\ln(IC_{50})$ values for MG132 in 3-Sigma cell lines (red, left) and all other cell lines (blue, right).

(FIG. 10A) Plot showing the distribution of IC50 values for MG132 across cancer cell lines of different cancer types in the GDSC database and identifying 3-Sigma cell lines. (FIG. 10B) Plot showing that the group of 3-Sigma cell lines is statistically enriched for blood cancers.

FIGS. 11A-11C: Plot showing deviation of PSMD5 expression from average expression of PSMD5 among the cancer cell lines in the GDSC database. Names of cell lines with at least a 3 SD lower expression of PSMD5 than the average expression level of PSMD5 are indicated. (FIG. 11A) Table showing, for each listed 19S subunit, the number of cell lines that showed at least 3 SD lower expression of that subunit compared to the average expression level of that subunit among cell lines in the GDSC database. (FIG. 11B) PSMD5 expression is frequently reduced in cancer cell lines in the GDSC. (FIG. 11C) PSMD4 expression is rarely lost in the cancer cell lines in the GDSC.

(FIG. 12A) Plot showing deviation of PSMD5 expression from average expression of PSMD5 among the cancer cell lines in the Cancer Cell Line Encyclopedia (CCLE) database. Names of cell lines with at least a 3 SD lower expression of PSMD5 than the average expression level of PSMD5 in the cancer cell lines in the CCLE are indicated. (FIG. 12B) Plot showing that PSMD5 expression loss among cell lines in the CCLE is not due to reduction in copy number. (FIG. 12C) PSMD4 expression is rarely lost in the cancer cell lines in the CCLE.

FIGS. 14A-14D: Reduced 19S subunit expression occurs in multiple settings of acquired and natural resistance to proteasome inhibitors. (FIG. 14A) Acquired resistance to bortezomib in HT-29 adenocarcinoma cells is accompanied by a decrease in expression of at least one 19S subunit. HT-29 cells resistant to bortezomib were obtained (by others) by culture in successively increasing concentrations of bortezomib (Suzuki E et al. (2011) Molecular Mechanisms of Bortezomib Resistant Adenocarcinoma Cells. PLoS ONE 6(12): e27996. Data in GSE29713 in NCBI GEO database). Plot shows $\log_2$(fold change) in expression level of each 19S and 20S subunit in bortezomib resistant versus wild type (bortezomib sensitive) HT-29 cells. Fold change (FC) values were obtained by dividing the expression level of each subunit in cells that have acquired bortezomib resistance by the expression level of that subunit in wild type HT-29 cells (i.e., parental HT-29 cells not exposed to bortezomib). Red dots (left) show $\log_2$(FC) values for 19S subunits. Blue dots (right) show $\log_2$(FC) values for 20S subunits. (FIG. 14B) Mantle cell lymphoma (MCL) cell lines derived from MCL with natural resistance to bortezomib show reduced expression of at least one 19S subunit relative to MCL cell lines derived from MCL tumors that are sensitive to bortezomib. (Data in GSE51371 in the NCBI GEO database) Plot shows $\log_2$(fold change) in expression level of each 19S and 20S subunit in bortezomib resistant versus bortezomib sensitive MCL cells. Fold change (FC) values were obtained by dividing the expression level of each subunit in bortezomib-resistant MCL cells by the expression level of that subunit in bortezomib-sensitive MCL cells. Red dots (left) show $\log_2$(FC) values for 19S subunits. Blue dots (right) show $\log_2$(FC) values for 20S subunits. (FIG. 14C) Multiple myeloma cells with acquired resistance to carfilzomib have reduced expression of three 19S subunits (PSMC6, PSMD5, and PSMD6) compared to the average expression of 19S subunits in parental cells not exposed to carfilzomib. Box plot shows $\log_2$(fold change) in expression level of all genes (left, black), $\log_2$(fold change) in expression level of the 19S subunits (middle, red), and $\log_2$(fold change) in expression level of the 20S subunits (right, blue) in carfilzomib resistant versus parental carfilzomib sensitive multiple myeloma cells. Fold change (FC) values for each gene were obtained by dividing the expression level of that gene in cells that have acquired carfilzomib resistance by the expression level of that gene in parental multiple myeloma cells not exposed to carfilzomib. (FIG. 14D) The relative expression of all proteasome subunits were plotted as the log 2 of the fold change in expression between the proteasome inhibitor resistant state and the control in a model of tumors derived from a bortezomib-resistant cell line (JBR (n=2)) compared to tumors derived from a bortezomib-sensitive cell line (JeKo-1 (n=5)).

(FIG. 15A) Progression-free survival of patients with relapsed multiple myeloma entered into phase II and III Bortezomib clinical trials (2007) comparing percentage of progression-free patients with 3-Sigma cancer versus controls (patients whose cancer had a sigma score less than 3). (All patients were treated with bortezomib.) (FIG. 15B) Reduced expression of 19S subunit expression is correlated with poor tumor suppression response to bortezomib in patients with relapsed myeloma enrolled in phase 2 and phase 3 clinical trials of bortezomib. Plotted is the time to relapse for patients that relapsed that were either treated with bortezomib, stratified by reduced expression of at least one subunit of the 19S proteasome complex or the dexamethasone treated group as a control.

FIG. 20: Plots showing effect of various concentrations of ABT-263 (upper panels) or ABT-199 (lower panels) in combination with various concentrations of bortezomib on viability of T47D cells with reduced expression of PSMD2 (KD) (right panels) or control cells (left panels). Fold viability refers to the number of viable cells of the indicated type (PSMD2 KD or control cells) after culture in the presence of the test compounds divided by the number of viable cells of that type after culture in the absence of the test compounds. The concentrations of ABT-263 or ABT-199 tested (in micromoles) are shown in the legend on the right side of each panel.

(FIG. 21A) Plot showing synergy of ABT-263 with ixazomib in T47D cells with reduced expression of PSMD2. (FIG. 21B) Plot showing synergy of ABT-263 with bortezomib in T47D cells with reduced expression of PSMD2. (FIG. 21C) Plot showing additive effect of ABT-199 with ixazomib in T47D cells with reduced expression of PSMD2. The y-axis on each plot is the calculated EC50 in micromoles for either ixazomib or bortezomib in the presence of sublethal doses of ABT-263 or ABT-199 as indicated. Compounds were added to the cells at the same time and cell viability was measured 72 hours later. The reduced EC50 in (FIG. 21A) and (FIG. 21B) relative to the dashed line (which connects the EC50 values of each agent alone) is indicative of synergy whereas maintenance of the same EC50 in (FIG. 21C) suggests an additive effect.

(FIG. 22A) Plot showing reduced expression of PSMD5 in IMR32 neuroblastoma cell line versus Kelly neuroblastoma cell line. (FIG. 22B) Plot showing that IMR32 cells have increased resistance to bortezomib compared to Kelly cells. P1 and P2 are two distinct experiments. (FIG. 22C) PSMD5 was overexpressed in IMR32 cells and the relative viability after 72 hours of treatment with indicated concentrations of ixazomib was plotted.

FIGS. 23A-23B: (FIG. 23A) PSMD5 promoter methylation in IMR32 cells (left) and in Kelly cells (right). The methylation status of each CpG for ten clones of each cell line is depicted (black circle=methylated, empty circle=unmethylated). (FIG. 23B) Schematic of the bisulfite sequencing protocol.

(FIG. 24A) Plot showing the effect of various concentrations of ABT-263 on IMR32 and Kelly cells. (FIG. 24B) Plot showing effect of various concentrations of disulfiram on IMR32 and Kelly cells. (FIG. 24C) Plot showing effect of various concentrations of elesclomol on IMR32 and Kelly cells. Fold viability refers to the number of viable cells of the indicated type after culture in the presence of the indicated test compound for 72 hours divided by the number of viable cells of that type after culture in the absence of the test compound.

(FIG. 25A) Analysis of primary tumor expression profiles taken from The Cancer Genome Atlas (TCGA) dataset. Overall number of times each proteasome 19S subunit expression is significantly reduced in all the different primary tumors analyzed. (FIG. 25B) Analysis of primary tumor expression profiles taken from The Cancer Genome Atlas (TCGA) dataset. The frequency that a significant drop of at least one 19S subunit occurs in the different primary tumors analyzed.

(FIG. 26A) TCGA dataset analysis for PSMD5 promoter methylation in low grade glioma (LGG) primary tumors. The data is aligned according to expression levels of the PSMD5 gene (on the right). Probes indicated correspond to genomic coordinates 123605229-123605666. (FIG. 26B) TCGA dataset analysis for PSMD5 promoter methylation in bladder urothelial carcinoma (BLCA) primary tumors. The data is aligned according to expression levels of the PSMD5 gene (on the right). Probes indicated correspond to genomic coordinates 123605229-123605666. (FIG. 26C and FIG. 26D) The average methylation score was calculated for the PSMD5 promoter region in low grade glioma (LGG) (FIG. 26C) and bladder urothelial carcinoma (BLCA) (FIG. 26D) primary tumors separately for tumors with a sigma score higher than 3 for the PSMD5 gene (3-sigma) and the rest (control). Plotted is the mean and SEM for every indicated probe corresponding to genomic coordinates 123605229-123605666. *** p-value <1e-5. In each plot in (FIG. 26C) and (FIG. 26D), the methylation score was higher for the 3-sigma tumors for each probe.

(FIGS. 30A-30B) Plotted is the relative viability following ABT-199 (FIG. 30A) or WEHI-539 (FIG. 30B) treatment of control T47D cells and cells expressing shRNA targeting the PSMD2 subunit of the proteasome. (FIG. 30C) PSMD5 was overexpressed in IMR32 cells and the relative viability of the cells (or cells with control plasmid) after 72 hours of treatment with indicated concentrations of ABT-263 are plotted.

(FIG. 31A) Schematic representation of the knockout strategy to generate the mutant PSMD12 and PSMC2 ES cells. Genetraps are in antisense (top), and sense (bottom) orientation. (FIG. 31B) Brightfield (top panels) and fluorescence (lower panels) microscopic imaging of FACS sorted PSMD12 and PSMC2 clones, stably expressing Cre ires mCherry fusion transcripts (40× mag.). (FIG. 31C) Genotyping of the ES clones by PCR before and after Cre-mediated inversion. (FIG. 31D) Relative gene expression of PSMD12 and PSMC2 in control and mutants as quantified by RT PCR (n=16-18 for each gene).

FIGS. 32A-32N: (FIGS. 32A-32D) Examining the effect of proteasome subunit knockdown in different cell lines. 80 shRNAs targeting 20 different proteasome subunits and control hairpins were expressed in HepG2 (FIG. 32A), H838 (FIG. 32B), T47D (FIG. 32C) and H1792 (FIG. 32D) cells by viral transduction. Each subunit was targeted by 4 different shRNAs. The relative cell number was measured 5 days after the initial introduction of the shRNAs. (FIGS. 32I-32N) The HepG2 cells with shRNAs targeting PSMC5, PSMD2 and GFP (described above) were further exposed to a short panel of stress inducers including bortezomib (FIG. 32I), tunicamycin (FIG. 32J), rohinitib-RHT (FIG. 32K), Hsp90 inhibition (FIG. 32L), withaferin A (FIG. 32M), and cyclohexamide (FIG. 32N) at indicated concentrations and the relative cell number (RFU) was examined after 4 days. The graphs represent the average of at least 4 different measurements and the SEM.

(FIG. 33A) Gene set enrichment analysis using the set of genes that are bound by HSF1 in MCF7 cancer cells under 37° basal conditions (Mendillo et al., 2012) was performed on genes negatively regulated in PSMD2 knockdown cells (siPSMD2) versus control cells (LacZ). (FIGS. 33B and 33C) Gene set enrichment analysis using the set of genes that are induced following heat shock (FIG. 33B), or genes that when knocked down confer resistance to bortezomib (FIG. 33C) was performed on genes negatively regulated in PSMD2 knockdown cells treated with bortezomib (siPSMD2_Velcade) versus control cells treated with bortezomib (LacZ_Velcade). Enrichment plot and statistics are displayed.

(FIGS. 34A-34F) PSMD2 shRNA was induced for 48 hours with 1 μg/ml doxycycline. Cells were then collected, washed and plated in the absence of doxycycline 24 hours prior to exposure to increasing concentration of bortezomib (FIG. 34A), MG132 (FIG. 34B), Cyclohexamide (FIG. 34C), Withaferin A (FIG. 34D), tunicamycin (FIG. 34E) and rotenone (FIG. 34F). (FIG. 34G) Lysosomal degradation rate was measured in control and PSMD2 knock down (Dox) cells in the presence or absence of 10 nM Bortezomib treatment for 20 hours.

FIG. 35: The relative expression level of each 19S complex subunit was analyzed in the MG132 resistant and sensitive groups. Expression levels with deviation of more than 2-fold from the average were color-coded (red—up green—down).

GLOSSARY

Figure 1A:
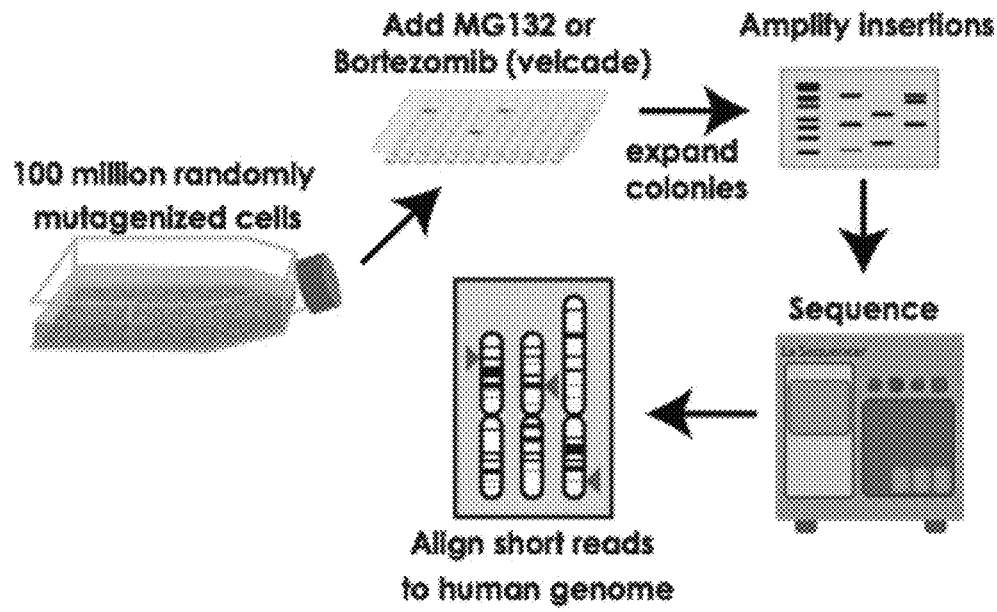

For convenience, certain terms used elsewhere in the present disclosure are collected below. It should be understood that wherever the disclosure refers to a term that is defined in the Glossary or defined elsewhere in the disclosure, the disclosure encompasses any and all embodiments of such term as defined in the Glossary or defined elsewhere in the disclosure, in the particular context(s) in which the term is used in the disclosure.

"Agent" is used herein to refer to any substance, compound (e.g., molecule), supramolecular complex, material, or combination or mixture thereof. The term "agent" is used interchangeably with "compound" herein. In some aspects, an agent can be represented by a chemical formula, chemical structure, or sequence. Example of agents, include, e.g., small molecules, polypeptides, nucleic acids (e.g., RNAi agents, antisense oligonucleotide, aptamers), lipids, polysaccharides, etc. In general, agents may be obtained using any suitable method known in the art. The ordinary skilled artisan will select an appropriate method based, e.g., on the nature of the agent. An agent may be at least partly purified. In some embodiments an agent may be provided as part of a composition, which may contain, e.g., a counter-ion, aqueous or non-aqueous diluent or carrier, buffer, preservative, or other ingredient, in addition to the agent, in various embodiments. In some embodiments an agent may be provided as a salt, ester, hydrate, or solvate. In some embodiments an agent is cell-permeable, e.g., within the range of typical agents that are taken up by cells and acts intracellularly, e.g., within mammalian cells, to produce a biological effect. Certain compounds may exist in particular geometric or stereoisomeric forms. Such compounds, including cis- and trans-isomers, E- and Z-isomers, R- and S-enantiomers, diastereomers, (D)-isomers, (L)-isomers, (−)- and (+)-isomers, racemic mixtures thereof, and other mixtures thereof are encompassed by this disclosure in various embodiments unless otherwise indicated. Certain compounds may exist in a variety or protonation states, may have a variety of configurations, may exist as solvates (e.g., with water (i.e. hydrates) or common solvents) and/or may have different crystalline forms (e.g., polymorphs) or different tautomeric forms. Embodiments exhibiting such alternative protonation states, configurations, solvates, and forms are encompassed by the present disclosure where applicable.

An "analog" of a first agent refers to a second agent that is structurally and/or functionally similar to the first agent. A "structural analog" of a first agent is an analog that is structurally similar to the first agent. Unless otherwise specified, the term "analog" as used herein refers to a structural analog. A structural analog of an agent may have substantially similar physical, chemical, biological, and/or pharmacological propert(ies) as the agent or may differ in at least one physical, chemical, biological, or pharmacological property. In some embodiments at least one such property differs in a manner that renders the analog more suitable for a purpose of interest, e.g., for inhibiting proliferation of cancer cells or treating cancer. In some embodiments a structural analog of an agent differs from the agent in that at least one atom, functional group, or substructure of the agent is replaced by a different atom, functional group, or substructure in the analog. In some embodiments, a structural analog of an agent differs from the agent in that at least one hydrogen or substituent present in the agent is replaced by a different moiety (e.g., a different substituent) in the analog.

The term "antibody" refers to an immunoglobulin, whether natural or wholly or partially synthetically produced. An antibody may be a member of any immunoglobulin class, including any of the mammalian, e.g., human, classes: IgG, IgM, IgA, IgD, and IgE, or subclasses thereof, and may be an antibody fragment, in various embodiments of the invention. An antibody can originate from any of a variety of vertebrate (e.g., mammalian or avian) organisms, e.g., mouse, rat, rabbit, hamster, goat, chicken, human, camelid, etc. As used herein, the term "antibody fragment" refers to a derivative of an antibody which contains less than a complete antibody. In general, an antibody fragment retains at least a significant portion of the full-length antibody's specific binding ability. Examples of antibody fragments include, but are not limited to, Fab, Fab', F(ab')2, scFv, Fv, dsFv diabody, Fd fragments, and domain antibodies. Standard methods of antibody identification and production known in the art can be used to produce an antibody that binds to a polypeptide of interest. In some embodiments, an antibody is a polyclonal antibody. In some embodiments, an antibody is a monoclonal antibody. Monoclonal antibodies can be identified and produced, e.g., using hybridoma technology or recombinant nucleic acid technology (e.g., phage or yeast display). In some embodiments, an antibody is a chimeric or humanized or fully human antibody. In some embodiments, an antibody is a polyclonal antibody. In some embodiments an antibody is affinity purified. It will be appreciated that certain antibodies, e.g., recombinantly produced antibodies, can comprise a heterologous sequence not derived from naturally occurring antibodies, such as an epitope tags. In some embodiments an antibody further has a detectable label attached (e.g., covalently attached) thereto (e.g., the label can comprise a radioisotope, fluorescent compound, enzyme, hapten).

A "biological sample" as used herein can be any biological specimen that contains one or more cells, tissue, or cellular material (e.g., cell lysate or fraction thereof). Unless otherwise specified or evident from the context, the term "sample" refers to a biological sample. A biological sample is often obtained from (i.e., originates from, was initially removed from) a subject. Methods of obtaining such samples are known in the art and include, e.g., tissue biopsy such as excisional biopsy, incisional biopsy, or core biopsy; fine needle aspiration biopsy; brushings; lavage; or collecting body fluids such as blood, sputum, lymph, mucus, saliva, urine, etc. In some embodiments, a biological sample contains at least some intact cells at the time it is removed from a subject and, in some embodiments, the sample retains at least some tissue microarchitecture. A "tumor sample" or "cancer sample" is a sample obtained from a cancer and typically includes at least some cancer cells. In some embodiments a tumor sample is obtained from a tumor either prior to or after removal of the tumor (or a portion thereof) from a subject. In some embodiments a sample (e.g., cancer sample) comprises circulating tumor cells (CTCs) that have shed into the vasculature from a solid tumor and circulate in the bloodstream. In some embodiments a sample is obtained prior to treatment of a subject with an anticancer agent. In some embodiments a sample is obtained after treatment of a subject with an anticancer agent. In some embodiments the subject has not been treated for the cancer prior to the sample being obtained and receives initial treatment for the cancer within 1, 2, 4, 6, or 8 weeks of the sample being obtained. A sample may be subjected to one or more processing steps after having been obtained from a subject and/or may be split into one or more portions which may entail removing or discarding part of the original sample. It will be understood that the term "biological sample" encompasses such processed samples, portions of samples, etc., and such samples are still considered to have been obtained from the subject from whom the initial sample was removed. In some embodiments, the biological sample is a tissue section, e.g., a formalin- or paraformalin-fixed, paraffin-embedded (FFPE) tissue section or a frozen tissue section.

"Cancer" refers to a class of diseases characterized by the development of abnormal cells (cancer cells) that proliferate uncontrollably and have the ability to infiltrate and destroy normal body tissues. The term "tumor" may be used interchangeably with "cancer" or "neoplasm" herein. Cancers include those diseases characterized by formation of malignant solid tumor masses (e.g., carcinomas, sarcomas) and also hematologic cancers such as leukemias in which there may be no detectable solid tumor mass. It will be understood that the term "cancer", "neoplasm", or "tumor" may be used to refer to a particular solid tumor mass or group of cancer cells in a subject as well as to the disease itself. As used herein, the term cancer includes, but is not limited to, the following types of cancer: breast cancer; biliary tract cancer; bladder cancer; brain cancer (e.g., glioblastomas (e.g., astrocytomas), medulloblastomas); cervical cancer; choriocarcinoma; colon cancer; endometrial cancer; esophageal cancer; gastric cancer; hematological cancers; intraepithelial neoplasms including Bowen's disease and Paget's disease; liver cancer (e.g., hepatocellular carcinoma); lung cancer (e.g., bronchogenic carcinoma, small cell lung cancer (SCLC), non-small cell lung cancer (NSCLC), adenocarcinoma of the lung); lymphomas including Hodgkin's disease and non-Hodgkin's lymphomas; neuroblastoma; melanoma; ocular cancer (e.g., intraocular melanoma, retinoblastoma); oral cancer (e.g., oral squamous cell carcinoma); ovarian cancer (e.g., arising from epithelial cells, stromal cells, germ cells, or mesenchymal cells); pancreatic cancer; prostate cancer; rectal cancer; anal cancer; sarcomas including angiosarcoma, gastrointestinal stromal tumors, leiomyosarcoma, rhabdomyosarcoma, liposarcoma, fibrosarcoma, and osteosarcoma; renal cancer including renal cell carcinoma and Wilms tumor; skin cancer including basal cell carcinoma and squamous cell cancer; testicular cancer including germinal tumors such as seminoma, non-seminoma (teratomas, choriocarcinomas), stromal tumors, and germ cell tumors; throat cancer (e.g., laryngeal cancer, pharyngeal cancer, nasopharyngeal cancer, oropharyngeal cancer), thyroid cancer (e.g., thyroid adenocarcinoma and medullary carcinoma). "Carcinoma" as used herein, refers to a cancer arising or believed to have arisen from epithelial cells, e.g., cells of the cancer possess various molecular, cellular, and/or histological characteristics typical of epithelial cells.

A "diverse panel of cancer cell lines" refers to a set of at least 50 cancer cell lines (e.g., 50, 100, 200, 300, or more), wherein at least 5% of the lines originate from hematologic cancers, wherein at least 8 different cancer types are included, and no single cancer type accounts for more than 15%, or in some embodiments no more than 20% of the cell lines, and in which the cell lines are selected without regard to resistance or sensitivity to a proteasome inhibitor and without regard to the level of expression or activity of any proteasome subunit or complex. In some embodiments a diverse panel of cancer cell lines is the set of cancer cell lines listed in Table S4 hereof or a subset thereof that satisfies the afore-mentioned criteria. In some embodiments a diverse panel of cancer cell lines is the NCI-60 cancer cell line panel (listed and discussed in Shoemaker, R H, Nat Rev Cancer. 2006; 6(10):813-23) or a subset thereof that meets the afore-mentioned criteria. A "diverse panel of cancers" refers to a set of at least 50 cancers (e.g., 50, 100, 200, 300, or more), wherein at least 10% of the lines originate from hematologic cancers, wherein at least 8 different cancer types are included, and no single cancer type accounts for more than 15%, or in some embodiments no more than 20% of the cell lines, and in which the cell lines are selected without regard to resistance or sensitivity to a proteasome inhibitor and without regard to the level of expression or activity of any proteasome subunit or complex. In some embodiments at least 50%, 60%, 70%, 80%, or more of the cell lines in a diverse panel of cancer cell lines or cancers are selected from breast, colon, CNS cancer, melanoma, ovarian cancer, prostate cancer, and non-small cell lung cancer cell lines or cancers.

A "drug label" is the official description of a drug product, which includes indication(s) (uses for which the drug has been approved), adverse reactions (side effects), dosage and administration instructions, and other information. Drug labels are often found inside drug product packaging in the form of a package insert.

"Genetic modification" refers to any of various processes that comprise (i) introducing a nucleic acid (e.g., a nucleic acid construct) into a cell or organism, wherein the nucleic acid comprises a portion that is stably or transiently expressed or capable of being stably or transiently expressed in the cell (and/or its descendants) or in at least one cell of the organism (and/or in at least one cell of the organism's descendants), in some cases after having been processed in the cell, e.g., reverse transcribed (in the case of introduced RNA), copied, and/or integrated into the genome of a cell, and/or (ii) producing an alteration in the sequence of the genome of a cell or in at least one cell of an organism by a method comprising introducing a targetable nuclease into a cell or organism and, optionally, introducing a nucleic acid (sometimes referred to as a donor) that serves as a template for homology directed repair/homologous recombination. Typically, a genetic modification is heritable. A nucleic acid or vector may be introduced into cells by transfection, infection, or other methods known in the art. Cells may be contacted with an appropriate reagent (e.g., a transfection reagent) to promote uptake of a nucleic acid or vector by the cells. In some embodiments a genetic modification is stable such that it is inherited by descendants of the cell into which a vector or nucleic acid construct was introduced. A stable genetic modification usually comprises alteration of a cell's genomic DNA, such as integration of exogenous nucleic acid into the genome or deletion of genomic DNA. A nucleic acid or vector may comprise a selectable marker that facilitates identification and/or isolation of genetically modified cells and, if desired, establishment of a stable cell line.

As will be appreciated by those of ordinary skill in the art, the term "genetic modification" can also refer to the particular change(s) in the nucleic acid content or genome sequence of the cell that result from the afore-mentioned process(es). An alteration may comprise an insertion of one or more nucleotide(s), a deletion of one or more nucleotide(s), a substitution of one or more nucleotide(s) by different nucleotide(s), or a combination thereof, in or into the genome. The term "genetic modification" as used herein excludes naturally occurring phenomena in which a nucleic acid enters a cell and/or in which the nucleic acid sequence of a genome is altered without intervention of man. Also excluded are selection techniques and physical and chemical mutagenesis techniques that do not involve introducing a nucleic acid or protein (e.g., a nuclease) into a cell or organism.

A "genetically modified cell" refers to an original cell in which a genetic modification has been made as well as descendants of the cell that inherit the genetic alteration(s). Thus a genetically modified cell used in methods or compositions described herein may be a descendant of an original genetically modified cell.

A "genetically modified organism" refers to a multicellular organism, at least some of whose cells (e.g., all or substantially all of the organism's cells) comprise a heritable genetic modification.

"Hematologic cancer", used interchangeably with "hematological cancer" refers to cancers of the hematopoietic and lymphoid tissues. Hematologic cancers include, e.g., leukemias, lymphomas, leukemias, multiple myeloma, other malignant plasma cell neoplasms such as extramedullary plasmacytoma, myelodysplastic syndromes, and myeloproliferative diseases. Leukemias include, e.g., myeloid leukemias (e.g., acute myeloid leukemia (AML) (also known as acute myelogenous leukemia or acute nonlymphocytic leukemia (ANLL), acute promyelocytic leukemia (APL), acute myelomonocytic leukemia (AMMoL)), chronic myeloid leukemia (CML)) and lymphoid leukemias (e.g., acute lymphocytic leukemia (ALL), chronic lymphocytic leukemia (CLL), hairy cell leukemia). Lymphomas include, e.g., non-Hodgkin's lymphomas (e.g., B cell lymphomas (e.g., mantle cell lymphoma, small B cell lymphoma, diffuse large B cell lymphoma, Burkitt's lymphoma, Waldenstrom's macroglobulinemia (also known as lymphoplasmacytic lymphoma)), T cell lymphomas (e.g., anaplastic large cell lymphoma (e.g., ALK positive or ALK negative), peripheral T cell lymphoma, adult T-cell leukemia/lymphoma), NK cell lymphomas) and Hodgkin's lymphoma. Other hematologic cancers are known to those of ordinary skill in the art.

"Modulate" as used herein means to decrease (e.g., inhibit, reduce) or increase (e.g., stimulate, activate) a level, response, property, activity, pathway, or process. A "modulator" is an agent capable of modulating a level, response, property, activity, pathway, or process. A modulator may be an inhibitor or activator.

The term "nucleic acid" refers to polynucleotides such as deoxyribonucleic acid (DNA) and ribonucleic acid (RNA). The terms "nucleic acid" and "polynucleotide" are used interchangeably herein and should be understood to include double-stranded polynucleotides, single-stranded (such as sense or antisense) polynucleotides, and partially double-stranded polynucleotides. A nucleic acid often comprises standard nucleotides typically found in naturally occurring DNA or RNA (which can include modifications such as methylated nucleobases), joined by phosphodiester bonds. In some embodiments a nucleic acid may comprise one or more non-standard nucleotides, which may be naturally occurring or non-naturally occurring (i.e., artificial; not found in nature) in various embodiments and/or may contain a modified sugar or modified backbone linkage. Nucleic acid modifications (e.g., base, sugar, and/or backbone modifications), non-standard nucleotides or nucleosides, etc., such as those known in the art as being useful in the context of RNA interference (RNAi), aptamer, CRISPR technology, polypeptide production, reprogramming, or antisense-based molecules for research or therapeutic purposes may be incorporated in various embodiments. Such modifications may, for example, increase stability (e.g., by reducing sensitivity to cleavage by nucleases), decrease clearance in vivo, increase cell uptake, or confer other properties that improve the translation, potency, efficacy, specificity, or otherwise render the nucleic acid more suitable for an intended use. Various non-limiting examples of nucleic acid modifications are described in, e.g., Deleavey G F, et al., Chemical modification of siRNA. Curr. Protoc. Nucleic Acid Chem. 2009; 39:16.3.1-16.3.22; Crooke, ST (ed.) Antisense drug technology: principles, strategies, and applications, Boca Raton: CRC Press, 2008; Kurreck, J. (ed.) Therapeutic oligonucleotides, RSC biomolecular sciences. Cambridge: Royal Society of Chemistry, 2008; U.S. Pat. Nos. 4,469,863; 5,536,821; 5,541,306; 5,637,683; 5,637,684; 5,700,922; 5,717,083; 5,719,262; 5,739,308; 5,773,601; 5,886,165; 5,929, 226; 5,977,296; 6,140,482; 6,455,308 and/or in PCT application publications WO 00/56746 and WO 01/14398. Different modifications may be used in the two strands of a double-stranded nucleic acid. A nucleic acid may be modified uniformly or on only a portion thereof and/or may contain multiple different modifications. Where the length of a nucleic acid or nucleic acid region is given in terms of a number of nucleotides (nt) it should be understood that the number refers to the number of nucleotides in a single-stranded nucleic acid or in each strand of a double-stranded nucleic acid unless otherwise indicated. An "oligonucleotide" is a relatively short nucleic acid, typically between about 5 and about 100 nt long.

"Nucleic acid construct" refers to a nucleic acid that is generated by man and is not identical to nucleic acids that occur in nature, i.e., it differs in sequence from naturally occurring nucleic acid molecules and/or comprises a modification that distinguishes it from nucleic acids found in nature. A nucleic acid construct may comprise two or more nucleic acids that are identical to nucleic acids found in nature, or portions thereof, but are not found as part of a single nucleic acid in nature.

The term "predictive method" generally refers to a method that provides information regarding the likely effect of a specified treatment, e.g., that can be used to predict whether a subject is likely to benefit from the treatment or to predict which subjects in a group will be likely or most likely to benefit from the treatment. It will be understood that a predictive method may be specific to a single treatment or to a class of treatments (e.g., a class of treatments having the same or a similar mechanism of action or that act on the same biological process, pathway or molecular target, etc., e.g., proteasome inhibitors). A predictive method may comprise classifying a subject or sample obtained from a subject into one of multiple categories, wherein the categories correlate, e.g., with different likelihoods that a subject will benefit from a specified treatment, with different likelihoods that a cancer will be sensitive or resistant to a treatment, etc. For example, categories can be low likelihood and high likelihood, wherein subjects in the low likelihood category have a lower likelihood of benefiting from the treatment than do subjects in the high likelihood category. Categories can be low likelihood and high likelihood wherein subjects in the high likelihood category have a cancer that has a high likelihood of being resistant to a therapeutic agent (e.g., a proteasome inhibitor) and subjects in the low likelihood category have a cancer with a lower likelihood of being resistant to a proteasome inhibitor (and thus a greater chance of benefiting from treatment with a proteasome inhibitor than subject in the high likelihood category). In some embodiments, a benefit is increased survival, increased progression-free survival, slowing of progression, clinical response, or decreased likelihood of recurrence. In some embodiments, a "suitable candidate for treatment" with a specified agent (or class of agents) refers to a subject for whom there is a reasonable likelihood that the subject would benefit from administration of the agent, e.g., in the context of treating a subject with cancer, the cancer has one or more characteristics that correlate with a beneficial effect resulting from administration of the agent (optionally together with one or more additional agents) as compared with, e.g., no treatment or as compared with treatment in the absence of the agent. In some embodiments, a "suitable candidate for treatment" with an agent refers to a subject for whom there is a reasonable likelihood that the subject would benefit from administration of the agent in combination with one or more other therapeutic interventions, e.g., in the context of treating a subject with cancer, the cancer has one or more characteristics that correlate with a beneficial effect from treatment with the agent and the other therapeutic interventions as compared with treatment with the other therapeutic interventions only. In some embodiments, a suitable candidate for treatment with an agent is a subject in need of treatment for cancer for whom there is a reasonable likelihood that the subject would benefit from addition of the agent to a standard regimen for treatment of cancer. See, e.g., De Vita, et al., supra for non-limiting discussion of standard regimens for treatment of cancer.

The term "RNA interference" (RNAi) encompasses processes in which a molecular complex known as an RNA-induced silencing complex (RISC) reduces gene expression in a sequence-specific manner in, e.g., eukaryotic cells, e.g., vertebrate cells, or in an appropriate in vitro system. RISC may incorporate a short nucleic acid strand (e.g., about 16-about 30 nucleotides (nt) in length) that pairs with and directs or "guides" sequence-specific degradation or translational repression of RNA (e.g., mRNA) to which the strand has complementarity. The short nucleic acid strand may be referred to as a "guide strand" or "antisense strand". An RNA strand to which the guide strand has complementarity may be referred to as a "target RNA". A guide strand may initially become associated with RISC components (in a complex sometimes termed the RISC loading complex) as part of a short double-stranded RNA (dsRNA), e.g., a short interfering RNA (siRNA). The other strand of the short dsRNA may be referred to as a "passenger strand" or "sense strand". The complementarity of the structure formed by hybridization of a target RNA and the guide strand may be such that the strand can (i) guide cleavage of the target RNA in the RNA-induced silencing complex (RISC) and/or (ii) cause translational repression of the target RNA. Reduction of expression due to RNAi may be essentially complete (e.g., the amount of a gene product is reduced to background levels) or may be less than complete in various embodiments. For example, mRNA and/or protein level may be reduced by 50%, 60%, 70%, 75%, 80%, 85%, 90%, 95%, or more, in various embodiments. As known in the art, the complementarity between the guide strand and a target RNA need not be perfect (100%) but need only be sufficient to result in inhibition of gene expression. For example, in some embodiments 1, 2, 3, 4, 5, or more nucleotides of a guide strand may not be matched to a target RNA. "Not matched" or "unmatched" refers to a nucleotide that is mismatched (not complementary to the nucleotide located opposite it in a duplex, i.e., wherein Watson-Crick base pairing does not take place) or forms at least part of a bulge. Examples of mismatches include, without limitation, an A opposite a G or A, a C opposite an A or C, a U opposite a C or U, a G opposite a G. A bulge refers to a sequence of one or more nucleotides in a strand within a generally duplex region that are not located opposite to nucleotide(s) in the other strand. "Partly complementary" refers to less than perfect complementarity. In some embodiments a guide strand has at least about 80%, 85%, or 90%, e.g., least about 91%, 92%, 93%, 94%, 95%, 96%, 97%, 98%, 99%, or 100% sequence complementarity to a target RNA over a continuous stretch of at least about 15 nt, e.g., between 15 nt and 30 nt, between 17 nt and 29 nt, between 18 nt and 25 nt, between 19 nt and 23 nt, of the target RNA. In some embodiments at least the seed region of a guide strand (the nucleotides in positions 2-7 or 2-8 of the guide strand) is perfectly complementary to a target RNA. In some embodiments, a guide strand and a target RNA sequence may form a duplex that contains no more than 1, 2, 3, or 4 mismatched or bulging nucleotides over a continuous stretch of at least 10 nt, e.g., between 10-30 nt. In some embodiments a guide strand and a target RNA sequence may form a duplex that contains no more than 1, 2, 3, 4, 5, or 6 mismatched or bulging nucleotides over a continuous stretch of at least 12 nt, e.g., between 10-30 nt. In some embodiments, a guide strand and a target RNA sequence may form a duplex that contains no more than 1, 2, 3, 4, 5, 6, 7, or 8 mismatched or bulging nts over a continuous stretch of at least 15 nt, e.g., between 10-30 nt. In some embodiments, a guide strand and a target RNA sequence may form a duplex that contains no mismatched or bulging nucleotides over a continuous stretch of at least 10 nt, e.g., between 10-30 nt. In some embodiments, between 10-30 nt is 10, 11, 12, 13, 14, 15, 16, 17, 18, 19, 20, 21, 22, 23, 24, 25, 26, 27, 28, 29, or 30 nt.

As used herein, the term "RNAi agent" encompasses nucleic acids that can be used to achieve RNAi in eukaryotic cells. Short interfering RNA (siRNA), short hairpin RNA (shRNA), and microRNA (miRNA) are examples of RNAi agents. siRNAs typically comprise two separate nucleic acid strands that are hybridized to each other to form a structure that contains a double stranded (duplex) portion at least 15 nt in length, e.g., about 15-about 30 nt long, e.g., between 17-27 nt long, e.g., between 18-25 nt long, e.g., between 19-23 nt long, e.g., 15, 16, 17, 18, 19, 20, 21, 22, 23, 24, 25, 26, 27, 28, 29, or 30 nucleotides. In some embodiments the strands of an siRNA are perfectly complementary to each other within the duplex portion. In some embodiments the duplex portion may contain one or more unmatched nucleotides, e.g., one or more mismatched (non-complementary) nucleotide pairs or bulged nucleotides. In some embodiments either or both strands of an siRNA may contain up to about 1, 2, 3, or 4 unmatched nucleotides within the duplex portion. In some embodiments a strand may have a length of between 15-35 nt, e.g., between 17-29 nt, e.g., 19-25 nt, e.g., 21-23 nt. Strands may be equal in length or may have different lengths in various embodiments. In some embodiments strands may differ by between 1-10 nt in length. A strand may have a 5' phosphate group and/or a 3' hydroxyl (—OH) group. Either or both strands of an siRNA may comprise a 3' overhang of, e.g., about 1-10 nt (e.g., 1-5 nt, e.g., 2 nt). Overhangs may be the same length or different in lengths in various embodiments. In some embodiments an overhang may comprise or consist of deoxyribonucleotides, ribonucleotides, or modified nucleotides or modified ribonucleotides such as 2'-O-methylated nucleotides, or 2'-O-methyl-uridine. An overhang may be perfectly complementary, partly complementary, or not complementary to a target RNA in a hybrid formed by the guide strand and the target RNA in various embodiments.

shRNAs are nucleic acid molecules that comprise a stem-loop structure and a length typically between about 40-150 nt, e.g., about 50-100 nt, e.g., 60-80 nt. A "stem-loop structure" (also referred to as a "hairpin" structure) refers to a nucleic acid having a secondary structure that includes a region of nucleotides which are known or predicted to form a double strand (stem portion; duplex) that is linked on one side by a region of (usually) predominantly single-stranded nucleotides (loop portion). Such structures are well known in the art and the term is used consistently with its meaning in the art. A guide strand sequence may be positioned in either arm of the stem, i.e., 5' with respect to the loop or 3' with respect to the loop in various embodiments. As is known in the art, the stem structure does not require exact base-pairing (perfect complementarity). Thus, the stem may include one or more unmatched residues or the base-pairing may be exact, i.e., it may not include any mismatches or bulges. In some embodiments the stem is between 15-30 nt, e.g., between 17-29 nt, e.g., 19-25 nt. In some embodiments the stem is between 15-19 nt. In some embodiments the stem is between 19-30 nt. The primary sequence and number of nucleotides within the loop may vary. Examples of loop sequences include, e.g., UGGU; ACUCGAGA; UUCAAGAGA. In some embodiments a loop sequence found in a naturally occurring miRNA precursor molecule (e.g., a pre-miRNA) may be used. In some embodiments a loop sequence may be absent (in which case the termini of the duplex portion may be directly linked). In some embodiments a loop sequence may be at least partly self-complementary. In some embodiments the loop is between 1 and 20 nt in length, e.g., 1-15 nt, e.g., 4-9 nt. The shRNA structure may comprise a 5' or 3' overhang. As known in the art, an shRNA may undergo intracellular processing, e.g., by the ribonuclease (RNase) III family enzyme known as Dicer, to remove the loop and generate an siRNA.

Mature endogenous miRNAs are short (typically 18-24 nt, e.g., about 22 nt), single-stranded RNAs that are generated by intracellular processing from larger, endogenously encoded precursor RNA molecules termed miRNA precursors (see, e.g., Bartel, D., Cell. 116(2):281-97 (2004); Bartel D P. Cell. 136(2):215-33 (2009); Winter, J., et al., Nature Cell Biology 11: 228-234 (2009). Artificial miRNA may be designed to take advantage of the endogenous RNAi pathway in order to silence a target RNA of interest. The sequence of such artificial miRNA may be selected so that one or more bulges is present when the artificial miRNA is hybridized to its target sequence, mimicking the structure of naturally occurring miRNA:mRNA hybrids. Those of ordinary skill in the art are aware of how to design artificial miRNA.

An RNAi agent that contains a strand sufficiently complementary to an RNA of interest so as to result in reduced expression of the RNA of interest (e.g., as a result of degradation or repression of translation of the RNA) in a cell or in an in vitro system capable of mediating RNAi and/or that comprises a sequence that is at least 80%, 90%, 95%, or more (e.g., 100%) complementary to a sequence comprising at least 10, 12, 15, 17, or 19 consecutive nucleotides of an RNA of interest may be referred to as being "targeted to" the RNA of interest. An RNAi agent targeted to an RNA transcript may also considered to be targeted to a gene from which the transcript is transcribed.

In some embodiments an RNAi agent is a vector (e.g., an expression vector) suitable for causing intracellular expression of one or more transcripts that give rise to a siRNA, shRNA, or miRNA in the cell. Such a vector may be referred to as an "RNAi vector". An RNAi vector may comprise a template that, when transcribed, yields transcripts that may form a siRNA (e.g., as two separate strands that hybridize to each other), shRNA, or miRNA precursor (e.g., pri-miRNA or pre-mRNA).

An RNAi agent may be produced in any of variety of ways in various embodiments. For example, nucleic acid strands may be chemically synthesized (e.g., using standard nucleic acid synthesis techniques) or may be produced in cells or using an in vitro transcription system. Strands may be allowed to hybridize (anneal) in an appropriate liquid composition (sometimes termed an "annealing buffer"). An RNAi vector may be produced using standard recombinant nucleic acid techniques.

The term "small molecule" refers to an organic molecule that is less than about 2 kilodaltons (kDa) in mass. In some embodiments, the small molecule is less than about 1.5 kDa, or less than about 1 kDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups.

The term "polypeptide" refers to a polymer of amino acids linked by peptide bonds. A protein is a molecule comprising one or more polypeptides. A peptide is a relatively short polypeptide, typically between about 2 and 100 amino acids (aa) in length, e.g., between 4 and 60 aa; between 8 and 40 aa; between 10 and 30 aa. The terms "protein", "polypeptide", and "peptide" may be used interchangeably. In general, a polypeptide may contain only standard amino acids or may comprise one or more non-standard amino acids (which may be naturally occurring or non-naturally occurring amino acids) and/or amino acid analogs in various embodiments. A "standard amino acid" is any of the 20 L-amino acids that are commonly utilized in the synthesis of proteins by mammals and are encoded by the genetic code. A "non-standard amino acid" is an amino acid that is not commonly utilized in the synthesis of proteins by mammals. Non-standard amino acids include naturally occurring amino acids (other than the 20 standard amino acids) and non-naturally occurring amino acids. An amino acid, e.g., one or more of the amino acids in a polypeptide, may be modified, for example, by addition, e.g., covalent linkage, of a moiety such as an alkyl group, an alkanoyl group, a carbohydrate group, a phosphate group, a lipid, a polysaccharide, a halogen, a linker for conjugation, a protecting group, a small molecule (such as a fluorophore), etc.

The term "subunit" or "protein subunit" refers to a polypeptide that assembles or is capable of assembling with one or more other polypeptides (which may have the same sequence or a different sequence) in a cell to form a protein or protein complex.

The term "vector" refers to a nucleic acid, virus, or portion thereof that is capable of mediating entry of, e.g., transferring, transporting, etc., a nucleic acid of interest between different genetic environments or into a cell. The nucleic acid of interest may be linked to, e.g., inserted into, the vector using, e.g., restriction and ligation. Vectors include, for example, DNA or RNA plasmids, cosmids, naturally occurring or modified viral genomes or portions thereof, nucleic acids that can be packaged into viral capsids, mini-chromosomes, artificial chromosomes, etc. Plasmid vectors typically include an origin of replication (e.g., for replication in prokaryotic cells). A plasmid may include part or all of a viral genome (e.g., a viral promoter, enhancer, processing or packaging signals, and/or sequences sufficient to give rise to a nucleic acid that can be integrated into the host cell genome and/or to give rise to infectious virus). Viruses or portions thereof that can be used to introduce nucleic acids into cells may be referred to as viral vectors. Viral vectors include, e.g., adenoviruses, adeno-associated viruses, retroviruses (e.g., lentiviruses), vaccinia virus and other poxviruses, herpesviruses (e.g., herpes simplex virus), and others. Viral vectors may or may not contain sufficient viral genetic information for production of infectious virus when introduced into host cells, i.e., viral vectors may be replication-competent or replication-defective. In some embodiments, e.g., where sufficient information for production of infectious virus is lacking, it may be supplied by a host cell or by another vector introduced into the cell, e.g., if production of virus is desired. In some embodiments such information is not supplied, e.g., if production of virus is not desired. A nucleic acid to be transferred may be incorporated into a naturally occurring or modified viral genome or a portion thereof or may be present within a viral capsid as a separate nucleic acid molecule. A vector may contain one or more nucleic acids encoding a marker suitable for identifying and/or selecting cells that have taken up the vector. Markers include, for example, various proteins that increase or decrease either resistance or sensitivity to antibiotics or other agents (e.g., a protein that confers resistance to an antibiotic such as puromycin, hygromycin or blasticidin), enzymes whose activities are detectable by assays known in the art (e.g., β-galactosidase or alkaline phosphatase), and proteins or RNAs that detectably affect the phenotype of cells that express them (e.g., fluorescent proteins). Vectors often include one or more appropriately positioned sites for restriction enzymes, which may be used to facilitate insertion into the vector of a nucleic acid, e.g., a nucleic acid to be expressed. An expression vector is a vector into which a desired nucleic acid has been inserted or may be inserted such that it is operably linked to regulatory elements (also termed "regulatory sequences", "expression control elements", or "expression control sequences") and may be expressed as an RNA transcript (e.g., an mRNA that can be translated into protein or a noncoding RNA such as an shRNA or miRNA precursor). Expression vectors include regulatory sequence(s), e.g., expression control sequences, sufficient to direct transcription of an operably linked nucleic acid under at least some conditions; other elements required or helpful for expression may be supplied by, e.g., the host cell or by an in vitro expression system. Such regulatory sequences typically include a promoter and may include enhancer sequences or upstream activator sequences. In some embodiments a vector may include sequences that encode a 5' untranslated region and/or a 3' untranslated region, which may comprise a cleavage and/or polyadenylation signal, and/or a vector may include a terminator. For example, a vector comprising an RNA pol III promoter may comprise an RNA pol III terminator sequence such as at least four-six consecutive T residues. In general, regulatory elements may be contained in a vector prior to insertion of a nucleic acid whose expression is desired or may be contained in an inserted nucleic acid or may be inserted into a vector following insertion of a nucleic acid whose expression is desired. As used herein, a nucleic acid and regulatory element(s) (e.g., a promoter) are said to be "operably linked" when they are covalently linked so as to place the expression or transcription of the nucleic acid under the influence or control of the regulatory element(s). For example, a promoter region would be operably linked to a nucleic acid if the promoter region were capable of effecting transcription of that nucleic acid. One of ordinary skill in the art will be aware that the precise nature of the regulatory sequences useful for gene expression may vary between species or cell types, but may in general include, as appropriate, sequences involved with the initiation of transcription, RNA processing, or initiation of translation. The choice and design of an appropriate vector and regulatory element(s) is within the ability and discretion of one of ordinary skill in the art. For example, one of skill in the art will select an appropriate promoter (or other expression control sequences) for expression in a desired species (e.g., a mammalian species) or cell type. A vector may contain a promoter capable of directing expression in mammalian cells, such as a suitable viral promoter, e.g., from a cytomegalovirus (CMV), retrovirus, simian virus (e.g., SV40), papilloma virus, herpes virus or other virus that infects mammalian cells, or a mammalian promoter from, e.g., a gene such as EF1alpha, ubiquitin (e.g., ubiquitin B or C), globin, actin, phosphoglycerate kinase (PGK), etc., or a composite promoter such as a CAG promoter (combination of the CMV early enhancer element and chicken beta-actin promoter). In some embodiments a human promoter may be used. In some embodiments, a promoter that ordinarily directs transcription by a eukaryotic RNA polymerase I (a "pol I promoter"), e.g., (a promoter for transcription of ribosomal RNA (other than 5S rRNA) or a functional variant thereof) may be used. In some embodiments, a promoter that ordinarily directs transcription by a eukaryotic RNA polymerase II (a "pol II promoter") or a functional variant thereof is used. In some embodiments, a promoter that ordinarily directs transcription by a eukaryotic RNA polymerase III (a "pol III promoter"), e.g., a promoter for transcription of U6, H1, 7SK or tRNA or a functional variant thereof is used. One of ordinary skill in the art will select an appropriate promoter for directing transcription of a sequence of interest. Examples of expression vectors that may be used in mammalian cells include, e.g., the pcDNA vector series, pSV2 vector series, pCMV vector series, pRSV vector series, pEF1 vector series, Gateway® vectors, etc. Examples of virus vectors that may be used in mammalian cells include, e.g., adenoviruses, adeno-associated viruses, poxviruses such as vaccinia viruses and attenuated poxviruses, retroviruses (e.g., lentiviruses), Semliki Forest virus, Sindbis virus, etc. In some embodiments, regulatable (e.g., inducible or repressible) expression control element(s), e.g., a regulatable promoter, is/are used so that expression can be regulated, e.g., turned on or increased or turned off or decreased. For example, the tetracycline-regulatable gene expression system (Gossen & Bujard, Proc. Natl. Acad. Sci. 89:5547-5551, 1992) or variants thereof (see, e.g., Allen, N, et al. (2000) Mouse Genetics and Transgenics: 259-263; Urlinger, S, et al. (2000). Proc. Natl. Acad. Sci. U.S.A. 97 (14): 7963-8; Zhou, X., et al (2006). Gene Ther. 13 (19): 1382-1390 for examples) can be used. Other inducible/repressible systems that may be used in various embodiments include those that can be regulated by artificial or naturally occurring hormone receptor ligands (e.g., steroid receptor ligands such as naturally occurring or synthetic estrogen receptor or glucocorticoid receptor ligands), metal-regulated systems (e.g., metallothionein promoter), and light-regulated systems. In some embodiments, tissue-specific or cell type specific regulatory element(s) may be used, e.g., in order to direct expression in one or more selected tissues or cell types. A tissue-specific or cell type specific regulatory element generally directs expression at a higher level in one or more tissues or cell types than in many or most other tissues or cell types (e.g., other cell types in the body or in an artificial environment). In some cases a cell type specific regulatory element directs detectable levels of expression only in a particular cell type of interest. However, useful cell type regulatory elements may not be and often are not absolutely specific for a particular cell type. In some embodiments a cell type specific regulatory element may direct expression of an operably linked nucleic acid at a level at least 2-, 5-, 10, 25, 50, or 100-fold greater in a particular cell type than the level at which it would direct expression of the same nucleic acid in a reference population of cells. One of ordinary skill in the art will be aware of tissue and cell type specific regulatory elements and will be able to select an appropriate element to achieve a useful level of expression in one or more selected tissues or cell types in which expression is desired while avoiding substantial levels of expression that might otherwise occur in tissues or cell types in which expression is not desired.

As used herein "19S subunit inhibitor" and "19S subunit inhibitors" refer to agents that inhibit (reduce, decrease) the expression and/or activity of one or more 19S subunits. "Activity of a 19S subunit" can refer to ATPase activity of those 19S subunits that have ATPase activity. Alternately or additionally, activity of a 19S subunit can refer to the ability of a 19S subunit to assemble with other 19S subunits (i.e., with one molecule of each of the other 19S subunits) to form a functional 19S proteasome complex. A "functional 19S proteasome complex" is a 19S proteasome complex that can assemble with a 20S proteasome complex to form a functional 26S proteasome. In some embodiments, 19S subunit inhibitors include molecules that bind directly to a functional region of one or more 19S subunits in a manner that interferes with one or more activities of such subunit(s). Examples of suitable inhibitors include, but are not limited to inhibitory nucleic acids such as interfering RNA (e.g., small interfering RNA (siRNA), small hairpin RNA (shRNA)), aptamers, ribozymes, antisense oligonucleotides, as well as oligopeptides, small molecule inhibitors, antibodies or fragments thereof, and combinations thereof.

As used herein "level", refers to a measure of the amount of, or a concentration of something, e.g., a biomolecule such as a mRNA or protein or protein complex.

As used herein "expression level" or "level of expression", refers to a measure of the amount of, or a concentration of an expression product, such as a transcription product, for instance an mRNA, or a translation product, for instance a protein or polypeptide.

As used herein "activity" refers to a biological effect or function that is produced or carried out by a product or substance, e.g., an expression product, small molecule, or the like.

As used herein "level of activity" refers to a measure of a biological effect or function of a product or substance, e.g., an expression product, small molecule, or the like. Activity of a molecule or complex typically refers to activity on a per molecule basis or per complex basis. It will be understood that a reduction in expression level typically results in a decrease in total level of activity.

As used herein, a "reduced level" of expression or activity is a level of expression or activity that is detectably lower than a reference level. In some embodiments, a reduced level of expression or activity is a modestly reduced level of expression or activity. A "modestly reduced level" of expression or activity is a level of expression or activity that is detectably lower than a reference level but in which expression or activity is not completely absent or undetectable. Typically, a modestly reduced level of expression or activity is between 10% and 90% of a reference level, although lesser and greater reductions are contemplated in some embodiments, so long as expression or activity is not completely abolished or rendered undetectable. In some embodiments a modestly reduced level of expression or activity is between 20% and 80%, e.g., between 25% and 75%, between 30% and 70%, or between 40% and 60% of a reference level. In some embodiments a modestly reduced level of expression or activity is between 25% and 50% or between 50% and 75% of a reference level. In some embodiments a modestly reduced level of expression or activity is about 10%, about 20%, about 25%, about 30%, about 35%, about 40%, about 45%, about 50%, about 55%, about 60%, about 65%, about 70%, about 75%, about 80%, about 85%, or about 90% of a reference level.

As used herein, a "reduction" in the level of expression or activity is a detectable decrease in the level of expression or activity relative to an initial level. In some embodiments a reduction in the level of expression or activity is a modest reduction in the level of expression or activity. A "modest reduction" in the level of expression or activity is a detectable decrease in the level of expression or activity relative to an initial level, provided that expression or activity is not completely abolished or rendered undetectable. Typically, a modest reduction is a decrease by between 10% and 90% of an initial level. A reduction by 10% means that the level is decreased to 90% of the initial level. In some embodiments a modest reduction in the level of expression or activity is a reduction by between 20% and 80%, e.g., by between 25% and 50%, between 30% and 70%, between 40% and 60%, or between 50% and 75% of an initial level. In some embodiments a modest reduction in the level of expression or activity is a reduction by about 10%, about 20%, about 25%, about 30%, about 35%, about 40%, about 45%, about 50%, about 55%, about 60%, about 65%, about 70%, about 75%, about 80%, about 85%, or about 90% of an initial level.

As used herein, the term "downregulating 19S subunit expression" refers to a detectable reduction in the expression of a 19S subunit in a cell or population of cells through any of the methods disclosed herein or those known to one of ordinary skill in the art, with the benefit of the present disclosure.

As used herein, the term "inhibiting 19S subunit translation" refers to causing a detectable reduction in the translation of a 19S subunit in a cell or population of cells from RNA encoding the 19S subunit.

As used herein, the term "inhibiting 19S subunit activity" refers to causing a measurable or observable reduction in the ability of a 19S subunit to carry out one or more of its biological activities through any of the methods disclosed herein or those known to one of ordinary skill in the art, with the benefit of the present disclosure.

An "effective amount" An "effective amount" or "effective dose" of a compound or other agent (or composition containing such compound or agent) refers to the amount sufficient to achieve a desired biological and/or pharmacological effect, e.g., when delivered to a cell or organism according to a selected administration form, route, and/or schedule. As will be appreciated by those of ordinary skill in this art, the absolute amount of a particular compound, agent, or composition that is effective may vary depending on such factors as the desired biological or pharmacological endpoint, the agent to be delivered, the target tissue, etc. Those of ordinary skill in the art will further understand that an "effective amount" may be contacted with cells or administered in a single dose, or the desired effect may be achieved by use of multiple doses. An effective amount of a composition may be an amount sufficient to reduce the severity of or prevent one or more symptoms or signs of a disorder.

"Contacting", "contacting a cell" and similar terms as used herein, refer to any means of introducing an agent (e.g., a nucleic acid, peptide, antibody, small molecule, etc.) into a target cell, including chemical and physical means, whether directly or indirectly or whether the agent physically contacts the cell directly or is introduced into an environment in which the cell is present. Contacting is intended to encompass methods of exposing a cell, delivering to a cell, or "loading" a cell with an agent by viral or non-viral vectors, wherein such agent is bioactive upon delivery. The method of delivery will be chosen for the particular agent and use (e.g., cancer being treated). Parameters that affect delivery, as is known in the medical art, can include, inter alia, the cell type affected, and cellular location. In some embodiments, contacting includes administering the agent to a subject.

DETAILED DESCRIPTION OF CERTAIN EMBODIMENTS

I. Proteasomes, Proteasome Inhibitors, and Proteasome Inhibitor Resistance

Proteasome function is essential for survival of mammalian cells. Proteasome inhibitors (PIs) are clinically useful in the treatment of cancer, particularly in the treatment of certain hematological malignancies. Most useful anticancer agents, including proteasome inhibitors, act by inducing cancer cell death and/or by inhibiting proliferation of cancer cells. For example, proteasome inhibitors have been shown to induce apoptosis of cancer cells via a number of different mechanisms. However, acquired or intrinsic resistance to proteasome inhibitors may limit their efficacy. Described herein are methods of identifying agents useful for reducing proteasome inhibitor resistance. Also described herein are cells, cell lines, and other products and compositions useful in performing such methods. Agents useful for reducing proteasome inhibitor resistance are also described herein. Also described herein are methods of classifying a cancer according to predicted sensitivity to a proteasome inhibitor, methods of predicting the likelihood that a cancer will be resistant to a proteasome inhibitor, methods of selecting a treatment for a subject with cancer, and methods of treating cancer.

The 26S proteasome is composed of a 20S catalytic core (also referred to herein as a "20S proteasome complex", "20S proteasome", or "20S complex") and a 19S regulatory complex (also referred to herein as a "19S proteasome complex", "19S proteasome", or "19S complex") at one or both ends of the 20S complex. The 20S proteasome complex is formed by two sets of $\alpha$ rings and two sets of $\beta$ rings arranged in a symmetrical manner with the $\alpha$ rings surrounding the $\beta$ rings. Each $\alpha$ or $\beta$ ring contains seven different subunits, named $\alpha 1$-$\alpha 7$ or $\beta 1$-$\beta 7$, respectively. The $\beta 1$-, $\beta 2$-, and $\beta 5$-subunits contain the proteolytic active sites. Each site cleaves preferentially after particular amino acid residues. The $\beta 1$ subunit is responsible for caspase-like (or peptidyl-glutamyl peptide-hydrolyzing-like/PGPH-like) activity that preferentially cleaves after acidic residues (e.g., aspartate and glutamate). The $\beta 2$ subunit has trypsin-like (T-L) activity that preferentially cleaves after basic residues (e.g., arginine and lysine). The $\beta 5$ subunit has chymotrypsin-like (CT-L) activity that preferentially cleaves after hydrophobic residues (e.g., tyrosine and phenylalanine). A subunit of the 20S proteasome complex may be referred to herein as a "20S subunit".

Mammals additionally possess inducible $\beta 1i$ (LMP2), $\beta 2i$ (MECL), $\beta 5i$ (LMP7), and $\beta 5t$ subunits, where "i" and "t" stand for immuno- and thymo-, respectively. These subunits are expressed in certain immune system tissues or are induced by particular stimuli, such as interferon-$\gamma$ exposure, and can replace the constitutively expressed $\beta 1$, $\beta 2$, and $\beta 5$ subunits. The proteasome assembled with these alternative subunits is known as the immunoproteasome or thymoproteasome, respectively, and has altered substrate specificity relative to the constitutive proteasome (i.e., the proteasome that contains $\beta 1$, $\beta 2$, and $\beta 5$ subunits).

The 19S regulatory complex can be split into two sub-complexes, termed the "lid" and the "base". The 19S proteasome lid contains at least nine non-ATPase subunits, which recognize polyubiquitinated proteins and remove the polyubiquitin chain from the substrate proteins (deubiquitination). The 19S base contains six ATPase subunits and several non-ATPase subunits. It serves to unfold substrate proteins and promote their entry into the 20S proteasome. A subunit of the 19S proteasome complex may be referred to herein as a "19S subunit".

Further information regarding the proteasome and its subunits, as well as proteasome-associated proteins such as proteasome-associated deubiquitinases, is found in Tomko, R J, et al., Annu. Rev. Biochem. (2013) 82:415-45, and references therein.

Table 1A lists the standardized gene symbols for subunits of the mammalian 19S proteasome complex together with the corresponding human Gene IDs (from the National Center for Biotechnology), and Reference Sequence (RefSeq) accession numbers of the transcript and polypeptide sequences. (Where multiple transcripts and isoforms exist, the corresponding isoform is adjacent to the transcript that encodes it.) Table 1B lists the NCBI Gene IDs for each subunit of the 20S proteasome complex. In general, NCBI Reference Sequences may be used for any aspect or embodiment described herein wherever relevant. However, one of ordinary skill in the art will appreciate that multiple alleles of a gene may exist among individuals of the same species. For example, differences in one or more nucleotides (e.g., up to about 1%, 2%, 3-5% of the nucleotides) of the nucleic acids encoding a particular protein may exist among individuals of a given species. Due to the degeneracy of the genetic code, such variations often do not alter the encoded amino acid sequence, although DNA polymorphisms that lead to changes in the sequence of the encoded proteins can exist. Examples of polymorphic variants can be found in, e.g., the Single Nucleotide Polymorphism Database (dbSNP), available at the NCBI website at www.ncbi.nlm.nih.gov/projects/SNP/. (Sherry S T, et al. (2001). "dbSNP: the NCBI database of genetic variation". Nucleic Acids Res. 29 (1): 308-311; Kitts A, and Sherry S, (2009). The single nucleotide polymorphism database (dbSNP) of nucleotide sequence variation in The NCBI Handbook [Internet]. McEntyre J, Ostell J, editors. Bethesda (Md.): National Center for Biotechnology Information (US); 2002 (www.ncbi.nlm.nih.gov/bookshelf/br.fcgi?book=handbook&part=ch5). Multiple isoforms of certain proteins may exist, e.g., as a result of alternative RNA splicing or editing. In general, where aspects of this disclosure pertain to a gene or gene product (e.g., a 19S subunit or mRNA encoding a 19S subunit, a BCL2 family member, an ALDH superfamily member, etc.), embodiments pertaining to transcript variants, allelic variants or isoforms are encompassed unless indicated otherwise. Certain embodiments may be directed to particular sequence(s), e.g., particular allele(s) or isoform(s), e.g., the most widely expressed isoform, an isoform expressed in a particular cell type of interest. In some embodiments, agents can be designed or selected that may be used to selectively detect or modulate one or more isoforms or that detect or modulate all isoforms. Further, it should be understood that a current or updated version of any accession number provided herein may be used where applicable.

TABLE 1A

19S Proteasome Subunits

| Gene Symbol | NCBI Gene ID | NCBI RefSeq (transcript) | NCBI RefSeq (protein) |
|---|---|---|---|
| PSMC1 | 5700 | NM_002802.2 | NP_002793.2 |
| PSMC2 | 5701 | NM_002803.3 | NP_002794.1 (isoform 1) |
|  |  | NM_001204453.1 | NP_001191382.1 (isoform 2) |
| PSMC3 | 5702 | NM_002804.4 | NP_002795.2 |
| PSMC4 | 5704 | NM_006503.3 | NP_006494.1 (isoform 1) |
|  |  | NM_153001.2 | NP_694546.1 (isoform 2) |
| PSMC5 | 5705 | NM_002805.5 | NP_002796.4 (isoform 1) |
|  |  | NM_001199163.1 | NP_001186092.1 (isoform 2 |
| PSMC6 | 5706 | NM_002806.3 | NP_002797.3 |
| PSMD1 | 5707 | NM_002807.3 | NP_002798.2 (isoform 1) |
|  |  | NM_001191037.1 | NP_001177966.1 (isoform 2) |
| PSMD2 | 5708 | NM_002808.4 | NP_002799.3 (isoform 1) |
|  |  | NM_001278708.1 | NP_001265637.1 (isoform 2) |
|  |  | NM_001278709.1 | NP_001265638.1 (isoform 3) |
| PSMD3 | 5709 | NM_002809.3 | NP_002800.2 |
| PSMD4 | 5710 | NM_002810.2 | NP_002801.1 |
| PSMD5 | 5711 | NM_005047.3 | NP_005038.1 |
|  |  | NM_001270427.1 | NP_001257356.1 (isoform 2) |
| PSMD6 | 9861 | NM_001271779.1 | NP_001258708.1 (isoform 1) |
|  |  | NM_014814.2 | NP_055629.1 (isoform 2) |
|  |  | NM_001271780.1 | NP_001258709.1 (isoform 3) |
|  |  | NM_001271781.1 | NP_001258710.1 (isoform 4) |
| PSMD7 | 5713 | NM_002811.4 | NP_002802.2 |
| PSMD8 | 5714 | NM_002812.4 | NP_002803.2 |
| PSMD9 | 5715 | NM_002813.6 | NP_002804.2 (isoform 1) |
|  |  | NM_001261400.2 | NP_001248329.1 (isoform 2) |
| PSMD10 | 5716 | NM_002814.3 | NP_002805.1 (isoform 1) |
|  |  | NM_170750.2 | NP_736606.1 (isoform 2) |
| PSMD11 | 5717 | NM_001270482.1 | NP_001257411.1 |
|  |  | NM_002815.3 | NP_002806.2 (same as NP_001257411.1) |
| PSMD12 | 5718 | NM_002816.3 | NP_002807.1 (isoform 1) |
|  |  | NM_174871.2 | NP_777360.1 (isoform 2) |
| PSMD13 | 5719 | NM_002817.3 | NP_002808.3 (isform 1) |
|  |  | NM_175932.2 | NP_787128.2 (isoform 2) |
| PSMD14 | 10213 | NM_005805.5 | NP_005796.1 |
| ADRM1 | 11047 | NM_007002.3 | NP_008933.2 (isoform 1) |
|  |  | NM_175573.2 | NP_783163.1 (isoform 1) |
|  |  | NM_001281438.1 | NP_001268367.1 (isoform 2) |
|  |  | NM_001281437.1 | NP_001268366.1 (isoform 2) |

TABLE 1B

20S Proteasome Subunits

| Gene Symbol | NCBI Gene ID |
|---|---|
| PSMA1 | 5862 |
| PSMA2 | 5683 |
| PSMA3 | 5684 |
| PSMA4 | 5685 |
| PSMA5 | 5686 |
| PSMA6 | 5687 |
| PSMA7 | 5688 |
| PSMB1 | 5689 |
| PSMB2 | 5690 |
| PSMB3 | 5691 |
| PSMB4 | 5692 |
| PSMB5 | 5693 |

TABLE 1B-continued

20S Proteasome Subunits

| Gene Symbol | NCBI Gene ID |
|---|---|
| PSMB6 | 5694 |
| PSMB7 | 5695 |

As described in the Examples, the function of the 19S proteasome complex is essential for sustained proliferation of mammalian cells. Complete loss of function of any of the subunits of the 19S proteasome complex causes mammalian cells to cease proliferating. Surprisingly, however, as described in the Examples, it was discovered that a modest reduction in the expression level of one or more subunits of the 19S proteasome complex protects cells against the toxic effects of proteasome inhibitors and increases the ability of cancer cells to survive and proliferate in the presence of proteasome inhibitors. Furthermore, analysis of transcriptional and drug resistance data from a collection of human cancer cell lines with diverse tissue origins and diverse oncogenic lesions revealed that cancer cell lines that are resistant to proteasome inhibitors have significantly lower average levels of mRNA transcripts encoding subunits of the 19S proteasome complex than do cancer cell lines that are proteasome inhibitor sensitive, whereas there was no significant difference in the average expression level of mRNA encoding subunits of the 20S proteasome complex between the proteasome inhibitor resistant and sensitive groups of cell lines.

The present disclosure provides the insight that compromising the 19S proteasome complex protects cells from proteotoxic stress due to proteasome inhibitors. As described herein, a modest reduction in the level of expression or activity of one or more subunits of the 19S proteasome complex confers increased resistance to proteasome inhibitors. As used herein, "resistant", "resistance" and like terms, in the context of a cell, e.g., a cancer cell, and an agent (e.g., an anticancer agent such as a proteasome inhibitor) refers to the ability of the cell to withstand the intended effect of such agent on the cell. Conversely, "sensitive", "sensitivity", and like terms, in the context of a cell, e.g., a cancer cell, and an agent (e.g., an anticancer agent such as a proteasome inhibitor) refer to the propensity of a cell to be affected by an agent, i.e., the propensity of the cell to exhibit the intended effect of the agent on the cell. Typically, the intended effect of an anticancer agent on a cell is a reduction in viability (survival) or proliferation (sometimes referred to as "proliferation rate", "growth" or "growth rate") of the cell. As used herein, an alteration in "survival or proliferation" (and like terms) refers to an alteration in viability, an alteration in proliferation, or both. Thus, a reduction in survival or proliferation of a cancer cell can be a reduction in viability, a reduction in proliferation, or both. Furthermore, it will be appreciated that if contacting a cell or cell population with an agent causes a reduction in the number of viable cells after a time period as compared with the number of viable cells that would be present had the cell or cell population not been contacted with the agent, the agent may be said to "inhibit growth". An agent may inhibit growth by killing a cell or by inhibiting its proliferation without killing it. The phrases "inhibit growth", "inhibit survival or proliferation", "reduce survival or proliferation", and "kill or inhibit proliferation" in reference to the effect of an agent or condition on cell(s) may be used interchangeably herein. It will be understood that the effect of an agent on a cancer cell is often determined by measuring the effect of the agent on a population of similar or substantially identical cancer cells that includes the cancer cell or of which the cancer cell is representative. The population of cancer cells may be, e.g., a population of cancer cells obtained from a cancer (which may be expanded in culture after being isolated from the cancer) or a population of cancer cells of a particular cancer cell line. Thus, resistance of a cancer cell typically refers to the resistance of a population of cancer cells of which the cancer cell is a member or of which the cancer cell is representative. A first cancer cell is said to be "more resistant" or to have "more resistance" or "increased resistance" to an agent than a second cancer cell if the first cancer cell is able to survive in the presence of the agent (or after exposure to the agent) at a concentration that would kill the second cancer cell and/or if the first cancer cell is able to survive and proliferate in the presence of the agent (or after exposure to the agent) at a concentration that would kill the second cell or at least prevent the second cell from proliferating.

Resistance of a cancer cell (e.g., in vitro) to an agent (e.g., a proteasome inhibitor) may be expressed in terms of the half maximal inhibitory concentration (IC50), the half maximal effective concentration (EC50), or both. As known in the art, the IC50 refers to the concentration of an agent that causes a 50% inhibition or reduction in the parameter being measured. In the context of resistance (or sensitivity) of a cell to an agent, IC50 refers to the concentration of the agent that causes a 50% reduction in the number of viable cells relative to the number of viable cells that would be present in the absence of the agent, as measured using a suitable assay at a particular time point. EC50 refers to the concentration of an agent that causes a response halfway between the baseline and maximum after a specified exposure time. It will be appreciated that in the context of resistance (or sensitivity) of a cell to an agent, the baseline refers to number of viable cells in the absence of the agent, and maximum response refers to the maximum effect of the agent on the number of viable cells, e.g., a reduction to no viable cells. The IC50 or EC50 can be determined by constructing a dose-response curve and examining the effect of the agent on the value of a parameter of interest, e.g., the number of viable cells, at different doses. In the context of an in vitro assay, dose refers to the concentration of the agent in a medium to which a cell is exposed.

Those of ordinary skill in the art are aware of values and ranges of IC50 and EC50 values that are considered indicative of resistance or sensitivity to a particular anticancer agent. In some aspects, whether a cancer cell is considered resistant or sensitive to a particular agent may be determined by comparing the IC50 of the agent for the cancer cell with the IC50 of the agent as measured for each cell line in a panel of diverse cancer cell lines. Cancer cells for which the agent has an IC50 in the $10^{th}$ percentile of IC50 values determined for the agent on a diverse panel of cancer cell lines may be considered sensitive, while cancer cells for which the agent has an IC50 in the $90^{th}$ percentile of IC50 values determined for the agent on a diverse panel of cancer cell lines may be considered resistant to the agent. In some embodiments, the panel of cancer cell lines is the set of 315 cancer cell lines listed in Table S4 hereof, for which drug sensitivity data for numerous anticancer drugs are available in the Genomics of Drug Sensitivity in Cancer (GDSC) database (available at http://www.cancerrxgene.org/). Drug sensitivity of these cell lines for bortezomib and MG132 (half maximal inhibitory (IC50) drug concentrations (natural log microMolar)) are listed in Table S4.

In some aspects, a cancer cell is considered to be resistant to an agent at a particular concentration if its survival or proliferation is not significantly reduced or inhibited or is only minimally reduced or inhibited (e.g., by no more than 5%, or in some embodiments by no more than 10%) by the presence of the agent at that concentration. In some aspects, a cancer cell is considered to be resistant to a particular agent if its survival or proliferation is reduced by no more than 15%, no more than 20%, no more than 25%, no more than 30%, no more than 40%, or no more than 50% by the presence of the agent at that concentration.

Cells that are sensitive to an anticancer agent, e.g., a proteasome inhibitor, can sometimes acquire increased resistance to the anticancer agent over time. In some aspects, a cell or cell population that is derived from a first cell or cell population that is sensitive to an agent is considered to have acquired increased resistance to the agent if the IC50 of the agent for the cell or cell population derived from the sensitive cell or cell population is at larger than the IC50 of the agent for the first cell or cell population, e.g., at least 1.5-fold, at least 2-fold, at least 3-fold, or at least 5-fold larger, e.g., between 2- and 5-fold larger, between 5- and 10-fold larger, between 10- and 25-fold larger, between 25- and 50-fold larger, between 50- and 100-fold larger, between 100- and 250-fold larger, between 250- and 500-fold larger, between 500-fold and 1000-fold larger, or more.

In some aspects, if the IC50 or EC50 of an agent, e.g., a proteasome inhibitor, for a cancer cell in vitro is greater than the peak plasma concentration that results from administering an agent to a mammalian subject (e.g., a human) at the maximum tolerated dose, then the cancer cell is considered to be resistant to the agent. Alternately or additionally, in some embodiments, a cancer cell is considered resistant to an agent if the ratio of the IC50 for normal cells to the IC50 for cancer cells is less than or equal to 2, or, in some embodiments, less than or equal to 1. The normal cells may be cells of the same cell type or may derive from the same cell lineage or may be found in the same organ or tissue as the cancer cells.

A cancer in a subject may be said to have acquired increased resistance to a chemotherapeutic agent, e.g., a proteasome inhibitor, if a subject who experienced improvement in his or her condition upon initial treatment with the agent (e.g., a subject whose cancer stabilized or responded during or soon after one or more courses of treatment with the agent) subsequently experiences a clinical relapse during treatment with the agent or experiences a worsening after treatment and does not experience improvement upon subsequent retreatment with the agent and/or requires a higher dose of the agent to keep the cancer under control. A cancer that is not controlled by treatment with a particular therapeutic agent at the maximum tolerated dose of the agent (or is not controlled by a combination of agents in which the particular therapeutic agent is used at its maximum tolerated dose in the context of the combination) may be considered to be resistant to the agent. In the case of a proteasome inhibitor that has been approved for use to treat one or more cancers by a regulatory agency such as the U.S. Food & Drug Administration (FDA), a cancer that is not controlled by treatment at the highest recommended dose of the agent is considered resistant. For example, the highest recommended dose of bortezomib according to its FDA-approved drug label is 1.3 mg/m$^2$, administered twice weekly (by intravenous or subcutaneous administration) with at least 72 hours between doses (VELCADE Prescribing Information, Millennium Pharmaceuticals, Inc., Cambridge Mass.). Accordingly, in some embodiments, if a cancer does not respond to treatment with bortezomib administered according to such a dosing regimen, the cancer may be considered to be resistant to bortezomib.

Those of ordinary skill in the art are aware of IC50 and/or EC50 values that are generally accepted in the art as indicating that a cancer cell is resistant or sensitive to an agent, e.g., a proteasome inhibitor. In some embodiments, a cell, e.g., a cancer cell, for which bortezomib has an IC50 of no more than 2-5 nM is considered sensitive to bortezomib. In some embodiments, a cell, e.g., a cancer cell, for which MG132 has an IC50 of no more than 200 nM is considered sensitive to MG132. In some embodiments, a cell, e.g., a cancer cell, that is able to survive and proliferate in the presence of 18 nM bortezomib is considered resistant to bortezomib. In some embodiments, a cell, e.g., a cancer cell, that is able to survive and proliferate in the presence of 700 nM MG132 is considered resistant to MG132.

Described herein are methods and products (e.g., cells and compositions) relating to the discovery that a modest reduction in the level of expression or activity of a 19S subunit increases the resistance of cancer cells to proteasome inhibitors. In some aspects, methods described herein comprise manipulating the level of expression or activity of a 19S subunit in order to modulate the level of resistance of a cell to a proteasome inhibitor. In some embodiments, a cell, e.g., a cancer cell, is rendered more resistant to proteasome inhibitors by manipulating it so as to reduce the level of expression or activity of a 19S subunit in the cell. The cell may be one that (prior to the manipulation) was relatively sensitive to the proteasome inhibitor. In some embodiments, a cell, e.g., a cancer cell, is rendered less resistant to proteasome inhibitors by manipulating it so as to increase the level of expression or activity of a 19S subunit in the cell. The cancer cell may be one that (prior to the manipulation) was relatively resistant to the proteasome inhibitor. In some embodiments the cell (prior to the manipulation) is one that has a reduced level of expression or activity of the 19S subunit as compared with a reference level.

In some aspects, described herein are cells (e.g., cancer cells) that have a modestly reduced level of expression or activity of a 19S subunit. Also described are methods of generating such cells. Cells that have a modestly reduced level of expression or activity of a 19S subunit may be used to identify candidate agents useful for reducing the acquisition of resistance to a proteasome inhibitor by a proteasome inhibitor sensitive cell. Cells that have a modestly reduced level of expression or activity of a 19S subunit may be used to identify candidate agents that are toxic to proteasome inhibitor resistant cancer cells. In some embodiments, such agents may be used to treat a subject suffering from a cancer, e.g., a cancer that comprises cancer cells that are resistant to a proteasome inhibitor or may acquire resistance to a proteasome inhibitor. In some embodiments, such agents may be used to treat a subject suffering from a cancer that comprising cancer cells that have acquired increased resistance to a proteasome inhibitor, e.g., as single agents, in combination with a proteasome inhibitor, and/or in combination with one or more other anticancer agents.

In some aspects, cells that have a modestly reduced level of expression or activity of a 19S subunit may be used to identify candidate agents that are selectively toxic to cancer cells that increased proteasome inhibitor resistance versus proteasome inhibitor sensitive cancer cells. In some embodiments, such agents may be used as anticancer agents, e.g., in combination with a proteasome inhibitor and/or in combination with one or more other anticancer agents. In some embodiments, such agents may be used to treat a subject suffering from a cancer, e.g., a cancer that is resistant to a proteasome inhibitor or may acquire resistance to a proteasome inhibitor. In some embodiments, such agents may be used to treat a subject suffering from a cancer that has acquired increased resistance to a proteasome inhibitor, e.g., as single agents, in combination with a proteasome inhibitor, and/or in combination with one or more other anticancer agents. In some embodiments, such agents restore proteasome inhibitor sensitivity to a cancer that has become resistant to a proteasome inhibitor. In some embodiments such agents overcome proteasome inhibitor resistance of a proteasome inhibitor resistant cancer.

In some aspects, the disclosure provides the insight that a modestly reduced level of expression or activity of a 19S subunit correlates with resistance to proteasome inhibitors. Thus, a cancer cell with a modestly reduced level of expression or activity of a 19S subunit is more likely to be resistant to a proteasome inhibitor as compared with a cancer cell that has a higher level of expression or activity of such subunit. In some embodiments a reduced level of expression or activity of a 19S subunit is a level of expression or activity that is detectable and sufficiently high to permit a cell to survive and proliferate (possibly more slowly than a comparable cell with a higher level of expression or activity of such 19S subunit) but is lower than the level found in a typical normal cell and/or is lower than the median level in a diverse panel of cancer cell lines or cancers and/or is lower than the average (mean) level in a diverse panel of cancer cell lines and/or is lower than a level (e.g., median level or average (mean) level) in a panel of cancer cell lines or cancers of the same type as a cancer cell or cancer of interest. "Resistance to a proteasome inhibitor" or "resistance to proteasome inhibitors" can refer to resistance to a specific proteasome inhibitor, resistance to proteasome inhibitors belonging to a particular structural class and/or having a particular mechanism of action or property (e.g., non-covalent binding, covalent binding) or resistance to multiple proteasome inhibitors (belonging to different structural classes and/or having different mechanisms of action). Without wishing to be bound by any theory, it is expected that the mechanism of increased proteasome resistance described herein (reduced level of expression or activity of a 19S subunit) is broadly relevant to proteasome inhibitor resistance across the range of proteasome inhibitors known in the art or discovered in the future.

In some embodiments, a reduced level of expression or activity of a 19S subunit is a level in the $25^{th}$ percentile of levels of expression or activity in a diverse panel of cancer cell lines (i.e., 25% of the cancer cell lines have the same or a lower level of expression or activity). In some embodiments, a reduced level of expression or activity of a 19S subunit is a level in the $20^{th}$ percentile of levels of expression or activity in a diverse panel of cancer cell lines (i.e., 20% of the cancer cell lines have the same or a lower level of expression or activity). In some embodiments, a reduced level of expression or activity of a 19S subunit is a level in the $15^{th}$ percentile, $10^{th}$ percentile, or $5^{th}$ percentile of levels of expression or activity in a diverse panel of cancer cell lines. In some embodiments the diverse panel of cancer cell lines is the set of cell lines listed in Table S4 hereof.

In some aspects, the level of expression or activity of one or more 19S subunits in a cancer sample may be used as a biomarker for proteasome inhibitor resistance. In some aspects, a measurement of the level or expression or activity may be used to classify a cancer according to predicted resistance or sensitivity to a proteasome inhibitor and/or may be used to select a treatment for a subject in need of treatment for cancer. For example, measurement of the level of expression or activity of one more 19S subunits may be used to determine whether a cancer is likely to be resistant to a proteasome inhibitor, or whether a cancer is potentially sensitive to a proteasome inhibitor. An appropriate treatment can be selected based on the determination and, optionally, administered to the subject. In some embodiments, the treatment comprises a proteasome inhibitor and an agent that reduces proteasome inhibitor resistance and thereby restores proteasome inhibitor sensitivity to a cancer that has become resistant to a proteasome inhibitor. In some embodiments the treatment comprises a proteasome inhibitor and an agent that reduces proteasome inhibitor resistance and thereby overcomes proteasome inhibitor resistance of a proteasome inhibitor resistant cancer. In some embodiments the treatment comprises an agent that is selectively toxic to proteasome inhibitor resistant cancer cells. In some embodiments the agent that is selectively toxic to proteasome inhibitor resistant cancer cells is administered in combination with a proteasome inhibitor.

II. Cells and Organisms with Reduced Expression or Activity of a 19S Subunit and Uses Thereof In some aspects, described herein are cells that have a reduced level of expression or activity of a 19S subunit as compared with a reference level. Also described herein are methods of generating such cells. In some embodiments the cells are cancer cells. In some embodiments the cells are immortalized non-tumorigenic cells. In some embodiments the reference level is a level measured in cells that are sensitive to a proteasome inhibitor. In some embodiments the reference level is a level measured in control cells that do not have a particular genetic modification that causes a reduction in the level of expression or activity of a 19S subunit and/or have not been subjected or exposed to a particular manipulation or agent that causes a reduction in the level of expression or activity of a 19S subunit. The control cells may be of the same cell type as the cells that have a reduced level of expression or activity of a 19S subunit. In some embodiments the cells that have a reduced level of expression or activity of a 19S subunit and control cells are genetically matched cells. Where the present disclosure refers to a reduction relative to a reference level, the reference level may be the level present in a cell or cell population before the cell or cell population was subjected to a manipulation that resulted in the reduction. It will be appreciated that the level of a parameter (e.g., expression or activity of a 19S subunit) in a cell population can be determined by measuring the level in a sample of cells from the population.

A cell may have or be manipulated to have a reduced level of expression or activity of any one or more 19S subunits. As mentioned above, the 19S proteasome includes subunits with ATPase activity and non-ATPase subunits. The 19S subunits named PSMC1, PSMC2, PSMC3, PSMC4, PSMC5, PSMC6 (sometimes referred to collectively as the PSMCs) are ATPases. The non-ATPase 19S subunits are named PSMD1-PSMD14 and ADRM1. PSMD14 has deubiquitinating activity. PSMD4 and ADRM1 function as ubiquitin receptors. PSMD2 and ADRM1 function in ubiquitin receptor docking. PSMD1 functions in ADRM1 docking. In some embodiments a cell has a reduced level of expression or activity of one or more PSMCs. In some embodiments a cell has or is manipulated to have a reduced level of expression or activity of one or more PSMDs. In some embodiments a cell has or is manipulated to have a reduced level of expression or activity of one or more 19S subunit(s) selected from the group consisting of: PSMC2, PSMC3, PSMC4, PSMC5, PSMC6, PSMD2, PSMD6, PSMD7, and PSMD12. In some embodiments a cell has or is manipulated to have a reduced level of expression or activity of one or more 19S subunit(s) selected from the group consisting of: PSMD3, PSMD6, PSMD7, PSMD11, PSMD2, PSMD9, PSMC5, PSMD8, PSMC3, PSMD14, PSMD10, PSMD5, PSMC6, ADRM1, or PSMD12. In some embodiments the 19S subunit is PSMD11. In some embodiments the 19S subunit is not PSMD11. In some embodiments the cell has or is manipulated to have a reduced level of expression or activity of PSMD11 and at least one other 19S subunit. In some embodiments a cell has or is manipulated to have a reduced level of expression or activity of one or more 19S subunit(s) selected from the group consisting of: PSMD5, PSMD1, PSMC6, PSMD10, PSMD14, PSMD6, PSMD13, PSMD7, PSMC1, PSMC5, PSMD12, PSMC3, PSMC4, PSMD4, and PSMD8. In some embodiments the 19S subunit is PSMD2. In some embodiments the 19S subunit is PSMD1, PSMC6, PSMD10, PSMD14, or PSMD6. In some embodiments the 19S subunit is PSMD5.

In some embodiments cells have a genetic modification that causes them to have a reduced level of expression or activity of a 19S subunit as compared with a reference level. A cell can comprise any of a variety of different genetic modifications that reduce the level of expression or activity of a 19S subunit. In some embodiments, a genetically modified cell comprises a nucleic acid construct comprising a promoter operably linked to a nucleic acid that encodes a polynucleotide or polypeptide that inhibits expression or activity of a 19S subunit. In some embodiments the polynucleotide that causes a cell to have a reduced level of expression of a 19S subunit is an RNAi agent. In some embodiments the RNAi agent is a short hairpin RNA (shRNA), short interfering RNA (siRNA), or microRNA (miRNA). In some embodiments the RNAi agent is a nucleic acid that comprises the sequence of a naturally occurring miRNA that has a predicted target site in a 19S subunit transcript. As described in the Examples, PSMD5, PSMD9, PSMD12, PSMD7, PSMD8, PSMD3, PSMD10, PSMD1, PSMD11, PSMD13, PSMD14, PSMD2, PSMC2, PSMC4, and PSMC6 transcripts have multiple predicted miRNA target sites. In some embodiments, a miRNA comprising a seed region (positions 2-7 of a mature miRNA) identical to that of a naturally occurring miRNA that has a predicted target site in a 19S subunit transcript is expressed in a cell in order to reduce the level of expression of such subunit.

In some embodiments the RNAi agent causes a modest reduction in the level of expression of a 19S subunit. The sequence and/or concentration of the RNAi agent used may be chosen such that the RNAi agent inhibits expression of the target 19S subunit by a selected amount. One of ordinary skill in the art appreciates that the extent to which an RNAi agent inhibits expression of a target gene may vary depending, e.g., on the sequence of the RNAi agent and the concentration of the RNAi agent. One or more RNAi agents and/or concentrations may be tested to identify an agent that inhibits expression by a selected amount when used at a particular concentration. One of ordinary skill in the art can design suitable RNAi agents. Knockdown of 19S subunit expression by RNAi agents is described in the Examples. It will be understood that other RNAi agents (e.g., targeting different sequences) could be used. In some embodiments two or more RNAi agents (e.g., shRNA, miRNA) that target different target sites of a 19S subunit transcript are expressed in a cell. In some embodiments two or more RNAi agents (e.g., shRNA, miRNA) that target different 19S subunit transcript are expressed in a cell.

In some aspects, described herein is a method that comprises: (a) contacting a cell with an agent that inhibits expression or activity of a 19S subunit; (b) contacting the cell with a proteasome inhibitor; (c) measuring the level of resistance of the cell to the proteasome inhibitor as compared with the level of resistance of a control cell not contacted with the agent; and (d) identifying the agent as suitable for generating a cell with increased proteasome inhibitor resistance if the resistance of the cell to the proteasome inhibitor is greater than the resistance of the control cell.

In some embodiments the polynucleotide that inhibits expression of a 19S subunit is an antisense nucleic acid. Antisense nucleic acids are single-stranded nucleic acids that are capable of hybridizing to a RNA target. Such hybridization may result in, e.g., degradation of mRNA by RNase H or blockage of mRNA translation. The polynucleotide may comprise a sequence at least about 80%, 85%, 90%, 95%, 99%, or 100% complementary to a RNA target over at least 10, 12, 14, 16, 18, 20, 22, 24, 26, 28, or 30 nucleotides (nt). In some embodiments, the sequence may be selected to minimize off-target effects. For example, a sequence that has less than about 70%, 75%, 80%, 85%, 90%, 95%, 99%, or 100% complementarity to known or predicted mRNAs (other than the target) of a species to which the antisense agent is to be administered over at least 10, 12, 14, 16, 18, 20, 22, 24, 26, 28, or 30 nt may be selected. In some embodiments the antisense nucleic acid hybridizes to a coding region, an intron, or a 5' or 3' untranslated region of a mRNA. One of ordinary skill in the art will be able to select a suitable antisense nucleic acid for inhibition of expression of a 19S subunit of interest.

In some embodiments an inhibitory nucleic acid (e.g., a shRNA or miRNA) that reduces expression of a 19S subunit is expressed intracellularly. The level of inhibition produced by the nucleic acid may vary depending on its level of expression. In some embodiments the level of expression of the inhibitory nucleic acid may be determined by the promoter that drives expression of the inhibitory nucleic acid. For example, a promoter that results in a moderate level of expression can be selected. One of ordinary skill in the art will appreciate that a variety of different promoters can be used to express a nucleic acid in a cell and will be able to select an appropriate promoter to result in a selected level of expression of the nucleic acid.

In some embodiments an agent that inhibits expression of a 19S subunit comprises a transcriptional repressor, e.g., an artificial transcriptional repressor that reduces transcription of RNA that encodes the 19S subunit. One of ordinary skill in the art is aware of suitable types of artificial transcriptional repressors capable of inhibiting expression of a gene of interest and methods for designing such agents. In some embodiments an artificial transcriptional repressor comprises a polypeptide comprising a sequence-specific DNA binding domain that binds to a suitable region of the gene of interest, e.g., a promoter, enhancer, or transcription start site of a gene of interest, resulting in transcriptional repression. DNA binding domains that bind to a desired target sequence may be designed based on the DNA binding domains of zinc finger proteins or transcription activator-like effectors (TALEs) using methods known in the art. In some embodiments an artificial transcriptional repressor comprises a polypeptide comprising a catalytically inactive Cas protein. Cas proteins (e.g., Cas9) are nucleases that can associate with a guide RNA (gRNA) that localizes the Cas protein to a selected DNA target site by complementary base pairing. Cas proteins are found in a variety of bacterial species including *S. pyogenes*, *S. thermophiles*, and *N. meningitidis* dCas proteins can be rendered catalytically inactive by appropriate amino acid substitution (e.g., D10A and H840A in *S. pyogenes* Cas9), thereby generating a Cas protein (sometimes referred to as dCas that has no endonuclease activity but maintains its RNA-guided DNA-binding capacity. In some embodiments, the polypeptide comprising a DNA binding domain or dCas may further comprise a transcriptional repression domain such as the Kruppel-associated box (KRAB) repressor domain or other repressor domain known in the art. Non-limiting discussion of the design of artificial transcriptional repressors, is found in Kabadi, A M and Gersbach, C M, Methods. 2014; 69(2): 188-197; Gilbert, L A, et al., Cell. 2013; 154(2):442-51.

In some embodiments an agent that inhibits expression of a 19S subunit acts post-transcriptionally, e.g., by causing mRNA degradation and/or repressing mRNA translation. One of ordinary skill in the art is aware of suitable types of agents capable of post-transcriptionally inhibiting expression of a gene of interest and methods for designing such agents. For example, shRNA, siRNA, and artificial miRNA can be used as described herein. In some embodiments an agent that inhibits expression of a gene post-transcriptionally comprises a polypeptide comprising a sequence-specific RNA binding domain that binds to a sequence in an mRNA (e.g., in the 5' untranslated region, coding sequence, or 3' UTR) wherein the polypeptide promotes mRNA degradation or represses mRNA translation. In some embodiments the polypeptide binds to the 5' UTR and represses translation, e.g., by preventing ribosome binding. In some embodiments the polypeptide may comprise a domain that recruits a deadenylase that removes at least part of the mRNA's polyA tail, thereby destabilizing the mRNA. In some embodiments the polypeptide comprises tristetraprolin (TTP), also known as zinc finger protein 36 homolog (ZFP36). In some embodiments an RNA binding domain capable of binding to an RNA sequence is designed based on pentatricopeptide repeat or Pumilio/fem-3 mRNA binding factor (PUF) proteins, which can be rationally modified for predictable RNA recognition. Non-limiting discussion of various types of polypeptides that can be used as post-transcriptional repressors is found in Abil, Z., et al. Journal of Biological Engineering, 2014, 8:7; Cao, J., et al., *Nucl. Acids Res*. (30 Apr. 2015) 43 (8): 4353-4362, and references therein.

A transcriptional repressor or post-transcriptional repressor may be expressed intracellularly, e.g., by introducing a nucleic acid that encodes it into the cell. In embodiments in which an artificial transcriptional repressor comprising a dCas protein, an appropriate gRNA may also be expressed in or otherwise introduced into the cells. In some embodiments the cell is genetically modified to stably express the transcriptional repressor or post-transcriptional repressor. In some embodiments in which dCas is used, the cell is genetically modified to stably express one or more gRNA. In some embodiments the cell transiently expresses the transcriptional repressor or post-transcriptional repressor. In some embodiments in which dCas is used, the cell transiently expresses stably one or more gRNA. The amount by which a transcriptional or post-transcriptional repressor reduces expression of a target gene may vary depending on the level of expression of the transcriptional or post-transcriptional repressor, which can be selected to produce a desired reduction in expression of a gene of interest.

Those of ordinary skill in the art are aware of suitable promoters useful for driving expression in mammalian cells. In some embodiments expression of the nucleic acid that encodes a 19S subunit inhibitor is under control of a constitutive promoter. In some embodiments expression of a nucleic acid that encodes a 19S subunit inhibitor is under control of a regulatable (inducible or repressible) promoter. One of ordinary skill in the art will appreciate that a variety of regulatable expression systems are available. In many of these systems expression is typically induced or repressed by a low molecular weight ligand (typically a small molecule or metal) that binds to a transcriptional regulator (which may be a transcriptional repressor or activator protein) that contains a sequence-specific DNA binding domain. Depending on the particular system, binding of the ligand may promote or inhibit binding of the transcriptional regulator to a promoter containing DNA sequences that mediate binding of the transcriptional regulator, thus permitting ligand-dependent regulation of the transcription directed by the promoter. In general, such regulation systems can be classified as OFF-type (expression occurs in the absence of the ligand) or ON-type (expression occurs in the presence of the ligand). For example, a tetracycline-regulatable gene expression system can be employed to provide inducible or repressible expression (see, e.g., Gossen & Bujard, Proc. Natl. Acad. Sci. 89:5547-5551, 1992; Allen, N, et al. (2000) Mouse Genetics and Transgenics: 259-263; Urlinger, S, et al. (2000). Proc. Natl. Acad. Sci. U.S.A. 97 (14): 7963-8; Zhou, X., et al (2006). Gene Ther. 13 (19): 1382-1390; Löw, R., et al., (2010) BMC Biotechnology 10:81; Schonig, K., et al., Methods Enzymol. 2010; 477:429-53). The promoter used in tetracycline-regulatable systems comprises one or more copies of the Tet operator (TetO) DNA sequence and a minimal promoter such as the CMV promoter. Small molecules such as tetracycline, doxycycline, etc. may be used as ligands. The cell in which a Tet-Off or Tet-On system is used should express a Tet-dependent transactivator (tTA; containing the *E. coli* Tet repressor fused to VP16 activation domain of herpes simplex virus) (for Tet-Off systems) or reverse transactivator (rtTA) or optimized variant thereof such as Tet-On Advanced transactivator (also known as rtTA2$^s$-M2) (for Tet-On systems). In a Tet-Off system, tTA is capable of binding the Tet operator only if not bound to tetracycline or an analog such as doxycycline, whereas in a Tet-On system, the rtTA or protein is capable of binding the operator only if bound by a ligand. Thus the introduction of ligand (e.g., doxycycline) initiates transcription in a Tet-On system. The T-REx™ System (Life Technologies) is a tetracycline-regulated mammalian expression system in which regulation is based on the binding of tetracycline or an analog thereof to the Tet repressor and resulting derepression of the promoter controlling expression of the gene of interest.

In some embodiments, a regulatable promoter is used to transiently express a 19S subunit inhibitor in a cell. Depending on the particular regulatable expression system employed, transient expression can be accomplished by contacting the cell with an appropriate inducing substance (e.g., tetracycline or an analog thereof) or culturing the cell in the absence of a substance that represses expression when present. A transient reduction in expression or activity of a 19S subunit can be sufficient to cause a temporary increase in resistance to a proteasome inhibitor that is of sufficient duration to permit the cell to be used in a method of identifying an agent that inhibits proteasome inhibitor resistance. One of ordinary skill in the art can select an appropriate duration for the transient reduction in expression so as to reduce the level of the 19S subunit sufficiently to increase resistance to a proteasome inhibitor for a sufficient period of time to perform a screen but not so much as to kill the cell. In some embodiments, expression of an inhibitory nucleic acid (e.g., an shRNA, artificial miRNA, or antisense RNA) that inhibits expression of a 19S subunit may be induced for between 8 hours (hr) and 72 hr, e.g., between 12 hr and 60 hr, e.g., between 24 hr and 54 hr, e.g., about 48 hr, prior to contacting cells with a test agent (e.g., as described further herein). In some embodiments, expression level of a 19S subunit may be reduced for at least 24 hours, e.g., between 24 hr and 2, 3, 4, 5, 6, 7 days, 2 weeks, etc.

In some embodiments the level of expression or activity of a 19S subunit is reduced by a modest amount relative to a reference level. In some embodiments the reference level is a control level. Wherever the present document refers to a reduction relative to a control level, the control level may be the level that was present before a manipulation or procedure that resulted in the reduction. For example, in some embodiments, a control level resulting from an RNAi agent is the level of expression in the absence of the agent. In some embodiments the reference level is a level present in a cancer cell that is sensitive to a proteasome inhibitor.

In some embodiments, the level of expression of at least one 19S subunit in a cell, cell population, or cell line (e.g., a cancer cell, cancer cell population, or cancer cell line) is reduced to a level at least 1.5 standard deviations (SD), at least 2 SD, at least 2.5 SD, or at least 3 SD lower than a reference level, wherein the reference level is (i) the average expression level of all 19S subunits in that cell, cell population, or cell line, (ii) the average expression level of all 20S subunits in that cell, cell population, or cell line, or (iii) the average expression level of all 19S and all 20S subunits in that cell, cell population, or cell line, and wherein the standard deviation is the standard deviation of the expression levels used to calculate the average expression level (i.e., the standard deviation is the standard deviation of the expression levels whose average value is the reference level). In some embodiments, the level of expression of at least one 19S subunit in a cancer cell, cancer cell population, or cancer cell line is reduced to a level at least 1.5 standard deviations (SD), at least 2 SD, at least 2.5 SD, or at least 3 SD lower than a reference level wherein the reference level is the average expression of that 19S subunit in a panel of cancer cell lines or cancers, e.g., a diverse panel of cancer cell lines or cancers. In some embodiments, the level of expression of at least one 19S subunit in a cell, cell population, or cell line (e.g., a cancer cell, cancer cell population, or cancer cell line) is reduced to a level at least 1.5 standard deviations (SD), at least 2 SD, at least 2.5 SD, or at least 3 SD lower than a reference level, wherein the reference level is the average expression of that 19S subunit in a panel of cancer cell lines or cancers of the same type as the cell, cell population, or cell line, and wherein the standard deviation is the standard deviation of the expression levels used to calculate the average expression level (i.e., the standard deviation is the standard deviation of the expression levels whose average value is the reference level). In certain of any of the afore-mentioned embodiments the level of expression is reduced to a level of up to 4.0 SD lower than the reference level, e.g., between 1.5 SD and 4.0 SD lower than the reference level, e.g., between 2.0 SD and 3.5 SD lower than the reference level, e.g., to a level of about 3.0 SD lower than the reference level.

Certain aspects of the present disclosure relate to determining a sigma score of a cell, cell population, cell line, or cancer. Certain aspects of the present disclosure relate to generating a cell, cell population, or cell line with a sigma score of at least 1.5, at least 2.0, at least 2.5, or at least 3.0. As used herein, the term "sigma score" in reference to a particular cell, cell population, cell line, or cancer of interest refers to the amount by which expression of the 19S subunit that has the lowest expression in that cell, cell population, cell line, or cancer differs from a reference level that is an average (mean) of a set of proteasome subunit expression levels, expressed in units of the standard deviation of the set of proteasome subunit expression levels. A sigma score may be calculated by (i) examining the expression level of all 19S subunits in a cell, cell line, cell population, or cancer of interest; (ii) selecting or determining a suitable reference level that is an average of a set of proteasome subunit expression levels; (iii) determining which 19S subunit has the lowest expression level, and (iv) expressing the difference between the reference level and the lowest expression level in terms of the standard deviation of the set of proteasome subunit expression levels that were used to calculate the reference level. A cell, cell population, cell line, or cancer in which the expression level of the 19S subunit with the lowest expression is X standard deviations lower than the reference level (where "X" is a number) is said to have a sigma score of X. For example, a cell line in which PSMD5 has the lowest expression level among the 19S subunits and such expression level is 3.0 standard deviations below the reference level has a sigma score of 3.0. A reference level that is based on the expression level(s) of one or more gene products, e.g., one or more proteasome subunits, in the particular cell, cell population, cell line, or cancer of interest may be referred to as an "internal reference level". Since the expression levels of the proteasome subunits in a cell are typically well correlated, by comparing the expression level of each 19S subunit with a reference level that is the average expression level of multiple proteasome subunits in a given cell, cell population, cell line, or cancer, one can identify cells, cell lines, or cancers that have reduced expression of one or up to a few (e.g., 2, 3, or 4) 19S subunits. In certain embodiments the reference level is an average expression level of at least 5, at least 10, at least 15, at least 20, at least 25, or 30 proteasome subunits, e.g., between 5 and 10, between 10 and 15, between 15 and 20, between 20 and 25, between 25 and 30, between 30 and 35 proteasome subunits. In certain embodiments the reference level is the average expression level of all 19S subunits (which subunits are listed in Table 1A) in the cell, cell population, cell line, or cancer of interest. In certain embodiments the reference level is the average expression level of all 20S subunits (which subunits are listed in Table 1B) in the cell, cell population, cell line, or cancer of interest. In certain embodiments the reference level is the average expression level of all 19S and 20S subunits in the cell, cell population, cell line, or cancer of interest. A reference level that is based on the expression level(s) of one or more gene products, e.g., one or more proteasome subunits, in one or more cells, cell populations, cell lines, or cancers other than the particular cell, cell population, cell line, or cancer of interest may be referred to as an "external reference level". For example, in certain embodiments the average expression level in a panel of cells, cell populations, cell lines, or cancers of the particular 19S subunit that has the lowest expression level in a particular cell, cell population, cell line, or cancer of interest is used as reference level for the particular cell, cell population, cell line, or cancer of interest, e.g., for determining a sigma score for the particular cell, cell population, cell line, or cancer of interest. For example, if PSMD5 is found to have the lowest expression level in a particular cancer of interest, the average expression level of PSMD5 in a panel of cancers may be used as the reference level. The panel of cells, cell populations, cell lines or cancers may or may not include the particular cell, cell population, cell line, or cancer of interest. If a reference level is based on the expression level(s) of one or more gene products, e.g., one or more proteasome subunits, in one or more cells, cell populations, cell lines, or cancers other than the particular cell, cell population, cell line, or cancer of interest and on the expression level(s) of one or more gene products, e.g., one or more proteasome subunits, in the particular cell, cell population, cell line, or cancer of interest, it will be considered an internal reference level if more than 50% of the expression levels used to calculate the reference level e.g., at least 60%, 70%, 80%, 90%, or 95% of the expression levels used to calculate the reference level, are from the particular cell, cell population, cell line, or cancer of interest and will be considered an external reference level if at least 50% of the expression levels used to calculate the reference level, e.g., at least 60%, 70%, 80%, 90%, or 95% of the expression levels used to calculate the reference level, are from one or more cells, cell populations, cell lines, or cancers other than the particular cell, cell population, cell line, or cancer of interest. In some embodiments, cells and cell lines useful for obtaining a reference level for a particular cell, cell population, cell line, or cancer of interest, e.g., for determining a sigma score for a cancer cell, cancer cell population, or cancer cell line of interest, are cancer cells or cancer cell lines. For example, a cancer cell line or panel of cancer cell lines for which data are available in the GDSC or Cancer Cell Line Encyclopedia (CCLE) may be used. In some embodiments a reference level is obtained from cancer cell(s) or cancer cell line(s) that are proteasome inhibitor sensitive. In some embodiments a reference level is obtained from cancer cell(s) or cancer cell line(s) that are proteasome inhibitor resistant. One of ordinary skill in the art will appreciate that a sigma score for a cancer or tissue of interest may be obtained from a sample of the cancer or tissue of interest.

In some embodiments a reference level is determined by a method comprising measuring multiple proteasome subunit expression levels (e.g., multiple 19S subunit expression levels, multiple 20S subunit expression levels, or at least one 19S subunit expression level and at least one 20S subunit expression level) and calculating the average. As described above, multiple proteasome subunit expression levels (e.g., multiple 19S subunit expression levels, multiple 20S subunit expression levels, or at least one 19S subunit expression level and at least one 20S subunit expression level) may be measured in a given cell, cell population, cell line, or cancer of interest or in a panel of cells, cell populations, cell lines, or cancer. In some embodiments a reference level is determined by a method comprising obtaining values of multiple proteasome subunit expression levels, e.g., multiple 19S subunit expression levels, multiple 20S subunit expression levels, or multiple 19S and multiple 20S subunit expression levels from previously performed measurements and calculating the average. In some embodiments the number of expression level values that are averaged to obtain a reference level is at least 10, 20, 30, 40, 50, 60, 70, 80, 90, 100, 125, 150, 175, 200, 250, 300, 400, 500, or more. In some embodiments a reference level is determined using proteasome subunit gene expression data, e.g., 19S subunit gene expression data, 20S subunit gene expression data, or both 19S and 20S subunit gene expression data, from a panel of cancers from patients who have participated in a clinical trial. In some embodiments the clinical trial includes treatment with a proteasome inhibitor. In some embodiments the proteasome subunit gene expression data are analyzed to identify a sigma score that is indicative of likely proteasome inhibitor resistance, e.g., as evidenced by lack of response to treatment with the drug. The sigma score may then be used to determine whether additional cancers are likely to be resistant to the same proteasome inhibitor or to a different proteasome inhibitor. A panel may include 5, 10, 20, 30, 40, 50, 100, 200, 300, or more cells, cell populations, cell lines or cancers. In some embodiments the cancer cells, cancer cell populations, cancer cell lines or cancers that make up a panel may be of the same cell type as the cancer cell, cancer cell line or cancer of interest. In some embodiments the panel may be a diverse panel of cancer cells, cancer cell populations, cancer cell lines or cancers. It will be appreciated that once a reference level or standard deviation has been calculated using expression levels from a particular cell line, cancer, panel of cell lines, panel of cancers, etc., it may subsequently be used without being calculated again.

As described in the Examples, sigma scores were determined for hundreds of cancer cell lines and were found to correlate strongly with proteasome inhibitor resistance. In some aspects, the present disclosure provides a method of generating a cancer cell, cancer cell population, or cancer cell line that has increased proteasome inhibitor resistance, the method comprising: providing a first cancer cell, cancer cell population, or cancer cell line and generating a second cancer cell, cancer cell population, or cancer cell line therefrom that has a higher sigma score. In some embodiments the sigma score of the second cancer cell, cancer cell population, or cancer cell line is greater than that of the first cancer cell, cancer cell population, or cancer cell line by at least 1.0, 1.5, 2, 2.5, or 3. In some embodiments the first cancer cell, cancer cell population, or cancer cell line has a sigma score of less than 1.5 and the second cancer cell, cancer cell population, or cancer cell line has a sigma score of at least 1.5, e.g., at least 2, at least 2.5, at least 3, at least 3.5, or at least 4. In some embodiments the cancer cell, cancer cell population, or cancer cell line generated has a sigma score between 1.5 and about 5, e.g., between 1.5 and 2.5, between 2.5 and 3.5, or between 3.5 and 4.5. In some embodiments the cancer cell, cancer cell population, or cancer cell line with a sigma score of at least 1.5 is generated by contacting the initial cancer cell, cancer cell population, or cancer cell line with an agent (e.g., an shRNA or artificial transcriptional repressor) that reduces expression of a selected 19S subunit. In certain embodiments the 19S subunit whose expression is reduced may be any 19S subunit. In some embodiments, the 19S subunit whose expression is reduced is PSMC2, PSMC3, PSMC4, PSMC5, PSMC6, PSMD2, PSMD6, or PSMD7. For example, in some embodiments, the 19S subunit whose expression is reduced is PSMD2. In some embodiments, the 19S subunit whose expression is reduced is PSMD12, PSMD5, PSMD1, PSMC6, PSMD10, PSMD14, PSMD6, PSMD13, PSMD7, PSMC1, PSMC5, PSMD12, PSMC3, PSMC4, PSMD4, or PSMD8. For example, in some embodiments, the 19S subunit whose expression reduced is PSMD5. In some embodiments the cancer cell, cancer cell population, or cancer cell line with a sigma score of less than 1.5 is proteasome inhibitor sensitive.

In some embodiments a cancer cell that is sensitive to a proteasome inhibitor is from a cell line selected from the following bortezomib sensitive cancer cell lines: LB771-HNC, CP66-MEL, OCUB-M, MFH-ino, OS-RC-2, HCE-T, ES1, LB2518-MEL, ACN, D-247MG, HCC2998, MZ2-MEL, ES8, KS-1, BB30-HNC, ONS-76, D-542MG, BB65-RCC, LOUCY, OVCAR-4, LXF-289, KNS-42, 8-MG-BA, NTERA-S-cl-D1, A101D, MMAC-SF, no-10, A253, TE-9, SK-UT-1, ES6. In some embodiments a cancer cell that is sensitive to a proteasome inhibitor is characterized in that the IC50 of the proteasome inhibitor for the cell falls within the range of IC50 values of the proteasome inhibitor for the afore-mentioned cell lines.

In some embodiments a cancer cell that is sensitive to a proteasome inhibitor is from a cell line selected from the group consisting of the MG132 sensitive cell lines listed in FIG. 35 (right panel). In some embodiments a cancer cell that is sensitive to a proteasome inhibitor is characterized in that the IC50 of the proteasome inhibitor for the cell falls within the range of IC50 of the proteasome inhibitor for the afore-mentioned cell lines.

In some embodiments, a cancer cell that is sensitive to a proteasome inhibitor is from a multiple myeloma cell line or T cell leukemia cell line that is sensitive to a proteasome inhibitor. MM.1S, MM.1R, RPMI-8226, U266, MM144, NCI-H929, and OPM-2 are examples of proteasome inhibitor sensitive multiple myeloma cell lines. CCRF-CEM cells are an example of a proteasome inhibitor sensitive human T-cell acute lymphoblastic leukemia. In some embodiments a cancer cell that is sensitive to a proteasome inhibitor is characterized in that the IC50 of the proteasome inhibitor for the cell falls within the range of IC50 values of the proteasome inhibitor for the afore-mentioned multiple myeloma cell lines.

In some embodiments an agent that reduces activity of a subunit of the 19S proteasome is a polypeptide that is expressed intracellularly. The agent may comprise, for example, a single chain antibody or a single domain antibody that binds to a 19S subunit. Such binding may, e.g., inhibit assembly of the subunit with other 19S subunits to form a 19S proteasome and/or inhibit ATPase activity of a 19S subunit. In some embodiments, an agent that reduces activity of a 19S subunit is a dominant negative variant of the subunit. A dominant negative variant may be a fragment or variant that is capable of assembling with other 19S subunits to form a 19S proteasome but lacks a domain or residue that is important for activity of the 19S proteasome. For example, a variant of a subunit that has a deletion or substitution of a catalytic residue may serve as a dominant negative.

In some embodiments, an agent that reduces the level of expression or activity of a subunit of the 19S proteasome is a small molecule.

Other methods of reducing the level of expression of a 19S subunit are also within the scope of the present disclosure. For example, a gene encoding a 19S subunit may be modified such that the gene encodes an mRNA that comprises a sequence that destabilizes the mRNA (an "mRNA-destabilizing sequence"). In some embodiments, the mRNA destabilizing sequence is an adenylate-uridylate-rich element (AU-rich elements; ARE). AREs are cis-acting elements found in the 3' untranslated region (UTR) of an estimated 5-8% of human mRNAs, including numerous cytokines, oncoproteins, and growth factors, and their presence generally accelerates mRNA turnover. ARE sequences are well known in the art (see, e.g., Wu, X & Brewer, G. Gene. 2012; 500(1): 10-21, and references therein). An exemplary ARE comprises 1-4 copies of the sequence UUAUUUAUU. In some embodiments a gene encoding a 19S subunit may be modified such that the encoded 19S subunit comprises a sequence that destabilizes the protein ("protein destabilizing sequence") such as a PEST sequence. In some embodiments a gene encoding a 19S subunit may be genetically modified so as to reduce transcription of RNA from the gene and/or reduce translation of the mRNA encoding the subunit. For example, in some embodiments a regulatory region of the gene (e.g., the promoter) may be modified so as to reduce binding of RNA polymerase and/or transcription factors or a portion of the gene that encodes the ribosome binding site may be modified so as to reduce ribosome binding. In some embodiments a stop codon, insertion, deletion or combination thereof resulting in a frameshift may be introduced into a gene encoding a 19S subunit, thereby preventing production of full length protein from transcripts transcribed from that copy of the gene. The stop codon, insertion, or deletion may be positioned so that any resulting polypeptide is non-functional or has reduced function relative to the non-genetically modified gene. Any of the genetic modifications that reduce 19S subunit expression and/or activity may be made to one or both copies of the gene that encodes a particular 19S subunit, so long as the reduction is compatible with cell survival for a sufficient period of time to use the cell for one or more purposes described herein, e.g., in screens to identify or characterize agents useful in reducing proteasome inhibitor resistance.

As used herein, a modest reduction in the level of expression or activity is typically a reduction of the level of expression or activity by between 10% and 90%. A reduction by 10% means that the level is reduced to 90% of the original level. In some embodiments a modest reduction in the level of expression is a reduction by between 20% and 80%, e.g., by between 25% and 50% or between 50% and 75%. In some embodiments a modest reduction in the level of expression is a reduction by about 10%, about 20%, about 25%, about 30%, about 35%, about 40%, about 45%, about 50%, about 55%, about 60%, about 65%, about 70%, about 75%, about 80%, about 85%, or about 90%. In some embodiments the level of expression or activity of a 19S subunit is reduced to about the level of expression or activity of such subunit that is present in a cancer cell that is resistant to a proteasome inhibitor. A modest reduction could be a steady state level or a transient reduction, as discussed herein.

In some embodiments a cancer cell that is resistant to a proteasome inhibitor is from a cell line selected from the following bortezomib-resistant cancer cell lines: NCI-H1838, IMR-5, U-698-M, COLO-824, P31-FUJ, KY821, RPMI-8866, TC-YIK, MS-1, DMS-153, SUP-T1, SCC-15, MSTO-211H, J-RT3-T3-5, NCI-H889, CPC-N, COLO-668, NCI-H226, TUR, DEL, CA46, SNU-C1, THP-1, SCH, NCI-H1522, LNCaP-Clone-FGC, NCI-H2171, KASUMI-1, SK-MEL-2, EW-22, NCI-H1299. In some embodiments a cancer cell that is resistant to a proteasome inhibitor is characterized in that the IC50 of the proteasome inhibitor for the cell falls within the range of IC50 of the proteasome inhibitor for the afore-mentioned cell lines.

In some embodiments a cancer cell that is resistant to a proteasome inhibitor is from a cell line selected from the group consisting of the MG132 resistant cell lines listed in FIG. 35 (left panel). In some embodiments a cancer cell that is resistant to a proteasome inhibitor is characterized in that the IC50 of the proteasome inhibitor for the cell falls within the range of IC50 of the proteasome inhibitor for the afore-mentioned cell lines.

In some embodiments the level of expression or activity of a particular 19S subunit in a first cancer cell that is sensitive to a proteasome inhibitor is reduced to about the level of expression or activity of such subunit that is present in a second cancer cell that has increased resistance to a proteasome inhibitor at least in part as a result of reduced expression or activity of such subunit, thereby increasing the resistance of the first cancer cell to a proteasome inhibitor. In some embodiments the average level of expression or activity of the 19S subunits in a first cancer cell that is sensitive to a proteasome inhibitor is reduced to about the average level of expression or activity of the 19S subunits present in a second cancer cell that is resistant to proteasome inhibition, thereby increasing the resistance of the first cancer cell to a proteasome inhibitor. In some embodiments the second cancer cell is from a cell line selected from the group of cancer cell lines that are sensitive to a proteasome inhibitor described herein. Different cancer cell lines or cancers may be proteasome inhibitor resistant as a result of a reduced level of expression or activity of different 19S subunits. For example, some proteasome inhibitor resistant cancer cell lines may have a reduced level of PSMC2 expression; some may have a reduced level of PSMC5 expression; some may have a reduced level of expression of PSMD3 expression; some may have a reduced level of expression of PSMD6 expression; some may have a reduced level of expression of PSMD12 expression, etc. If desired, one of ordinary skill in the art can measure the expression of the various 19S subunits in a cancer cell or cancer cell sample and determine which subunit(s) have reduced expression. One of ordinary skill in the art can identify which particular 19S subunit(s) have reduced expression in a given cancer cell line or cancer and can generate a cell population or cell line that has approximately the same level or expression or reduction in expression using the teachings of the present disclosure.

In some embodiments the level of expression of a proteasome subunit, e.g., a 19S subunit or 20S subunit, by cells is measured. In some embodiments, the level of expression is measured by measuring the level of mRNA that encodes the subunit. One of ordinary skill in the art appreciates that mRNA may be detected as cDNA after reverse transcription. One of ordinary skill in the art appreciates that a wide variety of methods of measuring nucleic acid levels (e.g., mRNA, cDNA) are available and can be used in methods described herein. Such methods include, e.g., e.g., PCR, e.g., real time PCR (also referred to as quantitative PCR), reverse transcription PCR (e.g., real-time reverse transcription PCR), nanostring technology (see, e.g., Geiss, G., et al., Nature Biotechnology (2008), 26, 317-325; U.S. Ser. No. 09/898,743 (U.S. Pat. Pub. No. 20030013091) for exemplary discussion of nanostring technology and general description of probes of use in nanostring technology), in situ hybridization, Northern blots, microarray hybridization (e.g., using cDNA or oligonucleotide microarrays), etc. In some embodiments the level of a target nucleic acid (e.g., mRNA encoding a 19S subunit or mRNA 20S subunit or a copy or reverse transcript thereof (e.g., cDNA) is determined by a method comprising contacting a biological sample (e.g., cells, cell lysate, or fraction thereof) with one or more nucleic acid probe(s) and/or primer(s) comprising a sequence that is substantially or perfectly complementary to the target nucleic acid over at least 10, 12, 15, 20, or 25 nucleotides, maintaining the sample under conditions suitable for hybridization of the probe or primer to its target nucleic acid, and detecting or amplifying a nucleic acid that hybridized to the probe or primer. In some embodiments, "substantially complementary" refers to at least 90% complementarity, e.g., at least 95%, 96%, 97%, 98%, or 99% complementarity. In some embodiments the sequence of a probe or primer is sufficiently long and sufficiently complementary to an mRNA of interest (or its complement) to allow the probe or primer to distinguish between such mRNA (or its complement) and at least 95%, 96%, 97%, 98%, 99%, or 100% of transcripts (or their complements) from other genes in a mammalian cell, e.g., a human cell, under the conditions of an assay. In some embodiments, a probe or primer may also comprise sequences that are not complementary to a mRNA of interest (or its complement). In some embodiments such additional sequences do not significantly hybridize to other nucleic acids in a sample and/or do not interfere with hybridization to a mRNA of interest (or its complement) under conditions of the assay. In some embodiments, an additional sequence may be used to immobilize a probe or primer to a support or to serve as an identifier or "bar code".

In some embodiments a probe or primer is labeled. A probe or primer may be labeled with any of a variety of detectable labels. In some embodiments a label is a radiolabel, fluorescent small molecule (fluorophore), quencher, chromophore, or hapten. Nucleic acid probes or primers may be labeled during synthesis or after synthesis. In some embodiments a nucleic acid to be detected is labeled prior to detection, e.g., prior to or after hybridization to a probe. For example, in microarray-based detection, nucleic acids in a sample may be labeled prior to being contacted with a microarray or after hybridization to the microarray and removal of unhybridized nucleic acids. Methods for labeling nucleic acids and performing hybridization and detection will be apparent to those of ordinary skill in the art. Microarrays are available from various commercial suppliers such as Affymetrix, Inc. (Santa Clara, Calif., USA) and Agilent Technologies, Inc. (Santa Clara, Calif., USA). For example, GeneChips® (Affymetrix) may be used, such as the GeneChip® Human Genome U133 Plus 2.0 Array or successors thereof. Microarrays may comprise one or more probes or probe sets designed to detect each of thousands of different RNAs. In some embodiments a microarray comprises probes designed to detect transcripts from at least 2,500, at least 5,000, at least 10,000, at least 15,000, or at least 20,000 different genes, e.g., human genes.

In some embodiments RNA level is measured using a sequencing-based approach such as serial analysis of gene expression (SAGE) (including modified versions thereof) or RNA-Sequencing (RNA-Seq). RNA-Seq refers to the use of any of a variety of high throughput sequencing techniques to quantify RNA molecules (see, e.g., Wang, Z., et al. Nature Reviews Genetics (2009), 10, 57-63). Other methods of use for detecting RNA include, e.g., electrochemical detection, bioluminescence-based methods, fluorescence-correlation spectroscopy, etc. Those of ordinary skill in the art are aware of how to perform these methods and will be able to obtain or generate appropriate reagents (e.g., nucleic acid probes and/or primers). It will be understood that these methods can be used to measure expression of any gene of interest.

In some embodiments, the level of expression of a proteasome subunit, e.g., a 19S subunit or 20S subunit, is measured by measuring the level of the subunit. Methods of measuring the level of a protein, e.g., a 19S subunit or 20S subunit include, e.g., immunological methods or other affinity-based method. In general, immunological detection methods involve detecting specific antibody-antigen interactions in a sample such as a tissue section or cell sample. The sample is contacted with an antibody that binds to the target antigen of interest. The binding is detected using any of a variety of techniques. In some embodiments, the antibody that binds to the antigen (primary antibody) or a secondary antibody that binds to the primary antibody has been tagged or conjugated with a detectable label, and the detectable label is detected as an indication of the binding. In some embodiments a label-free detection method is used. A detectable label may be, for example, a fluorescent dye (e.g., a fluorescent small molecule) or quencher, colloidal metal, quantum dot, hapten, radioactive atom or isotope, or enzyme (e.g., peroxidase). It will be appreciated that a detectable label may be directly detectable or indirectly detectable. For example, a fluorescent dye would be directly detectable, whereas an enzyme may be indirectly detectable, e.g., the enzyme reacts with a substrate to generate a directly detectable signal. Numerous detectable labels and strategies that may be used for detection, e.g., immunological detection, are known in the art. Examples of methods that may be used for protein detection include, e.g., immunoblot (Western blot), immunoprecipitation, ELISA assays, bead-based assays such as the Luminex® assay platform (Invitrogen), flow cytometry, protein microarrays, immunohistochemistry (IHC), surface plasmon resonance assays (e.g., using BiaCore technology). Antibodies that bind to a 19S subunit or 20S subunit are commercially available or can readily be generated using standard methods of antibody production. In some embodiments a monoclonal antibody may be used. One of ordinary skill in the art can select an appropriate assay method depending, e.g., on factors such as the amount and/or nature of the sample.

Suitable controls and normalization procedures may be used to accurately quantify expression and/or activity of 19S subunits, 20S subunits, or other gene products of interest, where appropriate. For example, measured values can be normalized based on, e.g., total mRNA expression or the expression of one or more RNAs or polypeptides whose expression is not correlated with a parameter of interest (e.g., cell survival or proliferation, proteasome activity, resistance or sensitivity to a proteasome inhibitor). In some embodiments expression level is normalized based on expression of a housekeeping gene. In some embodiments the expression level is normalized based on the level of actin or GAPDH protein or mRNA encoding actin or GAPDH.

In some embodiments, reducing the level of expression or activity of a 19S subunit causes the resistance of a cell, e.g., a cancer cell, to a proteasome inhibitor to increase by at least 1.1 fold, at least 1.2 fold, 1.3 fold, at least 1.4 fold, at least 1.5 fold, at least 1.6 fold, at least 1.7 fold, at least 1.8 fold, at least 1.9 fold, at least 2 fold, at least 3 fold, at least 4 fold, at least 5 fold, at least 10 fold, at least 20 fold, at least 30 fold, at least 40 fold, at least 50 fold, at least 100 fold, at least 250 fold, at least 500 fold, at least 1,000 fold, or more, relative to the resistance to the proteasome inhibitor of a control cell, e.g., a control cancer cell, in which the level of expression or activity of a 19S subunit has not been reduced. In some embodiments, reducing the level of expression or activity of a 19S subunit causes the resistance of a cell, e.g., a cancer cell to a proteasome inhibitor to increase by between 1.1 fold and 3 fold, between 3 fold and 5 fold, between 5 fold and 10 fold, between 10 fold and 25 fold, between 25 fold and at least 50 fold, between 50 fold and 100 fold, between 100 fold and 250 fold, between 250 fold and 500 fold, or between 500 fold and 1,000 fold, relative to the resistance to the proteasome inhibitor of a control cell, e.g., a control cancer cell, in which the level of expression or activity of a 19S subunit has not been reduced. In some embodiments the resistance of a cell, e.g., a cancer cell, to a proteasome inhibitor may be expressed in terms of the IC50 as measured using a suitable assay. Thus in some embodiments the IC50 of a proteasome inhibitor measured using cells, e.g., cancer cells, that have a reduced level of a 19S subunit is at least 1.1 fold, at least 1.2 fold, 1.3 fold, at least 1.4 fold, at least 1.5 fold, at least 1.6 fold, at least 1.7 fold, at least 1.8 fold, at least 1.9 fold, at least 2 fold, at least 3 fold, at least 4 fold, at least 5 fold, at least 10 fold, at least 20 fold, at least 30 fold, at least 40 fold, at least 50 fold, at least 100 fold, at least 250 fold, at least 500 fold, at least 1,000 fold, or more, as great as the IC50 of that proteasome inhibitor measured using control cells that do not have a reduced level of expression or activity of a 19S subunit. In some embodiments the IC50 of a proteasome inhibitor measured using cells, e.g., cancer cells, that have a reduced level of a 19S subunit is greater than the IC50 of that proteasome inhibitor measured using control cells, e.g., control cancer cells, by between 1.1 fold and 3 fold, between 3 fold and 5 fold, between 5 fold and 10 fold, between 10 fold and 25 fold, between 25 fold and at least 50 fold, between 50 fold and 100 fold, between 100 fold and 250 fold, between 250 fold and 500 fold, or between 500 fold and 1,000 fold.

Without wishing to be bound by any theory, it is reasonable to expect that (1) the precise extent of reduction in expression or activity of a particular 19S subunit that will result in a particular level of resistance or increase in resistance to a proteasome inhibitor may vary between different cancer cell populations (e.g., cancer cells obtained from different cancers) or cancer cell lines; (2) the 19S subunit(s) whose knockdown by a given amount is most effective in increasing proteasome inhibitor resistance may vary between different cancer cell populations (e.g., cancer cell samples obtained from different cancers) or cancer cell lines. For example, different 19S subunits may be expressed at different relative levels in different cancer cells or cancer types, and thus different 19S subunits may be limiting for formation of functional 19S proteasome complexes. Expression of a subunit that is expressed in excess relative to other subunits may need to be reduced by a greater amount (e.g., percentage) in order to achieve a given increase in proteasome inhibitor resistance as compared with the amount by which expression of a different, less highly expressed 19S subunit would need to be reduced to achieve the same increase in proteasome inhibitor resistance. Stated another way, the 19S subunit that is expressed at a relatively low level compared with other 19S subunits may require only a slight reduction in expression in order to reduce the level of functional 19S proteasomes (and thereby increase proteasome inhibitor resistance), while a 19S subunit that is expressed at relatively high level compared with the expression of other 19S subunits may require a greater reduction in expression (also referred to as "knockdown") in order to reduce the level of functional 19S proteasomes. One of ordinary skill in the art can select one or more 19S subunits to knock down and can select the appropriate level of knockdown to result in an increase in proteasome inhibitor resistance given the teachings of the present disclosure.

In some aspects, it is contemplated that agents that disrupt the integrity of the 26S proteasome may have similar effects as agents that reduce the level of expression or activity of a 19S subunit. Such agents may be, e.g., nucleic acids, polypeptides, or small molecules that interfere with physical association of the 19S and 20S subunits. In some aspects, a screen may be performed to identify such agents.

In some embodiments, genetic modification using targetable nucleases is used to reduce the level of expression or activity of a 19S subunit. The term "targetable nuclease" refers to a nuclease that can be programmed to produce site-specific DNA breaks, e.g., double-stranded breaks (DSBs), at a selected site in DNA. Such a site may be referred to as a "target site". The target site can be selected by appropriate design of the targetable nuclease or by providing a guide molecule (e.g., a guide RNA, e.g., sgRNA) that directs the nuclease to the target site. Examples of targetable nucleases include zinc finger nucleases (ZFNs), transcription activator-like effector nucleases (TALENs), and RNA-guided nucleases (RGNs) such as the Cas proteins of the CRISPR/Cas Type II system (e.g., Cas9), and engineered meganucleases. CRISPR/Cas systems are particularly convenient. A break created by a targetable nuclease can be repaired by non-homologous end joining, which can result in small deletions or by homology directed repair/homologous recombination in the presence of a suitable repair template to, e.g., create precise alterations in genomic sequence. Methods of using targetable nucleases, e.g., to perform genome modification, are described in numerous publications, such as *Methods in Enzymology*, Doudna J A, Sontheimer E J. (eds), The use of CRISPR/Cas9, ZFNs, and TALENs in generating site-specific genome alterations. *Methods Enzymol.* 2014, Vol. 546 (Elsevier); Carroll, D., Genome Editing with Targetable Nucleases, Annu. Rev. Biochem. 2014. 83:409-39, and references in either of these. See also U.S. Pat. Pub. Nos. 20140068797, 20140186919, 20140170753 and/or PCT/US2014/034387 (WO/2014/172470). One of ordinary skill in the art can select or design suitable nuclease, guide RNAs, and repair templates to create a genetic modification of interest. In some embodiments a targetable nuclease is used to modify a gene that encodes a 19S subunit, wherein the modification reduces the level of expression or activity of the subunit. Any of variety of genetic modifications could have such an effect, such as deletion of all or part of the gene, introduction of a frameshift mutation or stop codon into the coding region, an insertion or substitution of one or more nucleotides that disrupts a regulatory region (e.g., a promoter) or coding region, etc. In some embodiments, one of the two alleles of a gene encoding a 19S subunit is modified in a cell. In the case of modifications that essentially abolish expression or activity, this would be expected typically to result in an approximately 50% reduction in the total level of expression or activity of the subunit. Smaller reduction in expression or activity could be achieved by making modifications that have a less drastic effect on expression or activity. Larger reduction in expression or activity could be achieved by targeting both alleles.

In some aspects, described herein are methods for testing a cell that harbors a modification that reduces the level of expression or activity of a 19S subunit to determine if the cell exhibits resistance to a proteasome inhibitor. For example, cells that have been modified so as to reduce the level of expression or activity of a 19S subunit may be tested as described herein to determine the IC50, EC50, or both of one or more proteasome inhibitors. In some embodiments cancer cells are tested for proteasome inhibitor resistance in vivo by introducing them into a suitable animal host, administering a proteasome inhibitor to the animal host, and measuring the effect of the proteasome inhibitor on the formation and/or growth of tumors.

Aspects of the disclosure provide methods, test cells, and control cells, e.g., methods, test cells, and control cells that are useful for identifying inhibitors of proteasome inhibitor resistance, e.g., compounds that target (e.g., selectively target) proteasome inhibitor resistant cancer cells and/or that cause such cells to become more sensitive to proteasome inhibitors. The term "inhibitor of proteasome inhibitor resistance" refers to an agent that reduces resistance to a proteasome inhibitor of a cancer cell (e.g., a cancer cell that is proteasome inhibitor resistant) or reduces the likelihood that a proteasome inhibitor sensitive cell will acquire increased resistance to a proteasome inhibitor. In some embodiments, an inhibitor of proteasome inhibitor resistance is selectively toxic to cancer cells that have increased proteasome inhibitor resistance as compared to a reference value representative of proteasome inhibitor sensitive cells. An agent that is an inhibitor of proteasome inhibitor resistance may be characterized in that the IC50 of a proteasome inhibitor contacted with cells in the presence of the agent is lower than the IC50 of the proteasome inhibitor contacted with cells in the absence of the agent. An agent that is an inhibitor of proteasome inhibitor resistance may be characterized in that cells contacted with a proteasome inhibitor in the presence of the agent over a period of time (e.g., 2-8 weeks, 8 weeks-12 months, or more) have less likelihood of acquiring increased resistance to the proteasome inhibitor as compared with cells contacted with the same concentration of proteasome inhibitor in the absence of the agent.

In some embodiments, a method for identifying an agent that reduces proteasome inhibitor resistance or reduces the ability of a cell to acquire increased proteasome inhibitor resistance comprises: (a) contacting one or more test cells that has a modestly reduced level of expression or activity of a subunit of a 19S proteasome complex as compared to a reference level with a test agent; (b) detecting the level of inhibition of the survival or proliferation of the one or more test cells by the test agent; and (c) identifying the agent as an agent that reduces proteasome inhibitor resistance or reduces the ability of a cell to acquire increased proteasome inhibitor resistance if the test agent reduces the survival or proliferation of the test cells. In some embodiments the method comprises comparing the level of reduction of survival or proliferation of the test cells by the test agent with the level of reduction of survival or proliferation of control cells by the test agent, wherein the control cells do not have a reduced level of expression or activity of the 19S subunit as compared with the reference level.

In some embodiments, a method for identifying an agent that reduces proteasome inhibitor resistance or reduces the ability of a cell to acquire increased proteasome inhibitor resistance comprises: (a) contacting one or more test cells with a test agent in the presence of a proteasome inhibitor, wherein the one or more test cells has a modestly reduced level of expression or activity of a subunit of a 19S proteasome complex as compared to a reference level; (b) detecting the level of inhibition of the survival or proliferation of the one or more test cells by the test agent; and (c) identifying the test agent as an agent that reduces proteasome inhibitor resistance or reduces the ability of a cell to acquire increased proteasome inhibitor resistance if the test agent reduces the survival or proliferation of the test cells. In some embodiments the method comprises comparing the level of reduction of survival or proliferation of the test cells by the test agent with the level of reduction of survival or proliferation of control cells by the agent, wherein the control cells do not have a reduced level of expression or activity of the 19S subunit as compared with the reference level.

In some aspects, described herein is a method that comprises: (a) contacting a cell with an agent that increases level of expression or activity of a 19S subunit; (b) contacting the cell with a proteasome inhibitor; (c) measuring the level of resistance of the cell to the proteasome inhibitor as compared with the level of resistance of a control cell not contacted with the agent; and (d) identifying the agent as suitable for reducing proteasome inhibitor resistance if the resistance of the cell to the proteasome inhibitor is lower than the resistance of the control cell. In some embodiments, a screen may be performed to identify an agent that selectively increases expression or activity of a 19S subunit.

In some embodiments, cells of use in a composition or method described herein are cancer cells. In some embodiments the cells originate from a naturally occurring cancer.

In some embodiments the cells originate from an experimentally produced cancer. In some embodiments the cells are experimentally generated cancer cells. In some embodiments the cells are immortalized non-tumorigenic cells. In some embodiments the cells are cancer stem cells. In general, the cancer cells may originate from any type of cancer. In some embodiments the cancer is a carcinoma. In some embodiments the cancer is a sarcoma. In some embodiments the cancer is a hematological malignancy. As described herein, test cells and control cells can be cells or cell lines derived from malignant tumors, cells or cell lines derived from benign tumors, transformed immortalized cell lines, immortalized cell lines, non-immortalized cell lines, transgenic cell lines, primary cells, etc. In some embodiments the tumor is a metastatic tumor, in which case the cells may be derived from the primary tumor or a metastasis. More than one set of test cells and/or control cells may be provided, such as cancer cells derived from cancers of different types.

In some embodiments various methods described in the present disclosure comprise measuring one or more characteristics of a cell or tumor such as cell survival or proliferation, expression level of one or more genes, activity of one or more gene products, or tumor size or growth rate. In some embodiments one or more cells, biological samples, or tumors are contacted with an agent or combination of agents and one or more characteristics such as cell survival or proliferation, expression level of one or more genes, activity of one or more gene products, or tumor size or growth rate is measured.

In some embodiments cells are maintained and/or contacted with one or more agents in vitro (e.g., in cell culture). Cultured cells can be maintained in a suitable cell culture vessel under appropriate conditions (e.g., appropriate temperature, gas composition, pressure, humidity) and in appropriate culture medium. Methods, culture media, and cell culture vessels (e.g., plates (dishes), wells, flasks, bottles, tubes, or other chambers) suitable for culturing cells are known to those of ordinary skill in the art. Typically the vessels contain a suitable tissue culture medium. In some embodiments that involve test agent(s), the test agent(s) are present in the tissue culture medium, e.g., test agent(s) are added to the culture medium before or after the medium is placed in the culture vessels. One of ordinary skill in the art can select a medium appropriate for culturing a particular cell type. In some embodiments a medium is a chemically defined medium. In some embodiments a medium is free or essentially free of serum or tissue extracts. In some embodiments serum or tissue extract is present. In some embodiments cells are non-adherent. In some embodiments cells are adherent. Such cells may, for example, be cultured on a plastic or glass surface, which may in some embodiments be processed to render it suitable for mammalian cell culture. In some embodiments cells are cultured on or in a material comprising collagen, laminin, Matrigel®, or a synthetic polymer or other material that is intended to provide an environment that resembles in at least some respects the extracellular environment, e.g., extracellular matrix, found in certain tissues in vivo. In some embodiments cancer cells are cultured with non-cancerous stromal cells. In some embodiments cells are cultured in three-dimensional culture matrix.

In some embodiments mammalian cells are used. In some embodiments mammalian cells are primate cells (human cells or non-human primate cells), rodent (e.g., mouse, rat, rabbit, hamster) cells, canine, feline, bovine, or other mammalian cells. In some embodiments avian cells are used. A cell may be a primary cell, immortalized cell, normal cell, abnormal cell, tumor cell, non-tumor cell, etc., in various embodiments. A cell may originate from a particular tissue or organ of interest or may be of a particular cell type. Primary cells may be freshly isolated from a subject or may have been passaged in culture a limited number of times, e.g., between 1-5 times or undergone a small number of population doublings in culture, e.g., 1-5 population doublings. In some embodiments a cell is a member of a population of cells, e.g., a member of a non-immortalized or immortalized cell line. In some embodiments, a "cell line" refers to a population of cells that has been maintained in culture for at least 10 passages or at least 10 population doublings. In some embodiments, a cell line is derived from a single cell. In some embodiments, a cell line is derived from multiple cells (a polyclonal cell line). In some embodiments, cells of a cell line are descended from a cell or cells originating from a single sample (e.g., a sample obtained from a tumor) or individual. A cell may be a member of a cell line that is capable of prolonged proliferation in culture, e.g., for longer than about 3 months (with passaging as appropriate) or longer than about 25 population doublings). A non-immortalized cell line may, for example, be capable of undergoing between about 20-80 population doublings in culture before senescence. In some embodiments, a cell line is capable of indefinite proliferation in culture (immortalized). An immortalized cell line has acquired an essentially unlimited life span, i.e., the cell line appears to be capable of proliferating essentially indefinitely. For purposes hereof, a cell line that has undergone or is capable of undergoing at least 100 population doublings in culture may be considered immortal. In some embodiments, cells are maintained in culture and may be passaged or allowed to double once or more following their isolation from a subject (e.g., between 2-5, 5-10, 10-20, 20-50, 50-100 times, or more) prior to use in a method disclosed herein. In some embodiments, cells have been passaged or permitted to double no more than 1, 2, 5, 10, 20, or 50 times following isolation from a subject prior to use in a method described herein.

In some embodiments, cells may be tested to confirm whether they are derived from a single individual or belong to a particular cell line (or derived therefrom) by any of a variety of methods known in the art such as DNA fingerprinting (e.g., short tandem repeat (STR) analysis) or single nucleotide polymorphism (SNP) analysis (which may be performed using, e.g., SNP arrays (e.g., SNP chips) or sequencing. In any embodiment described herein, sequencing can comprise next generation sequencing.

In some aspects, a cell that is genetically engineered to have reduced (or increased) level of expression or activity of a 19S subunit is characterized in that it is genetically matched with a cell or cell line that does not have a modification that reduces (or increases) the level of expression or activity of a 19S subunit or with a subject whose cells do not harbor a mutation or epigenetic feature that reduces (or increases) the level of expression or activity of a 19S subunit.

Numerous cancer cell lines and non-cancer cell lines are known in the art and may be used in various methods described herein. Cell lines can be generated using methods known in the art or obtained, e.g., from depositories or cell banks such as the American Type Culture Collection (ATCC), Coriell Cell Repositories, Deutsche Sammlung von Mikroorganismen and Zellkulturen (German Collection of Microorganisms and Cell Cultures; DSMZ), European Collection of Cell Cultures (ECACC), Japanese Collection of Research Bioresources (JCRB), RIKEN, Cell Bank Australia, etc. The paper and online catalogs of the afore-mentioned depositories and cell banks are incorporated herein by reference. Table S4 provides a list of cancer cell lines that may be used in methods described herein.

Cells or cell lines (e.g., test cells and/or control cells) may be of any cell type or tissue of origin in various embodiments. Cancer cells or cancer cell lines may be of any cancer type or tissue of origin in various embodiments. In some embodiments cancer cells, e.g., a cancer cell line, originate from a human tumor. In some embodiments cancer cells, e.g., a cancer cell line, originates from a cancer of a non-human animal, e.g., a non-human mammal, e.g., cells of non-human primate, rodent (e.g., mouse, rat, guinea pig, rabbit) origin, or interspecies hybrids. In some embodiments cancer cells originate from a naturally arising cancer (i.e., a cancer that was not intentionally induced or generated for, e.g., experimental purposes). In some embodiments cancer cells originates from a primary tumor. In some embodiments a cancer cell line originates from a metastatic tumor. In some embodiments a cancer cell line originates from a metastasis. In some embodiments a cell line has become spontaneously immortalized in cell culture. In some embodiments a cancer cell line is capable of giving rise to tumors when introduced into an immunocompromised host, e.g., an immunocompromised rodent such as an immunocompromised mouse (e.g., a SCID mouse).

In certain embodiments cells, e.g., test and/or control cells, are obtained from a biopsy (e.g., tissue biopsy, fine needle biopsy, blood sample, etc.) or at surgery for a cancerous or noncancerous condition. In some embodiments the tissue biopsy is a bone marrow biopsy or lymph node biopsy.

A cancer from which cells (e.g., test cells and/or control cells) are derived may be of any type mentioned herein (see, e.g., the Glossary). In some embodiments, the cancer is a hematologic malignancy, e.g., multiple myeloma, leukemia, or lymphoma. In some embodiments the cancer is a cancer associated with a known or characteristic genetic mutation or polymorphism. In some embodiments the cancer is an experimentally produced cancer. In some embodiments cells are derived from an early stage cancer or precancerous lesion, e.g., a papilloma, adenoma, dysplastic lesion, etc., or a cancer in situ. In some embodiments the cancer is one that is responsive to a chemotherapeutic agent or combination thereof (e.g., any one or more of the chemotherapeutic agents discussed herein). In some embodiments the cancer is one that is resistant to a chemotherapeutic agent or combination thereof.

In some embodiments, cancer cells are experimentally produced. Cancer cells can be experimentally produced by a number of methods known in the art that result in transformation of a non-cancer cell (non-transformed cell) to a cancer cell (transformed cell). Such experimentally produced cancer cells may be metastatic or non-metastatic. In some embodiments cancer cells are produced from non-cancer cells by transfecting the non-cancer cells (transiently or stably) with one or more expression vector(s) encoding an oncogene. Such oncogenes, when expressed, lead to neoplastic hyperplastic transformation of a cell. The oncogene may be a complete sequence of the oncogene, preferably an oncogenic form of the oncogene, or it may be a fragment of the oncogene that maintains the oncogenic potential of the oncogene. Exemplary oncogenes include MYC, SRC, FOS, JUN, MYB, RAS, ABL, HOXI1, HOXI1 1L2, TAL1/SCL, LMO1, LMO2, EGFR, MYCN, MDM2, CDK4, GLI1, IGF2, activated EGFR, mutated genes, such as FLT3-ITD, mutated of TP53, PAX3, PAX7, BCR/ABL, HER2/NEU, FLT3R, FLT6-ITD, SRC, ABL, TAN1, PTC, B-RAF, PML-RAR-alpha, E2A-PRX1, and NPM-ALK, as well as fusion of members of the PAX and FKHR gene families. Other exemplary oncogenes are well known in the art. In some embodiments cancer cells can be produced from non-cancer cells by transfecting, the non-cancer cells (transiently or stably) with one or more expression vector(s) encoding an inhibitory molecule (e.g., shRNA, miRNA) capable of inhibiting the expression of a tumor suppressor gene. Such inhibitory molecules, when expressed, lead to neoplastic or hyperplastic transformation of a cell. Exemplary tumor suppressor genes include RB, TP53, APC, NF-1, BRCA-1, BRCA-2 and WT-1. Other exemplary tumor suppressor genes are well known in the art. In some cases, cancer cells can be produced from non-cancer cells by transfecting the non-cancer cells (transiently or stably) with one or more expression vector(s) encoding an inhibitory molecule (e.g., shRNA) capable of inhibiting the expression of a tumor suppressor gene and one or more expression vector(s) encoding an oncogene.

In some embodiments, cells (e.g., test cells, control cells) are derived from noncancerous tissue. For example, in some embodiments, the cells may be derived from a noncancerous hematologic tissue. In some embodiments, cells are B cells, T cells, plasma cells, peripheral blood mononuclear cells, or precursors of any of the foregoing. In some embodiments the cells may be derived from a noncancerous epithelial tissue. One of skill in the art will appreciate that "epithelium" refers to layers of cells that line the cavities and surfaces of structures throughout the body and is also the type of tissue of which many glands are at least in part formed. Such tissues include, for example, tissues found in the breast, gastrointestinal tract (stomach, small intestine, colon), liver, biliary tract, bronchi, lungs, pancreas, kidneys, ovaries, prostate, skin, cervix, uterus, bladder, ureter, testes, exocrine glands, endocrine glands, blood vessels, etc. In some embodiments the epithelium is endothelium or mesothelium.

In some embodiments the cells (test and/or control) have been modified, e.g., genetically modified, so as to express, inhibit, or delete one or more oncogenes or tumor suppressor genes. In some embodiments such modification immortalizes the cells. In some embodiments such modification transforms the cells to tumorigenic cells. For example, in certain embodiments test and/or control cells are immortalized by expressing telomerase catalytic subunit (e.g., human telomerase catalytic subunit; hTERT) therein. In certain embodiments test and/or control cells are transformed by expressing SV40 (e.g., early region) or Ras, optionally activated Ras such as H-rasV12, therein. In some embodiments cells are modified or treated so as to have reduced or essentially absent expression and/or functional activity of cell cycle checkpoint or DNA damage sensing proteins, e.g., p16, e.g., p16$^{INK4a}$, p53 and/or retinoblastoma (Rb) proteins. For example, cells can be modified to express a shRNA targeted to one or more of these genes, or to express a viral protein that binds to one or more of these proteins. Combinations of such modifications can be used. For example, cells may be modified to express SV40 large T (LT), hTERT, and H-rasV12. Other means of immortalizing and/or transforming cells are known in the art and are within the scope of the invention.

In certain embodiments test cells and control cells are derived from an initial population of substantially identical cells that have not undergone a manipulation causing them to have an altered (reduced or increased) level of expression or activity of a 19S subunit. In some embodiments, the cells have not undergone a manipulation causing them to have an altered (reduced or increased) level of expression or activity of a 20S subunit. In some embodiments, the cells have not undergone a manipulation causing them to have an altered (reduced or increased) level of expression or activity of any endogenous gene product. In some embodiments, one or more cells of the initial population are manipulated so as to render them suitable for use as test cells, e.g., by modifying them so cause them to have (or be induced to have) a reduced level of expression or activity of a 19S subunit. In some embodiments, one or more cells of the initial population are manipulated so as to render them suitable for use as test cells, e.g., by modifying them so as to be able to cause them to have a reduced level of expression or activity of a 19S subunit in a controlled manner and then causing a reduction in the level or activity of a 19S subunit, e.g., by contacting the cells with an agent that causes the cell to have a reduced level or activity of a 19S subunit, e.g., by inducing expression of an inhibitory nucleic acid or polypeptide.

In certain embodiments, the test and control cells are genetically matched but have one or several defined genetic differences such as those described herein that result in the test cells having or being capable of induction of a reduction in level of expression or activity of a 19S subunit, while the control cells are not. In certain embodiments, two populations of cells derived from the same starting population, wherein one population has been modified by introducing an expression construct that encodes a nucleic acid or protein that inhibits expression or activity of a 19S subunit and the other population has not been modified in such a way. In certain embodiments, two populations of cells derived from the same starting population, wherein one population has been modified by introducing an expression construct that encodes an nucleic acid or protein that inhibits expression or activity of a 19S subunit and the other population has been modified by introducing an expression construct encoding a control nucleic acid or protein (e.g., one that would not be expected to inhibit expression or activity of a proteasome subunit or proteasome-associated protein, e.g., one that would not be expected to inhibit expression or activity of an endogenous cellular gene or protein). Typically the expression constructs are otherwise similar or identical. In certain embodiments, the test cells and control cells are genetically matched and contain an expression construct (optionally integrated into the genome) comprising a sequence encoding a short interfering RNA capable of inhibiting expression of a 19S subunit (such as a shRNA or miRNA targeted to mRNA encoding such subunit), wherein the sequence is operably linked to a regulatable (e.g., inducible or repressible) promoter. In certain embodiments the test cells and control cells are genetically matched and contain an expression construct (optionally integrated into the genome) comprising a sequence encoding a protein capable of inhibiting activity of a 19S subunit, wherein the sequence is linked to a regulatable (e.g., inducible or repressible) promoter.

"Genetically matched" refers to cells or populations of cells that have largely identical genomes, e.g., their genomes are at least 95%, 98%, 99%, 99.5%, 99.9%, 99.99%, identical, or more. Typically, genetically matched cells are derived from the same subject (e.g., a human or non-human mammal such as a rodent). In some embodiments, e.g., in the case of certain species such as mice or rats that can be inbred, genetically matched cells may be derived from different subjects belonging to a particular inbred strain. In some embodiments genetically matched cells are derived from the same tissue sample. In some embodiments, test cells and control cells will have been derived from the same initial population of genetically matched cells and will have undergone no more than 2, 5, 10, 15, 20, 25, 30, 35, 40, 50, 60, 70, 80, 90, or 100 rounds of cell division before being used in a method described herein.

In some aspects, the disclosure provides genetically matched test cells and control cells and kits containing such cells, wherein the test cells and control cells differ in regard to the level of expression or activity of a 19S subunit. Without wishing to be bound by any theory and without limiting the disclosure in any way, methods that use test and control cells that are genetically matched and differ primarily or essentially in that the test cells have a reduced level of expression or activity of a 19S subunit as compared with control cells allows identification of compounds that differentially affect the test cells versus the control cells (e.g., compounds that inhibit survival or proliferation of the test cells to a significantly greater extent than the extent to which they inhibit survival or proliferation of the control cells) as a result of differences in the test cells and control cells that arise as a consequence of the reduced level of 19S subunit expression or activity (associated with acquiring increased resistance to proteasome inhibitors) in the test cells rather than because of other, possibly unknown, genetic or epigenetic differences in the test and control cells.

In some embodiments, methods described herein that use test cells and control cells could additionally or alternately be practiced using test cells that have a low level of expression or activity of a 19S subunit in the absence of manipulation and control cells that are manipulated so as to increase their level of expression or activity of such 19S subunit. For example, cancer cell lines can be tested to identify one or more lines that have a low level of expression or activity of a 19S subunit. Cells from such a cell line can be genetically modified by introduction of an expression construct comprising a nucleic acid encoding a 19S subunit, operably linked to a promoter. Expression of the nucleic acid results in increased level of the 19S subunit.

In some aspects, described herein are methods (e.g., screening methods) of use to test the ability of an agent to inhibit the survival or proliferation of a proteasome inhibitor resistant cell. In some aspects, described herein are methods of identifying agents that reduce the ability of a cell to acquire proteasome inhibitor resistance and/or reduce the level of proteasome inhibitor resistance of a cell. In some embodiments, a method for testing the ability of an agent to inhibit the survival or proliferation of a proteasome inhibitor resistant cancer cell comprises (a) contacting one or more test cells with the agent, wherein the one or more test cells has a modestly reduced level of expression or activity of a 19S subunit as compared to a reference level, and (b) detecting the level of inhibition of the survival or proliferation of the one or more test cells by the agent. If the test agent inhibits the survival or proliferation of the test cells, the test agent may be identified as an agent that inhibits survival or proliferation of proteasome inhibitor resistant cancer cells. In some embodiments the test cells are also contacted with a proteasome inhibitor. In some embodiments, the method comprises comparing the level of reduction of survival or proliferation of the test cells by the test agent with the level of reduction of survival or proliferation of control cells by the test agent, wherein the control cells do not have a reduced level of expression or activity of the 19S subunit as compared with the reference level.

In some aspects, an agent identified according to methods described herein may be referred to as a candidate agent. Such an agent may be further tested, e.g., by measuring its effect on survival or proliferation of cancer cells other than the test cells or control cells, e.g., in order to further validate the agent for use in treating cancer. Optionally, a candidate agent is tested in combination with a proteasome inhibitor, e.g., a proteasome inhibitor to which the cancer cell is determined or documented to be resistant. Such testing may be performed in cell culture or in an animal model of cancer.

In some embodiments the activity of an agent (e.g., a test agent) can be tested by contacting test cells and control cells that are in a co-culture. Co-cultures enable selective evaluation of the properties (e.g., survival or proliferation) of two or more populations of cells (e.g., test and control cells) in contact with an agent in a common growth chamber. Typically, each population of cells grown a co-culture will have an identifying characteristic that is detectable and distinct from an identifying characteristic of the other population(s) of cells in the co-culture. In some embodiments, the identifying characteristic comprises a level of expression of a fluorescent protein or other reporter protein or a protein expressed at the cell surface that could be detected using an antibody. Numerous fluorescent proteins are known in the art and may be used. Such proteins include, e.g., green, blue, yellow, red, orange, and cyan fluorescent proteins. In some embodiments, test cells and control cells express different, distinguishable FPs, e.g., a red FP and a green FP, or other pairs of FPs that have different emission spectra. Other reporter proteins include, e.g., enzymes such as luciferase, beta-galactosidase, alkaline phosphatase, etc. However, other identifying characteristics known in the art may be suitable, provided that the identifying characteristic enables measurement (e.g., by FACS or other suitable assay method) of the level of survival or proliferation of each of the two or more populations of cells in the co-culture. A cell can be modified to have an identifying characteristic using methods known in the art, e.g., by introducing into the cell a nucleic acid construct encoding an FP (or other detectable protein) operably linked to a promoter. In some embodiments, a nucleic acid construct that encodes an RNAi agent that reduces expression of a 19S subunit and a nucleic acid construct that encodes a FP are incorporated into the same vector. In some embodiments, they may be in different vectors. In some embodiments, the construct(s) may be integrated into the genome of the cell.

Compositions, e.g., co-cultures, comprising at least some test cells (e.g., between 1% and 99% test cells) and at least some control cells (e.g., between 1% and 99% control cells), are disclosed herein. In some embodiments the percentage of test cells is between 10% and 90%. In other embodiments the percentage of test cells is between 20% and 80%. In some embodiments the percentage of test cells is between 30% and 70%. In some embodiments the percentage of test cells is between 40% and 60%, e.g., about 50%. In some embodiments the composition further comprises a test agent.

In some embodiments, test cells and control cells are maintained in separate vessels (e.g., separate wells of a microwell plate) under substantially identical conditions.

Assay systems comprising test cells, control cells, and one or more test compounds, e.g., 10, 100, 1000, 10,000, or more test agents, wherein the cells and test agents are arranged in one or more vessels in a manner suitable for assessing effect of the test compound(s) on the cells, are aspects of the invention. Typically the vessels contain a suitable tissue culture medium, and the test compounds are present in the tissue culture medium. One of skill in the art can select a medium and culture environment appropriate for culturing a particular cell type.

In some embodiments, a first cell line (cells of which may be referred to as test cells) is provided that expresses a first fluorescent protein (e.g., a red fluorescent protein such as turboRFP) and an inducible 19S subunit-targeting shRNA and a second cell line (cells of which may be referred to as control cells) is provided that expresses a second fluorescent protein that is distinguishable from the first fluorescent protein (e.g., GFP) and a doxycycline-inducible control shRNA (e.g., an shRNA that does not target any endogenous gene). shRNA expression is induced in test cells and control cells for a selected time period (e.g., 12-72 hours, e.g., 48 hr). Test cells and control cells are mixed. In some embodiments, test cells and control cells may be mixed at different ratios (e.g., 1:1, 1:2, 1:5 or 1:10). In some embodiments, test cells (cells with reduced expression of a 19S subunit) may be added as the minority subpopulation. Mixed populations of cells are subsequently contacted with a proteasome inhibitor for a selected time period (e.g., 48 hours). In some embodiments, mixed populations may be contacted with various concentrations of proteasome inhibitor (e.g., 2, 3, 5, or more different concentrations). Cells are may be allowed to recover in the absence of the PI. The two groups of cells in the mixed population are quantified based on fluorescence (e.g., by FACS or fluorescence microscopy). In the absence of proteasome inhibitors, the initial ratios of the test cells and control cells is maintained. In contrast, if the mixed cell population is contacted with a PI, the population of surviving cells is enriched for test cells as compared with control cells. The extent of enrichment may increase with higher concentrations of the PI. In the presence of proteasome inhibitors, cells with modestly reduced levels of 19s subunit have a competitive advantage.

In some embodiments, a mixed population of test cells and control cells (such as those described above) in which shRNA expression has been induced is contacted with a test agent and not with a proteasome inhibitor. Mixed populations may be contacted with various concentrations of test agent (e.g., 2, 3, 5, or more different concentrations). Cells may be allowed to recover in the absence of the test agent. The two groups of cells in the mixed population are quantified based on fluorescence. In the absence of a test agent, the initial ratios of the test cells and control cells is maintained. If the test agent selectively inhibits survival or proliferation of cells with reduced level of 19S subunit expression or activity, the population of surviving cells is enriched for control cells as compared with test cells. The extent of enrichment may increase with higher concentrations of the test agent. A test agent that selectively inhibits survival or proliferation of cells with reduced level of 19S subunit expression or activity may be identified as a candidate inhibitor of 19S proteasome inhibitor resistance. Such an agent may selectively reduce survival or proliferation of cells that have increased proteasome inhibitor resistance or prevent such cells from emerging in a cell culture or cancer.

In some embodiments, a mixed population of test cells and control cells (such as those described above) in which shRNA expression has been induced is contacted with a test agent and a proteasome inhibitor. Mixed populations may be contacted with various concentrations of test agent and/or proteasome inhibitor. Cells may be allowed to recover in the absence of the test agent and PI. The two groups of cells in the mixed population are quantified based on fluorescence. In the absence of a test agent and PI, the initial ratios of the test cells and control cells is maintained. If the test agent is able to reduce proteasome inhibitor resistance, the initial ratios of the test cells and control cells is maintained or the population of surviving cells is enriched for control cells as compared with test cells. The extent of enrichment may increase with higher concentrations of the test agent. A test agent that causes the initial ratios of the test cells and control cells to be maintained in the presence of a proteasome inhibitor or causes the population of surviving cells to be enriched for control cells as compared with test cells in the presence of a proteasome inhibitor may be identified as a candidate inhibitor of 19S proteasome inhibitor resistance. In some embodiments, the effect of such an agent on test cells and/or control cells (or a mixed population) may be tested in the absence of a proteasome inhibitor to determine whether activity of the agent is dependent on or independent of the presence of a proteasome inhibitor.

In various embodiments the number of test agents is at least 10; 100; 1000; 10,000; 100,000; 250,000; 500,000 or more. In some embodiments test agents are tested in individual vessels, e.g., individual wells of a multiwell plate (sometimes referred to as microwell or microtiter plate or dish). In some embodiments a multiwell plate of use in performing an assay or culturing or testing cells or agents has 6, 12, 24, 96, 384, or 1536 wells. Cells (test cells and/or control cells) can be contacted with one or more test agents for varying periods of time and/or at different concentrations. In certain embodiments cells are contacted with test agent(s) for between 1 hour and 20 days, e.g., for between 12 and 48 hours, between 48 hours and 5 days, e.g., about 3 days, between 2 and 5 days, between 5 days and 10 days, between 10 days and 20 days, or any intervening range or particular value. Cells can be contacted with a test agent during all or part of a culture period. Cells can be contacted transiently or continuously. Test agents can be added to culture media at the time of replenishing the media and/or between media changes. If desired, test agent can be removed prior to assessing growth and/or survival. In some embodiments a test agent and/or proteasome inhibitor is tested at 1, 2, 3, 5, 8, 10 or more concentrations. Concentrations of test agent may range, for example, between about 1 nM and about 100 µM. For example, concentrations of 1 nM, 10 nM, 50 nM, 100 nM, 500 nM, 1 µM, 5 µM, 10 µM, 50 µM, 100 µM (or any subset of the foregoing) may be used. In some embodiments, any of the screening methods may include contacting cells (test cells and/or control cells) with a PI in addition to a test agent. Cells may be contacted with the PI prior to contacting them with the test agent, during at least part of the time they are contacted with the test agent, and/or after contacting them with the test agent. For example, in some embodiments cells may be contacted with test agent for between 12 hr and 5 days before contacting them with the PI. The cells may continue to be contacted with the test agent after addition of the PI. The cells can be contacted with the PI at different concentrations and/or for different time periods (e.g., as described for the test agent). All combinations of test agent, PI, concentrations, and time periods are contemplated.

In some embodiments of any aspect or embodiment in the present disclosure relating to cells, a population of cells, cell sample, or similar terms, the number of cells is between 10 and $10^{13}$ cells. In some embodiments the number of cells may be at least about $10^3$, $10^4$, $10^5$, $10^6$, $10^7$, $10^8$, $10^9$, $10^{10}$, $10^{11}$, $10^{12}$ cells, or more. In some embodiments, the number of cells is between $10^5$ and $10^{12}$ cells, e.g., at least $10^6$, $10^7$, $10^8$, $10^9$, $10^{10}$, $10^{11}$, up to about $10^{12}$ or about $10^{13}$. In some embodiments a screen is performed using multiple populations of cells and/or is repeated multiple times. In some embodiments, the number of cells is between $10^5$ and $10^{12}$ cells, e.g., at least $10^6$, $10^7$, $10^8$, $10^9$, $10^{10}$, $10^{11}$, up to about $10^{12}$. In some embodiments smaller numbers of cells are of use, e.g., between $1$-$10^4$ cells. In some embodiments a population of cells is contained in an individual vessel, e.g., a culture vessel such as a culture plate, flask, or well. In some embodiments a population of cells is contained in multiple vessels. In some embodiments two or more cell populations are pooled to form a larger population.

In some embodiments, each of one or more test cells is contacted with a different concentration of, and/or for a different duration with, a test agent than at least one other test cell; and/or each of the one or more control cells is contacted with a different concentration of, and/or for a different duration with, the test agent than at least one other control cell.

In some embodiments, a method may comprise generating a dose response curve for an agent test cells and/or control cells, wherein the dose response curve for test cells indicates the level of inhibition of survival or proliferation of the one or more test cells by the agent at a plurality of doses (optionally in the presence of a proteasome inhibitor at a specified dose) and wherein the dose response curve for control cells indicates the level of inhibition of survival or proliferation of the one or more control cells by the agent at a plurality of doses (optionally in the presence of a proteasome inhibitor at a specified dose).

In some embodiments, a method may comprise generating a dose response curve that indicates the relative level of inhibition of survival or proliferation of test cells versus control cells at a plurality of doses (optionally in the presence of a proteasome inhibitor at a specified dose). In some embodiments, similar dose response curves may be generated wherein an agent is used at a fixed dose and multiple different doses of PI in combination with the test agent are tested.

In some embodiments, a method may further comprise determining (e.g., by analyzing a dose response curve) an IC50, EC50, or both, for an agent, optionally a test agent in combination with a PI. In some embodiments, an agent is identified for which the IC50 value, the EC50 value, or both, for the agent on the one or more test cells is statistically significantly less than the EC50 value for the agent on the one or more control cells. In embodiments in which the test cells have reduced level of expression or activity of a 19S subunit as compared with control cells, such an agent may be identified as a candidate inhibitor of proteasome inhibitor resistance.

In some embodiments, an agent is identified for which the IC50 value, the EC50 value, or both, for the agent on the one or more control cells is statistically significantly less than the EC50 value for the agent on the one or more test cells. In embodiment in which the test cells have an increased level of expression or activity of a 19S subunit as compared with control cells, such an agent may be identified as a candidate inhibitor of proteasome inhibitor resistance.

In some aspects, described herein is a method of identifying a candidate agent for treatment of cancer, the method comprising identifying an agent that modulates the expression or activity of a subunit of a 19S proteasome complex. In some embodiments, identifying an agent that modulates the expression or activity of a subunit of a 19S proteasome complex comprises (a) contacting a cell with a test agent; (b) measuring the effect of the test agent on the level of expression or activity of a 19S subunit; and (c) identifying the agent as a modulator of expression or activity of the 19S subunit if the level of expression or activity of the 19S subunit differs from that which would be expected in the absence of the test agent. In some embodiments, the method of identifying a candidate agent for treatment of cancer comprises identifying an agent that reduces the level of expression or activity of a 19S subunit. As described herein, although a modest reduction in expression of a 19S subunit can confer proteasome inhibitor resistance, a complete knockout of expression of a 19S subunit can kill a cell. Thus an agent that reduces the level of expression or activity of a 19S subunit can be used to kill or inhibit proliferation of a cancer cell and/or to treat cancer, provided that the agent is capable of reducing the level of expression or activity of the 19S subunit sufficiently to kill or inhibit cancer cell proliferation. In some embodiments, the method comprises identifying an agent that reduces the level of expression or activity of a 19S subunit sufficiently to kill or inhibit cancer cell proliferation. In some embodiments, the method of identifying an agent that reduces the level of expression or activity of a 19S subunit comprises (a) contacting a cell with a test agent; (b) measuring the effect of the test agent on the level of expression or activity of a 19S subunit; and (c) identifying the agent as one that reduces the level of expression or activity of the 19S subunit if the level of expression or activity of the 19S subunit is lower than a suitable reference level. A suitable reference level may be the level that would be expected in the absence of the test agent (or a level lower than that). In some embodiments the agent is capable of reducing the level of expression or activity of a 19S subunit in a cancer cell to less than about 10% or, in some embodiments, less than about 5%, of the level found in a normal cell. In some embodiments, the agent is capable of reducing the level of expression or activity of the 19S subunit in the cancer cell by at least a factor of 10, or at least a factor of 20. In some embodiments the cancer cell is a proteasome inhibitor sensitive cell. In some embodiments the cancer cell is a proteasome inhibitor resistant cell. In some embodiments the proteasome inhibitor resistance is associated with reduced expression of a first 19S subunit, and the agent inhibits expression or activity of that subunit such that the level of expression or activity of the subunit is decreased sufficiently to kill the cell or inhibit its proliferation. In some embodiments the proteasome inhibitor resistance is associated with reduced expression of a first 19S subunit, and the agent inhibits expression or activity of a different subunit such that the level of expression or activity of that subunit is decreased sufficiently to kill the cell or inhibit its proliferation.

In some embodiments, a method of identifying a candidate agent for treatment of cancer comprises identifying an agent that increases the level of expression or activity of a 19S subunit. An agent that increases the level of expression or activity of a 19S subunit may be used in combination with a proteasome inhibitor to treat cancers that are proteasome inhibitor resistant due to reduced expression of that particular 19S subunit. By increasing the level of expression or activity of the 19S subunit, the agent may render the cancer sensitive to the proteasome inhibitor. In some embodiments, the method of identifying an agent that increases the level of expression or activity of a 19S subunit comprises (a) contacting a cell with a test agent; (b) measuring the effect of the test agent on the level of expression or activity of a 19S subunit; and (c) identifying the agent as one that increases the level of expression or activity of the 19S subunit if the level of expression or activity of the 19S subunit is at least as high as would be expected in the absence of the test agent. In some embodiments the agent is capable of increasing the level of expression or activity of a 19S subunit in a cancer cell by at least 10%, 25%, 50%, 75%, or 100%. In some embodiments the agent is capable of increasing the level of expression or activity of a 19S subunit in a cancer cell by between 1.2-fold and 10-fold, e.g., at least 1.2-fold, 1.5-fold, 2-fold, 3-fold, 4-fold, 5-fold, or more. In some embodiments the cancer cell is one that, absent the agent, has reduced level of expression or activity of that 19S subunit.

In some embodiments, a high throughput screen (HTS) is performed. A high throughput screen can utilize cell-free or cell-based assays. High throughput screens often involve testing large numbers of compounds with high efficiency, e.g., in parallel. For example, tens or hundreds of thousands of compounds can be routinely screened in short periods of time, e.g., hours to days. Often such screening is performed in multiwell plates containing, at least 96 wells or other vessels in which multiple physically separated cavities or depressions are present in a substrate. High throughput screens often involve use of automation, e.g., for liquid handling, imaging, data acquisition and processing, etc. Certain general principles and techniques that may be applied in embodiments of a HTS of the present invention are described in Macarrón R & Hertzberg R P. Design and implementation of high-throughput screening assays. Methods Mol Biol., 565:1-32, 2009 and/or An W F & Tolliday N J., Introduction: cell-based assays for high-throughput screening. Methods Mol Biol. 486:1-12, 2009, and/or references in either of these. Useful methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006) by Jorg Hvser.

The term "hit" generally refers to an agent that achieves an effect of interest in a screen or assay, e.g., an agent that has at least a predetermined level of inhibitory effect on cell survival, cell proliferation, gene expression, protein activity, or other parameter of interest being measured in the screen or assay. Test agents that are identified as hits in a screen may be selected for further testing, development, or modification. In some embodiments a test agent is retested using the same assay or different assays. For example, a candidate anticancer agent may be tested against multiple different cancer cell lines or in an in vivo tumor model to determine its effect on cancer cell survival or proliferation, tumor growth, etc. Additional amounts of the test agent may be synthesized or otherwise obtained, if desired. Physical testing or computational approaches can be used to determine or predict one or more physicochemical, pharmacokinetic and/or pharmacodynamic properties of compounds identified in a screen. For example, solubility, absorption, distribution, metabolism, and excretion (ADME) parameters can be experimentally determined or predicted. Such information can be used, e.g., to select hits for further testing, development, or modification. For example, small molecules having characteristics typical of "drug-like" molecules can be selected and/or small molecules having one or more unfavorable characteristics can be avoided or modified to reduce or eliminated such unfavorable characteristic(s).

Additional compounds, e.g., analogs, that have a desired activity can be identified or designed based on compounds identified in a screen. In some embodiments structures of hit compounds are examined to identify a pharmacophore, which can be used to design additional compounds. An additional compound may, for example, have one or more altered, e.g., improved, physicochemical, pharmacokinetic (e.g., absorption, distribution, metabolism and/or excretion) and/or pharmacodynamic properties as compared with an initial hit or may have approximately the same properties but a different structure. For example, a compound may have higher affinity for the molecular target of interest, lower affinity for a non-target molecule, greater solubility (e.g., increased aqueous solubility), increased stability, increased bioavailability, oral bioavailability, and/or reduced side effect(s), modified onset of therapeutic action and/or duration of effect. An improved property is generally a property that renders a compound more readily usable or more useful for one or more intended uses. Improvement can be accomplished through empirical modification of the hit structure (e.g., synthesizing compounds with related structures and testing them in cell-free or cell-based assays or in non-human animals) and/or using computational approaches. Such modification can make use of established principles of medicinal chemistry to predictably alter one or more properties. In some aspects, one or more analogs of ABT-263, disulfiram, and elesclomol may be designed or tested. An analog that has one or more improved properties may be identified and used in a composition or method described herein. In some embodiments a molecular target of a hit compound is identified or known. In some embodiments, additional compounds that act on the same molecular target may be identified empirically (e.g., through screening a compound library) or designed.

In certain embodiments an agent identified or tested using a method described herein displays selective activity (e.g., inhibition of survival or proliferation, or other manifestation of toxicity) against test cells that have reduced expression or activity of a 19S subunit, relative to its activity against control cells. For example, the $IC_{50}$ of an agent may be between about 2-fold and about 1000-fold lower, e.g., about 2, 5, 10, 20, 50, 100, 250, 500, or 1000-fold lower, for test cells versus control cells. In some embodiments, the agent has selective activity in the presence of a proteasome inhibitor. In some embodiments, the agent has selective activity in the presence of a proteasome inhibitor but not in the absence of a proteasome inhibitor. In some embodiments, the IC50 of an agent may be about 2, 5, 10, 20, 50, 100, 250, 500, or 1000-fold lower for cells that have at least 5-fold increased resistance to a proteasome inhibitor (e.g., as measured by IC50) as compared to control cells.

Data or results from testing an agent or performing a screen may be stored or electronically transmitted. Such information may be stored on a tangible medium, which may be a computer-readable medium, paper, etc. In some embodiments a method of identifying or testing an agent comprises storing and/or electronically transmitting information indicating that a test agent has one or more propert(ies) of interest or indicating that a test agent is a "hit" in a particular screen, or indicating the particular result achieved using a test agent. A list of hits from a screen may be generated and stored or transmitted. Hits may be ranked or divided into two or more groups based on activity, structural similarity, or other characteristics Once a candidate agent is identified, additional agents, e.g., analogs, may be generated based on it, and may be tested for anticancer effect, ability to inhibit acquisition of increased proteasome inhibitor resistance, ability to synergize with proteasome inhibitors, or other properties. An additional agent, may, for example, have increased cancer cell uptake, increased potency, increased stability, greater solubility, or any improved property. In some embodiments a labeled form of the agent is generated. The labeled agent may be used, e.g., to directly measure binding of an agent to a molecular target in a cell. In some embodiments, a molecular target of an agent identified as described herein may be identified. An agent may be used as an affinity reagent to isolate a molecular target. An assay to identify the molecular target, e.g., using methods such as mass spectrometry, may be performed. Once a molecular target is identified, one or more additional screens maybe performed to identify agents that act specifically on that target.

In certain embodiments of any method described herein, the survival or proliferation of cells, e.g., test cells and/or control cells, is determined by an assay selected from: a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, and a nuclear fragmentation assay. Exemplary assays include BrdU, EdU, or H3-Thymidine incorporation assays; DNA content assays using a nucleic acid dye, such as Hoechst Dye, DAPI, actinomycin D, 7-aminoactinomycin D or propidium iodide; cellular metabolism assays such as AlamarBlue, MTT, XTT, and CellTitre Glo; nuclear fragmentation assays; cytoplasmic histone associated DNA fragmentation assay; PARP cleavage assay; TUNEL staining; and Annexin staining. In some embodiments, gene expression analysis (e.g., microarray, cDNA array, quantitative RT-PCR, RNAse protection assay) may be used to measure the expression of genes whose products mediate or are correlated with cell cycle, cell survival (or cell death, e.g., apoptosis), and/or cell proliferation, as an indication of the effect of an agent on cell viability or proliferation. Alternately or additionally, expression of proteins encoded by such genes may be measured. In other embodiments, the activity of a gene, such as those disclosed herein, can be assayed in a compound screen. In some embodiments, cells are modified to comprise an expression vector that includes a regulatory region of a gene whose products mediate or are correlated with cell cycle, cell survival (or cell death), and/or cell proliferation operably linked to a sequence that encodes a reporter gene product (e.g., a luciferase enzyme), wherein expression of the reporter gene is correlated with transcriptional activity of the gene. In such embodiments assessment of reporter gene expression (e.g., luciferase activity) provides an indirect method for assessing cell survival or proliferation. Those of ordinary skill in the art are aware of genes whose products mediate or are correlated with cell cycle, cell survival (or cell death), and/or cell proliferation.

Any of a wide variety of agents may be used as a test agent in various embodiments. For example, a test agent may be a small molecule, polypeptide, peptide, nucleic acid, oligonucleotide, lipid, carbohydrate, or hybrid molecule. In some embodiments a nucleic acid used as a test agent comprises a siRNA, shRNA, antisense oligonucleotide, aptamer, or random oligonucleotide. In some embodiments a test agent is cell permeable or provided in a form or with an appropriate carrier or vector to allow it to enter cells.

Agents can be obtained from natural sources or produced synthetically. Agents may be at least partially pure or may be present in extracts or other types of mixtures. Extracts or fractions thereof can be produced from, e.g., plants, animals, microorganisms, marine organisms, fermentation broths (e.g., soil, bacterial or fungal fermentation broths), etc. In some embodiments, a compound collection ("library") is tested. A compound library may comprise natural products and/or compounds generated using non-directed or directed synthetic organic chemistry. In some embodiments a library is a small molecule library, peptide library, peptoid library, cDNA library, oligonucleotide library, or display library (e.g., a phage display library). In some embodiments a library comprises agents of two or more of the foregoing types. In some embodiments oligonucleotides in an oligonucleotide library comprise siRNAs, shRNAs, antisense oligonucleotides, aptamers, or random oligonucleotides.

A library may comprise, e.g., between 100 and 500,000 compounds, or more. In some embodiments a library comprises at least 10,000, at least 50,000, at least 100,000, or at least 250,000 compounds. In some embodiments compounds of a compound library are arrayed in multiwell plates. They may be dissolved in a solvent (e.g., DMSO) or provided in dry form, e.g., as a powder or solid. Collections of synthetic, semi-synthetic, and/or naturally occurring compounds may be tested. Compound libraries can comprise structurally related, structurally diverse, or structurally unrelated compounds. Compounds may be artificial (having a structure invented by man and not found in nature) or naturally occurring. In some embodiments compounds that have been identified as "hits" or "leads" in a drug discovery program and/or analogs thereof. In some embodiments a library may be focused (e.g., composed primarily of compounds having the same core structure, derived from the same precursor, or having at least one biochemical activity in common). Compound libraries are available from a number of commercial vendors such as Tocris BioScience, Nanosyn, BioFocus, and from government entities such as the U.S. National Institutes of Health (NIH). In some embodiments a test agent is not an agent that is found in a cell culture medium known or used in the art, e.g., for culturing vertebrate, e.g., mammalian cells, e.g., an agent provided for purposes of culturing the cells. In some embodiments, if the agent is one that is found in a cell culture medium known or used in the art, the agent may be used at a different, e.g., higher, concentration when used as a test agent in a method or composition described herein.

In some aspects, methods described herein may comprise measuring the effect of an agent (e.g., a test agent, proteasome inhibitor, or agent that reduces or increases the level of expression or activity of a 19S subunit) on the level of 19S, 20S, and/or 26S proteasomes in a cell. In some embodiments, native gel electrophoresis may be used to measure the level of 19S, 20S, and/or 26S proteasomes.

In some aspects, methods described herein may comprise measuring the effect of an agent (e.g., a test agent, proteasome inhibitor, or agent that reduces or increases the level of expression or activity of a 19S subunit) on one or more proteolytic activities of the proteasome. For example, the effect of an agent on the caspase-like activity, T-L activity, or CT-L activity may be measured. Those of ordinary skill in the art are aware of suitable substrates and methods for measuring proteasome activity. Suitable substrates and kits containing them are commercially available. For example, the Proteasome-Glo™ Cell-Based Assay (Promega) is a homogeneous, luminescent assay that measures the chymotrypsin-like, trypsin-like and caspase-like activities associated with the proteasome complex in cultured cells. The Proteasome-Glo™ Cell-Based Reagents each contain a specific luminogenic proteasome substrate in a buffer optimized for cell permeabilization, proteasome activity and luciferase activity. These peptide substrates are Suc-LLVY-aminoluciferin (Succinyl-leucine-leucine-valine-tyrosine-aminoluciferin), Z-LRR-aminoluciferin (Z-leucine-arginine-arginine-aminoluciferin) and Z-nLPnLD-aminoluciferin (Z-norleucine-proline-norleucine-aspartate-aminoluciferin) for the chymotrypsin-like, trypsin-like and caspase-like activities, respectively.

In some embodiments a method comprises preparing a composition comprising an identified candidate agent and a pharmaceutically acceptable carrier. In some embodiments a method comprises testing the effect of an identified candidate agent on cancer cell survival or proliferation. In some embodiments the agent is administered in combination with a proteasome inhibitor. In some embodiments a method comprises testing the effect of an identified candidate agent on a tumor in vivo, e.g., in a non-human animal that serves as a cancer model. An "in vivo" cancer model involves the use of one or more living non-human animals ("test animals"). For example, an in vivo cancer model may involve administration of an agent and/or introduction of cancer cells to one or more test animals. In some embodiments a test animal is a mouse, rat, or dog. Numerous in vivo cancer models are known in the art. By way of example, certain in vivo cancer models are described in U.S. Pat. No. 4,736,866; U.S. Ser. No. 10/990,993; PCT/US2004/028098 (WO/2005/020683); and/or PCT/US2008/085040 (WO/2009/070767). Introduction of one or more cells into a subject (e.g., by injection or implantation) may be referred to as "grafting", and the introduced cell(s) may be referred to as a "graft". In general, any cancer cells may be used in an in vivo cancer model in various embodiments. The number of tumor cells introduced may range, e.g., from 1 to about 10, $10^2$, $10^3$, $10^4$, $10^5$, $10^6$, $10^7$, $10^8$, $10^9$, or more. In some embodiments the cancer cells are of the same species or inbred strain as the test animal. In some embodiments cancer cells may originate from the test animal. In some embodiments the cancer cells are of a different species than the test animal. For example, the cancer cells may be human cells. In some embodiments, a test animal is immunocompromised, e.g., in certain embodiments in which the cancer cells are from a different species to the test animal or originate from an immunologically incompatible strain of the same species as the test animal. For example, a test animal may be selected or genetically engineered to have a functionally deficient immune system or may subjected to radiation or an immunosuppressive agent or surgery such as removal of the thymus) so as to reduce immune system function. In some embodiments, a test animal is a SCID mouse, NOD mouse, NOD/SCID mouse, nude mouse, and/or Rag1 and/or Rag2 knockout mouse, or a rat having similar immune system dysfunction. Cancer cells may be introduced at an orthotopic or non-orthotopic location. In some embodiments cancer cells are introduced subcutaneously, under the renal capsule, or into the bloodstream.

In some embodiments cancer cells are contacted with a candidate agent prior to grafting (in vitro) and/or following grafting (by administering the agent to the test animal). The agent may be administered to the test animal at around the same time as the cancer cells, and/or at one or more subsequent times. The number, size, growth rate, metastasis, or other properties of resulting tumors (if any) may be assessed at one or more time points following grafting and, if desired, may be compared with a control in which cancer cells of the same type are grafted without contacting them with the agent or using a higher or lower concentration or dose of the agent.

In some embodiments a test animal is a tumor-prone animal. The test animal may, for example, be of a species or strain that naturally has a predisposition to develop tumors and/or may be a genetically modified tumor-prone animal. For example, in some embodiments the animal is a genetically engineered animal at least some of whose cells comprise, as a result of genetic modification, at least one activated oncogene and/or in which at least one tumor suppressor gene has been functionally inactivated. Standard methods of generating genetically modified animals, e.g., transgenic animals that comprises exogenous genes or animals that have an alteration to an endogenous gene, e.g., an insertion or an at least partial deletion or replacement can be used.

Any of a wide variety of methods and/or devices known in the art may be used to assess tumors in vivo. Tumor number, size, growth rate, or metastasis may, for example, be assessed using various imaging modalities, e.g., 1, 2, or 3-dimensional imaging (e.g., using X-ray, CT scan, ultrasound, or magnetic resonance imaging, etc.) and/or functional imaging (e.g., PET scan) may be used to detect or assess lesions (local or metastatic), e.g., to measure anatomical tumor burden, detect new lesions (e.g., metastases), etc. In some embodiments PET scanning with the glucose analog fluorine-18 (F-18) fluorodeoxyglucose (FDG) as a tracer is used. In some embodiments tumor(s) may be removed from the body (e.g., at necropsy) and assessed (e.g., tumors may be counted, weighed, and/or size (e.g., dimensions) measured). In some embodiments the size and/or number of tumors may be determined non-invasively. For example, in certain cancer models, tumor cells that are fluorescently labeled (e.g., by expressing a fluorescent protein such as GFP) can be monitored by various tumor-imaging techniques or instruments, e.g., non-invasive fluorescence methods such as two-photon microscopy. The size of a tumor implanted or developing subcutaneously can be monitored and measured underneath the skin (e.g., by estimated volume or weight).

In some aspects, cells that have a modestly reduced level of expression or activity of a 19S subunit (e.g., cells generated as described herein) may be used to identify new proteasome inhibitors that may be less prone to development of proteasome inhibitor resistance versus proteasome inhibitors currently known or used in the art.

In some aspects, cancer cells that have a modestly reduced level of expression or activity of a 19S subunit (e.g., cancer cells generated as described herein) may be introduced into test subjects (non-human animals) and used to assess the ability of an anticancer agent or candidate anticancer agent to inhibit development or growth of tumors in the animal. The agent may be a proteasome inhibitor. In some embodiments the candidate agent is tested for ability to reduce proteasome inhibitor resistance. The candidate agent may be administered in combination with a proteasome inhibitor, e.g., one to which the introduced cells are resistant.

In some aspects, non-human mammals (e.g., rodents), cells of which harbor a genetic modification that reduces the level of expression or activity of a 19S subunit (either constitutively or upon induction) are provided. In some embodiments, such genetically modified animals may be used as test subjects in the testing and/or identification of anticancer agents or candidate anticancer agents or as sources of cells that may be used in other methods described herein. The non-human mammals may be generated using methods known in the art for generating genetically modified non-human mammals, e.g., transgenic animals, genome edited animals, knock-out animals. The animal may have reduced level of expression or activity of a 19S subunit in one or more cell types. For example cells may harbor a nucleic acid construct comprising a sequence encoding a shRNA targeted to a 19S subunit, operably linked to a cell type specific promoter. In some embodiments a regulatable promoter may be used. Expression from the promoter may be induced by administering an appropriate inducing agent (e.g., doxycycline) to the animal, e.g., in drinking water.

III. Proteasome Inhibitors

Numerous proteasome inhibitors (PIs) are known in the art. In some aspects, any proteasome inhibitor may be used in or relevant to a composition or method described herein. In some embodiments a proteasome inhibitor inhibits one or more proteolytic activities of the 20S proteasome complex. For example, in some embodiments a proteasome inhibitor inhibits at least the chymotrypsin-like activity of the proteasome. In some embodiments a proteasome inhibitor additionally or alternately inhibits the caspase-like activity, the trypsin-like activity, or both. In some embodiments a proteasome inhibitor binds to the 20S proteasome complex, e.g., to a particular subunit of the 20S proteasome complex. In some embodiments the proteasome inhibitor binds non-covalently to the 20S proteasome complex, e.g., to a particular subunit of the 20S proteasome complex. In some embodiments the proteasome inhibitor binds covalently to the 20S proteasome complex, e.g., to a particular subunit of the 20S proteasome complex.

In some embodiments a proteasome inhibitor is a natural product. Chemically diverse natural product inhibitors of the ubiquitin-proteasome pathway are elaborated by organisms as diverse as terrestrial and marine bacteria, fungi, and plants (Kisselev et al., 2006; Kisselev et al., 2012; Schneekloth and Crews, 2011). In some embodiments a proteasome inhibitor is a synthetic analog of a natural product. In some embodiments a proteasome inhibitor comprises a boronate as an active moiety. Boronates act as an electron acceptor, forming reversible tetrahedral boronic esters with the $NH_2$-terminal threonine side chain of the catalytic β subunits. In some embodiments a PI comprises an epoxyketone as an active moiety. Examples of such PIs include, e.g., carfilzomib and oprozomib.

In some embodiments a proteasome inhibitor is bortezomib or an analog thereof. Bortezomib is an N-protected dipeptide boronate and its formula can be written as Pyz-Phe-boroLeu, which stands for pyrazinoic acid, phenylalanine and leucine with a boronic acid instead of a carboxylic acid. Bortezomib targets the β5 and β1 activity of the proteasome. It primarily inhibits the β5-subunit with low nanomolar potency but also inhibits the β1-subunit to a lesser extent. The structure of bortezomib is as follows:

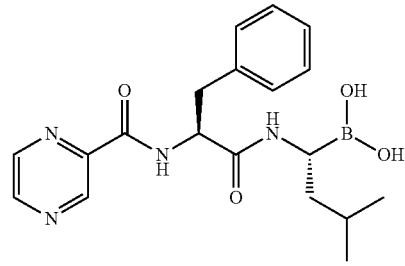 [SMILES: CC(C)C[C@H](NC(=O)[C@H](Cc1ccccc1)NC(=O)c1cnccn1)B(O)O]

Bortezomib and certain analogs thereof are described in U.S. Pat. Nos. 5,780,454; 6,083,903; 6,297,217; 6,617,317; 6,713,446; 6,747,150; 6,958,319; and/or 7,119,080. The present disclosure encompasses proteasome inhibitors described in any one or more of the foregoing patents.

In some embodiments the proteasome inhibitor is MG132 (N-(benzyloxycarbonyl)leucinylleucinylleucinal) or an analog thereof. The structure of MG132 is as follows:

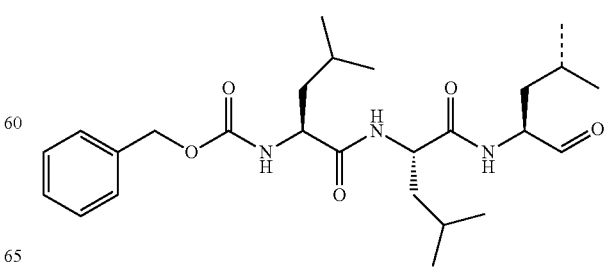

In some embodiments the proteasome inhibitor in a composition or method described herein is delanzomib (CEP-18770) or an analog thereof. The structure of delanzomib is as follows:

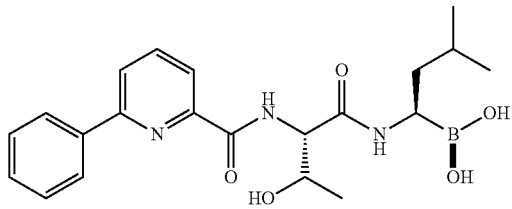

In some embodiments the proteasome inhibitor in a composition or method described herein is ixazomib (MLN-2238) or an analog thereof. The structure of ixazomib is as follows:

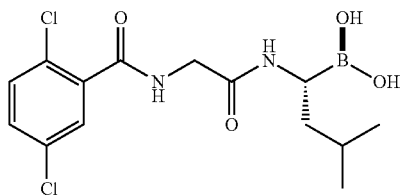

In some embodiments ixazomib is provided as ixazomib citrate (MLN-9708). The structure of ixazomib citrate is as follows:

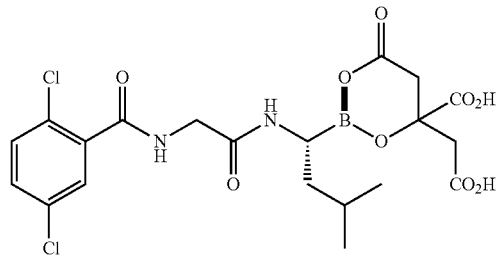

of such PIs include, e.g., carfilzomib and oprozomib.

In some embodiments the proteasome inhibitor is carfilzomib (Kyprolis) or an analog thereof. The structure of carfilzomib is as follows:

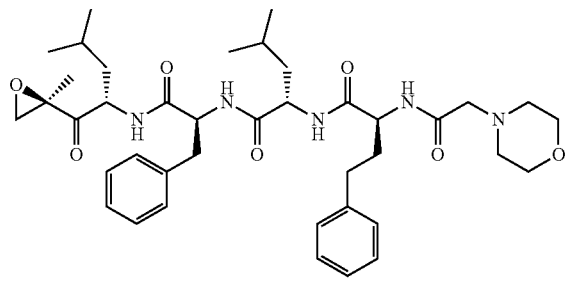 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

Carfilzomib and certain analogs thereof are described in U.S. Pat. Nos. 7,232,818; 7,417,042; 7,491,704; 7,737,112; 8,129,346; 8,207,125; 8,207,126; 8,207,127; and/or 8,207,297. The present disclosure encompasses proteasome inhibitors described in any one or more of the foregoing patents.

In some embodiments a proteasome inhibitor is oprozomib (ONX0912; PR-047) or an analog thereof. The structure of oprozomib is as follows:

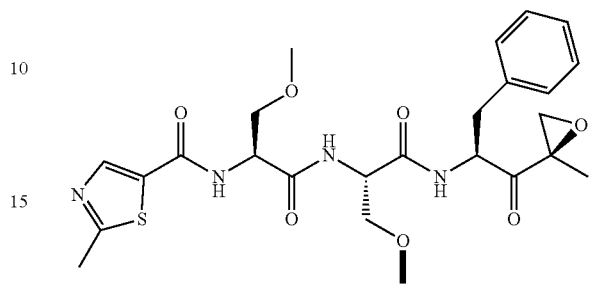

In some embodiments a proteasome inhibitor is ONX 0914 or an analog thereof.

In some embodiments the proteasome inhibitor is a compound described in U.S. Pat. No. 6,831,099 or is an analog or prodrug of a compound described in U.S. Pat. No. 6,831,099. In some embodiments the proteasome inhibitor is described in U.S. Pat. No. 7,232,818 or is an analog or prodrug of a compound described in U.S. Pat. No. 7,232,818.

In some embodiments a proteasome inhibitor is a salinosporamide, e.g., salinosporamide A (NPI-0052 marizomib) or an analog thereof. Salinosporamide A is an orally active irreversible inhibitor of the three catalytic activities of the proteasome. Salinosporamide A and certain analogs thereof are described in U.S. Pat. No. 7,176,232. The structure of salinosporamide A is as follows:

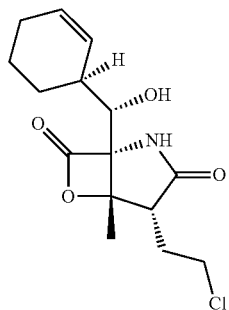 [SMILES: C[C@@]12OC(=O)[C@]1([C@@H](O)[C@@H]1C=CCCC1)NC(=O)[C@@H]2CCCl]

In some embodiments a proteasome inhibitor is NSC310551, NSC321206, NSC310551, NSC99671, NSC3907 or an analog of any of these. See U.S. Patent Application Pub. Nos. 20120083477 and/or 20130225547.

In some embodiments a proteasome inhibitor is an 8-hydroxylquinoline such as clioquinol or an analog thereof, e.g., AHQ (5-amino-8-hydroxyquinoline), HNQ (8-hydroxy-5-nitroquinoline), BCQ (7-bromo-5-chloro-8-hydroxyquinoline), or COQ (5-chloro-8-hydroxyquinoline). Exemplary 8-hydroxylquinolines are described in U.S. Patent Application Pub. Nos. 20110123617 and/or 20110144155.

In some embodiments a proteasome inhibitor is LU-102 (azido-Phe-Leu-Leu-4-aminomethyl-Phe-methyl vinyl sulfone), a selective inhibitor of β2 activity (Guerink, P P, et al., J Med Chem. 2013; 56(3):1262-75).

In some embodiments a proteasome inhibitor is PI-1833 or an analog thereof (Kazi, A., et al., J Biol Chem. 2014; 289(17):11906-15).

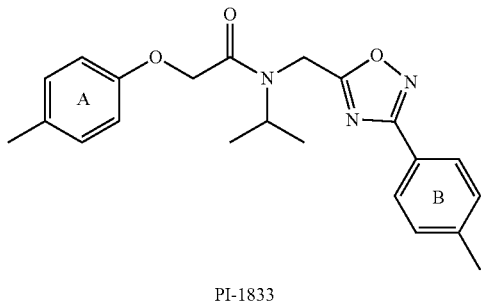

PI-1833

In some embodiments a proteasome inhibitor is an 8-hydroxylquinoline such as clioquinol or an analog thereof.

In some embodiments the analog comprises a modification to ring A and/or ring B of PI-1883. For example, the proteasome inhibitor may be PI-1840, the structure of which is depicted below:

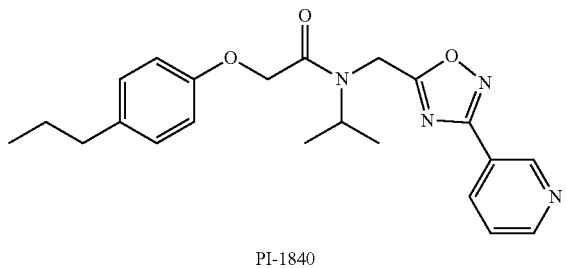 [SMILES: CCCc1ccc(OCC(=O)N(Cc2nc(-c3cccnc3)no2)C(C)C)cc1]

PI-1840

In some embodiments a proteasome inhibitor is G4 or an analog thereof such as G4-1 (Miller, Z, et al., J. Med. Chem., 2015, 58 (4): 2036-2041).

In some embodiments a proteasome inhibitor is a macyranone, e.g., macyranone A from Cystobacter fuscus MCy9118, or an analog thereof. Macyranone A is an epoxyketone that binds covalently to the β5 subunit of the 20S proteasome (Keller L., et al., J Am Chem Soc. 2015 Jun. 17. [Epub ahead of print]).

In some embodiments a proteasome inhibitor preferentially targets the immunoproteasome as compared with the constitutive proteasome. A proteasome inhibitor that displays an IC50 that is at least 25-fold lower, e.g., at least 100-fold lower, for the inhibition of one or more activities of the 20Si proteasome as compared to the constitutive 20S proteasome may be referred to as an immunoproteasome-specific inhibitor. For example, the proteasome inhibitor may be IPSI-001 (carbobenzoxy-leucyl-norleucinal (Z-LnL-CHO, or IPSI-001), also known as calpeptin), PR-924, PR-957, ML604440, or UK-101, or an analog of any of the foregoing.

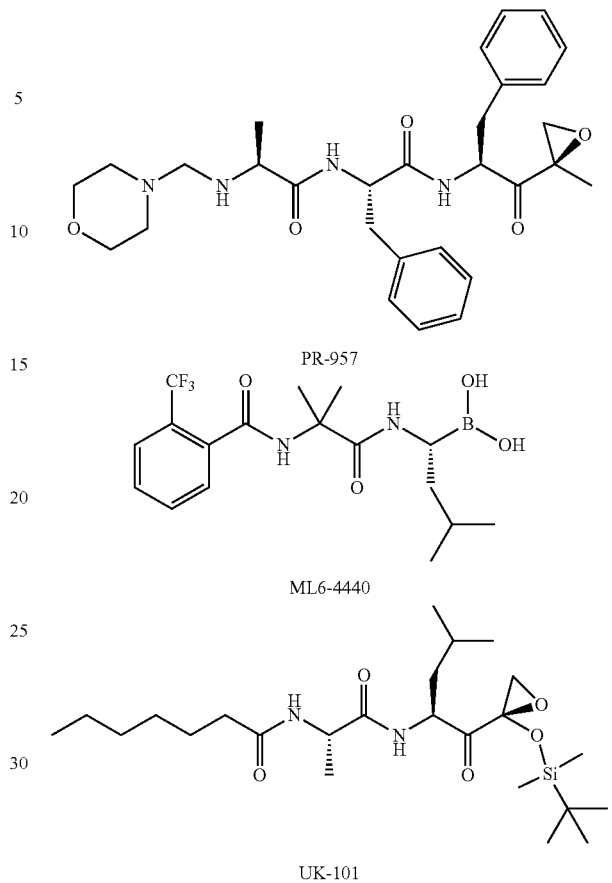

In some embodiments a proteasome inhibitor comprises a nucleic acid, e.g., siRNA, miRNA, nucleic acid aptamer, antisense nucleic acid, that inhibits expression of a gene that encodes a subunit of the 20S proteasome or 20Si proteasome.

In some embodiments a proteasome inhibitor inhibits one or more deubiquitinases, e.g., one or more 19S proteasome-associated deubiquitinases (UCHL5, USP14, and POU1). Examples of such PIs include, e.g., b-AP15.

IV. Methods of Classifying Cancers and Selecting Cancer Treatment

In some aspects, described herein are methods of classifying a cancer according to predicted level of resistance or sensitivity to a proteasome inhibitor. Such a classification can be used, e.g., to predict whether a subject with cancer is likely to experience a clinical response to therapy with a proteasome inhibitor and/or to select an appropriate therapy for a subject in need of treatment for cancer. For example, if a cancer is classified as likely to be resistant to a PI, the subject may be treated with a different therapy or may be treated with an inhibitor of proteasome inhibitor resistance in addition to treatment with the PI. On the other hand, if the cancer is classified as potentially (e.g., likely to be) sensitive to a proteasome inhibitor, the subject may be treated with a proteasome inhibitor. The subject may or may not also be treated with an inhibitor of PI resistance.

In some embodiments a method of classifying a cancer according to predicted level of resistance or sensitivity to a proteasome inhibitor comprises (a) measuring the level of expression or activity of a subunit of a 19S proteasome complex in a sample obtained from the cancer; (b) comparing the level measured in (a) with a reference level; and (c) classifying the cancer as likely to be proteasome inhibitor resistant or as potentially (e.g., likely to be) proteasome inhibitor sensitive based on the comparison of (b). In some embodiments, the reference level represents the level of expression or activity of said 19S subunit in a sample from a proteasome inhibitor sensitive cancer, wherein if the level determined in (a) is lower than the reference level, the cancer is classified as likely to be proteasome inhibitor resistant, and wherein if the level determined in (a) is greater than or about the same as the reference level, the cancer is classified as potentially (e.g., likely to be) proteasome inhibitor sensitive. In some embodiments, the reference level represents the level of expression or activity of said 19S subunit in a sample from normal (non-cancer) cells, wherein if the level determined in (a) is lower than the reference level, the cancer is classified as likely to be proteasome inhibitor resistant, and wherein if the level determined in (a) is greater than or about the same as the reference level, the cancer is classified as potentially (e.g., likely to be) proteasome inhibitor sensitive. In some embodiments the reference level represents the level of expression or activity of said 19S subunit in a sample from a proteasome inhibitor resistant cancer, wherein if the level determined in (a) is lower than or about the same as the reference level, the cancer is classified as likely to be proteasome inhibitor resistant, and wherein if the level determined in (a) is greater than the reference level, the cancer is classified as potentially (e.g., likely to be) proteasome inhibitor sensitive. In some embodiments, any of the methods may comprise determining an average level of expression or activity of at least 2, 3, 4, 5, 10, 15, or all of the subunits of the 19S proteasome complex and classifying the cancer as likely to be proteasome inhibitor resistant or as potentially (e.g., likely to be) proteasome inhibitor sensitive based on a comparison of the average level of expression or activity with a reference level. In some embodiments, a cancer may be classified as likely to be proteasome inhibitor resistant if at least one 19S subunit is expressed at a 2-fold lower level (e.g., relative to other genes) than a reference level (i.e., level is reduced by a factor of 2). In some embodiments, a cancer may be classified as likely to be proteasome inhibitor resistant if at least one 19S subunit is expressed at more than a 2-fold lower level (e.g., relative to other genes) than a reference level (i.e., level is reduced by more than factor of 2). The reference level may be, e.g., a level present in a typical proteasome inhibitor sensitive cancer or a level present in a diverse panel of cancers (e.g., median level or average (mean) level) or a level (e.g., median level or average (mean) level) present in a panel of cancers of the same type as the cancer.

In some embodiments, a method of classifying a cancer according to predicted level of resistance or sensitivity to a proteasome inhibitor comprises (a) measuring the level of expression or activity of at least 5 subunits of a 19S proteasome complex in a sample obtained from the cancer; (b) determining whether the level of expression or activity of at least one of the subunits is at least a predetermined number of standard deviations (SD) lower than a reference level; and (c) classifying the cancer as likely to be proteasome inhibitor resistant or as potentially proteasome inhibitor sensitive based on the result of step (b). In some embodiments, if the level of expression or activity of at least one of the subunits is at least a predetermined number of SD lower than the reference level, then the cancer is deemed likely to be proteasome inhibitor resistant. In some embodiments, if the level of expression or activity of none of the subunits is at least a predetermined number of SD lower than the reference level, then the cancer is deemed potentially proteasome inhibitor sensitive. In some embodiments the method comprises (a) measuring the level of expression or activity of at least 6, 7, 8, 9, 10, 11, 12, 13, 14, 15, 16, 17, 18, 19, 20, or 21 19S subunits and (b) comparing, for each of the subunits, the level of expression or activity measured for that subunit with the reference level. In some embodiments the reference level is an internal reference level, as described herein. In some embodiments the reference level is an external reference level, as described herein. In some embodiments the predetermined value is between 1.5 and 2.0. In some embodiments the predetermined value is 1.5, 1.6, 1.7, 1.8, 1.9, or 2.0 when rounded to one decimal point. In some embodiments the predetermined value is between 2.0 and 2.5. In some embodiments the predetermined value is 2.0, 2.1, 2.2, 2.3, 2.4, or 2.5 when rounded to one decimal point. In some embodiments the predetermined value is between 2.5 and 3.0. In some embodiments the predetermined value is 2.5, 2.6, 2.7, 2.8, 2.9, or 3.0 when rounded to one decimal point. In some embodiments the predetermined value is between 3.0 and 3.5. In some embodiments the predetermined value is 3.0, 3.1, 3.2, 3.3, 3.4, or 3.5 when rounded to one decimal point. In some embodiments the predetermined value may be selected based at least in part on the particular type of reference level used. For example, in some embodiments the reference level is an internal reference level (e.g., the average expression level of all 19S subunits in the cancer, the average expression level of all 20S subunits in the cancer, or the average expression level of all 19S and 20S subunits in the cancer) and the predetermined number of standard deviations is between 1.5 and 2.0. In some embodiments the reference level is an external reference level (e.g., the average expression level of a particular 19S subunit in a panel of cancers) and the predetermined number of standard deviations is between 3.0 and 3.5, or in some aspects is 3.0.

In some aspects, a method of selecting a treatment for a subject in need of treatment for cancer comprises (a) determining that the level of expression or activity of at least one 19S subunit is reduced by at least a predetermined number of standard deviations relative to a reference level, wherein said reduced level indicates that the cancer is likely to be proteasome inhibitor resistant; and (b) selecting a treatment based on the determination of step (a). In some embodiments the method comprises selecting a proteasome inhibitor and an agent that reduces proteasome inhibitor resistance as treatment for the subject or (ii) selecting at least one anti-cancer therapy other than a proteasome inhibitor (e.g., a therapy that is recognized in the art as an alternative to proteasome inhibitor therapy) as treatment for the subject. In some embodiments the method comprises selecting an agent that is selectively toxic to proteasome inhibitor resistant cancer cells. In some embodiments the method further comprises administering the selected treatment to the subject. In some embodiments the reference level is an internal reference level, as described herein. In some embodiments the reference level is an external reference level, as described herein.

In some aspects, a method of selecting a treatment for a subject in need of treatment for cancer comprises determining the sigma score of the cancer and selecting an agent for treating the subject based on the sigma score. In certain embodiments the sigma score indicates that the cancer is likely to be resistant to a proteasome inhibitor, and the method comprises selecting a proteasome inhibitor and an agent that reduces proteasome inhibitor resistance as treatment for the subject. In certain embodiments the sigma score indicates that the cancer is likely to be resistant to a proteasome inhibitor, and the method comprises selecting at least one anti-cancer agent other than a proteasome inhibitor (e.g., a therapy that is recognized in the art as an alternative to proteasome inhibitor therapy) as treatment for the subject. In some embodiments the sigma score indicates that the cancer is likely to be resistant to a proteasome inhibitor, and the method comprises selecting an agent that is selectively toxic to proteasome inhibitor resistant cancer cells. In some embodiments the method further comprises administering the selected treatment to the subject. In some embodiments the sigma score is calculated using an internal reference level, as described herein. In some embodiments the sigma score is calculated using an external reference level, as described herein.

In some aspects, a method of selecting a treatment for a subject in need of treatment for cancer comprises measuring the expression of at least 10, 11, 12, 13, 14, 15, 16, 17, 18, 19, 20, or 21 19S subunits in the cancer, and selecting a proteasome inhibitor as a treatment for the subject if the cancer is found not to have reduced expression of any 19S subunit whose expression was measured.

In certain embodiments, the level of expression or activity of a 19S subunit in a cancer may be used in selecting an appropriate dose or dosing regimen for a proteasome inhibitor for treatment of the cancer. For example, in certain embodiments a subject in need of treatment for a cancer that is deemed likely to be proteasome inhibitor resistant may be treated with a higher dose and/or more frequent administration of a proteasome inhibitor than would be the case if the cancer is deemed not likely to be proteasome inhibitor resistant.

In some embodiments of any aspect described in the present disclosure that relates to a reference level, the reference level may be an internal reference level unless otherwise indicated. In some embodiments of any aspect described in the present disclosure that relates to a reference level, the reference level may be an external reference level unless otherwise indicated. In some embodiments of any aspect described in the present disclosure that relates to an average of multiple values (e.g., an average of multiple proteasome subunit expression levels) an average value that is computed excluding one or more values that lie furthest from the average or median value may be used. For example, the 1, 2, or 3 highest values and/or the 1, 2, or 3 lowest values may be excluded in some embodiments. In some embodiments the highest and lowest 10%, 15%, 20%, or 25% of values may be excluded.

In some embodiments of any aspect described in the present disclosure that relates to an average expression level of all 19S subunits in a cell, cell population, cell line, or cancer, an estimated average expression level may be used. In some embodiments an estimated average expression level of all 19S subunits may be calculated using the expression levels of between 5 and 20 of the 19S subunits, e.g., between 5 and 10, between 10 and 15, or between 15 and 20 of the 19S subunits, e.g., 10, 11, 12, 13, 14, 15, 16, 17, 18, 19, or 20 of the 19S subunits. In some embodiments an estimated average expression level of all 19S subunits may be calculated using the expression levels of between 5 and 21 of the 20S subunits and the expression levels of up to 4 of the 20S subunits. In some embodiments of any aspect described in the present disclosure that relates to an average expression level of all 20S subunits in a cell, cell population, cell line, or cancer, an estimated average expression level may be used. In some embodiments an estimated average expression level of all 20S subunits may be calculated using the expression levels of between 5 and 13 of the 20S subunits, e.g., between 5 and 9 or between 10 and 13 of the 20S subunits, e.g., 5, 6, 7, 8, 9, 10, 11, 12, or 13 of the 20S subunits. In some embodiments an estimated average expression level of all 20S subunits may be calculated using the expression levels of between 5 and 13 of the 20S subunits and the expression levels of up to 4 of the 19S subunits. In some embodiments of any aspect described in the present disclosure that relates to an average expression level of all 19S and all 20S subunits in a cell, cell population, cell line, or cancer, an estimated average expression level may be used. In some embodiments an estimated average expression level of all 19S and all 20S subunits in a cell, cell population, cell line, or cancer may be calculated using the expression levels of between 5 and 21 of the 19S subunits, e.g., between 5 and 10, between 10 and 15, or between 15 and 21 of the 19S subunits, e.g., 10, 11, 12, 13, 14, 15, 16, 17, 18, 19, 20, or 21 of the 19S subunits, and between 5 and 14 of the 20S subunits, e.g., between 5 and 9 or between 10 and 14 of the 20S subunits, e.g., 5, 6, 7, 8, 9, 10, 11, 12, 13, or 14 of the 20S subunits, with the proviso that the total number of 19S and 20S subunit expression levels used to calculate the average is less than 35.

In some embodiments an estimated average expression level of all 19S subunits may be calculated using a set of expression levels characterized in that at least 50%, 60%, 70%, 80%, 90%, or more of the expression levels that are used to compute the estimated average expression level are 19S subunit expression levels. The other expression levels (i.e., the expression levels that are not 19S subunit expression levels) may be, e.g., expression levels of 20S subunits, expression levels of proteasome-associated proteins, or expression levels of any gene product whose expression level is approximately the same as the expression level of a 19S subunit or 20S subunit or is correlated with the expression level of a 19S subunit or 20S subunit. In some embodiments an estimated average expression level of all 20S subunits may be calculated using a set of expression levels characterized in that at least 50%, 60%, 70%, 80%, 90%, or more of the expression levels that are used to compute the estimated average expression level are 20S subunit expression levels. The other expression levels (i.e., the expression levels that are not 20S subunit expression levels) may be, e.g., expression levels of 19S subunits, expression levels of proteasome-associated proteins, or expression levels of any gene product whose expression level is approximately the same as the expression level of a 19S subunit or 20S subunit or is correlated with the expression level of a 19S subunit or 20S subunit. In some embodiments an estimated average expression level of all 19S and 20S subunits may be calculated using a set of expression levels characterized in that at least 50%, 60%, 70%, 80%, 90%, or more of the expression levels that are used to compute the estimated average expression level are 19S or 20S subunit expression levels. The other expression levels (i.e., the expression levels that are not 19S or 20S subunit expression levels) may be, e.g., expression levels of proteasome-associated proteins or expression levels of any gene product whose expression level is approximately the same as the expression level of a 19S subunit or 20S subunit or is correlated with the expression level of a 19S subunit or 20S subunit. In some embodiments, no more than 1%, no more than 5%, no more than 10%, no more than 15%, or no more than 20% of the expression levels that are used to calculate an estimated average expression level of 19S subunits and/or 20S subunits are not proteasome subunit expression levels.

In some embodiments of any aspect described in the present disclosure that relates to a sigma score, an estimated sigma score may be used. In some embodiments, an estimated sigma score may be calculated using an internal reference level that is an average of the measured expression levels of fewer than all 19S and 20S subunits. For example, in some embodiments an estimated sigma score may be calculated using as a reference level the average expression level of between 5 and 20 of the 19S subunits, e.g., between 5 and 10, between 10 and 15, or between 15 and 20 of the 19S subunits, e.g., 10, 11, 12, 13, 14, 15, 16, 17, 18, 19, or 20 of the 19S subunits and at least 5 of the 20S subunits, e.g., 2, 3, 4, 5, 6, 7, 8, 9, 10, 11, 12, 13, or 14 of the 20S subunits. In some embodiments an estimated sigma score may be calculated using as a reference level the average expression level of at least 5 of the 19S subunits, e.g., 5, 6, 7, 8, 9, 10, 11, 12, 13, 14, 15, 16, 17, 18, 19, 20, or 21 of the 19S subunits and between 5 and 13 of the 20S subunits, e.g., 5, 6, 7, 8, 9, 10, 11, 12, or 13 of the 20S subunits. In some embodiments the total number of 19S and 20S subunit expression levels is between 10 and 34.

It should be noted that wherever the present disclosure relates to multiple proteasome subunits and/or multiple proteasome subunit expression or activity levels (e.g., examining, measuring, or determining an average of such levels), all different subsets of the 19S subunits, all different subsets of the 20S subunits, and all different combinations of one or more 19S subunits and one or more 20S subunits are encompassed and are to be understood as being expressly disclosed herein.

In some embodiments, an estimated sigma score for a cell, cell line, or cancer of interest may be calculated using an external reference level that is the average expression level in a panel of cells, cell lines, or cancers of (i) a different 19S subunit than the particular 19S subunit that has the lowest expression level in the cell, cell line, or cancer of interest or (ii) two or more 19S subunits or (iii) one or more 20S subunits or (iv) at least one 19S subunit and at least one 20S subunit. In some embodiments, an estimated sigma score for a cell, cell line, or cancer of interest may be calculated using an internal or external reference level that is an estimated average expression level of all 19S subunits, an estimated average expression level of all 20S subunits, or an estimated average expression level of all 19S and all 20S subunits.

As described above, calculating a sigma score generally comprises examining the expression level of all 19S subunits in a cell, cell line, or cancer of interest, determining which 19S subunit has the greatest deviation (in the direction of lower expression) from the reference level and expressing the deviation in units of the standard deviation of a set of expression level values that were used to compute the reference level. In certain embodiments, determining an estimated average expression level or estimated sigma score comprises examining (e.g., measuring) the expression levels of fewer than all 19S subunits in the cell, cell line, or cancer of interest. In some embodiments the subunits whose expression levels are examined include PSMD5. In certain embodiments the 19S subunits whose expression levels are examined include PSMD5 and at least 1, at least 2, or at least 3 subunits selected from the group consisting of PSMD1, PSMC6, PSMD10, PSMD14, PSMD6, PSMD8, and PSMD9. For example, in certain embodiments the 19S subunits whose expression levels are examined include PSMD5, PSMD1, and PSMC6. In certain embodiments the 19S subunits whose expression levels are examined include PSMD5 and at least 4, at least 5, or at least 6 subunits selected from the group consisting of PSMD1, PSMC6, PSMD10, PSMD14, PSMD6, PSMD8, and PSMD9. For example, in certain embodiments the 19S subunits whose expression levels are examined include PSMD5, PSMD1, PSMC6, PSMD10, PSMD14, and PSMD6. In certain embodiments the 19S subunits whose expression levels are examined include PSMD5, PSMD1, PSMC6, PSMD10, PSMD14, PSMD6, PSMD8, and PSMD9. In certain embodiments the 19S subunits whose expression levels are examined include PSMD5, PSMD1, PSMC6, PSMD10, PSMD14, PSMD6, PSMD8, PSMD9, PSMD13, PSMD7, PSMC1, PSMD12, PSMC3, PSMC4, and PSMD4. In certain embodiments the 19S subunits whose expression levels are examined include PSMD5, PSMC3, PSMD3, PSMD4, PSMD6, PSMD7, PSMC5, PSMD1, PSMD11, PSMD13, PSMD8, and PSMD10.

In some embodiments an estimated sigma score may be calculated using an average expression level value that is computed excluding one or more values that lie furthest from the average or median value. For example, the 1, 2, or 3 highest values and/or the 1, 2, or 3 lowest values may be excluded in some embodiments. In some embodiments the highest and lowest 10%, 15%, 20%, or 25% of values may be excluded.

In some embodiments an estimated sigma score may be calculated using the median of multiple proteasome subunit expression levels instead of the average as the reference level and/or as the central point from which the standard deviation is calculated. In some embodiments an estimated sigma score may be calculated using the mean or median absolute deviation of the expression levels that are used to calculate the reference level rather than the standard deviation, where the central point from which the absolute deviation may be the mean or median of the expression levels in various embodiments. In some embodiments, any of a variety of other measures of central tendency and/or deviation therefrom could be used. Furthermore, it will be appreciated that in some embodiments the expression level values may be subjected to any of a variety of mathematical transformations before calculating a reference level or measure of central tendency. Examples of such transformations are squaring the values or taking logarithms. In some embodiments an estimated sigma score may be calculated using an internal reference level or an external reference level that is an estimated average expression level of all 19S subunits, all 20S subunits, or all 19S and 20S subunits, as described herein. Thus, it will be appreciated that an estimated sigma score may be computed using a variety of approaches. More generally, one of ordinary skill in the art will appreciate that any value or score that correlates with a sigma score or can otherwise indicate that one or more 19S subunits has a reduced level of expression equivalent to or greater than that indicated by a particular sigma score may be used in a method described herein. For example, certain 19S subunits may only rarely, if ever, naturally exhibit reduced expression in proteasome resistant cancers. In certain embodiments, the expression level of any such 19S subunit may be used as an internal or external reference level and compared with the expression level of the other 19S subunits to determine whether any of the other 19S subunits has reduced expression.

In some embodiments the expression level of many or most 19S subunits may be higher in a proteasome-resistant cell, cell line, cell population, or cancer, than in a control proteasome-sensitive cell, cell line, cell population, or cancer while the expression level of one or a few (e.g., 2, 3, 4, 5) of the 19S subunits is lower than the expression level of such subunit(s) in a control proteasome-sensitive cell, cell line, cell population, or cancer. For example, the average expression level of the 19S subunits may be higher by a factor of between 1.1 and 1.5, between 1.5 and 2, between 2 and 2.5, between 2.5 and 3 in a proteasome-resistant cell, cell line, cell population, or cancer than in a control proteasome-sensitive cell, cell line, cell population, or cancer while the expression level of one or a few (e.g., 2, 3, 4, 5) of the 19S subunits in the proteasome-resistant cell, cell line, cell population, or cancer is modestly lower than the expression level of such subunit(s) in the control proteasome-sensitive cell, cell line, cell population, or cancer. Without wishing to be bound by any theory, selective reduced relative expression of one or more 19S subunits may result in an increased ratio of 20S proteasomes to 26S proteasomes, which may be responsible for conferring proteasome inhibitor resistance.

Various categories of likelihood of resistance or sensitivity to a proteasome inhibitor may be defined. For example, cancer may be classified as at low, intermediate, or high risk of resistance to a proteasome inhibitor. In some embodiments a cancer may be classified as having at least a 50%, 75%, or 90% likelihood of being proteasome inhibitor resistant. A variety of statistical methods may be used to correlate the risk of poor outcome (e.g., that the cancer is likely to be resistant to treatment with a proteasome inhibitor) with the relative or absolute level of expression or activity of one or more 19S subunits or the average level of expression or activity of two or more 19S subunits.

In some embodiments, any of the methods may further comprise treating a subject with one or more anticancer agents based on the classification. In some embodiments, the treating comprises (i) treating a subject having a cancer that is classified as likely to be proteasome inhibitor resistant with a proteasome inhibitor and an agent that increases expression or activity of a subunit of a 19S proteasome complex whose expression or activity is reduced in the cancer or (ii) treating a subject having a cancer that is classified as likely to be proteasome inhibitor resistant with a proteasome inhibitor and an agent that reduces proteasome inhibitor resistance and/or is selectively toxic to cancer cells that have reduced level or activity of a subunit of a 19S proteasome complex; (iii) treating a subject having a cancer that is classified as likely to be proteasome inhibitor resistant with an anticancer agent other than a proteasome inhibitor; or (iv) treating a subject having a cancer that is classified as potentially proteasome inhibitor sensitive with a proteasome inhibitor (optionally in combination with an inhibitor of proteasome inhibitor resistance).

In some aspects, described herein is a method of determining whether a subject with cancer is a suitable candidate for treatment with a proteasome inhibitor, the method comprising: (a) measuring the level of expression or activity of a subunit of a 19S proteasome complex in a cancer sample obtained from the subject; and (b) comparing the level measured in (a) with a reference level; and (c) determining whether the cancer is likely to be resistant to a proteasome inhibitor based on the comparison, wherein the subject is not a suitable candidate for treatment with a proteasome inhibitor in the absence of an inhibitor of proteasome inhibitor resistance if the cancer is determined to be likely to be resistant to a proteasome inhibitor, optionally wherein the method further comprises treating the subject for the cancer based on the determination of (c). In some embodiments, a method comprises treating a subject having a cancer that is classified as likely to be proteasome inhibitor resistant with a proteasome inhibitor and an agent that increases expression or activity of a subunit of a 19S proteasome complex whose expression or activity is reduced in the cancer or (ii) treating a subject having a cancer that is classified as likely to be proteasome inhibitor resistant with a proteasome inhibitor and an agent that is selectively toxic to cancer cells that have reduced level or activity of a subunit of a 19S proteasome complex; (iii) treating a subject having a cancer that is classified as likely to be proteasome inhibitor resistant with an anti-cancer agent other than a proteasome inhibitor; or (iv) treating a subject having a cancer that is classified as potentially proteasome inhibitor sensitive with a proteasome inhibitor.

In some aspects, described herein is a method of determining whether a subject with cancer is a suitable candidate for treatment with a proteasome inhibitor, the method comprising: (a) measuring the level of expression or activity of a subunit of a 19S proteasome complex in a cancer sample obtained from the subject; and (b) comparing the level measured in (a) with a reference level; and (c) determining whether the cancer is likely to be resistant to a proteasome inhibitor based on the comparison, wherein the subject is a suitable candidate for treatment with a proteasome inhibitor if the cancer is determined to be likely to be resistant to a proteasome inhibitor, optionally wherein the method further comprises treating the subject for the cancer based on the determination of (c).

Any of the methods of measuring level of expression or activity described herein may be used in the methods of classification, prediction, and/or treatment selection described herein.

Mutations and/or epigenetic changes may result in reduced expression or activity of one or more 19S subunits in a cancer cell and thereby cause the cancer cell (or cancer comprising the cancer cell) to acquire proteasome inhibitor resistance. For example, a mutation in a promoter or other regulatory region of a gene that encodes a 19S subunit could result in reduced expression of the subunit. A mutation in a coding region of a gene that encodes a 19S subunit could result in reduced expression or activity of the encoded subunit. A deletion of all or part of a gene that encodes a 19S subunit could result in reduced expression or activity of the subunit. Epigenetic changes such as promoter methylation could result in reduced expression. In some aspects, a cancer cell, a cancer cell line, a cell population comprising cancer cells, or a cancer may be classified according to predicted level of resistance or sensitivity to a proteasome inhibitor based on detecting one or more such genetic or epigenetic changes in said cancer cell, cancer cell line, cell population, or cancer. In some aspects, a cancer may be classified according to predicted level of resistance or sensitivity to a proteasome inhibitor based on detecting one or more such genetic or epigenetic changes in a nucleic acid (e.g., DNA) obtained from a cancer sample. Such changes may be detected by, e.g., sequencing, microarrays, or other methods known in the art. For example bisulfite reaction based methods such as methylation specific PCR, bisulfite sequencing, methylation-sensitive single-nucleotide primer extension, may be used to detect methylation of a regulatory region, e.g., a promoter region or enhancer region, of a gene that encodes a 19S subunit. In some embodiments, methylation of one of the promoters of one of the two alleles of a gene that encodes a 19S subunit causes a modest reduction in expression of such subunit and results in proteasome inhibitor resistance. In some embodiments, methylation of the promoter of both alleles of a gene that encodes a 19S subunit causes a reduction in expression of such subunit and results in proteasome inhibitor resistance. In some embodiments, the gene is PSMD5. In embodiments relating to expression of a 19S subunit, methylation of the promoter region of the gene encoding such subunit may serve as an indicator of reduced expression of the subunit. As used herein, the term "promoter region" refers to the region of a gene that extends from 2000 nt upstream of the transcriptional start site (TSS) to 500 nt downstream of the TSS. A promoter region comprises a core promoter, which is the minimal portion of the promoter required to properly initiate transcription, and includes the TSS and elements located within up to about 50-100 nt upstream of the TSS that comprise binding sites for RNA polymerase and general transcription factors. A promoter region may also comprise a proximal promoter that comprises binding sites for specific transcription factors and is located upstream of the core promoter at a location up to about position 250 nt upstream of the TSS. A promoter region may also comprise a distal promoter located further upstream from the TSS. In some embodiments, e.g., when the start codon of a gene is located within 500 nt downstream of the TSS, a promoter region may comprise the start codon. The location of a TSS or start codon of a gene that encodes a 19S subunit may be determined based on the RefSeq transcript and protein sequences.

DNA methylation in mammalian somatic cells mainly occurs at the 5 position of cytosine in CpG dinucleotides and reduces gene expression. DNA methylation is carried out by DNA methyltransferases. DNMT1 is the proposed maintenance methyltransferase, which preserve DNA methylation after every cellular DNA replication cycle. DNMT3A and DNMT3B are the de novo methyltransferases that establish DNA methylation patterns early in development. DNA methylation is an important regulator of gene transcription, and considerable evidence indicates that transcription of genes with high levels of 5-methylcytosine in their promoter region is typically low or absent. CpGs are often clustered in CpG-rich regions of DNA called CpG islands that are often associated with the transcription start sites of genes and may also be found in gene bodies and intergenic regions. CpG islands have been defined as DNA regions at least 200 bp long with a GC fraction greater than 0.5 and an observed-to-expected ratio of CpG greater than 0.6 (Gardiner-Garden, M. & Frommer, M. CpG islands in vertebrate genomes. *J. Mol. Biol.* 196, 261-282 (1987). Locations of CpG islands in the human genome are known in the art. CpG islands are identified in the UCSC Genome Browser in the "CpG Islands" tracks. In cancer, CpG islands associated with promoter regions can acquire abnormal hypermethylation, which results in transcriptional silencing that can be inherited by daughter cells following cell division.

As described in Example 24, the IMR32 neuroblastoma cell line was found to have both reduced PSMD5 expression and increased resistance to proteasome inhibitors relative to a second neuroblastoma cell line (Kelly). Bisulfite sequencing revealed that the PSMD5 promoter region in IMR32 cell lines is extensively methylated (~98% of CpGs in the region 50-382 bps upstream of the PSMD5 gene ATG were methylated in IMR32 cells), whereas the same region is almost entirely unmethylated in Kelly cells (4% of CpGs in the region 50-382 bp downstream of the PSMD5 gene ATG were methylated in Kelly cells), strongly suggesting that promoter methylation is responsible for the reduced PSMD5 expression observed in IMR32 cells and confirming that methylation within the promoter region of genes encoding 19S subunits can be used as a biomarker for proteasome inhibitor resistance. In some aspects, the present disclosure provides the recognition that hypermethylation within a promoter region of a gene that encodes a 19S subunit can be used as a biomarker for proteasome inhibitor resistance. In some aspects, the present disclosure provides the recognition that hypermethylation within a promoter region of a gene that encodes a 19S subunit can be used as a biomarker for sensitivity to agents that selectively inhibit survival and/or proliferation of proteasome inhibitor resistant cells. As used herein, "hypermethylation" of a portion of genomic DNA in a cell, cell population, or cancer of interest refers to an increased level of methylation of that portion of DNA in the cell, cell population, or cancer of interest as compared with the level of methylation of that portion of DNA in control cells or a control cancer. The control cells may be normal cells, e.g., normal cells of the same cell type as the cancer cell, cancer cell population, or cancer. The normal cells may be of the cell type from which the cancer arose or that it most closely resembles, or may be the dominant cell type, in the organ in which the cancer is located. In some embodiments in which methylation of a portion of a promoter region of a gene that encodes a 19S subunit is measured, control cells are cells of a cancer cell line or cancer that is sensitive to bortezomib, such as IMR32 cells or any of the other bortezomib-sensitive cell lines disclosed herein. In some embodiments, if a portion of DNA is unmethylated or almost entirely unmethylated (i.e., less than 10% or, in some embodiments, less than 5%, of the CpG dinucleotides in the region are methylated) in control cells, the portion is considered to be "hypermethylated" in a cell, cell population, or cancer of interest if at least 50%, 75%, 80%, 85%, 90%, or more of the CpG dinucleotides in the portion are methylated in the cell, cell population, or cancer of interest. In some embodiments, if a portion of DNA is between 10% and 50% methylated (i.e., between 10% and 50% of the CpG nucleotides in the region are methylated) in control cells, the region is considered to be "hypermethylated" in a cell, cell population, or cancer of interest if at least 75%, 80%, 85%, 90% or more of the CpG dinucleotides in the portion are methylated in the cell, cell population, or cancer of interest.

In some aspects, the disclosure provides a method of classifying a cancer cell, cancer cell population, or cancer comprising: (a) providing genomic DNA obtained from a cancer cell, cancer cell population, or cancer; and (b) measuring methylation of a portion of the promoter region of a gene that encodes a 19S subunit in the genomic DNA. The cancer cell, cancer cell population, or cancer may be classified as having or not having hypermethylation of a portion of the promoter region of a gene that encodes a 19S subunit. In some embodiments the method comprises determining the extent to which the portion of the promoter region is methylated. In some embodiments the method comprises determining that the portion of the promoter region is hypermethylated. In some embodiments the method comprises detecting methylation of at least 80%, at least 85%, at least 90%, or at least 95% of the CpGs in the portion of the promoter region. In some embodiments the method further comprises identifying the cancer or cancer cell as likely to be resistant to a proteasome inhibitor if the portion of the promoter region is hypermethylated. In some embodiments the method further comprises identifying the cancer or cancer cell as likely to be resistant to a proteasome inhibitor if at least 80%, at least 85%, at least 90%, or at least 95% of the CpGs in the portion of the promoter region are methylated. In some embodiments the method comprises identifying the cancer or cancer cell as likely to be sensitive to an agent that inhibits proteasome inhibitor resistance if at least 80%, at least 85%, at least 90%, or at least 95% of the CpGs in the portion of the promoter region are methylated. In some embodiments the method comprises identifying the cancer or cancer cell as likely to be sensitive to an agent that inhibits proteasome inhibitor resistance if at least 80%, at least 85%, at least 90%, or at least 95% of the CpGs in the portion of the promoter region are methylated. In some embodiments the method comprises contacting the cancer cell or cancer with an agent that selectively inhibits survival and/or proliferation of cancer cells that have reduced expression or activity of one or more 19S subunits if the portion of the promoter region is hypermethylated. In some embodiments the method comprises contacting the cancer cell or cancer with an agent that selectively inhibits survival and/or proliferation of cancer cells that have reduced expression or activity of one or more 19S subunits if at least 80%, at least 85%, at least 90%, or at least 95% of the CpGs in the portion of the promoter region are methylated. In some embodiments the method comprises contacting the cancer cell or cancer with an agent that inhibits proteasome inhibitor resistance if the portion of the promoter region is hypermethylated. In some embodiments the method comprises contacting the cancer cell or cancer with an agent that selectively inhibits survival and/or proliferation of cancer cells that have reduced expression or activity of one or more 19S subunits if at least 80%, at least 85%, at least 90%, or at least 95% of the CpGs in the portion of the promoter region are methylated. In some embodiments the method comprises contacting the cancer cell or cancer with a proteasome inhibitor and an agent that inhibits proteasome inhibitor resistance if the portion of the promoter region is hypermethylated. In some embodiments the method comprises contacting the cancer cell or cancer with a proteasome inhibitor and an agent that inhibits proteasome inhibitor resistance if at least 80%, at least 85%, at least 90%, or at least 95% of the CpGs in the portion of the promoter region are methylated A portion of DNA over which methylation is measured is typically at least 50 nt in length, e.g., between 50 nt and 100 nt, between 100 nt and 300 nt, between 300 nt and 500 nt, between 500 nt and 1 kb, or between 1 kb and 2 kb long. In some embodiments the portion comprises at least 10, 15, 20, 25, 30, 40, 50, 60, 70, 80, 90, 100, or more CpG dinucleotides. In some embodiments, the portion comprises or lies within or overlaps a CpG island. The portion selected for measurement may be one that is normally unmethylated or almost entirely unmethylated (i.e., less than 10% or, in some embodiments, less than 5%, of the CpG dinucleotides in the region are methylated) in control cells.

In some embodiments the portion of the promoter region over which methylation is measured comprises at least part of the core promoter. In some embodiments the portion of the promoter region over which methylation is measured comprises at least part of the core promoter and at least part of the proximal promoter. In some embodiments the portion of the promoter region over which methylation is measured comprises at least a 100, 200, 300, 400, or 500 nt region located within 1 kb upstream of the transcription start site (TSS) of the gene. In some embodiments the region encompasses the TSS. In some embodiments the region encompasses positions-1 to -50, positions-50 to -100, positions-100 to -150, positions-150 to -200, and/or positions-200 to -250, where position-1 is the position immediately upstream of the TSS.

In some embodiments the portion of the promoter region over which methylation is measured comprises at least a 100, 200, 300, 400, or 500 nt region located within 1 kb upstream of the start codon of the gene. In some embodiments the region encompasses positions 1 to 50 nt upstream of the start codon, positions 50 to 100 nt upstream of the start codon, positions 100 to 150 nt upstream of the start codon, positions 150 to 200 nt upstream of the start codon, positions 200 to 250 nt upstream of the start codon, and/or positions 200 to 250 nt upstream of the start codon. In some embodiments the region is within or overlaps a CpG island located at chr9:120842766-120843307 (as annotated in the human genome GRCh38/hg38 Assembly available at the UCSC Genome Browser) which is associated with the promoter of the PSMD5 gene. In some embodiments methylation is measured over two or more portions of the promoter region of a gene that encodes a 19S subunit, wherein the portions may have any of the lengths and/or positions described herein. In some embodiments methylation is measured over portions of the promoter region of two or more genes that encode 19S subunits.

As described in the Examples, many 19S subunit transcripts, including PSMD5, PSMD12, PSMD7, PSMD8, PSMD3, PSMD10, PSMD1, PSMD11, PSMD13, PSMD14, PSMD2, PSMC2, PSMC4, and PSMC6, contain multiple predicted miRNA target sites. In some embodiments, the disclosure provides a method of classifying a cancer comprising: (a) providing a biological sample comprising RNA obtained from one or more cancer cells obtained from a subject in need of treatment for cancer; and (b) measuring the expression level of a miRNA that has a predicted target site in the transcript of a 19S subunit, e.g., PSMD5, PSMD12, PSMD7, PSMD8, PSMD3, PSMD10, PSMD1, PSMD11, PSMD13, PSMD14, PSMD2, PSMC2, PSMC4, or PSMC6 in the sample. The cancer cell, cancer cell population, or cancer may be classified as having or not having overexpression of one or more miRNAs that have a predicted target site in a 19S subunit transcript. Without wishing to be bound by any theory, overexpression of one or more miRNAs that have a predicted target site in a 19S subunit transcript may be at least in part responsible for reduced expression of that subunit in a cell (e.g., a cancer cell), cell line (e.g., a cancer cell line), cell population (e.g., a cell population comprising cancer cells), or cancer. In some aspects, a cancer cell, a cancer cell line, a cell population comprising cancer cells, or a cancer, may be classified according to predicted level of resistance or sensitivity to a proteasome inhibitor based on detecting the expression level of a miRNA that has a predicted target site in the transcript of a 19S subunit, e.g., PSMD5, PSMD12, PSMD7, PSMD8, PSMD3, PSMD10, PSMD1, PSMD11, PSMD13, PSMD14, PSMD2, PSMC2, PSMC4, or PSMC6. The level of expression of a miRNA may be detected by any suitable method, e.g., methods comprising sequencing, reverse transcription quantitative PCR, hybridization to complementary probes or primers, primer extension, microarrays, and/or other methods known in the art. In some embodiments mature miRNA may be detected. In some embodiments precursor miRNA may be detected. In some embodiments the miRNA is a member of a miRNA family listed in Table 3. In certain embodiments the miRNA is a member of one of the following miRNA families: miR-4282, miR-570, miR-3120-3p, miR-545, miR-30abcdef/30abe-5p/384-5p, miR-2355-5p, miR-763/1207-3p/1655, miR-802, miR-452/4676-3p, miR-4680-3p, and miR-3600/4277. These miRNA families were predicted to be most likely to differentially regulate the PSMC and PSMD subunits (19S subunits) versus the PSMA and PSMB (20S) proteasome subunits.

In some embodiments, sensitivity of a cancer in a human subject to a therapy (e.g., a therapeutic agent or combination of agents) may be evaluated at least in part using objective criteria that can be used to determine when or whether cancer patients improve, remain about the same ("stable disease"), or worsen ("progressive disease"). If a cancer patient receives treatment, an improvement or (sometimes) stabilization of disease that had been progressing may be referred to as a "response" provided that it meets defined response criteria. A response may be a complete response, near complete response, or partial response. Examples of guidelines that describe criteria for, e.g., response, stable disease, and progression include IMWG Uniform Response Criteria (Durie B G, et al. International uniform response criteria for multiple myeloma. Leukemia 2006; 20(9):1467-1473j and the European Group for Blood and Marrow Transplantation (EBMT) criteria (Blade J, et al. Criteria for evaluating disease response and progression in patients with multiple myeloma treated by high-dose therapy and haematopoietic stem cell transplantation: Myeloma Subcommittee of the EBMT. European Group for Blood and Marrow Transplant. Br J Haematol 1998; 102(5):1115-1123), the original or revised Response Evaluation Criteria In Solid Tumors (RECIST), a guideline based on anatomical tumor burden (e.g., measured using physical examination and/or imaging techniques). The original RECIST guideline is described in Therasse P, et al. J Natl Cancer Inst (2000) 92:205-16. A revised RECIST guideline (Version 1.1) is described in Eisenhauer, E., et al., Eur J Cancer. (2009) 45(2):228-47). In the case of lymphomas or leukemias, response criteria known in the art can be used (see, e.g., Cheson B D, et al. Revised response criteria for malignant lymphoma. J Clin Oncol 2007; 10:579-86). It will be appreciated that the guidelines and criteria mentioned herein for assessing tumor sensitivity are merely exemplary. Modified or updated versions thereof or other reasonable criteria (e.g., as determined by a person of ordinary skill in the art) may be used. Clinical assessment of symptoms or signs associated with tumor presence, stage, regression, progression, or recurrence may be used. In certain embodiments criteria based on anatomic tumor burden and/or other markers such as paraprotein levels in the blood should reasonably correlate with a clinically meaningful benefit such as increased survival (e.g., increased progression-free survival, increased cancer-specific survival, or increased overall survival) or at least improved quality of life such as reduction in one or more symptoms. In some embodiments a response lasts for at least 2, 3, 4, 5, 6, 8, 12 months, or more. In some embodiments tumor response or recurrence may be assessed at least in part by testing a sample comprising a body fluid such as blood for the presence of cancer cells and/or for the presence or level or change in level of one or more substances (e.g., microRNA, protein) produced or secreted by tumor cells. A normal level or a reduction in level over time of one or more substances derived from tumor cells may indicate a response or maintenance of remission. An abnormally high level or an increase in level over time may indicate progression or recurrence.

V. Methods of Increasing 20S Proteasome Level and Activity

As described in the Examples, it was observed that, in addition to increasing proteasome inhibitor resistance, a modest reduction in the level of expression of a 19S subunit results in a reduced level of 26S proteasomes and a considerable increase in the level of 20S proteasomes and 20S proteasome activity in cells exposed to proteasome inhibitors. Furthermore, in the absence of proteasome inhibitors, protein degradation was not reduced, polyubiquitinated substrates were not elevated and hallmark stress responses were not activated. Thus, the present disclosure provides the recognition that a reduction in the level of expression or activity of a 19S subunit can increase the level of 20S proteasomes and 20S proteasome activity and can protect cells against proteotoxic stress.

In some aspects, described herein is a method of increasing the level of 20S proteasomes and 20S proteasome activity in a cell comprising: (a) providing a cell; and (b) modestly reducing the level of expression or activity of a subunit of a 19S proteasome complex in the cell. In some embodiments the cell is characterized by reduced flux through the proteasome. In some embodiments, described herein is a method of reducing the level of proteotoxic stress in a cell comprising: (a) providing a cell; and (b) modestly reducing the level of expression or activity of a subunit of a 19S proteasome complex in the cell. In some embodiments, the cell has an abnormally high level of proteotoxic stress. In some embodiments the cell has an abnormally high level of proteotoxic stress due to exposure to an agent or condition that inhibits expression or activity of a chaperone or cochaperone or inhibits expression or activity of one or more components of the ubiquitin-proteasome system. In some embodiments the cell is characterized by reduced flux through the proteasome. "Chaperone" refers to any of a variety of proteins that assist with the non-covalent folding and/or unfolding of other proteins and/or the assembly/disassembly and protein complexes. Examples of chaperones include, e.g., heat shock proteins such as HSP90. "Cochaperone" refers to a protein that assists a chaperone in protein folding and other functions. Examples of co-chaperones include, e.g., CDC37. Those of ordinary skill in the art will be aware of other chaperones and co-chaperones. In some embodiments the cell has an abnormally high level of proteotoxic stress due to abnormal protein aggregation. In some embodiments the cell is a mammalian cell, e.g., a human cell. In some embodiments the cell is a non-neoplastic cell. In some embodiments the cell is a member of a cell line. In general, the cell may be of any cell type, e.g., any of the cell types mentioned herein. In some embodiments the cell is in a cell culture. In some embodiments the cell is in a subject.

In some embodiments, reducing the level of expression or activity of a subunit of a 19S proteasome complex comprises contacting the cell with an agent that causes a modest reduction in the level of expression or activity of said subunit. The agent may be any of the various agents herein that reduce the level of expression or activity of a 19S subunit. For example, the agent may be an RNAi agent that inhibits expression of the subunit by, e.g., causing degradation and/or inhibiting translation of mRNA encoding the subunit. The RNAi agent may be an siRNA or a vector that encodes a shRNA. In some embodiments the agent is a small molecule. In some embodiments, the level of expression or activity of a 19S subunit is reduced to between 20% and 80% of the level present in the cell prior to contacting the cell with the agent. In some embodiments the level of expression or activity of a 19S subunit is reduced to between 25% and 75%, e.g., e.g., between 25% and 50% or between 30% and 70% of the level present in the cell prior to contacting the cell with the agent. In some embodiments the level of expression or activity of a 19S subunit is reduced to between 40% and 60%, e.g., about 50% of the level present in the cell prior to contacting the cell with the agent. In some embodiments the level of expression or activity of a 19S subunit is reduced sufficiently to detect an increase in the level of 20S proteasomes and/or an increase in 20S proteasome activity (e.g., in the presence of a proteasome inhibitor). In some embodiments the level of expression or activity of a 19S subunit is reduced sufficiently to detect a decrease in at least one indicator of proteotoxic stress.

Proteotoxic stress can occur in a variety of different disorders. In some aspects, described herein is a method of treating a subject in need of treatment for a condition characterized by proteotoxic stress comprising: administering an agent that modestly reduces the level of expression or activity of a 19S subunit to the subject. In some embodiments the condition is characterized by reduced flux through the proteasome. In general, the agent can be any of the agents described herein that reduce the level or activity of a 19S subunit. For example, in some embodiments, the agent is an inhibitory oligonucleotide or a nucleic acid engineered to cause a cell to express an inhibitory RNA that selectively inhibits expression of a gene that encodes a 19S subunit. In some embodiments, the agent is a peptide or a nucleic acid engineered to cause a cell to express a polypeptide that inhibits expression of a gene that encodes a 19S subunit, inhibits activity of a 19S subunit, or disrupts integrity of the 26S proteasome. In some embodiments, the agent is a compound (e.g., a small molecule) that inhibits the expression or activity of a 19S subunit or disrupts integrity of the 26S proteasome. In some embodiments the condition is caused by or associated with exposure to a substance that causes proteotoxic stress, e.g., by inhibiting flux through the proteasome.

VI. Kits and Systems

In some aspects, described herein are kits comprising one or more cells or cell populations described herein. In some embodiments, the kit comprises cells that are genetically modified to have (constitutively or upon induction) altered (reduced or increased) expression or activity of a 19S subunit. In some embodiments, a kit comprises a first cell or cell population that has a first level of expression or activity of a 19S subunit and a second cell or cell population that has (constitutively or upon induction) a reduced level of expression or activity of a 19S subunit as compared to the first cell or cell population. In some embodiments the cells or cell populations are genetically matched. In some embodiments, the second cell or cell population has increased resistance to a proteasome inhibitor as compared with the first cell or cell population. In some embodiments, a kit comprises a first cell or cell population that has a first level of expression or activity of a 19S subunit which is relatively low (sufficiently low to confer increased resistance to a proteasome inhibitor) and a second cell or cell population that has (constitutively or upon induction) an increased level of expression or activity of a 19S subunit as compared to the first cell or cell population. In some embodiments the cells or cell populations are genetically matched. In some embodiments, the first cell or cell population has increased resistance to a proteasome inhibitor as compared with the second cell or cell population.

In some embodiments, a kit comprises test cells and control cells that have (constitutively or upon induction), different levels of expression or activity of a 19 S subunit, wherein optionally, test cells and control cells each have an identifying characteristic, as described herein, and/or wherein test cells and control cells are genetically matched.

In some embodiments a kit may further comprise one or more of the following: (i) a proteasome inhibitor, (ii) one or more reagents useful for measuring the level of expression or activity of a 19S subunit and/or useful for measuring proteasome activity, (iii) instructions for use of the kit to perform a screen to identify a modulator (e.g., an inhibitor) of proteasome inhibitor resistance.

In some aspects, described herein are kits comprising one or more reagents suitable for performing an assay to measure the level of expression or activity of one or more 19S subunits, e.g., for use in a method described herein. Such kits may contain, e.g., (i) a probe, primer, or primer pair for detecting, reverse transcribing, and/or amplifying a nucleic acid (e.g., mRNA, cDNA) encoding a 19S subunit (or probes, primers, or primer pairs for detecting, reverse transcribing, and/or amplifying nucleic acid encoding any one or more 19S subunits); (ii) an antibody or other specific binding agent that binds to a 19S subunit; (iii) one or more control reagents; (iv) a detectably labeled secondary antibody; (v) one or more control or reference samples that can be used for comparison purposes or to verify that a procedure for detecting expression or activity of a 19S subunit is performed appropriately or yields accurate results. A control reagent can be used for negative or positive control purposes. A control reagent may be, for example, a probe or primer that does not detect or amplify mRNA encoding a 19S subunit, an antibody that does not detect a 19S subunit, a purified 19S subunit or portion thereof. In some embodiments, a kit comprises a probe, primer, or primer pair suitable for detecting a gene product for normalization purposes. A probe, primer, antibody, or other reagent may be attached to a support, e.g., a bead, slide, chip, etc. In some embodiments a kit may further comprise one or more reagents suitable for performing an assay to measure the level of expression or activity of one or more 20S subunits.

One of ordinary skill in the art would appreciate that the particular probes, primers, and/or other reagents for use in a given assay would, in general, depend on the particular type of assay. For example, an assay in which mRNA is detected using nanostring (nCounter) technology may utilize at least two probes that hybridize to mRNA of each assay target gene. An assay in which mRNA is detected using PCR may utilize a pair of primers and, in some embodiments, a probe. In some embodiments a kit comprises reagents suitable for measuring expression of at least 2, 3, 4, 5, 6, 7, 8, 9, 10, 11, 12, 13, 14, 15, 16, 17, 18, 19, 20, or all 21 subunits of the 19S proteasome. In some embodiment the kit comprises primers suitable for performing a multiplex PCR assay for measuring expression of multiple 19S subunits. The primer design for all primers pairs may be optimized so that all primer pairs have a similar Tm (varying within up to about 3° C.-5° C.), do not form primer dimers, and are specific to a particular subunit sequence. In some embodiments, a kit comprises beads with nucleic acids and/or antibodies attached thereto for performing a bead-based assay such as a Luminex® assay. In some embodiments, a kit comprises primers (and, optionally one or more probes) for performing quantitative PCR or a nanostring assay. In some embodiments, at least 50%, 60%, 70%, 80%, 90%, or more, of the gene products measurable using the kit are 19S subunits. In some embodiments a kit further comprises reagents suitable for measuring expression of at least 1, 2, 3, 4, 5, 6, 7, 8, 9, 10, or more subunits of the 20S proteasome, e.g., 11, 12, 13, or 14 20S subunits. In some embodiments, at least 50%, 60%, 70%, 80%, 90%, or more, of the gene products measurable using the kit are either a 19S subunit or a 20S subunit. In some embodiments a kit may comprise one or more control reagents (e.g., probe(s) and/or primer(s)) suitable for measuring the level of expression of one or more control genes or the level of activity of one or more control proteins. A control gene or protein may be one whose expression or activity is not expected to differ significantly between proteasome inhibitor resistant and proteasome inhibitor sensitive cancer cells. The level of expression or activity of a control gene or protein may be used for normalization. In some embodiments at least 50%, 60%, 70%, 80%, 90%, or more, of the gene products measurable using the kit are either a 19S subunit or a 20S subunit or a control gene product.

In some embodiments a kit may comprise one or more enzymes for use in an assay implemented using the kit. For example, an assay that includes a step of reverse transcribing mRNA may comprise a reverse transcriptase. An assay that includes a nucleic acid amplification step may contain a polymerase, e.g., a DNA polymerase. For example, a kit for performing, e.g., a PCR assay, may include a thermostable DNA polymerase such as Taq polymerase or Pfu DNA polymerase. In some embodiments a kit may comprise dNTPs for reverse transcribing RNA and/or for amplifying DNA, rNTPs for transcribing RNA, oligodT primers for reverse transcribing mRNA, random hexamer primers for reverse transcribing RNA. In some embodiments a kit may comprise a buffer solution for extracting RNA from a biological sample comprising cells, an agent for stabilizing RNA prior to or after its extraction from cells, an agent for degrading or removing genomic DNA, or a combination thereof. A set of primers or probes may comprise one or more primers and/or probes included for control purposes, e.g., to confirm that appropriate kit components (e.g., enzymes) are active and present in an assay reaction. In some embodiments a kit may comprise a buffer solution for isolating DNA from cells and/or one or more restriction enzyme(s) for digesting genomic DNA into smaller fragments. The kit may comprise a protease for digesting such as proteinase K. In some embodiments a kit may comprise a buffer solution suitable for denaturing DNA or maintaining DNA in a single-stranded state. In some embodiments a kit may comprise suitable reagents for performing an assay to detect and/or quantify DNA methylation. For example, a kit may comprise bisulfite, e.g., sodium bisulfite. In some embodiments the kit may contain an aqueous medium for dissolving bisulfite. In some embodiments, a kit may comprise a desulfonation buffer, spin column(s), wash buffer(s), and/or suitable buffers to promote the binding and elution of DNA from the spin column. In some embodiments, a kit may comprise a primer pair suitable for amplifying (e.g., using PCR) at least a portion of a promoter region of a gene that encodes a 19S subunit (e.g., PSMD5), e.g., after bisulfite treatment. In some embodiments the portion of the promoter region is between 0.1 kb and 2 kb long, e.g., between about 300 nt and about 500 nt long. In some embodiments the portion of the regulatory region comprises at least a 100, 200, 300, 400, or 500 nt region located within 1 kb upstream of the start codon of the gene. In some embodiments the portion of the regulatory region comprises at least a 100, 200, 300, 400, or 500 nt region located within 1 kb upstream of the transcription start site of the gene. In some embodiments the region comprises at least 10, 15, 20, 25, 30, 35, 40, 45, or 50 CpG dinucleotides. In some embodiments the kit comprises at least 2, 3, 5, 10, 15, or more such primer pairs, each suitable for amplifying at least a portion of a promoter region of a different 19S subunit gene. In some embodiments a kit may comprise a DNA polymerase that can use templates containing uracil, such as a Taq polymerase, e.g., a hot start Taq polymerase. In some embodiments a kit may comprise a fragment of methylated DNA that serves a methylated DNA standard, which may be used for evaluation of bisulfite-mediated conversion of DNA. The methylated DNA standard may be, e.g., mammalian genomic DNA (e.g., human genomic DNA) with at least 90%, at least 95%, or more (e.g., all) of the CpG sites methylated. The DNA may be, e.g., between about 0.1 kb and about 5 kb long and may contain at least 20 CpG dinucleotides. A kit may contain collection vessels (e.g., tubes) for collecting RNA or DNA.

Individual kit components may be packaged in separate containers (e.g., tubes, bottles, etc.) The individual component containers may be packaged together in a larger container such as a box for commercial supply. Optionally the kit comprises written material, e.g., instructions, e.g., in a paper or electronic format (e.g., on a computer-readable medium). Instructions may comprise directions for performing the assay and/or for interpreting results, e.g., in regard to cancer classification, prediction, or treatment selection. Such material could be provided online.

In some aspects, a kit is useful to classify a cancer, to determine whether a subject is a suitable candidate for treatment with a proteasome inhibitor, and/or to select a treatment for a subject in need of treatment for cancer.

In some aspects, a kit is useful to classify a cancer, to determine whether a subject is a suitable candidate for treatment with an agent that reduces proteasome inhibitor resistance. In some aspects, a kit is useful to classify a cancer, to determine whether a subject is a suitable candidate for treatment with a BCL2 family inhibitor, to select a BCL2 family inhibitor as a treatment for a subject in need of treatment for cancer, and/or to treat a subject with a BCL2 family inhibitor. In some aspects, a kit is useful to classify a cancer, to determine whether a subject is a suitable candidate for treatment with a dithiocarbamate (e.g., disulfiram), to select a dithiocarbamate (e.g., disulfiram) as a treatment for a subject in need of treatment for cancer, and/or to treat a subject with a dithiocarbamate (e.g., disulfiram). In some aspects, a kit is useful to classify a cancer, to determine whether a subject is a suitable candidate for treatment with a bis(thio-hydrazide amide) (e.g., elesclomol), to select a bis(thio-hydrazide amide) (e.g., elesclomol) as a treatment for a subject in need of treatment for cancer, and/or to treat a subject with a bis(thio-hydrazide amide) (e.g., elesclomol).

In some aspects, a method comprising measuring the level of expression or activity of one or more 19S subunits, or a kit useful for performing such a method, may be used as a "companion diagnostic" to determine, for example, whether a cancer is likely to be resistant or sensitive to a proteasome inhibitor, whether a subject is a suitable candidate for treatment with a proteasome inhibitor, whether a subject is a suitable candidate for treatment with an inhibitor of proteasome inhibitor resistance. In some embodiments, such a method or kit measures promoter methylation of a gene encoding a 19S subunit, e.g., PSMD5. In some embodiments, such a method or kit measures promoter methylation of the promoter of any 1, 2, 3, 4, 5, or 6 of the genes encoding the following 19S subunits: PSMD5, PSMD1, PSMC6, PSMD10, PSMD14, PSMD6.

In some aspects, the invention provides a system which is adapted or programmed to measure expression or activity of one or more 19S subunits e.g., for use in a method of the invention. In some embodiments the system may include one or more instruments (e.g., a PCR machine), an automated cell or tissue staining apparatus, an imaging device (i.e., a device that produces an image), and/or one or more computer processors. The system may be programmed with parameters that have been selected or optimized for detection and/or quantification of a 19S subunit, e.g., in cancer samples. The system may be adapted to perform the assay on multiple samples in parallel and/or may have appropriate software to analyze samples (e.g., using computer-based image analysis software) and/or provide an interpretation of the result. The system can comprise appropriate input and output devices, e.g., a keyboard, display, etc. In certain embodiments the system comprises a non-transitory computer-readable medium encoded with computer-executable instructions for comparing a measured 19S subunit expression or activity level with a reference level, computing an average 19S subunit expression or activity level, or computing a sigma score.

In some embodiments, an assay (e.g., an assay comprising measuring the level of expression or activity of one or more 19S subunits in a sample) may be performed at one or more testing facilities, which may be specially qualified or accredited (e.g., by a national or international organization which, in some embodiments, is a government agency or organization or a medical or laboratory professional organization) to perform the assay and, optionally, provide a result. For example, a sample can be sent to the laboratory, and a result of the assay, optionally together with an interpretation, are subsequently provided to a requesting individual or entity. In some embodiments, a method determining the likelihood of resistance to a proteasome inhibitor comprises providing a sample to a testing facility. In some embodiments a method comprises: providing to a testing facility (a) a sample obtained from a subject and instructions to perform an assay comprising measuring the level of expression or activity of one or more 19S subunits; and (b) receiving results of an assay that comprises measuring the level of expression or activity of one or more 19S subunits. In some embodiments such assay comprises measuring promoter methylation of a gene that encodes a 19S subunit. A result can comprise one or more measurements, scores and/or a narrative description. In some embodiments, a result provided comprises a measurement or score, together with associated classification, prediction, or treatment selection information. In some embodiments, a result provided comprises a measurement, score, or image of the sample, without associated classification, prediction, or treatment selection. In some embodiments an assay may be performed at a testing facility which is remote from the site where the sample is obtained from a subject (e.g., at least 1 kilometer away). It is contemplated that samples and/or results may be transmitted to one or more different entities, which may carry out one or more steps of an assay or a method or transmit or receive results thereof. All such activities are within the scope of various embodiments of methods described herein.

In some embodiments an agent described herein, e.g., an agent that inhibits growth of proteasome resistant cancer cells, such as a BCL2 family inhibitor (e.g., ABT-263), a dithiocarbamate (e.g., disulfiram), or a bis(thio-hydrazide amide) (e.g., elesclomol), may be approved by the FDA and/or by a government agency having similar functions in a different jurisdiction, such as the European Medicines Agency, the Pharmaceutical and Medical Devices Agency (Japan), etc., for use in treating patients with cancers that have reduced expression or activity of one or more 19S subunits, e.g., as demonstrated by one or more assays. In some embodiments the drug label of the agent specifies that the agent is approved for treatment of cancers that have reduced expression or activity of one or more 19S subunits (e.g., 2.5, 2.6, 2.7, 2.8, 2.9, or 3-sigma cancers). In some embodiments, a drug label may specify a particular assay, system, reagent(s), and/or kit to be used to demonstrate that a cancer has reduced expression or activity of one or more 19S subunits. In some embodiments the drug label of the agent specifies that the agent is approved for treatment of cancers that have promoter hypermethylation of a gene encoding a 19S subunit. In some embodiments, a drug label may specify a particular assay, system, reagent(s), and/or kit to be used to demonstrate that a cancer has promoter hypermethylation of a gene encoding a 19S subunit. In some embodiments a kit, system, reagent(s) or testing facility may be approved by the FDA and/or by a government agency having similar functions in a different jurisdiction for use in performing an assay to determine whether a patient falls within the subset of patients for treatment of which a particular agent was approved (e.g., patients needing treatment for a cancer that has reduced expression or activity of one or more 19S subunits). In some embodiments an agent and a particular assay (test) are approved together, wherein the assay serves as a companion diagnostic that provides information that is essential for the safe and effective use of the agent. The test helps a health care professional determine whether the agent's benefits to a patient will outweigh any potential serious side effects or risks. In some embodiments, the assay may be developed or approved during or after a drug is made available on the market.

VII. Compositions and Methods of Treatment

In some aspects, methods are provided herein for treating subjects having or at risk of having cancer. In some embodiments, the methods involve administering one or more agents that reduce proteasome inhibitor resistance in cells (e.g., cancer cells) of the subject and/or are selectively toxic to proteasome inhibitor resistant cells. In some embodiments, the agent increases the level of expression or activity of a 19S subunit. In some embodiments the agent is selectively toxic to cells that have a reduced level of expression or activity of a 19S subunit.

According to certain methods provided herein for treating subjects having or at risk of having cancer, a treatment that reduces proteasome inhibitor resistance and/or is selectively toxic to proteasome inhibitor resistant cells may be administered to the subject within particular period of time of at least one other treatment for the cancer in the subject (e.g., a proteasome inhibitor). The particular period of time may be within 12 months, within 6 months, within 3 months, within 1 month, within 3 weeks, within 2 weeks, within 1 week, within 5 days, within 4 days, within 3 days, within 2 days, within 1 day, within 12 hours, within 6 hours, within 2 hours, within 1 hour or less time. The treatment affecting proteasome inhibitor resistance may be administered to the subject prior to or after the at least one other treatment for the cancer in the subject. The other treatment may be any appropriate treatment, including, for example, a surgery to remove malignant or premalignant cells from the subject; or radiation therapy directed at eradicating malignant or premalignant cells from the subject; or a chemotherapy treatment; or other appropriate treatment.

In some embodiments, methods of treatment provided herein are employed in conjunction with methods provided herein for cancer classification, prediction, or treatment selection. For example, in some embodiments, the methods involve first determining that a subject has cancer or is at risk of having or developing cancer and then, having established that the subject has cancer, or is at risk of having or developing cancer, treating the subject according to the methods provided herein. In some embodiments, the methods involve determining that the subject has a cancer that contains cells that are proteasome inhibitor resistant or are likely to acquire proteasome inhibitor resistance. In some embodiments, the determination comprises evaluating the level of expression or activity of one or more 19S subunits in cells isolated from the subject, e.g., isolated from a region of the subject suspected of containing cancerous tissue. In some embodiments the method comprises contacting cells obtained from the subject with a proteasome inhibitor and measuring the effect of the proteasome inhibitor on cell survival or proliferation. For example, the cells may be isolated from the blood or from a lymph node or from the bone marrow in the case of a hematologic cancer. In some embodiments, the methods involve determining that the cancer contains cells that exhibit a reduced level of expression or activity of a 19S subunit and, having determined that the cancer contains such cells, treating the subject according to one or more methods disclosed herein. In some embodiments, the 19S subunit is any of the 19S subunits. In some embodiments, the method comprises administering to the subject an agent that increases expression or activity of a particular 19S subunit whose level of expression or activity is reduced in the cancer. In some embodiments, the method comprises administering to the subject an agent identified as an inhibitor of proteasome inhibitor resistance as described herein.

In some embodiments, methods of treatment provided herein that comprise administering an inhibitor of PI resistance are employed for treating a subject who has received at least one course of therapy with a proteasome inhibitor. In some embodiments, the subject has experienced a clinical response to the proteasome inhibitor. In some embodiments, the subject has experienced a clinical response to the proteasome inhibitor and subsequently experienced disease progression or relapse.

In some embodiments, methods for treating a subject in need of treatment for cancer comprise subjecting a sample of the cancer obtained from the subject to a gene expression analysis to determine expression levels of one or more genes encoding 19S subunits in the sample; and comparing the expression levels to reference expression levels of said gene(s) in appropriate reference cells, wherein the results of the comparison are indicative of whether the cancer contains cells that are proteasome inhibitor resistant or likely to acquire proteasome inhibitor resistance. In such embodiments, the methods may further comprise determining that the cancer contains cells that are proteasome inhibitor resistant or likely to acquire proteasome inhibitor resistance and treating the subject with an agent that inhibits proteasome inhibitor resistance and a proteasome inhibitor.

In some aspects, methods described herein have broad application to treating cancer. In certain embodiments, a cancer may be any of the cancers mentioned herein (see, e.g., Glossary). In some embodiments of particular interest, a cancer is a hematologic cancer. In some embodiments of particular interest, the hematologic cancer is multiple myeloma. In some embodiments of particular interest, the hematologic cancer is mantle cell lymphoma.

In some aspects, described herein are methods of treating a subject having, or suspected of having, cancer comprising administering to the subject an effective amount of a compound that selectively targets cells that are resistant to a proteasome inhibitor, e.g., by increasing the expression or activity of a 19S subunit. In some embodiments, the treatment methods of the invention involve treatment of a subject having (e.g., harboring) or at risk of having a proteasome inhibitor resistant cancer cell. In some embodiments, the subject has a hematologic cancer. In some embodiments, the subject has a hematologic cancer that has been treated with a proteasome inhibitor. In some embodiments the subject has relapsed or experienced disease progression after or during treatment with a proteasome inhibitor. In some embodiments the proteasome inhibitor is bortezomib or carfilzomib or an analog of either of these.

In some aspects, a method of killing or inhibiting proliferation of a cancer cell or cancer cell population comprises contacting the cancer cell or cancer cell population with a proteasome inhibitor and an agent that reduces proteasome inhibitor resistance, wherein the cancer cell or cancer cell population has been determined to have reduced expression or activity of at least one 19S subunit. In some embodiments the agent is selectively toxic to proteasome inhibitor resistant cancer cells. In some embodiments, it has been determined that the level of expression or activity of at least one 19S subunit is reduced by at least a predetermined number of standard deviations relative to a reference level, wherein said reduced level indicates that the cancer is likely to be proteasome inhibitor resistant. In some embodiments the sigma score of the cancer cell or cancer cell population has been determined, and found to be at least as great as a predetermined value indicative that the cancer cell or cancer cell population is likely to be proteasome inhibitor resistant. In some embodiments the cancer cell or cancer cell population is contacted with the proteasome inhibitor and the agent in vitro. In some embodiments the cancer cell or cancer cell population is contacted with the proteasome inhibitor and the agent in vivo.

In some aspects, a method of killing or inhibiting proliferation of a cancer cell or cancer cell population that has been determined to have reduced expression or activity of a 19S subunit comprises contacting the cancer cell or cancer cell population with a proteasome inhibitor and an agent that increases the level of expression of said 19S subunit. In some embodiments, it has been determined that the level of expression or activity of the 19S subunit is reduced by at least a predetermined number of standard deviations relative to a reference level, wherein said reduced level indicates that the cancer is likely to be proteasome inhibitor resistant. In some embodiments the sigma score of the cancer cell or cancer cell population has been determined, and found to be at least as great as a predetermined value indicative that the cancer cell or cancer cell population is likely to be proteasome inhibitor resistant. In some embodiments the cancer cell or cancer cell population is contacted with the proteasome inhibitor and the agent in vitro. In some embodiments the cancer cell or cancer cell population is contacted with the proteasome inhibitor and the agent in vivo.

In some aspects, a method of killing or inhibiting proliferation of a cancer cell or cancer cell population comprises determining the sigma score of the cancer cell population and contacting the cancer cell or cancer cell population with a proteasome inhibitor and an agent that reduces proteasome inhibitor resistance if the sigma score is above a predetermined value. In some embodiments the agent increases the level of expression of the 19S subunit that has the lowest level of expression in the cancer cell or cancer cell population. In some embodiments the cancer cell or cancer cell population is contacted with the proteasome inhibitor and the agent in vitro. In some embodiments the cancer cell or cancer cell population is contacted with the proteasome inhibitor and the agent in vivo.

In some aspects, a method of killing or inhibiting proliferation of a cancer cell or cancer cell population comprises contacting the cancer cell or cancer cell population with a proteasome inhibitor, wherein the expression of one or more 19S subunits, e.g., at least 5 19S subunits, in the cancer cell or cancer cell population has been measured, and the cancer cell or cancer cell population has been determined not to have reduced expression of any 19S subunit whose expression was measured. In some aspects, a method of killing or inhibiting proliferation of a cancer cell or cancer cell population comprises contacting the cancer cell or cancer cell population with a proteasome inhibitor, wherein the expression of at least 10, 11, 12, 13, 14, 15, 16, 17, 18, 19, 20, or 21 19S subunits in the cancer cell or cancer cell population has been measured, and the cancer cell or cancer cell population has been determined not to have reduced expression of any 19S subunit whose expression was measured. In some embodiments the cancer cell or cancer cell population is contacted with the proteasome inhibitor in vitro. In some embodiments the cancer cell or cancer cell population is contacted with the proteasome inhibitor in vivo.

In some aspects, a method of treating a subject in need of treatment for cancer comprises determining that the level of expression or activity of at least one 19S subunit is reduced by at least a predetermined number of standard deviations relative to a reference level, wherein said reduced level indicates that the cancer is likely to be proteasome inhibitor resistant; treating the subject with a proteasome inhibitor and an agent that reduces proteasome inhibitor resistance or treating the subject with at least one anti-cancer agent other than a proteasome inhibitor (e.g., a therapy that is recognized in the art as an alternative to proteasome inhibitor therapy). In some embodiments the method comprises treating the subject with an agent that is selectively toxic to proteasome inhibitor resistant cancer cells.

In some aspects, a method of treating a subject in need of treatment for cancer comprises determining the sigma score of the cancer and treating the subject with an agent selected based on the sigma score. In certain embodiments the sigma score indicates that the cancer is likely to be resistant to a proteasome inhibitor, and the treatment comprises a proteasome inhibitor and an agent that reduces proteasome inhibitor resistance. In certain embodiments the sigma score indicates that the cancer is likely to be resistant to a proteasome inhibitor, and the treatment comprises at least one anti-cancer agent other than a proteasome inhibitor (e.g., a therapy that is recognized in the art as an alternative to proteasome inhibitor therapy). In some embodiments the method comprises treating the subject with an agent that is selectively toxic to proteasome inhibitor resistant cancer cells.

In some aspects, a method of treating a subject in need of treatment for cancer comprises treating the subject with a proteasome inhibitor, wherein the expression of one or more 19S subunits, e.g., at least 5 19S subunits, in the cancer has been measured, and the cancer has been determined not to have reduced expression of any 19S subunit whose expression was measured. In some aspects, a method of treating a subject in need of treatment for cancer comprises treating the subject with a proteasome inhibitor, wherein the expression of at least 10, 11, 12, 13, 14, 15, 16, 17, 18, 19, 20, or 21 19S subunits in the cancer has been measured, and the cancer has been determined not to have reduced expression of any 19S subunit whose expression was measured.

In some aspects, a method of treating a subject in need of treatment for cancer, e.g., a proteasome inhibitor resistant cancer, comprises administering an agent that reduces or counteracts a post-transcriptional mechanism by which 19S subunit expression can be reduced in the cancer. In certain embodiments a method of treating a subject in need of treatment of cancer comprises administering to the subject an agent that increases expression of a 19S subunit, wherein expression of such 19S subunit is reduced in the cancer. For example, in instances in which reduced expression of a 19S subunit (e.g., PSMD5), is associated with proteasome inhibitor resistance, increasing the expression of the 19S subunit may reduce such resistance. In some embodiments, expression of a 19S subunit may be increased by contacting a cell with an agent that reduces the level or activity of an endogenous miRNA that has a predicted target site in the transcript of a 19S subunit. In some embodiments, for example, reduced expression of a 19S subunit is due at least in part to overexpression of one or more endogenous miRNAs that has a predicted target site in the transcript of the 19S subunit, and the method comprises increasing expression of such 19S subunit by contacting a cell with an agent that reduces the level or activity of the miRNA. In some embodiments the endogenous miRNA is a member of a miRNA family listed in Table 3. In certain embodiments the miRNA is a member of one of the following miRNA families: miR-4282, miR-570, miR-3120-3p, miR-545, miR-30abcdef/30abe-5p/384-5p, miR-2355-5p, miR-763/1207-3p/1655, miR-802, miR-452/4676-3p, miR-4680-3p, and miR-3600/4277.

An agent suitable for reducing the activity of a miRNA may be referred to as a "miRNA inhibitor". miRNA inhibitors include any of a variety of agents that bind to a miRNA of interest and inhibit its activity. Such agents include, e.g., nucleic acids that have complementarity to a miRNA, hybridize to it, and prevent it from hybridizing to its target site in a transcript. Examples of such agents are known in the art as anti-miRNA oligonucleotides, antimiRs, and miRNA sponges. mRNA sponges are RNA molecules harboring complementary binding sites to one or more miRNA(s) of interest that are transcribed from transgenes within cells, which transgenes may in some embodiments be introduced using a suitable vector (e.g., a viral vector). In some embodiments a nucleic acid (e.g., an oligonucleotide) that hybridizes to a miRNA target site in a mRNA that encodes a 19S subunit, and blocks hybridization of an endogenous miRNA to the mRNA target, may be used as a miRNA inhibitor to selectively reduce the activity of the miRNA against the particular mRNA transcripts in which the target site is found.

In certain embodiments an anti-miRNA oligonucleotide is between 8 and 30 nucleotides, e.g., between 8 and 15 or between 15 and 30. In certain embodiments an anti-miRNA oligonucleotide comprises a sequence of at least 6, 7, 8, 9, 10, 11, 12, 13, 14, 15, or more consecutive nucleotides that is at least 90% complementary, e.g., perfectly complementary, to a miRNA to be inhibited.

One of ordinary skill in the art will appreciate that a variety of miRNA inhibitor technologies are available that use various chemical modifications, conjugation, and/or encapsulation/impregnation to enhance the activity of the miRNA inhibitor by, e.g., protecting the miRNA inhibitor from biological degradation and/or clearance, by increasing cell uptake, increasing binding affinity and/or specificity for particular target(s) of interest, etc. Any such technologies may be used in the methods described herein that comprise inhibiting a miRNA. Examples of useful chemical modifications of anti-miRNA oligonucleotides include, e.g., modifications of the nucleic acid backbone, e.g., 2'-modifications of the sugar (ribose or deoxyribose) such as introduction of 2'-O-methyl (2'-O-Me), 2'-O-methoxyethyl groups (2'-MOE), or 2'-fluoro (2'-F). miRNA inhibitor oligonucleotides may harbor phosphorothioate (PS) backbone linkages. Other nucleic acid modifications include use of locked nucleic acids, peptide nucleic acids, or morpholinos. As mentioned above, a nucleic acid (e.g., an anti-miRNA oligonucleotide) may be modified uniformly or on only a portion thereof and/or may contain multiple different modifications. For example, in certain embodiments between 5% and 25%, between 25% and 50%, between 50% and 75%, or between 75% and 100% of the sugars may be modified and/or between 5% and 25%, between 25% and 50%, between 50% and 75%, or between 75% and 100% of the internucleoside linkages may be modified, as compared with the usual structure of sugars or internucleoside linkages in RNA or DNA. Conjugation approaches include conjugation to cholesterol, to N-Acetylgalactosamine (GalNAC), or to ligands for cell surface receptors or other proteins exposed at the surface of target cells of interest (e.g., cancer cells). In some embodiments, such receptors or other cell surface markers (e.g., cell surface-exposed proteins) may be expressed selectively by cancer cells. In some embodiments such receptor or other cell surface marker may be expressed selectively by cells of the type from which the cancer arose (and by the cancer cells). Encapsulation approaches include encapsulating the miRNA inhibitor in lipids (e.g., neutral lipids) or organic polymers. In some embodiments the miRNA inhibitor is encapsulated by or otherwise physically associated with (e.g., attached to), which may be composed at least in part of a lipid or organic polymer. The microparticle or nanoparticle may have a targeting moiety at its surface that targets the particle to cell surface markers on cancer cells.

In some embodiments, a method of treating a subject in need of treatment for cancer comprises (a) determining that the cancer has reduced expression of at least one 19S subunit, wherein the mRNA that encodes the 19S subunit in the cancer has at least one target site for an endogenous miRNA; and (b) administering to the patient a miRNA inhibitor that inhibits activity of the miRNA. In general, the 19S subunit may be any 19S subunit. For example, in some embodiments a cancer is determined to have reduced expression of PSMD5, and the method comprises administering an inhibitor of a miRNA that has a target site in a PSMD5 transcript. In certain embodiments the 19S subunit is PSMD5, PSMD9, PSMD12, PSMD7, PSMD8, PSMD3, PSMD10, PSMD1, PSMD11, PSMD13, PSMD14, PSMD2, PSMC2, PSMC4, or PSMC6. In some embodiments 2, 3, 4, 5, or more miRNA inhibitors that inhibit different miRNA that have target sites in a transcript encoding a particular 19S subunit may be administered. For example in some embodiments 2, 3, 4, 5, or more miRNA inhibitors that inhibit different miRNA that have target sites in PSMD5 transcripts may be administered. In some embodiments two or more miRNA inhibitors that inhibit different miRNAs may be administered. In some embodiments the endogenous miRNA is a member of a miRNA family listed in Table 3. In certain embodiments the miRNA is a member of one of the following miRNA families: miR-4282, miR-570, miR-3120-3p, miR-545, miR-30abcdef/30abe-5p/384-5p, miR-2355-5p, miR-763/1207-3p/1655, miR-802, miR-452/4676-3p, miR-4680-3p, miR-3600/4277.

As described herein, a cancer cell or cancer may have reduced expression of a 19S subunit as a result of methylation within the promoter region of the gene that encodes the subunit. In some embodiments, expression of a 19S subunit whose expression is reduced as a result of promoter methylation may be increased by contacting the cancer cell or cancer with an agent that reduces DNA methylation (a "hypomethylating agent"). In some embodiments the hypomethylating agent is a DNA methyltransferase inhibitor (DNMTi). The term "DNA methyltransferase inhibitor" refers to a compound that inhibits expression or activity of at least one DNA methyltransferase. DNA methyltransferase inhibitors can be classified as nucleoside analogs (e.g., cytidine analogs) and non-nucleoside analogs. In some embodiments the cytidine analog is azacitidine (also known as 5-azacitidine), its deoxy derivative, decitabine (also known as 5-aza-2'deoxycytidine), zebularine, 5-fluoro-2'-deoxycytidine (5-F-CdR), 5,6-dihydro-5-azacytidine (DHAC)) or a prodrug of any of these. In some embodiments the DNMTi is guadecitabine (SGI-110), a hypomethylating prodrug whose active metabolite is decitabine. Guadecitabine is a dinucleotide in which decitabine is linked through a phosphodiester bond to deoxyguanosine. In some embodiments the agent is a 2'-deoxycytidine analog with 4'-thio and/or other modifications (US Pat. App. Pub. No. 20110218170). Non-nucleoside DNA methyltransferase inhibitors include hydralazine, procainamide, N-acetylprocainamide, procaine, EGCG ((−)-epigallocatechin-3-gallate), laccaic acid, psammaplin A, MG98, RG108, and analogs of any of these. In some embodiments the non-nucleoside DNMTi is a quinolone-based compound such as SGI-1027 (N-(4-(2-amino-6-methylpyrimidin-4-ylamino) phenyl)-4-(quinolin-4-ylamino)benzamide) or an analog thereof. For example, certain analogs of SGI-1027 are described in Rilova, E., et al., ChemMedChem. 2014; 9(3): 590-601. In some embodiments the DNMTi is an oligonucleotide that inhibits expression of DNMT1, DNMT3A, and/or DNMT3B. For example, US Pat. App. Pub. No. 20150167004 discloses oligonucleotide DNMT inhibitors that contains at least one modified CpG dinucleotide target sequence for DNMT, in which the CpG is modified by replacing the cytosine (C) in one strand by a cytosine analogue and the C in the opposite strand is either unmodified or it is replaced by methylated cytosine (such as 5-methylcytosine) to create a hemi-methylated target for DNMT In some embodiments the oligonucleotide is an siRNA that inhibits expression of DNMT1, DNMT3A, or DNMT3B. In some embodiments the DNMTi is a siRNA that inhibits expression of DNMT1, DNMT3A, and/or DNMT3B.

In certain embodiments expression of a 19S subunit in a proteasome inhibitor resistant cancer that exhibits reduced expression of a 19S subunit may be increased by administering translatable RNA or translatable modified RNA to the subject, wherein the RNA encodes the 19S subunit.

As used herein, a "subject" is a mammal, including but not limited to a primate (e.g., a human), rodent (e.g., mouse or rat) dog, cat, horse, cow, pig, sheep, goat, chicken. Preferred subjects are human subjects. The human subject may be a pediatric or adult subject. In some embodiments the adult subject is a geriatric subject. Whether a subject is deemed "at risk" of having or developing cancer or recurrence of cancer is a determination that may be within the discretion of the skilled practitioner caring for the subject. Any suitable diagnostic test and/or criteria can be used. For example, a subject may be considered "at risk" of having or developing cancer if (i) the subject has a mutation, genetic polymorphism, gene or protein expression profile, and/or presence of particular substances in the blood, associated with increased risk of developing or having cancer relative to other members of the general population not having mutation or genetic polymorphism; (ii) the subject has one or more risk factors such as having a family history of cancer, having been exposed to a carcinogen or tumor-promoting agent or condition, e.g., asbestos, tobacco smoke, aflatoxin, radiation, chronic infection/inflammation, etc., advanced age; (iii) the subject has one or more symptoms of cancer, (iv) the subject has a medical condition that is known to increase the likelihood of cancer, etc. For example, monoclonal gammopathy of undetermined significance (MGUS) is a condition in which a paraprotein is present in the blood but the levels of antibody and the number of plasma cells in the bone marrow are lower than in multiple myeloma and there are no symptoms. MGUS may progress to multiple myeloma, Waldenstrom's macroglobulinemia, primary amyloidosis, B-cell lymphoma, or chronic lymphocytic leukemia.

In some embodiments, if the agent is one that has been previously (prior to the present disclosure) administered to subjects for purposes other than treating cancer or disclosed to be useful for administration to subjects for purposes other than treating cancer, e.g., for treatment of a condition other than cancer, the subject is not one to whom the compound would normally be administered for such other purpose and/or the compound is administered in a formulation or at a dose distinct from that known in the art to be useful for such other purpose.

As used herein "treatment" or "treating", in reference to a subject, includes amelioration, cure, and/or maintenance of a cure (i.e., the prevention or delay of relapse and/or reducing the likelihood of recurrence) of a disorder (e.g., cancer). Treatment after a disorder has started aims to reduce, ameliorate or altogether eliminate the disorder, and/or its associated symptoms, to prevent it from becoming worse, to slow the rate of progression, or to prevent the disorder from re-occurring once it has been initially eliminated (i.e., to prevent a relapse). Treating encompasses administration of an agent that may not have an effect on the disorder by itself but increases the efficacy of a second agent administered to the subject. A suitable dose and therapeutic regimen may vary depending upon the specific agent used, the mode of delivery of the compound, and whether it is used alone or in combination.

As used herein, in the context of treatment for cancer, a therapeutically effective amount generally refers to an amount of an agent that inhibits formation, progression, proliferation, growth and/or spread (e.g., metastasis) of a cancer cell or cancer and/or enhances the ability of a second agent (e.g., a proteasome inhibitor) to inhibit formation, progression, proliferation, growth and/or spread (e.g., metastasis) of a cancer cell or cancer. In some embodiments, a therapeutically effective amount is an amount of an agent sufficient to inhibit proliferation of a cancer cell. In some embodiments, a therapeutically effective amount is an amount of an agent sufficient to inhibit proliferation of a cancer cell that has been exposed to or is exposed to a proteasome inhibitor. In some embodiments, a therapeutically effective amount is an amount of an agent sufficient to reduce (e.g. by at least 5%, 10%, 20%, 25%, 30%, 40%, 50%, 60%, 70%, 80%, 90%, or more) the likelihood that a cell exposed to a proteasome inhibitor for a selected period of time will acquire increased resistance to the proteasome inhibitor or that a subject treated with a proteasome inhibitor for a cancer that is sensitive to the proteasome inhibitor will develop a proteasome inhibitor resistant cancer (e.g., a recurrence of the cancer that has acquired proteasome inhibitor resistance) over a selected time period. The selected period of time may be, e.g., between 1 week and 2 years. The cell or subject may be exposed to or treated with the proteasome inhibitor continuously or intermittently during the time period.

A therapeutically effective amount can refer to any one or more of the agents or compositions described herein, or discovered using the methods described herein, that inhibit the survival and/or proliferation of cancer cells (e.g., selectively inhibits the survival or proliferation of proteasome inhibitor resistant cancer cells), that increase the sensitivity of a cancer cell to a proteasome inhibitor, and/or that reduces the likelihood of a cancer acquiring proteasome inhibitor resistance (e.g., as evidenced by treatment failure).

In some embodiments, a therapeutically effective amount is an amount of an agent sufficient to increase the expression or activity of a 19S subunit in a cell by at least 5%, e.g., by at least 10%, 20%, 30%, 40%, 50%, 60%, 70%, 80%, 90%, or 100% (i.e., a 2-fold increase), e.g., by between 25% and 100%. In some embodiments, a therapeutically effective amount increases the expression or activity of a 19S subunit in a cell by at least 3-fold, 5-fold, 10-fold, 25-fold, 50-fold, or more. In some embodiments, a therapeutically effective amount increases the expression or activity of a 19S subunit in a cell that has a reduced level of expression or activity of said subunit to a normal level. In some embodiments, a therapeutically effective amount increases the expression or activity of a 19S subunit in a cell that has a reduced level of expression or activity of said subunit by at least 5%, 10%, 20%, 30%, 40%, 50%, 60%, 70%, 80%, 90%, or 100% of a normal level.

In some aspects, as described herein, although a modest and/or transient reduction in expression of a 19S subunit is associated with proteasome inhibitor resistance, complete knockout of expression of a 19S subunit can kill a cell. It is expected that an agent that causes a sufficiently strong reduction in the level of expression or activity of a 19S subunit will kill cancer cells or at least inhibit their proliferation and will therefore be useful in treating cancer. Thus in some aspects, described herein is a method of killing or inhibiting proliferation of a cancer cell comprising contacting the cancer cell with an agent that reduces the level of expression or activity of a 19S subunit. The agent should be capable of reducing the level of expression or activity of the 19S subunit sufficiently to kill the cell or inhibit its proliferation. In some embodiments, the agent reduces the level of expression or activity of the 19S subunit in the cancer cell to less than about 10% or, in some embodiments, less than about 5%, of the level found in a normal cell. In some embodiments, the agent reduces the level of expression or activity of the 19S subunit in the cancer cell by at least a factor of 5, at least a factor of 10, or at least a factor of 20. In some embodiments the cancer cell is a proteasome inhibitor sensitive cell. In some embodiments the cancer cell is a proteasome inhibitor resistant cell. In some embodiments the proteasome inhibitor resistance is associated with reduced expression of a first 19S subunit, and the agent inhibits expression or activity of that subunit such that the level of expression or activity of the subunit is decreased sufficiently to kill the cell or inhibit its proliferation. In some embodiments the proteasome inhibitor resistance is associated with reduced expression of a first 19S subunit, and the agent inhibits expression or activity of a different subunit such that the level of expression or activity of that subunit is decreased sufficiently to kill the cell or inhibit its proliferation. In some embodiments the agent that inhibits expression or activity of a 19S subunit is contacted with the cancer cell in combination with a proteasome inhibitor.

In some aspects, described herein is a method of treating cancer comprising administering an agent that reduces the level of expression or activity of a 19S subunit to a subject in need of treatment of cancer. The agent should be capable of reducing the level of expression or activity of the 19S subunit sufficiently to kill or inhibit proliferation of cancer cells. In some embodiments, the agent reduces the level of expression or activity of the 19S subunit to less than about 10% or, in some embodiments, less than about 5%, of the level found in normal cells. In some embodiments, the agent reduces the level of expression or activity of the 19S subunit in the cancer cell by at least a factor of 5, at least a factor of 10, or at least a factor of 20. In some embodiments the cancer is a proteasome inhibitor sensitive cell. In some embodiments the cancer is a proteasome inhibitor resistant cancer. In some embodiments the proteasome inhibitor resistance is associated with reduced expression of a first 19S subunit in cancer cells of the cancer, and the agent inhibits expression or activity of that subunit such that the level of expression or activity of the subunit is decreased sufficiently to kill or inhibit proliferation of such cells. In some embodiments the proteasome inhibitor resistance is associated with reduced expression of a first 19S subunit in cancer cells of the cancer, and the agent inhibits expression or activity of a different subunit such that the level of expression or activity of that subunit is decreased sufficiently to kill or inhibit proliferation of the cancer cells. In some embodiments the agent that inhibits expression or activity of a 19S subunit is administered in combination with a proteasome inhibitor.

Methods for establishing a therapeutically effective amount for any agents or compositions described herein will be known to one of ordinary skill in the art. The effective amount can vary depending on such factors as the cancer being treated, the particular compound being administered, the size of the subject, or the severity of the disease or condition. One of ordinary skill in the art can empirically determine the effective amount of a particular agent without undue experimentation. In light of the teachings provided herein, by choosing among the various active compounds and weighing factors such as potency, relative bioavailability, patient body weight, severity of adverse side-effects and preferred mode of administration, an effective prophylactic or therapeutic treatment regimen can be planned with the goal of avoiding substantial toxicity and yet effective to treat the particular subject. In some embodiments a useful agent or composition increases the average length of survival, increases the average length of progression-free survival, increases the 1-year, 2-year, 3-year, or 5-year survival rate of subjects with cancer and/or reduces the rate of recurrence of cancer of subjects treated with the compound in a statistically significant manner. As used herein, "statistically significant" refers to a p-value of less than 0.05, e.g., a p-value of less than 0.025 or a p-value of less than 0.01, using an appropriate statistical test (e.g., ANOVA, t-test, etc.).

Subject doses of agents described herein typically range from about 0.1 µg to 10,000 mg, more typically from about 1 µg to 8000 mg, e.g., from about 10 µg to 100 mg or from 100 mg to about 500 mg, once or more per day, week, month, or other time interval. Stated in terms of subject body weight, typical dosages in certain embodiments may range from about 0.1 µg/kg/day to 20 mg/kg/day, e.g., from about 1 to 10 mg/kg/day, e.g., from about 1 to 5 mg/kg/day. It will be appreciated that dosages can be expressed in terms of mass of the agent per surface area of the subject (e.g., mg/m$^2$). In certain embodiments a reduced dose may be used when two or more agents are administered in combination either concomitantly or sequentially. The absolute amount will depend upon a variety of factors including other treatment, the number of doses and the individual patient parameters including age, physical condition, size and weight. These are factors well known to those of ordinary skill in the art and can be addressed with no more than routine experimentation. In some embodiments, a maximum tolerated dose may be used, that is, the highest safe and tolerable dose according to sound medical judgment.

The dose used may be the maximal tolerated dose or a sub-therapeutic dose or any dose therebetween. Multiple doses of agents described herein are contemplated. In some embodiments, when agents are administered in combination a sub-therapeutic dosage of one or more of the agents may be used in the treatment of a subject having, or at risk of developing, cancer. A "sub-therapeutic dose" as used herein refers to a dosage which is less than that dosage which would produce a therapeutic result in the subject if administered in the absence of the other agent. In some aspects, a sub-therapeutic dose of an anticancer agent (e.g., a proteasome inhibitor) is one which would not produce a useful therapeutic result in the subject in the absence of the administration of an agent described herein that inhibits proteasome inhibitor resistance. Therapeutic doses of anticancer agents are well known in the field of medicine for the treatment of cancer.

As used herein, pharmaceutical compositions comprise one or more agents or compositions that have therapeutic utility, and a pharmaceutically acceptable carrier, e.g., a carrier that facilitates delivery of agents or compositions. Agents and pharmaceutical compositions disclosed herein may be administered by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or as an aerosol. Depending upon the type of condition (e.g., cancer) to be treated, compounds of the invention may, for example, be inhaled, ingested or administered by systemic routes. Thus, a variety of administration modes, or routes, are available. The particular mode selected will typically depend on factors such as the particular compound selected, the particular condition being treated and the dosage required for therapeutic efficacy. The methods described herein, generally speaking, may be practiced using any mode of administration that is medically acceptable, meaning any mode that produces acceptable levels of efficacy without causing clinically unacceptable adverse effects. Preferred modes of administration are parenteral and oral routes. The term "parenteral" includes subcutaneous, intravenous, intramuscular, intraperitoneal, and intrasternal injection, or infusion techniques. In some embodiments, inhaled medications are of particular use because of the direct delivery to the lung, for example in lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. In some embodiments agents are delivered by pulmonary aerosol. Other appropriate routes will be apparent to one of ordinary skill in the art.

Agents described herein may be administered in a pharmaceutical composition. In addition to the active agent, the pharmaceutical compositions typically comprise a pharmaceutically-acceptable carrier. The term "pharmaceutically-acceptable carrier", as used herein, means one or more compatible solid or liquid vehicles, fillers, diluents, or encapsulating substances which are suitable for administration to a human or non-human animal. In preferred embodiments, a pharmaceutically-acceptable carrier is a non-toxic material that does not interfere with the effectiveness of the biological activity of the active ingredients. The term "compatible", as used herein, means that the components of the pharmaceutical compositions are capable of being comingled with an agent, and with each other, in a manner such that there is no interaction which would substantially reduce the pharmaceutical efficacy of the pharmaceutical composition under ordinary use situations. Pharmaceutically-acceptable carriers should be of sufficiently high purity and sufficiently low toxicity to render them suitable for administration to the human or non-human animal being treated.

Some examples of substances which can serve as pharmaceutically-acceptable carriers are pyrogen-free water; isotonic saline; phosphate buffer solutions; sugars such as lactose, glucose, and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobrama; polyols such as propylene glycol, glycerin, sorbitol, mannitol, and polyethylene glycol; sugar; alginic acid; cocoa butter (suppository base); emulsifiers, such as the Tweens; as well as other non-toxic compatible substances used in pharmaceutical formulation. Wetting agents and lubricants such as sodium lauryl sulfate, as well as coloring agents, flavoring agents, excipients, tableting agents, stabilizers, antioxidants, and preservatives, can also be present. It will be appreciated that a pharmaceutical composition can contain multiple different pharmaceutically acceptable carriers.

A pharmaceutically-acceptable carrier employed in conjunction with the compounds described herein is used at a concentration or amount sufficient to provide a practical size to dosage relationship. The pharmaceutically-acceptable carriers, in total, may, for example, comprise from about 60% to about 99.99999% by weight of the pharmaceutical compositions, e.g., from about 80% to about 99.99%, e.g., from about 90% to about 99.95%, from about 95% to about 99.9%, or from about 98% to about 99%.

Pharmaceutically-acceptable carriers suitable for the preparation of unit dosage forms for oral administration and topical application are well-known in the art. Their selection will depend on secondary considerations like taste, cost, and/or shelf stability, which are not critical for the purposes of the subject invention, and can be made without difficulty by a person skilled in the art.

Pharmaceutically acceptable compositions can include diluents, fillers, salts, buffers, stabilizers, solubilizers and other materials which are well-known in the art. The choice of pharmaceutically-acceptable carrier to be used in conjunction with the compounds of the present invention is basically determined by the way the compound is to be administered. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof in certain embodiments. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. It will also be understood that a compound can be provided as a pharmaceutically acceptable pro-drug, or an active metabolite can be used. Furthermore it will be appreciated that agents may be modified, e.g., with targeting moieties, moieties that increase their uptake, biological half-life (e.g., pegylation), etc.

The agents may be administered in pharmaceutically acceptable solutions, which may routinely contain pharmaceutically acceptable concentrations of salt, buffering agents, preservatives, compatible carriers, adjuvants, and optionally other therapeutic ingredients.

The agents may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

In some embodiments, agents may be administered directly to a tissue, e.g., a tissue in which the cancer cells are found or one in which a cancer is likely to arise. Direct tissue administration may be achieved by direct injection. The agents may be administered once, or alternatively they may be administered in a plurality of administrations. If administered multiple times, the agents may be administered via different routes. For example, the first (or the first few) administrations may be made directly into the affected tissue while later administrations may be systemic.

For oral administration, compositions can be formulated readily by combining the active agent(s) with pharmaceutically acceptable carriers well known in the art. Such carriers enable the agents to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration. For buccal administration, the compositions may take the form of tablets or lozenges formulated in conventional manner.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In certain embodiments, the preferred vehicle is a biocompatible microparticle or implant that is suitable for implantation into the mammalian recipient. Exemplary bioerodible implants that are useful in accordance with this method are described in PCT International Application Publication No. WO 95/24929, entitled "Polymeric Gene Delivery System", which reports on a biodegradable polymeric matrix for containing a biological macromolecule. The polymeric matrix may be used to achieve sustained release of the agent in a subject. In some embodiments, an agent described herein may be encapsulated or dispersed within a biocompatible, preferably biodegradable polymeric matrix. The polymeric matrix may be in the form of a microparticle such as a microsphere (wherein the agent is dispersed throughout a solid polymeric matrix) or a microcapsule (wherein the agent is stored in the core of a polymeric shell). Other forms of polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the peptide, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for prophylactic treatment of subjects at risk of developing a recurrent cancer. Long-term release, as used herein, means that the implant is constructed and arranged to delivery therapeutic levels of the active agent for at least 30 days, and preferably 60 days. Long-term sustained release implants are well-known to those of ordinary skill in the art and include some of the release systems described above.

In some embodiments, it may be advantageous to formulate oral or parenteral compositions in dosage unit form for ease of administration and uniformity of dosage. Unit dosage form as used herein refers to physically discrete units suited as unitary dosages for the subject to be treated; each unit containing a predetermined quantity of active compound calculated to produce the desired therapeutic effect in association with the required pharmaceutical carrier.

If desired, toxicity and therapeutic efficacy of an agent or combination of agents can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. In some embodiments, a compound that exhibits a high therapeutic index may be selected. The data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in a method of treatment, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

Generally, treatment of a subject can include a single treatment or, in many cases, can include a series of treatments. A pharmaceutical composition can be administered at various intervals and over different periods of time as required, e.g., multiple times per day, daily, every other day, once or more a week for between about 1 to 10 weeks, between 2 to 8 weeks, between about 3 to 7 weeks, about 4, 5, or 6 weeks, etc. It will be appreciated that multiple cycles of administration may be performed. Numerous variations are possible. The skilled artisan will appreciate that certain factors can influence the dosage and timing required to effectively treat a subject, including but not limited to the severity of the disease or disorder, previous treatments, the general health and/or age of the subject, and other diseases present.

In some aspects, described herein are methods comprising administering to a subject therapeutically effective amounts of a proteasome inhibitor and an inhibitor of proteasome inhibitor resistance. "Administered in combination" means that two or more agents are administered to a subject. Such administration is sometimes referred to herein as "combination therapy", "combined administration", or "coadministration". The agents may be administered in the same composition or separately. When they are coadministered, agents may be administered simultaneously or sequentially and in either instance, may be administered separately or in the same composition, e.g., a unit dosage form that includes both a proteasome inhibitor and an inhibitor of proteasome inhibitor resistance. When administered separately, the agents may be administered in any order, provided that they are given sufficiently close in time to have a desired effect such as, e.g., inhibiting cancer cell proliferation or survival. For example, a proteasome inhibitor and an inhibitor of proteasome inhibitor resistance may be administered to a subject sufficiently close together in time so as to increase the sensitivity of cancer cells in the subject to the proteasome inhibitor. "Therapeutically effective amounts" of agents administered in combination means that the amounts administered are therapeutically effective at least when the agents are administered in combination or as part of a treatment regimen that includes the agents and one or more additional agents. In some embodiments, administration in combination of first and second agents (e.g., a proteasome inhibitor and an inhibitor of proteasome inhibitor resistance), is performed such that (i) a dose of the second agent is administered before more than 90% of the most recently administered dose of the first agent has been metabolized to an inactive form or excreted from the body; or (ii) doses of the first and second agent are administered within 48 hours of each other, or (iii) the agents are administered during overlapping time periods (e.g., by continuous or intermittent infusion); or (iv) any combination of the foregoing. In some embodiments, three or more agents are administered and the afore-mentioned criteria are met with respect to all agents, or in some embodiments, the criteria are met if each agent is considered a "second agent" with respect to at least one other agent of the combination. In some embodiments, agents may be administered individually at substantially the same time (e.g., within less than 1, 2, 5, or 10 minutes of one another). In some embodiments they may be administered individually within a short time of one another (by which is meant less than 3 hours, sometimes less than 1 hour, sometimes within 10 or 30 minutes apart). In some embodiments, agents may be administered one or more times within 1, 2, 3, 4, 5, or 6 weeks of each other. In certain embodiments of combination therapy, the first agent is administered during the entire course of administration of the second agent; where the first agent is administered for a period of time that is overlapping with the administration of the second agent, e.g. where administration of the first agent begins before the administration of the second agent and the administration of the first agent ends before the administration of the second agent ends; where the administration of the second agent begins before the administration of the first agent and the administration of the second agent ends before the administration of the first agent ends; where the administration of the first agent begins before administration of the second agent begins and the administration of the second agent ends before the administration of the first agent ends; where the administration of the second agent begins before administration of the first agent begins and the administration of the first agent ends before the administration of the second agent ends. In some embodiments, agents may be administered in alternate weeks. The agents may, but need not, be administered by the same route of administration. A treatment course might include one or more treatment cycles, each of which may include one or more doses of a first agent, e.g., a proteasome inhibitor, and one or more doses of a second agent, e.g., an agent that inhibits proteasome inhibitor resistance. In some embodiments, an inhibitor of proteasome inhibitor resistance may be added to any chemotherapy regimen that includes a proteasome inhibitor.

Certain aspects of the present disclosure encompasses gene therapy, in which a nucleic acid vector that encodes a therapeutic effector agent, e.g., a therapeutic nucleic acid or a therapeutic polypeptide, operably linked to regulatory elements sufficient to direct expression of the operably linked nucleic acid, is introduced into a subject. Nucleic acids can be introduced into a subject by any of a number of methods. For instance, a pharmaceutical preparation of a nucleic acid (e.g., a nucleic acid vector) can be introduced systemically, e.g., by intravenous injection. Expression of the nucleic acid in particular target cells may result from specificity of transfection provided by the vector (e.g., cell tropism of a virus or viral capsid), cell-type or tissue-type expression due to the transcriptional regulatory sequences controlling expression of the gene, or a combination thereof. Alternatively, initial delivery of the nucleic acid can be more limited. For example, a genetic vector can be locally administered.

A pharmaceutical composition can comprise a nucleic acid or a genetic vector in an acceptable diluent or carrier, or can comprise a slow release matrix in which the nucleic acid or genetic vector is encapsulated, entrapped, or embedded. The genetic vector can be a plasmid, virus, or other vector. Alternatively, the pharmaceutical composition can comprise one or more cells which produce a therapeutic nucleic acid or polypeptide. Preferably such cells secrete the nucleic acid or polypeptide into the extracellular space or bloodstream.

Viral vectors that are of use include, but are not limited to, retroviruses, lentiviruses, other RNA viruses such as poliovirus or Sindbis virus, adenovirus, adeno-associated virus, herpes viruses, SV 40, vaccinia and other DNA viruses. Replication-defective murine retroviral or lentiviral vectors are widely utilized gene transfer vectors. Chemical methods of gene delivery can involve carrier-mediated gene transfer through the use of fusogenic lipid vesicles such as liposomes or other vesicles for membrane fusion. A carrier harboring a nucleic acid of interest can be introduced into the vascular system or other body fluids or administered locally. The carrier can be site specifically directed to a target organ or tissue in the body. Cell or organ-specific DNA-carrying liposomes, for example, can be developed and the foreign nucleic acid carried by the liposome becomes attached to or taken up by those specific cells. Carrier mediated gene transfer may also involve the use of lipid-based compounds which are not liposomes. For example, lipofectins and cytofectins are lipid-based compounds containing positive ions that bind to negatively charged nucleic acids and form a complex that can ferry the nucleic acid across a cell membrane. Cationic polymers are known to spontaneously bind to and condense nucleic acids such as DNA into nanoparticles. For example, naturally occurring proteins, peptides, or derivatives thereof have been used. Synthetic cationic polymers such as polyethylenimine (PEI), polylysine (PLL) etc., are also known to condense DNA and are useful delivery vehicles. Dendrimers can also be used.

Many of the useful polymers contain both chargeable amino groups, to allow for ionic interaction with the negatively charged DNA phosphate, and a degradable region, such as a hydrolyzable ester linkage. Examples of these include poly(alpha-(4-aminobutyl)-L-glycolic acid), network poly(amino ester), and poly (beta-amino esters). These complexation agents can protect DNA against degradation, e.g., by nucleases, serum components, etc., and create a less negative surface charge, which may facilitate passage through hydrophobic membranes (e.g., cytoplasmic, lysosomal, endosomal, nuclear) of the cell. Certain complexation agents facilitate intracellular trafficking events such as endosomal escape, cytoplasmic transport, and nuclear entry, and can dissociate from the nucleic acid.

In some embodiments an agent that inhibits proteasome inhibitor resistance is administered in combination with another treatment for cancer. In some embodiments an agent that inhibits proteasome inhibitor resistance is administered in combination with a proteasome inhibitor and another treatment for cancer. The terms "chemotherapeutic agent" or "anticancer agent" are used interchangeably to refer to a compound or composition that is administered in the treatment of cancer. Chemotherapeutic agents useful in methods, compositions, and/or kits disclosed herein include, but are not limited to, alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, bendamustine, chlorozotocin, fotemustine, lomustine, nimustine, ranimustine; antibiotics such as aclacinomysins, actinomycin, authramycin, azaserine, bleomycins, dactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; antiadrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside (Ara-C); taxoids, e.g. paclitaxel and docetaxel; chlorambucil; gemcitabine; 6-thioguanine; mercaptopurine; platinum analogs such as cisplatin and carboplatin; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine; retinoic acid; esperamicins; capecitabine; and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide, and irinotecan, as well as pharmaceutically acceptable salts, acids, or derivatives of any of these. In some embodiments, the chemotherapeutic agent is an antimetabolite. An anti-metabolite is a chemical with a structure that is similar to a metabolite required for normal biochemical reactions, yet different enough to interfere with one or more normal functions of cells, such as cell division. Antimetabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain e embodiments, the antimitotic agent comprises a *vinca* alkaloid, such as vincristine, binblastine, vinorelbine, or vindesine, or pharmaceutically acceptable salts, acids, or derivatives thereof. In some embodiments the chemotherapeutic agent is an angiogenesis inhibitor, e.g., an anti-VEGF agent such as avastin or aflibercept.

In some embodiments the chemotherapeutic agent is thalidomide, an immunomodulatory agent that has been approved by the FDA for treatment of multiple myeloma, one or more types of lymphoma, or both.

In some embodiments the chemotherapeutic agent is lenalidomide, an immunomodulatory agent that has been approved by the FDA for treatment of MM, deletion 5q myelodysplastic syndrome, and mantle cell lymphoma. In some embodiments lenalidomide is administered to a subject in need of treatment for one of the afore-mentioned diseases in combination with an inhibitor of proteasome inhibitor resistance described herein.

In some embodiments, a method includes administering a proteasome inhibitor, an agent that inhibits proteasome inhibitor resistance, and a chemotherapeutic agent or chemotherapy regimen suitable for treatment of MM and/or NHL to a subject in need thereof.

In some embodiments the chemotherapeutic agent binds to a cell surface marker expressed by cancer cells. For example, the chemotherapeutic agent may be rituximab, a chimeric monoclonal antibody that binds to the protein CD20, which is primarily found on the surface of immune system B cells. Rituximab destroys B cells and is therefore used to treat diseases which are characterized by excessive numbers of B cells, including B cell lymphomas and B cell leukemias.

In some embodiments, the method includes administering a targeted anticancer therapy. The expression "targeted cancer therapy" includes the use of therapeutic agents that can alter the expression and/or activation state of proteins or other molecules that are deregulated (e.g., mutated or overexpressed) in a disease state, e.g., cancer. The skilled artisan will be able to readily determine suitable targeted inhibitor therapies based, e.g., on the type of cancer to be treated and/or the presence of particular mutations or dysregulated expression levels of a particular protein or molecule in the cancer, the presence of which can be determined using methods known in the art. In certain embodiments a targeted inhibitor therapy comprises a kinase inhibitor that inhibits activity of a kinase that is mutated or overexpressed in the cancer or that is known to contribute to dysregulated growth of the cancer. In some embodiments the targeted anticancer therapy is a monoclonal antibody, e.g., Herceptin.

In some embodiments the method includes administering an immune checkpoint inhibitor, e.g., an antibody that binds to PD-1, PD-L1, CTLA-4, or another immune checkpoint protein.

In some aspects, pharmaceutical compositions comprising two or more agents described herein are provided. For example, in some embodiments a pharmaceutical composition comprises therapeutically effective amounts of a proteasome inhibitor and a BCL2 family inhibitor. In some embodiments a pharmaceutical composition comprises therapeutically effective amounts of a proteasome inhibitor and an ALDH inhibitor and a bis(thio-hydrazide amide), e.g., elesclomol. In some embodiments a pharmaceutical composition comprises In some embodiments a pharmaceutical composition comprises therapeutically effective amounts of a BCL2 family inhibitor and an ALDH inhibitor. In some embodiments a pharmaceutical composition comprises therapeutically effective amounts of a BCL2 family inhibitor and a bis(thio-hydrazide amide), e.g., elesclomol.

VIII. Compositions and Methods Relating to Compounds that Inhibit Proteasome Inhibitor Resistance In some aspects, the present disclosure provides compounds that selectively inhibit growth of cancer cells that have reduced expression of one or more 19S proteasome subunits as compared to their ability to inhibit growth of control cells (cells that do not have reduced expression of such 19S subunit(s) but are otherwise similar). In some aspects, the compounds selectively inhibit growth of cancer cells that are proteasome inhibitor resistant as compared to their ability to inhibit growth of control cells (cells that are proteasome inhibitor sensitive but otherwise similar). In some aspects, the compounds increase proteasome inhibitor sensitivity of cancer cells that are proteasome inhibitor resistant. In some aspects, the compounds restore proteasome inhibitor sensitivity to cancer cells that have acquired proteasome inhibitor resistance and/or inhibit the acquisition of proteasome inhibitor resistance by cancer cells that are proteasome inhibitor sensitive.

In some aspects, the disclosure provides compounds that selectively inhibit growth of cancer cells characterized by reduced expression or activity of one or more 19S subunits. In some aspects, the disclosure provides methods of using such compounds to inhibit the growth of cancer cells characterized by reduced expression or activity of one or more 19S subunits and/or to treat cancers characterized by reduced expression or activity of one or more 19S subunits. In some aspects, the present disclosure provides the insight that reduced expression or activity of 19S subunit(s), e.g., PSMD5, is associated with increased sensitivity of cancer cells to a variety of different agents. In some aspects, the present disclosure provides the insight that increased resistance to proteasome inhibitors is associated with increased sensitivity of cancer cells to a variety of different agents. In some aspects, this increased sensitivity provides new methods of treating cancers characterized by proteasome inhibitor resistance. In some aspects, the proteasome inhibitor resistant state and/or the mechanisms that give rise to a proteasome inhibitor resistant state (e.g., reduced absolute or relative expression of one or more 19S subunits and/or the mechanisms that result in reduced absolute or relative expression of one or more 19S subunit) produce new vulnerabilities in cancer cells. These new vulnerabilities can be exploited to effectively treat proteasome inhibitor resistant cancers and/or other cancers in which such mechanisms are operative. For example, as described herein, proteasome inhibitor resistant cancer cells are highly sensitive to ABT-263, disulfiram, and elesclomol, as compared to proteasome inhibitor sensitive counterpart cells.

In some aspects, the present disclosure provides the insight that biomarkers that can identify proteasome inhibitor resistant cancer cells or cancers can additionally or alternately be used to identify cancer cells and/or cancers that are susceptible to a variety of agents. For example, detecting reduced expression or activity of one or more 19S subunits can be used to identify cancer cells and cancers that are proteasome inhibitor resistant. In some aspects, detecting reduced expression or activity of one or more 19S subunits can additionally or alternately be used to identify cancer cells and/or cancers that are sensitive to any of a variety of agents described herein, e.g., ABT-263, disulfiram, elesclomol, or analogs, prodrugs, active metabolites, of any of these, and/or other compounds that act on the same biological target or process as any of these agents. In some aspects, a subject in need of treatment for a cancer that has been determined to have reduced expression or activity of one or more 19S subunits may be treated with any of a variety of agents described herein, e.g., ABT-263, disulfiram, elesclomol, or analogs, prodrugs, active metabolites, of any of these, and/or other compounds that act on the same biological target or process as any of these agents. In some aspects, a subject in need of treatment for a cancer that has been determined to have reduced expression or activity of one or more 19S subunits may be treated with a BCL2 family inhibitor, an ALDH inhibitor, or both. In some embodiments the subject may be treated with a BCL2 family inhibitor and a proteasome inhibitor. In some embodiments the subject may be treated with an ALDH inhibitor and a proteasome inhibitor. In some aspects, a subject in need of treatment for a cancer that has been determined to have increased methylation of the promoter region of one or more 19S subunits (e.g., PSMD5) may be treated with any of a variety of agents described herein, e.g., ABT-263, disulfiram, elesclomol, or analogs, prodrugs, active metabolites, of any of these, and/or other compounds that act on the same biological target or process as any of these agents. In some aspects, a subject in need of treatment for a cancer that has been determined to have increased methylation of the promoter region of one or more 19S subunits (e.g., PSMD5) may be treated with a BCL2 family inhibitor, an ALDH inhibitor, or both. In some embodiments the subject may be treated with a BCL2 family inhibitor and a proteasome inhibitor. In some embodiments the subject may be treated with an ALDH inhibitor and a proteasome inhibitor.

As described in the Examples, a screen of the Selleck anti-cancer compound library identified ABT-263 as a compound that selectively inhibits growth of T47D cancer cells that have a reduced level of PSMD2 as compared to control T47D cancer cells. ABT-263 is an inhibitor of BCL2 (B-cell CLL/lymphoma 2) and certain other members of the BCL2 family of proteins. In some aspects, the present disclosure provides the recognition that BCL2 family inhibitors can selectively inhibit proliferation of or kill proteasome inhibitor resistant cancer cells as compared to their proteasome inhibitor sensitive counterparts. The disclosure further provides the recognition that BCL2 family inhibitors can restore proteasome inhibitor sensitivity to proteasome inhibitor resistant cancer cells.

In some aspects, a BCL2 family inhibitor and a proteasome inhibitor exhibit an additive effect. As used herein, the term "synergy" refers to the ability of two or more agents to produce a combined effect greater than the sum of their separate effects. In some aspects, a BCL2 family inhibitor and a proteasome inhibitor exhibit synergy. For example, in some embodiments, contacting cancer cell(s) that have reduced expression or activity of at least one 19S proteasome subunit with a BCL2 family inhibitor and a proteasome inhibitor has a synergistic effect, e.g., in regard to inhibiting growth (reducing survival or proliferation) of the cancer cell(s). In some embodiments, contacting proteasome resistant cancer cell(s) with a BCL2 family inhibitor and a proteasome inhibitor has a synergistic effect, e.g., in regard to inhibiting growth (reducing survival or proliferation) of the cancer cell(s). In some embodiments, contacting a proteasome resistant cancer cell with a BCL2 family inhibitor and a proteasome inhibitor has a synergistic effect in regard to killing the cancer cell(s). In some embodiments a BCL2 family inhibitor and a proteasome inhibitor have an additive or synergistic effect in regard to killing cancer cell(s) that have reduced expression or activity of at least one 19S proteasome subunit. In some embodiments a BCL2 family inhibitor and a proteasome inhibitor have an additive or synergistic effect in regard to inhibiting tumor growth, causing tumor growth delay, or causing tumor regression. In some embodiments, whether or not an additive or synergistic effect exists may be assessed using the Bliss independence model (M. Wong, M., et al. Mol. Cancer Ther. 11, 1026-1035 (2012); Berenbaum, M C, et al. Adv. Cancer Res. 35, 269-335 (1981); Borisy, A A, et al. Proc. Natl. Acad. Sci. U.S.A. 100, 7977-7982 (2003), Leverson, J D et al (cited below), According to this model, the Bliss expectation is calculated with the equation (A+B)−A×B, in which A and B are the fractional growth inhibitions induced by agents A and B, respectively, at a given concentration or dose. The difference between the Bliss expectation and the observed growth inhibition induced by the combination of agent A and B at the same dose is the Bliss score. Negative Bliss score values indicate antagonism, a value of zero indicates additive activity, and positive values indicate synergy. In some embodiments, whether or not an additive or synergistic effect exists may be assessed using the combination index (CI) (Chou, T.-C. & Talalay, P. (1984) Adv. Enzyme Regul. 22, 27-55).

In some embodiments, administering a BCL2 family inhibitor and a proteasome inhibitor to a subject in need of treatment for a cancer that has reduced expression or activity of at least one 19S proteasome subunit with a BCL2 family inhibitor and a proteasome inhibitor has a synergistic effect in regard to one or more indicators of treatment efficacy. In some embodiments, administering a BCL2 family inhibitor and a proteasome inhibitor to a subject in need of treatment for a proteasome inhibitor resistant cancer has a synergistic effect in regard to one or more indicators of tumor efficacy.

Members of the BCL2 family regulate the intrinsic pathway of apoptosis, a process of programmed cell death that plays important roles in normal development and tissue homeostasis. The BCL2 family includes three subgroups with distinct structures and functions: the anti-apoptotic (pro-survival) proteins, the pro-apoptotic effector proteins, and the BH3-only proteins. The six human anti-apoptotic BCL2 family members are BCL2, BCL-$X_L$ (the longer of two protein isoforms encoded by the BCL-X gene, also known as BCL2L1 or BCL2-like 1), BCL-W (also known as BCL2L2 or BCL2-like 2), MCL1, BCL2-A1 (also known as BFL1 or A1) and BCL-B (also known as BCL2L10 or BCL2-like 10). Unless otherwise indicated, the term "MCL1" as used herein in reference to a protein refers to MCL1L, the longest isoform encoded by the myeloid cell leukemia sequence 1 (MCL1) gene. The pro-apoptotic effector proteins include BAX (BCL-2-associated X) and BAK (BCL-2 antagonist/killer). BCL2 family proteins contain one or more regions of sequence homology known as BCL2 homology (BH) domains. The anti-apoptotic BCL2 family members and the pro-apoptotic proteins BAX and BAK have four BH domains (termed BH1, BH2, BH3, and BH4). BCL2 family members that contain only a BH3 domain are referred to as "BH3-only" proteins and include BIM, PUMA, BAD, BID, tBID, BIK, BMF, HRK, and NOXA. The BH3 domain contains an alpha-helical region that can bind to a hydrophobic groove present in anti-apoptotic family members.

The main functional activity of the anti-apoptotic BCL-2 family members is to bind and sequester the pro-apoptotic proteins BAX and BAK. Certain BCL-2 family members can also directly interact with certain BH3-only proteins and restrain their pro-apoptotic activity. Apoptotic stimuli result in upregulation of BH3-only proteins and/or downregulation of anti-apoptotic BCL2 family proteins. The BH3-only proteins promote initiation of apoptosis by engaging anti-apoptotic BCL-2 family members, resulting in release of bound BAX and BAK and their activation. Additionally, binding of certain BH3-only proteins (sometimes referred to as "sensitizer" BH3 proteins) to anti-apoptotic BCL-2 family members can cause release of other BH-3 proteins (sometimes referred to as "activator" BH3 proteins) that can directly bind and activate BAX and BAK. In both of these mechanisms, the binding of BH3-only proteins to anti-apoptotic BCL2 family members results in BAX and BAK activation. Activated BAK and BAX assemble into multimeric pores in the mitochondrial membrane and promote mitochondrial outer membrane permeabilization and release of cytochrome c release into the cytosol, leading to caspase activation and eventual cell death.

In certain embodiments, compounds that selectively inhibit growth of cancer cells that have reduced expression of one or more 19S proteasome subunits are BCL2 family inhibitors. In certain embodiments, compounds that selectively inhibit growth of cancer cells that are proteasome inhibitor resistant as compared to their ability to inhibit growth of cells that are proteasome inhibitor sensitive are BCL2 family inhibitors. As used herein, "BCL2 family inhibitor" refers to an agent that inhibits expression and/or activity of at least one anti-apoptotic member of the BCL2 family, i.e., an agent that inhibits expression and/or activity of at least one of BCL2, BCL-$X_L$, BCL-W, MCL1, BCL2-A1, and BCL-B. In some aspects, described herein is a method of killing or inhibiting proliferation of a cancer cell that has reduced expression of one or more 19S proteasome subunits, the method comprising: contacting the cancer cell with a BCL2 family inhibitor. In some embodiments the cancer cell has been determined to have reduced expression of one or more 19S subunits before being contacted with the BCL2 family inhibitor. In some embodiments the method further comprises contacting the cell with a proteasome inhibitor. In some aspects, described herein is a method of killing or inhibiting proliferation of a proteasome inhibitor resistant cancer cell, the method comprising: contacting the proteasome inhibitor resistant cancer cell with a BCL2 family inhibitor. In some embodiments the cancer cell has been determined to be proteasome inhibitor resistant before being contacted with the BCL2 family inhibitor. In some embodiments the method further comprises contacting the cancer cell with a proteasome inhibitor.

In some aspects, described herein is a method of treating a subject in need of treatment for a cancer characterized by reduced expression of one or more 19S subunits, the method comprising: administering a BCL2 family inhibitor to the subject. In some embodiments the cancer has been determined to have reduced expression of one or more 19S subunits prior to administration of the BCL2 family inhibitor. In some embodiments the method further comprises administering a proteasome inhibitor to the subject.

Also described herein is a method of treating a subject in need of treatment for a proteasome inhibitor resistant cancer, the method comprising: administering a BCL2 family inhibitor to the subject. In some embodiments the cancer has been determined to be proteasome inhibitor resistant prior to administration of the BCL2 family inhibitor. In some embodiments the subject has been treated with a proteasome inhibitor prior to administration of the BCL2 family inhibitor. In some embodiments the cancer did not respond to treatment with the proteasome inhibitor or has progressed during treatment with a proteasome inhibitor or the subject has experienced a relapse after treatment with a proteasome inhibitor. In some embodiments the method further comprises administering a proteasome inhibitor to the subject.

It should be understood that the teachings of the other sections of the present specification are applicable to this Section VIII ("*Compositions and Methods Relating to Compounds that Inhibit Proteasome Inhibitor Resistance*") and vice versa. For example, the teachings regarding pharmaceutical compositions, administration routes, and other teachings pertaining to administration of compounds to subjects described in the section entitled "*Compositions and Methods of Treatment*" (Section VII) are applicable to the compositions and methods that comprise administering a BCL2 family inhibitor to a subject.

In some embodiments a method of inhibiting growth of a cancer cell comprises determining that the cancer cell has reduced expression or activity of one or more 19S subunits and contacting the cancer cell with a BCL2 family inhibitor. In some embodiments the method further comprises contacting the cancer cell with a proteasome inhibitor. In some embodiments a method of treating a subject in need of treatment for cancer comprises determining that the cancer has reduced expression or activity of one or more 19S subunits and administering a BCL2 family inhibitor to the subject. In some embodiments the method further comprises administering a proteasome inhibitor to the subject. In some embodiments, the level of expression or activity of 19S subunits may be determined, or may have been determined, using any of the methods described herein. In some embodiments a cancer cell or cancer may be determined, or may have been determined, to have reduced expression or activity of one or more 19S subunits using any of the methods described herein.

In some aspects, a method of treating a subject in need of treatment for cancer comprises treating the subject with a BCL2 family inhibitor, wherein the expression of one or more 19S subunits, e.g., at least five 19S subunits, in the cancer has been measured, and the cancer has been determined to have reduced expression of at least one 19S subunit whose expression was measured. In some embodiments the method further comprises administering a proteasome inhibitor to the subject. In some aspects, a method of treating a subject in need of treatment for cancer comprises treating the subject with a proteasome inhibitor, wherein the expression of at least 10, 11, 12, 13, 14, 15, 16, 17, 18, 19, 20, or 21 19S subunits in the cancer has been measured, and the cancer has been determined to have reduced expression of at least one 19S subunit whose expression was measured. In some embodiments the method further comprises administering a proteasome inhibitor to the subject.

In some embodiments of any of the methods that comprise contacting a cancer cell or cancer with a BCL2 family inhibitor, the cancer cell or cancer has reduced expression or activity of at least one 19S subunit selected from PSMD12, PSMD5, PSMD1, PSMC6, PSMD10, PSMD14, PSMD6, PSMD13, PSMD7, PSMC1, PSMC5, PSMD12, PSMC3, PSMC4, PSMD4, or PSMD8. For example, in some embodiments the cancer cell or cancer has reduced expression or activity of PSMD5, PSMD1, PSMC6, PSMD10, PSMD14, or PSMD6. In some embodiments the cancer cell or cancer has reduced expression or activity of PSMD5.

In some embodiments the cancer cell or cancer has a sigma score of at least 1.5, e.g., between 1.5 and 5.0. In some embodiments the cancer cell or cancer has a sigma score of at least 2.0, e.g., between 2.0 and 5.0. In some embodiments the cancer cell or cancer has a sigma score of at least 2.5, e.g., between 2.5 and 5.0. In some embodiments the cancer cell or cancer has a sigma score of at least 3.0, e.g., between 3.0 and 5.0. In some embodiments of any of the methods, the sigma score of the cancer cell or cancer has been determined prior to contacting the cancer cell or cancer with the BCL2 family inhibitor.

In some embodiments any of the methods may be practiced on a cancer cell population. In some embodiments any of the methods may be practiced on a cell or cell population from a cancer cell line. In some embodiments any of the methods may be practiced on a cell or cell population in culture. In some embodiments any of the methods may be practiced on a cell or cell population in a cancer. In some embodiments a cancer cell is a member of a cancer cell population or cancer cell line or cancer that has reduced expression or activity of one or more 19S subunits. In some embodiments such cancer cell population or cancer cell line or cancer has been determined to have reduced expression of one or more 19S subunits using any of the methods described herein. In some embodiments such cancer cell population or cancer cell line or cancer has been determined to have reduced expression of one or more 19S subunits using any of the methods described herein.

In some embodiments of any of the methods that comprise contacting a cancer cell or cancer with a BCL2 family inhibitor, the cancer cell or cancer may be of any cancer type, e.g., any of the cancer types described herein. In some embodiments the cancer is a hematological malignancy. In some embodiments the cancer is not a hematological malignancy.

In some embodiments, contacting a cancer cell that has reduced expression or activity of at least one 19S proteasome subunit with a BCL2 family inhibitor causes the cell to undergo apoptosis. In some embodiments, contacting a cancer cell that has reduced expression or activity of at least one 19S proteasome subunit with a BCL2 family inhibitor and a proteasome inhibitor causes the cell to undergo apoptosis. In some embodiments apoptosis may be measured. One of ordinary skill in the art is aware of suitable assays to measure apoptosis. For example, apoptosis may be measured by measuring cytosolic cytochrome c (released from mitochondria), accumulation of caspase-dependent sub-GO-G1 DNA content, caspase activation, poly(ADP-ribose) polymerase (PARP) cleavage, TUNEL assay, cell surface exposure of phosphatidylserine (which may be measured using Annexin V staining), etc. In some embodiments caspase activation may be measured by measuring cleavage of a caspase substrate, e.g., a procaspase (e.g., procaspase 3, procaspase 7, and/or procaspase 9). In some embodiments a Caspase-Glo® assay (Promega) may be used.

In general, any BCL2 family inhibitor may be used in methods and compositions described herein. In certain embodiments a BCL2 family inhibitor comprises a small molecule, a polypeptide, or a nucleic acid. A number of BCL2 family inhibitors are known in the art and may be used in compositions and methods described herein. Certain anti-apoptotic BCL2 family members are overexpressed in a variety of cancers, and inhibition of these proteins has been proposed as a therapeutic strategy. Several BCL2 family inhibitors have entered clinical trials and some show promise in a variety of oncologic indications. However, the present disclosure is believed to represent the first description of the particular utility of BCL2 family inhibitors for inhibiting growth of cancer cells that have reduced expression or activity of one or more 19S proteasome subunits and for treating cancers that have reduced expression or activity of one or more 19S proteasome subunits.

As discussed above, anti-apoptotic BCL2 family proteins contain a hydrophobic groove to which the alpha-helical BH3 region of the pro-apoptotic BCL2 family proteins binds, resulting in activation of BAX and BAK. In some embodiments, a BCL2 family inhibitor is an agent that binds to the BH3-binding groove of anti-apoptotic BCL2 proteins and induces apoptosis. Such agents, when distinct from naturally occurring BH3 domains, may be referred to as "BH3 mimetics". In some embodiments a BH3 mimetic induces apoptosis in a manner that is dependent at least in part on BAX and/or BAK, in that the compound is less potent against cells that are deficient in BAX and BAK than against cells that are not deficient in BAX and BAK. In some embodiments a BH3 mimetic is a peptide. In some embodiments a BH3 mimetic is a small molecule.

In some embodiments the BCL2 family inhibitor is a BCL2 inhibitor, which term refers to an agent that inhibits expression and/or activity of BCL2. The agent may or may not also inhibit one or more other anti-apoptotic members of the BCL2 family.

In some embodiments the BCL2 family inhibitor is ABT-263 (navitoclax) or an analog thereof. ABT-263 is a small molecule BH3 mimetic that binds to the BH3-binding groove of BCL2, BCL-$X_L$, and BCL-W and prevents binding of pro-apoptotic BCL2 family members such as BIM, BID, and BAD (Tse, C., et al., Cancer Res 2008, 68(9): 3421-3428). The structure of ABT-263 is as follows:

20140113910, 20140275082, 20150072978, 20150152097, 20150183775, 20150246914, 20150299197 (all entitled "APOPTOSIS-INDUCING AGENTS FOR THE TREATMENT OF CANCER AND IMMUNE AND AUTOIMMUNE DISEASES"). Such compounds (other than ABT-263) are considered ABT-263 analogs for purposes of the present disclosure.

In some embodiments the BCL2 family inhibitor is a compound that falls within the scope of any one or more formulae (e.g., Formula I, Formula II, Formula III, Formula IV, Formula V, or Formula VI) as described in any one or more of US Patent Application Pub. Nos. 20100152183, 20100298321, 20130296295, 20140057889, 20140057890,

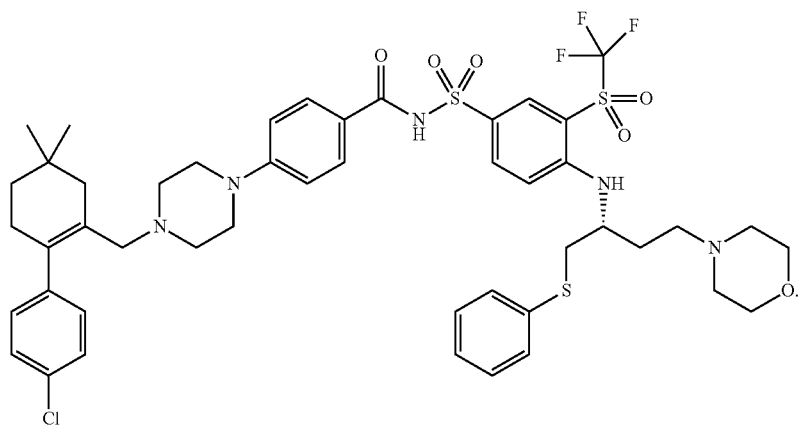 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C1]

In some embodiments the BCL2 family inhibitor is ABT-199 (venetoclax) or an analog thereof. ABT-199 is a small molecule BH3 mimetic that selectively binds to BCL2 as compared with its binding to BCL-$X_L$ and BCL-W. The structure of ABT-199 is as follows:

20140107119, 20160009687 (all entitled BCL-2-SELECTIVE APOPTOSIS-INDUCING AGENTS FOR THE TREATMENT OF CANCER AND IMMUNE DISEASES). Such compounds (other than ABT-199) are considered ABT-199 analogs for purposes of the present disclosure. In certain

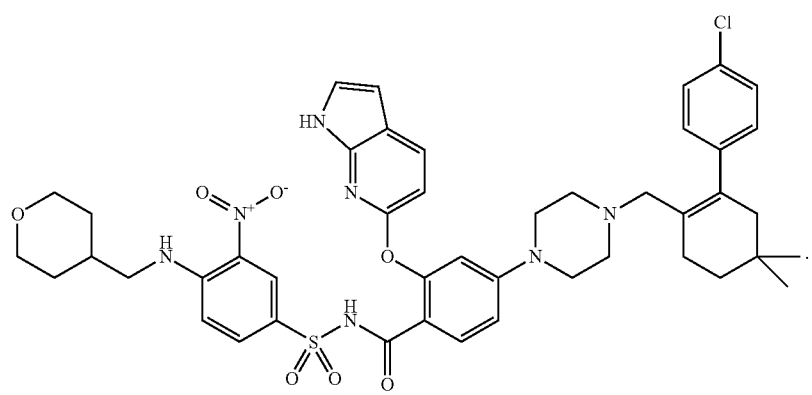 [SMILES: CC1(C)CCC(CN2CCN(c3ccc(C(=O)NS(=O)(=O)c4ccc(NCC5CCOCC5)c([N+](=O)[O-])c4)c(Oc4ccc5cc[nH]c5n4)c3)CC2)=C(c2ccc(Cl)cc2)C1]

In some embodiments the BCL2 family inhibitor is a compound that falls within the scope of any one or more formulae (e.g., Formula I, Formula II, Formula III, Formula IV, Formula V, or Formula VI) as described in any one or more of US Patent Application Pub. Nos. 20070027135 (entitled "Apoptosis Inhibitors), 20100160322, 20100184750, 20100184766, 20100298323, 20110124628, 20110237553, 20120028925, 20120190688, 20120214796, 20130096121, 20130184278, 20130267514, 20130267534, 20140066621, 20140073640, 20140088106, 20140094471, embodiments the BCL2 family inhibitor is a member of a subgenus of any one or more formulae described in any one or more of the aforementioned US patent application publications. In certain embodiments the BCL2 family inhibitor is a particular species named in any one or more of the aforementioned US patent application publications.

In some embodiments the BCL2 family inhibitor is obatoclax (also called GX15-070) or an analog thereof. The structure of obatoclax is as follows:

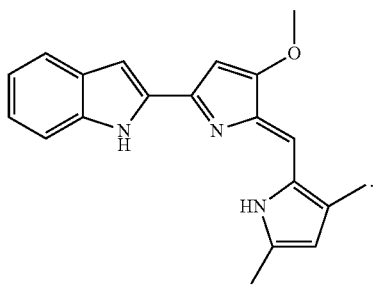 [SMILES: COC1=CC(c2cc3ccccc3[nH]2)=N/C1=C\c1[nH]c(C)cc1C]

In some embodiments obatoclax is provided as obatoclax mesylate (also known as GX15-070). In some embodiments the BCL2 family inhibitor is a compound that falls within the scope of any one or more of Formula Ia, Formula Ib, and Formula Ic as described in US Patent Application Pub. No. 2012004224 (entitled "Triheterocyclic Compounds and Compositions Thereof"). Such compounds (other than obatoclax) are considered obatoclax analogs for purposes of the present disclosure.

In some embodiments the BCL2 family inhibitor is gossypol (2,2'-Bis(formyl-1,6,7-trihydroxy-5-isopropyl-3-methylnaphthalene)) or a gossypol derivative. In some embodiments, the BCL2 family inhibitor is AT-101 (R-(−)-gossypol acetic acid), an enantiomer of racemic gossypol. AT-101 has been reported to bind to the BH3 domain of BCL2, BCL-$X_L$, MCL1, and BCL-W. In some embodiments the BCL2 family inhibitor is a gossypol derivative. In some embodiments the gossypol derivative is apogossypol or apogossypolone (ApoG2). In some embodiments the gossypol derivative is a benzoylsulfonide derivative such as TW37. In some embodiments the gossypol derivative is sabutoclax (also known as BI-97C1), BI97D6, or BI112D1 (((−)BI97D6)) (Wei, J., et al. J Med Chem. 2010; 53(10): 4166-76; Wei J, et al., Front Oncol. 2011; 1:28).

In some embodiments the BCL2 family inhibitor is a compound described in US Pat. Pub. No. 20140135318 (SUBSTITUTED SULFONAMIDES USEFUL AS ANTIAPOPTOTIC BCL INHIBITORS).

In some embodiments the BCL2 family inhibitor is a "BCL-$X_L$ inhibitor", which term refers to an agent that inhibits expression and/or activity of BCL-$X_L$. The agent may or may not also inhibit one or more other anti-apoptotic members of the BCL2 family. In some embodiments the BCL-$X_L$ inhibitor also inhibits at least BCL2. For example, in some embodiments the BCL-$X_L$ inhibitor is ABT-263. As discussed above, ABT-263 inhibits BCL2, BCL-$X_L$, and BCL-W. In some embodiments the BCL-$X_L$ inhibitor is selective for binding to BCL-$X_L$ as compared with BCL2. Such an inhibitor may be referred to as a BCL-$X_L$ selective inhibitor. In some embodiments the BCL-$X_L$ inhibitor is selective for binding to BCL-$X_L$ as compared with MCL1.

In some embodiments the BCL2 family inhibitor is a compound described in Sleebs, B E, et al., (J Med Chem. 2011; 54(6):1914-26) comprising a quinazoline sulfonamide core (compound 21, 28, 29, 30, 31, 32, 33, or 34). These compounds selectively inhibit BCL2 and BCL-$X_L$ as compared to MCL1 and BCL-W.

In some embodiments the BCL-$X_L$ inhibitor is a compound described in U.S. Pat. No. 8,232,273.

In some embodiments the BCL2 family inhibitor is JY-1-106 or an analog thereof (Cao, X, et al., Molecular Cancer 2013; 12: 42). The structure of JY-1-106 is as follows:

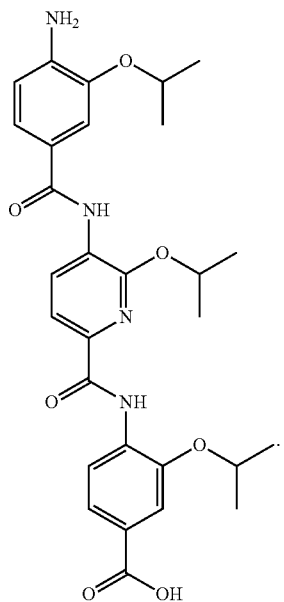 [SMILES: CC(C)Oc1cc(C(=O)Nc2ccc(C(=O)Nc3ccc(C(=O)O)cc3OC(C)C)nc2OC(C)C)ccc1N]

JY-1-106 is a BH3 mimetic reported to bind to BCL-$X_L$ and MCL1, with selectivity for BCL-$X_L$ (Cao, cited above).

In some embodiments, the BCL2 family inhibitor, e.g., the BCL-$X_L$ selective inhibitor, is a compound described in US Pat. Pub. No. 20140005190 of the following formula:

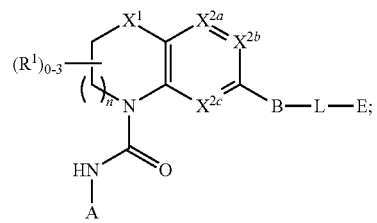

in which the variables $X^1$, $X^{2a}$, $X^{2b}$, $X^{2c}$, $R^1$, B, L, E, A and the superscript n are as defined therein.

In some embodiments the BCL-$X_L$ selective inhibitor is a BH3 mimetic compound described in Petros, A M, et al., J Med Chem. 2006; 49(2):656-63.

In some embodiments the BCL-$X_L$ selective inhibitor is A-385358 ([(R)-4-(3-dimethylamino-1-phenylsulfanylmethyl-propylamino)-N-[4-(4,4-dimethyl-piperidin-1-yl)-benzoyl]-3-nitro-benzenesulfonamide) or an analog thereof (Shoemaker, A R, et al., Cancer Res. 2006; 66(17):8731-9).

In some embodiments the BCL2 family inhibitor is a compound described in US Pat. Pub. No. 20090137585. In some embodiments the compound is a BCL-$X_L$ selective inhibitor.

In some embodiments the BCL2 family inhibitor is a compound described in US Pat. Pub. No. 20120189539.

In some embodiments the BCL2 family inhibitor is a compound described in Table 1, Table 2, or Table 3 of Chen, J., et al., J Med Chem. 2012 Oct. 11; 55(19): 8502-8514. In some embodiments the compound has the following structure:

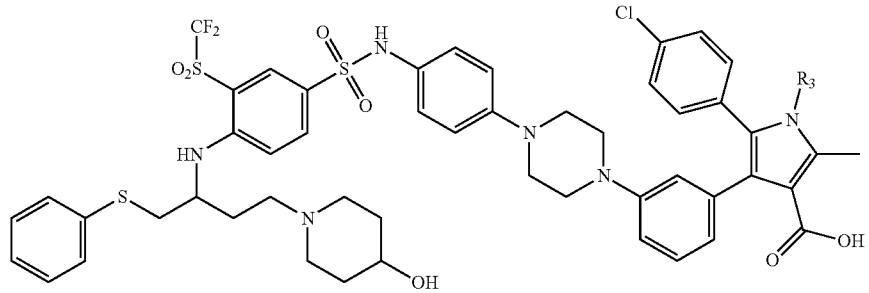

wherein R³ is C₁₋₆ alkyl, e.g., methyl, ethyl, isopropyl, propyl. In some embodiments the compound is BM-957 (R³ is ethyl).

In some embodiments the BCL2 family inhibitor is a compound described in Aguilar, A., et al., J Med Chem. 2013; 56(7):3048-67. In some embodiments the compound has the following structure:

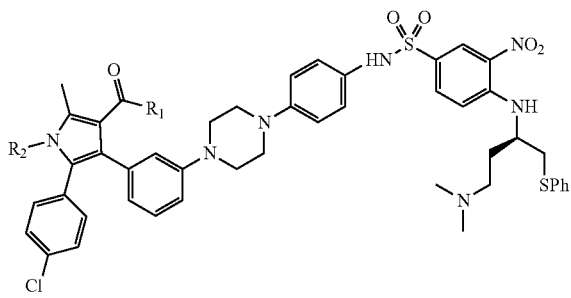

wherein $R_1$ is OH or NHSO₂CH₃ and wherein $R_2$ is C₁₋₆ alkyl. For example, in some embodiments $R_1$ is NHSO₂CH₃ and $R_2$ is ethyl (compound BM-1075). In some embodiments $R_1$ is NHSO₂CH₃ and $R_2$ is isopropyl (compound BM-1074).

In some embodiments the BCL2 family inhibitor is a compound described in US Pat. Pub. No. 20140199234.

In some embodiments the BCL2 family inhibitor is BM-1197 or an analog thereof (Bai, L., et al. PLoS One. 2014; 9(6):e99404). The structure of BM-1197 is as follows:

In some embodiments the BCL2 family inhibitor is a compound described in US Patent Application Pub. No. 20140187531, e.g., a BCL-X$_L$ selective inhibitor described therein.

In some embodiments the BCL-X$_L$ selective inhibitor is BXI-61 or BXI-72 or an analog of BXI-61 or BXI-72 (Park, D., et al., Cancer Res. 2013; 73(17):5485-96. doi: 10.1158/ 0008-5472).

In some embodiments the BCL-X$_L$ selective inhibitor is a compound listed in Table 5 of Wendt, M D, et al., J. Med. Chem. 2006, 49, 1165-1181 or an analog thereof. In some embodiments the compound is 73R (4-((R)-3-Dimethyl-amino-1-phenylsulfanylmethylpropylamino)-N-[4-(4,4-di-methylpiperidin-1-yl)benzoyl]-3-nitrobenzenesulfonamide) or 79R (4-((R)-3-Dimethylamino-1-phenylsulfanylmethyl-propylamino)-N-[2'-methoxy-4'-(3-morpholin-4-ylpropyl) biphenyl-4-carbonyl]-3-nitrobenzenesulfonamide).

In some embodiments the BCL-X$_L$ selective inhibitor is WEHI-539 (Lessene, G., et al., Nat. Chem. Biol. 2013, 9, 390-397) or an analog thereof. The structure of WEHI-539 is as follows:

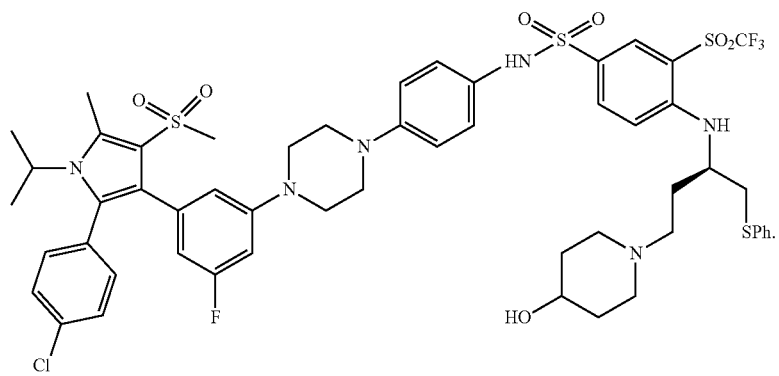

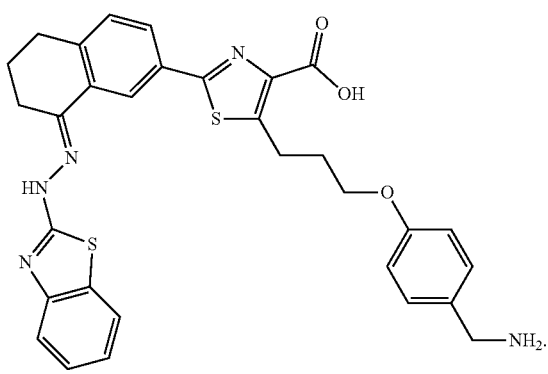 [SMILES: NCc1ccc(OCCCc2sc(-c3ccc4c(c3)/C(=N/Nc3nc5ccccc5s3)CCC4)nc2C(=O)O)cc1]

In some embodiments the analog of WEHI-539 is a compound in which the hydrazone linkage present in WEHI-539 is replaced by a more stable moiety.

In some embodiments the BCL-$X_L$ selective inhibitor is a compound described in Koehler, M F, et al., ACS Med Chem Lett. 2014, 5(6):662-7, e.g., any of compounds 13-23 or an analog thereof. Compounds 13-23 have the following structure:

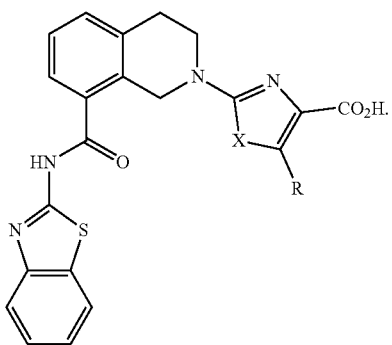

For example, in some embodiments the compound is 13 (X is CH=CH and R is H), 14 (X is S and R is H), or 22 (X is S and R is (CH$_2$)$_3$,OPh). In some embodiments the BCL-$X_L$ selective inhibitor is A-1155463 (Tao et al, ACS Med. Chem. Lett., 2014, 5(10): 1088-1093) or an analog thereof. The structure of A-1155463 is as follows:

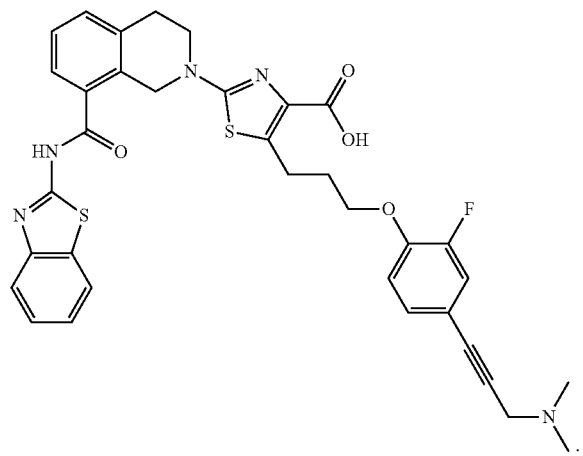 [SMILES: CN(C)CC#Cc1ccc(OCCCc2sc(N3CCc4cccc(C(=O)Nc5nc6ccccc6s5)c4C3)nc2C(=O)O)c(F)c1]

In some embodiments the BCL-$X_L$ selective inhibitor is A-1331852 or an analog thereof (Leverson, J D, et al., Sci Transl Med. 2015; 7(279):279ra40). The structure of A-1331852 is as follows:

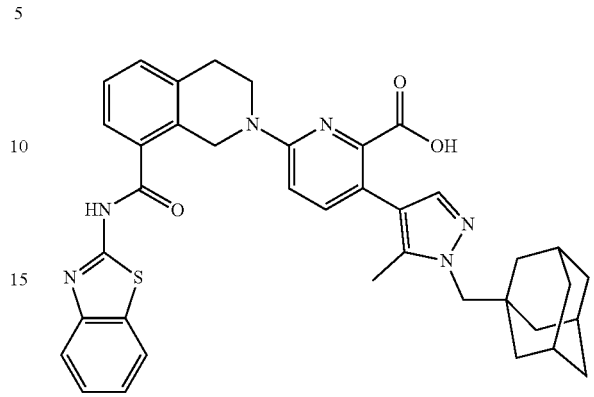

NMR solution structures and X-ray co-crystal structures have shown that there exists a lipophilic P4 pocket within the hydrophobic BH3 binding groove of BCL-$X_L$ (Lee, E F, et al. Cell Death and Differentiation (2007) 14, 1711-1713) that contributes to tight binding of BH3 peptides and small molecule inhibitors. In some embodiments the BCL-$X_L$ inhibitor is a compound that binds to the P4 pocket of BCL-$X_L$. Examples of such compounds and approaches to designing such compounds are described in Tao et al. (cited above) and Koehler, et al. (cited above).

In some embodiments the BCL2 family inhibitor is an "MCL1 inhibitor", which term refers to an agent that inhibits expression and/or activity of MCL1. The agent may or may not also inhibit one or more other anti-apoptotic members of the BCL2 family. In some embodiments the MCL1 inhibitor is selective for inhibiting MCL1 as compared with BCL-$X_L$. In some embodiments the MCL1 inhibitor is selective for inhibiting MCL1 as compared with BCL2.

In some embodiments the BCL2 family inhibitor is a compound of Formula I or Formula II as described in PCT/US2014/053148 (WO/2015/031608), entitled SUBSTITUTED INDOLE MCL-1 INHIBITORS. In some embodiments the BCL2 family inhibitor is described in PCT/US2015/022841 (WO/2015/148854), entitled SUBSTITUTED INDOLE MCL-1 INHIBITORS. In some embodiments the BCL2 family inhibitor is described in US Pat. Pub. No. 20150336925 (SUBSTITUTED BENZOFURAN, BENZOTHIOPHENE AND INDOLE MCL-1 INHIBITORS). In some embodiments the BCL2 family inhibitor is described in one or more of US Pat. Pub. Nos. 20090054402, 20140051683, and/or 20150284328 (all entitled 7-SUBSTITUTED INDOLE MCL-1 INHIBITORS). In some embodiments the BCL2 family inhibitor is described in US Pat. Pub. No. 20120172285 (METHODS AND COMPOSITIONS FOR SPECIFIC MODULATION OF MCL-1), 20130035304 (SMALL MOLECULES FOR THE MODULATION OF MCL-1 AND METHODS OF MODULATING CELL DEATH, CELL DIVISION, CELL DIFFERENTIATION AND METHODS OF TREATING DISORDERS), and/or 20150051249 (INHIBITION OF MCL-1 AND/OR BFL-1/A1).

In some embodiments the BCL2 family inhibitor is an indole-2-carboxylic acid described in (Leverson, D., et al., Potent and selective small-molecule MCL-1 inhibitors demonstrate on-target cancer cell killing activity as single agents and in combination with ABT-263 (navitoclax). Cell Death Dis. 2015; 6:e1590). For example, in some embodiments the BCL2 family inhibitor is A-1210477, the structure of which is as follows:

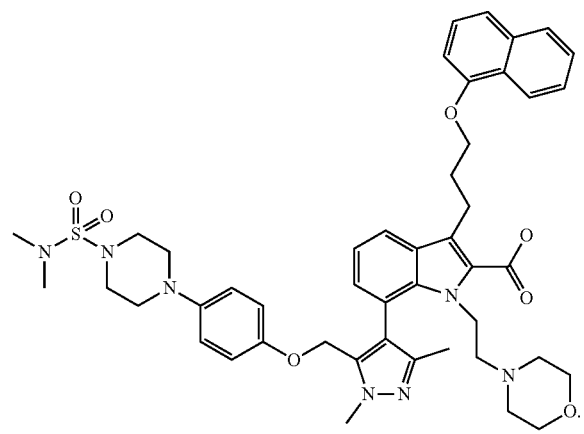 [SMILES: Cc1nn(C)c(COc2ccc(N3CCN(S(=O)(=O)N(C)C)CC3)cc2)c1-c1cccc2c(CCCOc3cccc4ccccc34)c(C(=O)O)n(CCN3CCOCC3)c12]

In some embodiments the BCL2 family inhibitor is a marinopyrrole, e.g., marinopyrrole A (maritoclax) or a marinopyrrole A analog. Marinopyrroles are described in, e.g., Li, R., et al., Design, synthesis and evaluation of marinopyrrole derivatives as selective inhibitors of Mc1-1 binding to pro-apoptotic Bim and dual Mc1-1/Bc1-xL inhibitors. Eur J Med Chem. 2015; 90:315-31 PCT/US2015/016336 (WO/2015/126912), entitled MARINOPYRROLE DERIVATIVES AND METHODS OF MAKING AND USING SAME; Cheng, C., et al., Marinopyrrole derivatives with sulfide spacers as selective disruptors of Mc1-1 binding to pro-apoptotic protein Bim. Mar Drugs. 2014; 12(8):4311-25 and/or U.S. Pat. App. Pub. No. 20150080632 (MARINOPYRROLE DERIVATIVES AS ANTICANCER AGENTS).

In some embodiments an MCL1 inhibitor is an agent that inhibits transcription. Transcriptional repression results in the rapid downregulation of mRNA transcripts and proteins with short half-lives, such as MCL1. In certain embodiments an agent that inhibits transcription is a cyclin dependent kinase (CDK) inhibitor that inhibits CDK7 and/or CDK9 In some embodiments the CDK inhibitor is dinaciclib (MK-7965, formerly SCH-727965), the structure of which is as follows:

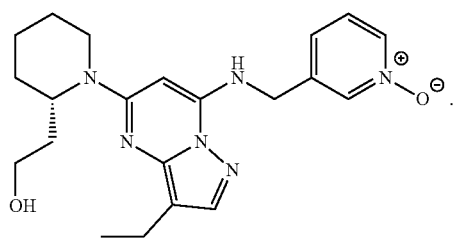 [SMILES: CCc1cnn2c(NCc3ccc[n+]([O-])c3)cc(N3CCCC[C@H]3CCO)nc12]

In some embodiments the BCL2 inhibitor comprises a nucleic acid that hybridizes to mRNA encoding BCL2, BCL-$X_L$, BCL-W, MCL1, BCL2-A1, or BCL-B and inhibits its translation or promotes its degradation. In some embodiments the nucleic acid is an RNAi agent, e.g., an siRNA, shRNA, or miRNA. In some embodiments the nucleic acid is an antisense oligonucleotide. In some embodiments the RNAi agent specifically inhibits BCL-$X_L$ expression as compared with expression of BCL2.

In some embodiments the BCL2 inhibitor comprises a nucleic acid aptamer that binds to at least one anti-apoptotic BCL2 family member. In some embodiments the aptamer binds in the BH3 binding groove of at least one anti-apoptotic BCL2 family member.

In some embodiments the BCL2 family inhibitor comprises a polypeptide that binds to at least one anti-apoptotic BCL2 family member. In some embodiments the polypeptide that binds to at least one anti-apoptotic BCL2 family member comprises a BH3 domain or variant thereof. Such a polypeptide may be referred to as "BH3 peptide". In some embodiments a polypeptide that binds to at least one anti-apoptotic BCL2 family member is distinct from naturally occurring polypeptides in sequence. For example, a BH3 peptide may comprise a sequence that has at least one substitution, insertion, or deletion as compared to the sequence of a naturally occurring BH3 domain.

In some embodiments the BCL2 inhibitor comprises an artificial transcriptional repressor that represses transcription of at least one anti-apoptotic BCL2 family member. In some embodiments an artificial transcriptional repressor that represses transcription of at least one anti-apoptotic BCL2 family member is expressed in cancer cells.

In some embodiments a polypeptide that binds to at least one anti-apoptotic BCL2 family member comprises or is conjugated to a moiety that stabilizes the polypeptide and/or enhances uptake of the polypeptide by mammalian cells. In some embodiments the polypeptide comprises at least one non-standard amino acid (i.e., an amino acid other than the 20 amino acids most commonly found in naturally occurring polypeptides). In some embodiments the polypeptide comprises at least one non-natural amino acid.

In some embodiments the polypeptide that is a BCL2 family inhibitor is a stapled BH3 peptide. Stapled peptides comprise a linking moiety connecting a pair of the peptide's amino acid side chains. For example, hydrocarbon stapled alpha-helical peptides contain two alpha,alpha-disubstituted unnatural amino acids that are cross-linked by a hydrocarbon chain. Exemplary stapled BH3 peptides are described in Muppidi, A., et al. J Am Chem Soc. 2012; 134(36):14734-7, Muppidi, A., et al., Tetrahedron. 2014; 70(42):7740-7745 and/or US Pat. Pub. No. 20150045310 (NOVEL ENGINEERED POTENT CYTOTOXIC STAPLED BH3 PEPTIDES). Other BH3 peptides are known in the art. For example, certain BH3 peptides that bind selectively to MCL1 as compared to their binding to BFL1, BCL-$X_L$, BCL2, and BCL-W are described in Foight, G W, et al., ACS Chem Biol. 2014; 9(9):1962-8.

In some embodiments the polypeptide that binds to at least one anti-apoptotic BCL2 family member comprises a single domain antibody (e.g., a nanobody) or a single chain antibody. In some embodiments the polypeptide that binds to at least one anti-apoptotic BCL2 family member comprises an engineered binding protein having a structure distinct from that of antibodies, such as an affibody, affimer, adnectin, DARPin, knottin, or anticalin. In some embodiments an antibody or non-antibody polypeptide that binds to at least one anti-apoptotic BCL2 family member may be identified using a display technique, such as phage display, bacterial display, yeast display, ribosome display, or yeast display.

In some embodiments, a nucleic acid that encodes a polypeptide that binds to at least one anti-apoptotic BCL2 family member or that encodes an artificial transcriptional repressor that represses transcription of at least one anti-apoptotic BCL2 family member is contacted with cancer cells in vitro or administered to a subject in need of treatment for cancer, leading to synthesis of the encoded polypeptide by cancer cells that take up the nucleic acid. In some embodiments the nucleic acid that encodes a polypeptide that binds to at least one anti-apoptotic BCL2 family member or that encodes an artificial transcriptional repressor that represses transcription of at least one anti-apoptotic BCL2 family member comprises synthetic messenger RNA (mRNA). As used herein, "synthetic mRNA" refers to RNA that encodes a polypeptide and is produced using in vitro transcription, chemical synthesis, or combinations thereof, or otherwise by the hand of man. In some embodiments the synthetic mRNA is modified RNA, i.e., it comprises at least one modification relative to naturally occurring RNA. In some embodiments the modification increases the stability and/or cellular uptake of the mRNA and/or reduces immune response against the mRNA. In some embodiments the modified mRNA incorporates one or more modified ribonucleoside bases, e.g., as described in Warren et al. (Cell Stem Cell 7(5):618-30, 2010, Mandal P K, Rossi D J. Nat Protoc. 2013 8(3):568-82, US Pat. Pub. No. 20120046346 and/or PCT/US2011/032679 (WO/2011/130624), e.g., substitution of 5-methylcytidine (5mC) for cytidine and/or pseudouridine (psi) for uridine at one or more positions. In some embodiments the modified mRNA comprises a 5' cap and/or a polyA tail.

In some embodiments a nucleic acid construct comprising a promoter operably linked to a sequence that comprises a template for transcription of mRNA that encodes a polypeptide that binds to at least one anti-apoptotic BCL2 family member or that comprises a template for transcription of mRNA that encodes an artificial transcriptional repressor that represses transcription of at least one anti-apoptotic BCL2 family member is contacted with cancer cells in vitro or administered to a subject in need of treatment for cancer, leading to synthesis of the mRNA and the encoded polypeptide by cancer cells that take up the nucleic acid construct. In some embodiments a vector comprising such a nucleic acid construct is contacted with cancer cells in vitro or administered to a subject in need of treatment for cancer, leading to synthesis of the mRNA and the encoded polypeptide by cancer cells that take up the vector.

In some embodiments of any of the compositions or methods described herein that relate to a BCL2 family inhibitor, the BCL2 family inhibitor may be any of the BCL2 family inhibitors known in the art, e.g., any of the BCL2 family inhibitors described herein. In certain embodiments of any of the compositions or methods described herein that relate to a proteasome inhibitor, the proteasome inhibitor may be any of the proteasome inhibitors known in the art, e.g., any of the proteasome inhibitors described herein. In certain embodiments of any of the methods described herein that relate to a BCL2 family inhibitor and to a proteasome inhibitor, the BCL2 family inhibitor may be any of the BCL2 family inhibitors known in the art, e.g., any of the BCL2 family inhibitors described herein, and the proteasome inhibitor may be any of the proteasome inhibitors known in the art, e.g., any of the proteasome inhibitors described herein. All different pairs and combinations of BCL2 family inhibitor and proteasome inhibitor are encompassed and expressly disclosed herein. For example, in some embodiments the BCL2 family inhibitor is ABT-263 or an analog thereof, and the proteasome inhibitor is bortezomib, carfilzomib, oprozomib, ixazomib, or an analog of any of these compounds.

In some embodiments a composition comprising a BCL2 family inhibitor and a proteasome inhibitor may be contacted with cells in vitro or administered to a subject. In some embodiments a BCL2 family inhibitor and to a proteasome inhibitor may be contacted with cells or administered to a subject in separate compositions. When administered separately, they may be administered via the same route or different routes. For example, in some embodiments the proteasome inhibitor is administered intravenously, subcutaneously, or intramuscularly, and the BCL2 family inhibitor is administered orally. In some embodiments they are administered in a unit dosage form that includes both a BCL2 family inhibitor and a proteasome inhibitor. A BCL2 family inhibitor and a proteasome inhibitor may be administered to a subject in combination according to any of the teachings described herein.

In some embodiments of any of the compositions or methods described herein that relate to a BCL2 family inhibitor, the BCL2 family inhibitor binds to at least one of BCL2, BCL-$X_L$, BCL-W, MCL1, BCL2-A1, and BCL-B and inhibits its activity. Commonly used measures of binding affinity of an agent, e.g., a small molecule or polypeptide, to a target protein (e.g., an anti-apoptotic BCL2 family member) are the dissociation constant (Kd) or the inhibition constant (Ki). The inhibition constant (Ki) is the dissociation constant of an agent/protein complex under conditions in which the agent is competing with a second agent for binding to the target protein. Thus, the larger the Kd or Ki of an agent/protein complex, the lower the binding affinity of the agent to the protein. The smaller the Kd or Ki of an agent/protein complex, the higher the binding affinity of the agent to the protein. For example, a small molecule that binds to BCL2 with a Kd of 10 nM has a higher binding affinity for BCL2 than a small molecule that binds to BCL2 with a Kd of 100 nM. If an agent binds to a first protein to form a complex that has a Kd or Ki that is less than the Kd or Ki of a complex of the agent with a second protein, the agent is considered to selectively bind to the first protein. The degree of selectivity may be expressed as the ratio of the two Kd or Ki values. For example, if a small molecule binds to BCL2 with a Kd of 10 nM and binds to BCL-$X_L$ with a Kd of 100 nM, the small molecule is selective for BCL2.

In certain embodiments the Kd of a BCL2 family inhibitor is determined using a surface plasmon resonance Biacore assay as described in Sleebs, B E, et al. J. Med. Chem. 2013, 56, 5514-5540. In certain embodiments the Ki of a BCL2 family inhibitor is determined using a fluorescence polarization assay in which a fluorescently labeled BH3 peptide is used as the competing agent. In certain embodiments the BH3 peptide is a BAK or BAX peptide. In certain embodiments the assay is performed and the Ki value calculated as described in U.S. Patent Application Publication 20070027135. In certain embodiments the assay is a time resolved fluorescence resonance energy transfer (TR-FRET) binding assay and is performed, and the Ki value calculated, as described in U.S. Patent Application Publication 20140005190 or 20150299197. In certain embodiments the assay is a fluorescence polarization assay and is performed, and the Ki value is calculated, as described in U.S. Patent Application Publication 20140199234 or Aguilar, A., et al. (cited above).

In some embodiments of any of the compositions or methods described herein that relate to a BCL2 family inhibitor, the BCL2 family inhibitor binds to at least one anti-apoptotic BCL2 family member with a Kd of less than or equal to 1 uM, e.g., between 10 nM and 100 nM or between 100 nM and 500 nM or between 500 nM and 1 uM. In some embodiments a BCL2 family inhibitor binds to at least one of BCL2, BCL-W, and MCL1 with a Kd of less than or equal to 1 uM, e.g., between 0.1 nM and 1 nM, between 1 nM and 10 nM between 10 nM and 100 nM or between 100 nM and 500 nM or between 500 nM and 1 uM. In some embodiments, binding may be measured using a surface plasmon resonance assay (e.g., using BiaCore technology), fluorescence polarization assay, isothermal titration calorimetry, fluorescence quenching assay, fluorescence resonance energy transfer (FRET) assay, or other methods known in the art.

In some embodiments of any of the compositions or methods described herein that relate to a BCL2 family inhibitor, the BCL2 family inhibitor binds to BCL-$X_L$ with a Kd of ≤100 nM, e.g., 50 nM-100 nM. In some embodiments the BCL2 family inhibitor binds to BCL-$X_L$ with a Kd of ≤50 nM, e.g., 10 nM-50 nM. In some embodiments the BCL2 family inhibitor binds to BCL-$X_L$ with a Kd of ≤10 nM, e.g., 1 nM-10 nM. In some embodiments the BCL2 family member binds to BCL-$X_L$ with a Kd of ≤1 nM, e.g., 0.1 nM-1 nM or 0.01 nM-0.1 nM. In some embodiments of any of the compositions or methods described herein that relate to a BCL2 family inhibitor, the BCL2 family inhibitor binds to BCL2 with a Kd of ≤100 nM, e.g., 50 nM-100 nM. In some embodiments the BCL2 family inhibitor binds to BCL2 with a Kd of ≤50 nM, e.g., 10 nM-50 nM. In some embodiments the BCL2 family inhibitor binds to BCL2 with a Kd of ≤10 nM, e.g., 1 nM-10 nM. In some embodiments the BCL2 family inhibitor binds to BCL2 with a Kd of ≤1 nM, e.g., 0.1 nM-1 nM or 0.01 nM-0.1 nM. In some embodiments the BCL2 family inhibitor binds to MCL1 with a Kd of ≤100 nM, e.g., 50 nM-100 nM. In some embodiments the BCL2 family inhibitor binds to MCL1 with a Kd of ≤50 nM, e.g., 10 nM-50 nM. In some embodiments the BCL2 family inhibitor binds to MCL1 with a Kd of ≤10 nM, e.g., 1 nM-10 nM. In some embodiments the BCL2 family inhibitor binds to MCL1 with a Kd of ≤1 nM, e.g., 0.1 nM-1 nM or 0.01 nM-0.1 nM. In some embodiments the BCL2 family inhibitor binds to BCL-W with a Kd of ≤100 nM, e.g., 50 nM-100 nM. In some embodiments the BCL2 family inhibitor binds to BCL-W with a Kd of ≤50 nM, e.g., 10 nM-50 nM. In some embodiments the BCL2 family inhibitor binds to BCL-W with a Kd of ≤10 nM, e.g., 1 nM-10 nM. In some embodiments the BCL2 family inhibitor binds to BCL-W with a Kd of ≤1 nM, e.g., 0.1 nM-1 nM or 0.01 nM-0.1 nM.

In some embodiments of any of the compositions or methods described herein that relate to a BCL2 family inhibitor, the BCL2 family inhibitor binds to BCL-$X_L$ with a Ki of ≤100 nM, e.g., 50 nM-100 nM. In some embodiments the BCL2 family inhibitor binds to BCL-$X_L$ with a Ki of ≤50 nM, e.g., 10 nM-50 nM. In some embodiments the BCL2 family inhibitor binds to BCL-$X_L$ with a Ki of ≤10 nM, e.g., 1 nM-10 nM. In some embodiments the BCL2 family inhibitor binds to BCL-$X_L$ with a Ki of ≤1 nM, e.g., 0.1 nM-1 nM or 0.01 nM-0.1 nM. In some embodiments of any of the compositions or methods described herein that relate to a BCL2 family inhibitor, the BCL2 family inhibitor binds to BCL2 with a Ki of ≤100 nM, e.g., 50 nM-100 nM. In some embodiments the BCL2 family inhibitor binds to BCL2 with a Ki of ≤50 nM, e.g., 10 nM-50 nM. In some embodiments the BCL2 family inhibitor binds to BCL2 with a Ki of ≤10 nM, e.g., 1 nM-10 nM. In some embodiments the BCL2 family member binds to BCL2 with a Ki of ≤1 nM, e.g., 0.1 nM-10 nM or 0.01 nM 0.1 nM. In some embodiments the BCL2 family inhibitor binds to MCL1 with a Ki of ≤100 nM. In some embodiments the BCL2 family inhibitor binds to MCL1 with a Ki of ≤50 nM. In some embodiments the BCL2 family inhibitor binds to MCL1 with a Ki of ≤10 nM. In some embodiments the BCL2 family inhibitor binds to MCL1 with a Ki of ≤1 nM. In some embodiments the BCL2 family inhibitor binds to BCL-W with a Ki of ≤100 nM, e.g., 50 nM-100 nM. In some embodiments the BCL2 family inhibitor binds to BCL-W with a Ki of ≤50 nM, e.g., 10 nM-50 nM. In some embodiments the BCL2 family inhibitor binds to BCL-W with a Ki of ≤10 nM, e.g., 1 nM-10 nM. In some embodiments the BCL2 family inhibitor binds to BCL-W with a Ki of ≤1 nM, e.g., 0.1 nM-10 nM or 0.01 nM-0.1 nM.

In some embodiments the BCL2 family inhibitor binds to BCL-$X_L$ with a Kd that is between 1 and 5 times the Kd of binding of ABT-263 to BCL-$X_L$. In some embodiments the BCL2 family inhibitor binds to BCL-$X_L$ with a Kd that is less than the Kd of binding of ABT-263 to BCL-$X_L$, e.g., between 1 and 5 times lower than the Kd of binding of ABT-263 to BCL-$X_L$. In some embodiments the BCL2 family inhibitor binds to BCL2 with a Kd that is between 1 and 5 times the Kd of binding of ABT-263 to BCL2. In some embodiments the BCL2 family inhibitor binds to BCL2 with a Kd that is less than the Kd of binding of ABT-263 to BCL-2, e.g., between 1 and 5 times lower than the Kd of binding of ABT-263 to BCL-2. In some embodiments the BCL2 family inhibitor binds to BCL-$X_L$ with a Ki that is between 1 and 5 times the Ki of binding of ABT-263 to BCL-$X_L$. In some embodiments the BCL2 family inhibitor binds to BCL-$X_L$ with a Ki that is less than the Ki of binding of ABT-263 to BCL-$X_L$, e.g., between 1 and 5 times lower. In some embodiments the BCL2 family inhibitor binds to BCL2 with a Ki that is between 1 and 5 times the Ki of binding of ABT-263 to BCL2. In some embodiments the BCL2 family inhibitor binds to BCL2 with a Ki that is less than the Ki of binding of ABT-263 to BCL-2, e.g., between 1 and 5 times lower.

In some embodiments the BCL2 family inhibitor binds selectively to BCL-$X_L$ as compared to MCL1. In some embodiments the BCL2 family inhibitor binds selectively to BCL-$X_L$ as compared to BCL2. In some embodiments, the binding affinity of a BCL-$X_L$ selective inhibitor for BCL-$X_L$ is at least 5-fold, at least 10-fold, at least 100-fold, at least 1000-fold, at least 10,000-fold, at least 20,000-fold, at least 30,000-fold, or at least 50,000-fold higher than the binding affinity of such inhibitor for BCL2. In other words, the Kd or Ki of the inhibitor/BCL-$X_L$ complex is at least 5-fold, at least 10-fold, at least 100-fold, or at least 1000-fold lower than the Kd or Ki of a complex of the inhibitor and BCL2. In some embodiments, the binding affinity of a BCL-$X_L$ selective inhibitor for BCL-$X_L$ is at least 5-fold, at least 10-fold, at least 100-fold, at least 1000-fold, at least 10,000-fold, at least 20,000-fold, at least 30,000-fold, or at least 50,000-fold higher than the binding affinity of such inhibitor for MCL1. In other words, the Kd or Ki of the inhibitor/BCL-$X_L$ complex is at least 5-fold, at least 10-fold, at least 100-fold, at least 1000-fold, at least 10,000-fold, at least 20,000-fold, at least 30,000-fold, or at least 50,000-fold lower than the Kd or Ki of a complex of the inhibitor and BCL-$X_L$.

In some aspects, the disclosure provides a method for testing the ability of a BCL2 family inhibitor to inhibit the survival or proliferation of a proteasome inhibitor resistant cancer cell, comprising (a) contacting one or more test cells with the BCL2 family inhibitor, wherein the one or more test cells has a modestly reduced level of expression or activity of a subunit of a 19S proteasome complex as compared to a reference level, and (b) detecting the level of inhibition of the survival or proliferation of the one or more test cells by the BCL2 family inhibitor. In some embodiments the method comprised determining the IC50 of the BCL2 family inhibitor. In some embodiments the cancer cells are contacted with the BCL2 family inhibitor in vitro. In some embodiments the cancer cells are in a subject and the BCL2 family inhibitor is administered to the subject. In some aspects, the method may be used to identify BCL2 family inhibitors that are particularly effective in killing or inhibiting proliferation of cancer cells that have reduced expression of one or more 19S subunits and/or that are particularly effective in inhibiting tumor growth, causing tumor growth delay, or causing tumor regression. The method may be performed with two or more BCL2 family inhibitors, and the ability of the various BCL2 family inhibitors to inhibit growth of such cells may be compared. In some embodiments, one or more BCL2 family inhibitors with greater ability to inhibit growth of such cells as compared to ABT-199 may be identified and may be used in any of the compositions or methods relating to BCL2 family inhibitors described herein. In some embodiments, one or more BCL2 family inhibitors with greater ability to inhibit growth of such cells as compared to ABT-263 may be identified and may be used in any of the compositions or methods relating to BCL2 family inhibitors described herein. In some embodiments, at least 5, 10, 50, 100, or more BCL2 family inhibitors may be tested for ability to inhibit survival or proliferation of a proteasome inhibitor resistant cancer cell. In some embodiments, at least 5, 10, 50, 100, or more BCL2 family inhibitors may be tested for ability to inhibit survival or proliferation of a cancer cell that has reduced expression or activity of one or more 19S subunits (e.g., PSMD5) and/or for ability to inhibit tumor growth, cause tumor growth delay, or cause tumor regression of a tumor that has reduced expression or activity of one or more 19S subunits (e.g., PSMD5). In some embodiments one or more BCL2 family inhibitors described herein may be tested. In some embodiments the method comprises identifying one or more BCL2 family inhibitors using, e.g., physical compound screening, virtual compound screening, structure-based drug design, or combinations thereof. In some embodiments the cancer cells are contacted both with a BCL2 family inhibitor and a proteasome inhibitor in the same composition in vitro. In some embodiments cancer cells are contacted with a BCL2 family inhibitor and a proteasome inhibitor in vivo in combination. In some embodiments the level of synergy of the BCL2 family inhibitor and proteasome inhibitor with respect to inhibiting growth of, e.g., killing, the cancer cells or with respect to inhibiting tumor growth, causing tumor growth delay, or causing tumor regression is determined. In some embodiments of any of the compositions or methods described herein, the cancer cell or cancer does not have a defect in the intrinsic pathway of apoptosis. In some embodiments the cancer cell or cancer does not have a mutation in or loss of a gene that encodes a pro-apoptotic BCL2 family member, wherein said mutation reduces expression or activity of the pro-apoptotic BCL2 family member. In some embodiments the cancer cell or cancer does not have a mutation in or near a gene that encodes an anti-apoptotic BCL2 family member, wherein said mutation increases expression or activity of the anti-apoptotic BCL2 family member. For example, in some embodiments the cancer cell or cancer does not have a t(14;18) chromosomal translocation, which translocation results in overexpression of BCL2. In some embodiments the cancer cell or cancer does not have an increased copy number of a gene that encodes an anti-apoptotic BCL2 family member. In some embodiments the cancer cell or cancer does not overexpress BCL-$X_L$. In some embodiments the cancer cell or cancer does not overexpress BCL2. In some embodiments the cancer cell does not have an increased BCL2/BAX ratio. In some embodiments the cancer cell or cancer does not overexpress MCL1. In some embodiments the cancer cell or cancer does not overexpress BCL-W. In some embodiments the cancer cell or cancer does not overexpress BCL-XL and does not overexpress BCL2. In some embodiments the cancer cell or cancer does not overexpress any of BCL-$X_L$, BCL2, and MCL1. In some embodiments the cancer cell or cancer does not overexpress any of the anti-apoptotic BCL2 family members. Whether or not a cancer cell overexpresses an anti-apoptotic BCL2 family member or has an increased BCL2/BAX ratio may be determined by comparing the level in the cancer cell or cancer with the level found in normal cells or tissue of the same type as the cancer cell or cancer. In some embodiments, increased expression of an anti-apoptotic BCL2 family member or an increased BCL2/BAX ratio refers to an increase by at least a factor of at least 1.2, 1.5, 2, 2.5, 3, or more relative to a normal level.

In some embodiments of any of the compositions or methods described herein, the cancer cell or cancer has a defect in the intrinsic pathway of apoptosis. In some embodiments the cancer cell or cancer has a mutation in or loss of a gene that encodes a pro-apoptotic BCL2 family member, wherein said mutation reduces expression or activity of the pro-apoptotic BCL2 family member. In some embodiments the cancer cell or cancer has mutation in or near a gene that encodes an anti-apoptotic BCL2 family member, wherein said mutation increases expression or activity of the anti-apoptotic BCL2 family member. For example, in some embodiments the cancer cell or cancer has a t(14;18) chromosomal translocation, which translocation results in overexpression of BCL2 by juxtaposing the gene encoding it to the immunoglobulin heavy chain gene enhancer. In some embodiments the cancer cell or cancer has an increased copy number of a gene that encodes an anti-apoptotic BCL2 family member. In some embodiments the cancer cell or cancer overexpresses BCL-$X_L$. In some embodiments the cancer cell or cancer overexpresses BCL2. In some embodiments the cancer cell or cancer overexpresses MCL1.

In some embodiments of any of the methods described herein that relate to contacting a cancer cell with a BCL2 family inhibitor and a proteasome inhibitor, the cancer cell is contacted with a proteasome inhibitor and a BCL2 family inhibitor at a concentration of the BCL2 family inhibitor that would not (in the absence of the proteasome inhibitor) effectively inhibit growth (kill or inhibit proliferation) of the cancer cell. In some embodiments the cancer cell is contacted with a proteasome inhibitor and a BCL2 family inhibitor at a concentration of the BCL2 family inhibitor that is above the IC50 of the BCL2 family inhibitor when contacted with cancer cells in the absence of the proteasome inhibitor. In some embodiments of any of the methods described herein that relate to administering a BCL2 family inhibitor and a proteasome inhibitor to a subject in need of treatment for cancer, the BCL2 family inhibitor is administered at a dose that is lower than the maximum tolerated dose or a dose that is below the optimum dose as established in a clinical trial in which the BCL2 family inhibitor was administered to cancer patients as a single agent or in combination with one or more agent(s) that are not proteasome inhibitors.

In some embodiments the cancer is of a type for which the BCL2 family inhibitor has not shown efficacy in at least one clinical trial, e.g., the cancer is of a type for which the BCL2 inhibitor has shown a lack of efficacy sufficient to justify further development or approval of the BCL2 inhibitor for that type of cancer. In some embodiments the cancer is of a type for which the BCL2 family inhibitor has shown a lack of efficacy as a single agent in at least one clinical trial. In some embodiments the cancer is of a type for which the BCL2 family inhibitor has shown a lack of additional beneficial effect when administered in combination with one or more other agents as compared with the effect of the agent(s) when administered not in combination with the BCL2 family inhibitor. In some embodiments the cancer is of a type for which the BCL2 family inhibitor has shown efficacy in at least one clinical trial.

In some embodiments a BCL2 family inhibitor is administered as first-line therapy for treating a cancer of a type for which the BCL2 family inhibitor would otherwise not be used as first-line therapy, wherein the cancer has reduced expression or activity of one or more 19S subunits. In some embodiments a BCL2 family inhibitor is administered for treating a cancer of a type for which the risk/benefit ratio in a patient population that is not selected based on 19S subunit expression is too high to justify such treatment. In some embodiments a BCL2 family inhibitor is administered for treating a cancer that has reduced expression or activity of one or more 19S subunits, wherein the cancer is of a type for which the risk/benefit ratio in a patient population that is not selected based on reduced 19S subunit expression or activity is too high to justify such treatment. In some embodiments a BCL2 family inhibitor is administered for treating a cancer that has reduced expression or activity of one or more 19S subunits, wherein the dose of BCL2 inhibitor administered is lower than would be expected to be efficacious in treating the cancer in a patient population that is not selected based on reduced 19S subunit expression or activity. In some embodiments the BCL2 family inhibitor is administered in combination with a proteasome inhibitor. In some embodiments the BCL2 family inhibitor is administered not in combination with a proteasome inhibitor.

The screen that identified ABT-263 also identified a number of other compounds that selectively inhibit growth of T47D cancer cells that have a reduced level of PSMD2 as compared to control T47D cancer cells, including disulfiram, elesclomol, cladribine, and Ku-0063794. Accordingly, in certain embodiments any of these compounds or analogs thereof, or other compounds that act on the same biological process, pathway, or molecular target or by the same mechanism may be used in any of the compositions or methods in which BCL2 family inhibitors may be used. For example, in certain embodiments any of these compounds or analogs thereof, or other compounds that act on the same biological process, pathway, or molecular target or by the same mechanism may be used to treat a subject in need of treatment for a proteasome inhibitor resistant cancer. In certain embodiments any of these compounds or analogs thereof, or other compounds that act on the same biological process, pathway, or molecular target or by the same mechanism may be used to treat a subject in need of treatment for a cancer that has been determined to have reduced expression of one or more 19S subunits. In certain embodiments any of these compounds or analogs thereof, or other compounds that act on the same biological process, pathway, or molecular target or by the same mechanism may be used to treat a subject in need of treatment for a cancer that has been determined to have methylation of the promoter of a gene that encodes a 19S subunit, e.g., PSMD5. In certain embodiments any of these compounds or analogs thereof, or other compounds that act on the same biological process, pathway, or molecular target or by the same mechanism may be used in combination with a proteasome inhibitor, e.g., bortezomib, carfilzomib, oprozomib, ixazomib, or an analog of any of these compounds.

In some embodiments, a compound that selectively inhibits growth of cancer cells that have reduced expression of one or more 19S proteasome subunits is a dithiocarbamate. In some embodiments the dithiocarbamate is tetraethylthiuram disulfide (disulfiram; CAS Registry Number 97-77-8), the structure of which is shown below.

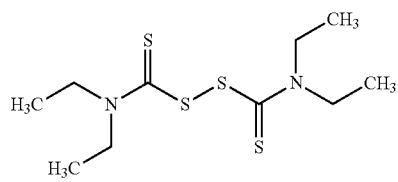 [SMILES: CCN(CC)C(=S)SSC(=S)N(CC)CC]

In some embodiments the compound is a disulfiram analog referred to as compound 339 (Sharma, V., et al. Mol Carcinog. 2015 Nov. 24. doi: 10.1002/mc.22433. [Epub ahead of print]). In some embodiments the compound is a disulfiram metabolite. In some embodiments the dithiocarbamate is pyrrolidine dithiocarbamate (PDTC).

In some embodiments, a compound that selectively inhibits growth of cancer cells that have reduced expression of one or more 19S proteasome subunits is a bis(thio-hydrazide amide). Exemplary bis(thio-hydrazide amides) are described in U.S. Patent Application Publication No. 20080119440. In some embodiments the bis(thio-hydrazide amide) is elesclomol, the structure of which is as follows:

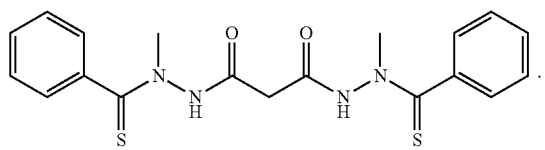 [SMILES: CN(NC(=O)CC(=O)NN(C)C(=S)c1ccccc1)C(=S)c1ccccc1]

In some embodiments a compound that selectively inhibits growth of cancer cells that have reduced expression of one or more 19S proteasome subunits is a compound capable of forming a complex with copper, e.g., Cu(II). Without wishing to be bound by any theory, the copper-agent complex may generate copper-mediated oxidative stress. In some embodiments, the compound that is capable of forming a complex with copper is a bis(thiohydrazide) amide or dithiocarbamate. In some embodiments the compound is additionally or alternately capable of forming a complex with zinc.

In some embodiments, a compound that selectively inhibits growth of cancer cells that have reduced expression or activity of one or more 19S subunits is an agent that causes an increased level of one or more reactive oxygen species (ROS) in cells with which it is contacted. ROS are chemically reactive molecules containing oxygen. Exemplary ROS are peroxides (e.g., hydrogen peroxides), superoxide, hydroxyl radical, and singlet oxygen. A compound that causes an increased level of one or more ROS may be referred to as "ROS inducer". A ROS inducer may, for example, inhibit an enzyme or biological pathway or process that would normally be responsible for reducing ROS (e.g., converting a ROS into a less reactive species) or may activate an enzyme or biological pathway or process that generates ROS in cells. Increased levels of ROS often result in, among other things, lipid peroxidation, which can generate numerous aldehyde species that are toxic to cells. In some embodiments a compound that selectively inhibits growth of cancer cells that have reduced expression or activity of one or more 19S subunits is an agent that is an oxidative stress promoting agent. The term "oxidative stress promoting agent" refers to ROS inducers and agents that impair the ability of a cell or organism to metabolize, inhibit, or remove harmful species that are generated as a result of ROS. For example, an oxidative stress promoting agent may inhibit an enzyme such as aldehyde dehydrogenase (ALDH) that would normally be responsible for converting a reactive protein or lipid species that has been generated through oxidation by ROS into a less reactive form.

In some embodiments, a compound that selectively inhibits growth of cancer cells that have reduced expression or activity of one or more 19S subunits is an aldehyde dehydrogenase (ALDH) inhibitor. Aldehyde dehydrogenases catalyze the irreversible oxidation of aldehydes to their corresponding carboxylic acid, thereby protecting cells from aldehyde-induced cytotoxicity. The human ALDH superfamily comprises 19 ALDH polypeptides: ALDH1A1, ALDH1A2, ALDH1A3, ALDH1B1, ALDH1L1, ALDH1L2, ALDH2, ALDH3A1, ALDH3A2, ALDH3B1, ALDH3B2, ALDH4A1, ALDH5A1, ALDH6A1, ALDH7A1, ALDH8A1, ALDH9A1, ALDH16A1, and ALDH18A1. These enzymes catalyze the oxidation of an aldehyde (e.g., an endogenously produced aldehyde such as those generated during metabolism or an exogenous aldehyde) to its respective carboxylic acid in an $NAD^+$-dependent or $NADP^+$-dependent reaction. Exemplary amino acid sequences of ALDH polypeptides (e.g., human sequences) and nucleic acids that encode them are known in the art and available in public databases such as the NCBI RefSeq database.

"ALDH inhibitor" refers to an agent that inhibits expression or activity of at least one member of the ALDH superfamily. In some embodiments of any of the methods or compositions described herein relating to ALDH inhibitors, the ALDH inhibitor inhibits the expression and/or activity of one or more of ALDH1A1, ALDH1A2, ALDH1A3, ALDH1B1, ALDH1L1, ALDH1L2, ALDH2, ALDH3A1, ALDH3A2, ALDH3B1, ALDH3B2, ALDH4A1, ALDH5A1, ALDH6A1, ALDH7A1, ALDH8A1, ALDH9A1, ALDH16A1, and ALDH18A1. In some embodiments, an ALDH inhibitor inhibits the expression and/or activity of one or more members of the ALDH1 family (ALDH1A1, ALDH1A2, ALDH1A3, ALDH1B1, ALDH1L1, and ALDH1L2). In some embodiments, an ALDH inhibitor inhibits the expression and/or activity of at least ALDH1A1. In some embodiments, an ALDH inhibitor inhibits the expression and/or activity of at least ALDH1A2. In some embodiments an ALDH inhibitor inhibits the expression and/or activity of ALDH2. In some embodiments an ALDH inhibitor inhibits the expression and/or activity of one or more members of the ALDH3 family (ALDH3A1, ALDH3A2, ALDH3B1, and ALDH3B2). In some embodiments an ALDH inhibitor inhibits the expression and/or activity of ALDH4A1, ALDH5A 1, ALDH6A1, ALDH7A1, ALDH8A1, ALDH9A1, ALDH16A1, and/or ALDH18A1. In some embodiments, an ALDH inhibitor inhibits the expression and/or activity of one or more members of the ALDH1 family and ALDH2.

An ALDH inhibitor may comprise a small molecule, nucleic acid (e.g., siRNA, aptamer), or protein (e.g., an antibody or non-antibody polypeptide). In some embodiments, the ALDH inhibitor binds to an ALDH polypeptide and inhibits its activity. In some embodiments the binding is reversible. In some embodiments a stable covalent bond between the ALDH inhibitor and ALDH is formed. For example, a covalent bond to an amino acid in the active site of the enzyme (e.g., Cys302) may be formed. In some embodiments the ALDH inhibitor is metabolized to one or more active metabolite(s) that at least in part mediate its inhibitory activity. Any of a wide variety of ALDH inhibitors are known in the art and may be used in compositions and methods described herein. Further information regarding ALDHs and certain ALDH inhibitors is found in Koppaka, V., et al., Pharmacological Reviews, (2012) 64: 520-539.

In certain embodiments an ALDH inhibitor is a dithiocarbamate, e.g., disulfiram, or an analog or metabolite of a dithiocarbamate, e.g., a disulfiram metabolite. Disulfiram inhibits ALDH1A1 and ALDH2. Disulfiram metabolites that are ALDH inhibitors include, e.g., N,N-diethyldithiocarbamate, S-methyl N,N-diethyldithiocarbamate, S-methyl N,N-diethyldithiocarbamate sulfoxide, S-methyl N,N-diethylthiocarbamate sulfoxide, S-methyl N,N-diethyldithiocarbamate sulfone, and S-methyl N,N-diethylthiocarbamate sulfone. Disulfiram and certain other ALDH inhibitors are used clinically in the treatment of alcoholism. Alcohol consumption by patients being treated with disulfiram results in acetaldehyde accumulation, leading to a number of unpleasant symptoms that discourage the patient from consuming alcohol. Disulfiram is also an inhibitor of dopamine-β-hydroxylase and has use in treating cocaine addiction.

In some embodiments an ALDH inhibitor is a quinazolinone derivative described in US Pat. App. Pub. No. 20080249116 of the following formula, where $R^1$, $R^2$, $R^3$, W, and V are as described therein:

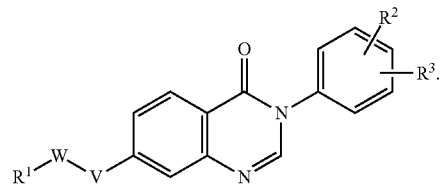

In some embodiments an ALDH inhibitor is a compound described in US Pat. Pub. No. 20040068003 of the following formula, wherein R1, R2, R3, R4, R5, R6, and R7 are as described therein:

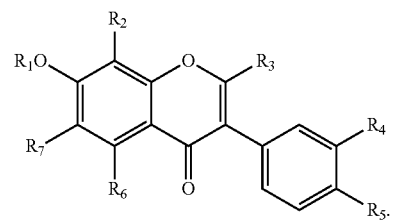

In some embodiments an ALDH inhibitor is a compound of the formula:

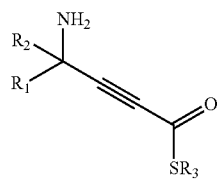

wherein $R_1$, $R_2$ and R3, independently represent a saturated or unsaturated linear or branched $C_1$-$C_6$ alkyl radical, or a salt thereof.

In some embodiments an ALDH inhibitor is a compound described in PCT/US2014/067943 (WO/2015/084731), entitled ALDEHYDE DEHYDROGENASE INHIBITORS AND METHODS OF USE THEREOF). In some embodiments the compound is of the following Formula I:

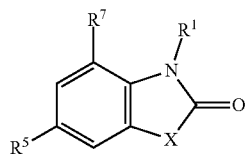

Formula I wherein X is O or —C=O; le is H, alkyl, substituted alkyl, alkenyl, substituted alkenyl, alkynyl, substituted alkynyl, cycloalkyl, substituted cycloalkyl, heterocycloalkyl, substituted heterocycloalkyl, aryl, substituted aryl, heteroaryl or substituted heteroaryl; $R^5$ is H, alkyl, substituted alkyl, halo, alkoxy or substituted alkoxy; and $R^7$ is H or halo.

In some embodiments the compound is of the following Formula II:

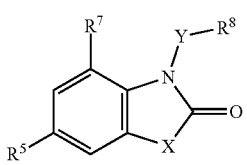

Formula II wherein X is O or —C=O; Y is alkyl, substituted alkyl, alkenyl, substituted alkenyl, alkynyl or substituted alkynyl; $R^5$ is H, alkyl, substituted alkyl, halo, alkoxy or substituted alkoxy; $R^7$ is H or halo; and $R^8$ is cycloalkyl, substituted cycloalkyl, heterocycloalkyl, substituted heterocycloalkyl, aryl, substituted aryl, heteroaryl or substituted heteroaryl.

In some embodiments the compound is of the following Formula III:

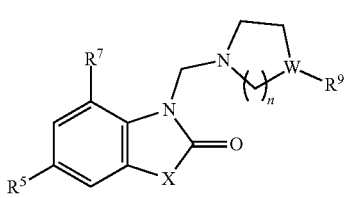

Formula III wherein n is 1 or 2; X is O or —C=O; W is N or O, and when W is O, then $R^9$ is not present; $R^5$ is H, alkyl, substituted alkyl, halo, alkoxy or substituted alkoxy; $R^7$ is H or halo; $R^9$ is H or —$(CH_2)_m R^{10}$, where m is an integer from 1 to 6; and $R^{10}$ is H, cycloalkyl, substituted cycloalkyl, heterocycloalkyl, substituted heterocycloalkyl, aryl, substituted aryl, heteroaryl or substituted heteroaryl.

Other ALDH inhibitors include coprine, cyanamide, 1-aminocyclopropanol (ACP), daidzin (i.e., the 7-glucoside of 4',7-dihydroxyisoflavone), CVT-10216 (3-[[[3-4-[(Methylsulfonyl)amino]phenyl]-4-oxo-4H-1-benzopyran-7-yl]oxy]methyl]benzoic acid; CAS Registry number 1005334-57-5), cephalosporins, antidiabetic sulfonylureas, metronidazole, diethyldithiocarbamate, phenethyl isothiocyanate (PEITC), prunetin (4',5-dihydroxy-7-methoxyisoflavone), 5-hydroxydaidzin (genistin), trichloroacetaldehyde monohydrate (or chloral), 4-amino-4-methyl-2-pentynethioic acid (S)-methyl ester. In some embodiments an ALDH inhibitor comprises 4-amino-4-methyl-2-pentyne-1-al (AMPAL) or 2-methyl-5-(methylsulfanyl)-5-oxopentan-2-aminium, which are irreversible inhibitors of the ALDH1 and ALDH3 enzymes. In some embodiments an ALDH inhibitor comprises benomyl (methyl-[1-[(butylamino)carbonyl]-1H-benzimidazol-2-yl]carbamate). In some embodiments an ALDH inhibitor is an oral hypoglycemic agent such as chlorpropamide or tolbutamide. In some embodiments an ALDH inhibitor is gossypol or an analog thereof. In some embodiments, an ALDH inhibitor is 2,2'-bis-(formyl-1,6,7-trihydroxy-5-isopropyl-3-methylnaphthalene). In some embodiments an ALDH inhibitor is a compound with any of the following CAS Registry numbers: 1069117-57-2, 1069117-56-1, 10691 17-55-0, 1055417-23-6, 1055417-22-5, 1055417-21-4, 1055417-20-3, 1055417-19-0, 1055417-18-9, 1055417-17-8, 1055417-16-7, 1055417-15-6 and 1055417-13-4.

In some embodiments an ALDH inhibitor is an aromatic lactone described in Buchman, C D, et al., Chemico-Biological Interactions (2015) 234:38-44.

In some embodiments an ALDH inhibitor comprises a nucleic acid that inhibits ALDH gene expression or activity. In some embodiments the nucleic acid is an RNAi agent (e.g., an siRNA) that inhibits ALDH gene expression. Exemplary nucleic acid ALDH inhibitors and formulations comprising them are described in US Pat. Pub. No. 20140248338.

In some embodiments an ALDH inhibitor is selective for one or more ALDH enzymes as compared to one or more other ALDH enzymes. As used herein, an inhibitor is considered selective for a first enzyme as compared to a second enzyme if the IC50 of the agent for the first enzyme is at least 5-fold lower than the IC50 of the agent for the second enzyme. In some embodiments the difference in IC50 values is at least 10-fold, at least 100-fold, or at least 1000-fold. In some embodiments an ALDH inhibitor is selective for one or more ALDH1 family members (e.g., ALDH1A1) as compared to ALDH2. In some embodiments an ALDH inhibitor is selective for one or more ALDH1 family members (e.g., ALDH1A1) and for ALDH2 as compared to at least some of the other ALDH superfamily members (e.g., ALDH3A1). In some embodiments an ALDH inhibitor is selective for one or more ALDH enzymes as compared with other dehydrogenases such as 15-hydroxyprostaglandin dehydrogenase (HPGD) and type 4 hydroxysteroid dehydrogenase (HSD17β4) HPGD and HSD17β4.

In some embodiments of any of the compositions or methods described herein that relate to an ALDH inhibitor, the ALDH inhibitor binds to at least one ALDH superfamily member with a Kd of ≤100 nM, e.g., 50 nM-100 nM. In some embodiments the ALDH inhibitor binds to at least one ALDH polypeptide with a Kd of ≤50 nM, e.g., 10 nM-50 nM. In some embodiments the ALDH inhibitor binds to at least one ALDH superfamily member with a Kd of ≤10 nM, e.g., 1 nM-10 nM. In some embodiments the ALDH inhibitor binds to at least one ALDH superfamily member with a Kd of ≤1 nM, e.g., 0.1 nM to 1 nM or 0.01 nM to 0.1 nM. In some embodiments the ALDH inhibitor binds to at least one ALDH1 family member with a Kd of ≤100 nM, e.g., 50 nM-100 nM. In some embodiments the ALDH inhibitor binds to at least one ALDH1 family member with a Kd of ≤50 nM, e.g., 10 nM-50 nM. In some embodiments the ALDH inhibitor binds to at least one ALDH1 family member with a Kd of ≤10 nM, e.g., 1 nM-10 nM. In some embodiments the ALDH inhibitor binds to at least one ALDH1 family member with a Kd of ≤1 nM, e.g., 0.1 nM to 1 nM or 0.01 nM to 0.1 nM. In some embodiments the ALDH inhibitor binds to ALDH2 with a Kd of ≤100 nM, e.g., 50 nM-100 nM. In some embodiments the ALDH inhibitor binds to ALDH2 with a Kd of ≤50 nM, e.g., 10 nM-50 nM. In some embodiments the ALDH inhibitor binds to ALDH2 with a Kd of ≤10 nM, e.g., 1 nM-10 nM. In some embodiments the ALDH inhibitor binds to ALDH2 with a Kd of ≤1 nM, e.g., 0.1 nM to 1 nM or 0.01 nM to 0.1 nM.

In some embodiments of any of the compositions or methods described herein that relate to a ALDH inhibitor, the ALDH inhibitor inhibits one or more ALDH polypeptides with an IC50 of 1 nM-5 μM, e.g., 1 nM-5 nM, 5 nM-10 nM, 10 nM-20 nM, 20 nM-30 nM, 30 nM-50 nM, 50 nM-100 nM, 100 nM-500 nM, 500 nM-1 μM, or 1 μM-5 μM. In some embodiments the ALDH inhibitor inhibits one or more ALDH1 polypeptides with an IC50 of 1 nM-5 μM, e.g., 1 nM-5 nM, 5 nM-10 nM, 10 nM-20 nM, 20 nM-30 nM, 30 nM-50 nM, 50 nM-100 nM, 100 nM-500 nM, 500 nM-1 μM, or 1 μM-5 μM. In some embodiments the ALDH inhibitor inhibits ALDH1A1 with an IC50 of 1 nM-5 μM, e.g., 1 nM-5 nM, 5 nM-10 nM, 10 nM-20 nM, 20 nM-30 nM, 30 nM-50 nM, 50 nM-100 nM, 100 nM-500 nM, 500 nM-1 μM, or 1 μM-5 μM. In some embodiments the ALDH inhibitor inhibits ALDH1A2 with an IC50 of 1 nM-5 μM, e.g., 1 nM-5 nM, 5 nM-10 nM, 10 nM-20 nM, 20 nM-30 nM, 30 nM-50 nM, 50 nM-100 nM, 100 nM-500 nM, 500 nM-1 μM, or 1 μM-5 μM. In some embodiments the ALDH inhibitor inhibits ALDH2 with an IC50 of 1 nM-5 μM, e.g., 1 nM-5 nM, 5 nM-10 nM, 10 nM-20 nM, 20 nM-30 nM, 30 nM-50 nM, 50 nM-100 nM, 100 nM-500 nM, 500 nM-1 μM, or 1 μM-5 μM.

In some aspects, the disclosure provides a method for testing the ability of an ALDH inhibitor to inhibit the survival or proliferation of a proteasome inhibitor resistant cancer cell, comprising (a) contacting one or more test cells with the ALDH inhibitor, wherein the one or more test cells has a modestly reduced level of expression or activity of a subunit of a 19S proteasome complex as compared to a reference level, and (b) detecting the level of inhibition of the survival or proliferation of the one or more test cells by the ALDH inhibitor. In some embodiments the method comprises determining the IC50 of the ALDH inhibitor. In some embodiments the cancer cells are contacted with the ALDH inhibitor in vitro. In some embodiments the cancer cells are in a subject and the ALDH inhibitor is administered to the subject. In some aspects, the method may be used to identify ALDH family inhibitors that are particularly effective in killing or inhibiting proliferation of cancer cells that have reduced expression of one or more 19S subunits and/or that are particularly effective in inhibiting tumor growth, causing tumor growth delay, or causing tumor regression. The method may be performed with two or more ALDH inhibitors, and the ability of the various ALDH inhibitors to inhibit growth of such cells may be compared. In some embodiments, one or more ALDH inhibitors with greater ability to inhibit growth of such cells as compared to disulfiram may be identified and may be used in any of the compositions or methods relating to ALDH inhibitors described herein. In some embodiments, one or more ALDH inhibitors with greater ability to inhibit growth of such cells as compared to disulfiram may be identified and may be used in any of the compositions or methods relating to ALDH inhibitors described herein. In some embodiments, at least 5, 10, 50, 100, or more ALDH inhibitors may be tested. In some embodiments the cancer cells are contacted both with an ALDH inhibitor and a proteasome inhibitor in the same composition in vitro. In some embodiments cancer cells are contacted with an ALDH inhibitor and a proteasome inhibitor in vivo in combination. In some embodiments the level of synergy of the ALDH inhibitor and proteasome inhibitor with respect to inhibiting growth of, e.g., killing, the cancer cells or with respect to inhibiting tumor growth, causing tumor growth delay, or causing tumor regression is determined.

In some embodiments an ROS inducer is a dithiocarbamate (e.g., disulfiram or an analog or active metabolite thereof) or a bis(thio-hydrazide amide) (e.g., elesclomol or an analog or active metabolite thereof). In some embodiments a ROS inducer is a metal such as iron, copper, chromium, vanadium, and cobalt that is capable of redox cycling in which a single electron may be accepted or donated by the metal. This action catalyzes production of reactive radicals and reactive oxygen species. In some embodiments a ROS inducer is a compound that forms a complex with such a metal.

In some embodiments, a compound that selectively inhibits growth of cancer cells that have reduced expression of one or more 19S proteasome subunits is a purine analog. Purine analogs are compounds that mimic the structure of naturally occurring purines such as adenosine. In some embodiments the purine analog is cladribine (2-chlorodeoxyadenosine), pentostatin, or EHNA (erythro-9-(2-hydroxy-3-nonyl)adenine), which mimic the nucleoside adenosine and inhibit the enzyme adenosine deaminase.

In some embodiments, a compound that selectively inhibits growth of cancer cells that have reduced expression of one or more 19S proteasome subunits is a mammalian target of rapamycin (mTOR) inhibitor. As known in the art, mTOR can form complexes that include mTOR protein along with either raptor or rictor, which, together with other proteins, form mTOR complex 1 (mTORC1) and mTOR complex 2 (mTORC2), respectively. In some embodiments the mTOR inhibitor inhibits mTORC1, mTORC2, or both. In some embodiments the mTOR inhibitor is a small molecule that binds to mTOR and inhibits its kinase activity. In some embodiments the mTOR inhibitor is a small molecule that binds to the ATP-binding site of mTOR. In some embodiments the mTOR inhibitor is Ku-0063794. In some embodiments the mTOR inhibitor is AZD2104, OSI-027, INK128, CC-223, Torin2, or an analog of any of these compounds. In some embodiments the mTOR inhibitor inhibits the kinase activity of mTORC1, mTORC2, or both with an IC50 of <20 nM.

In certain embodiments a BCL2 family inhibitor (e.g., ABT-263 or an analog thereof), an ALDH inhibitor (e.g., disulfiram), a dithiocarbamate (e.g., disulfiram), a bis(thio-hydrazide amide) (e.g., elesclomol), a purine analog such as cladribine, or a mTOR inhibitor or other compounds that act on the same biological process, pathway, or molecular target or by the same mechanism as any of these compounds may be used to treat a subject in need of treatment for a cancer that has increased methylation of the promoter region of at least one 19S subunit gene, e.g., the PSMD5 gene. In some embodiments the cancer has been determined to have increased methylation of the promoter region of at least one 19S subunit gene, e.g., the PSMD5 gene, prior to administration of the agent. In certain embodiments, methylation of the promoter region of a 19S subunit gene, e.g., the PSMD5 gene, may be used as a biomarker to predict the likelihood that a cancer will be sensitive to a BCL2 family inhibitor (e.g., ABT-263 or an analog thereof, a dithiocarbamate (e.g., disulfiram), a bis(thio-hydrazide amide) (e.g., elesclomol), a purine analog such as cladribine, or a mTOR inhibitor, or other compounds that act on the same biological process, pathway, or molecular target or by the same mechanism.

In some aspects, the present disclosure provides the insight that the increased sensitivity to BCL2 family inhibitors or ALDH inhibitors, dithiocarbamates, or bis(thio-hydrazide amides) associated with reduced 19S subunit expression (e.g., associated with promoter methylation of a gene that encodes a 19S subunit, e.g., PSMD5), may not be directly driven by such 19S subunit expression loss (or such loss may be only partially responsible for the increased sensitivity). Without wishing to be bound by any theory, such 19S subunit expression loss (e.g., associated with promoter methylation of a gene that encodes a 19S subunit, e.g., PSMD5) may be associated with an altered global epigenetic state, wherein cells in such altered epigenetic state exhibit increased sensitivity to a variety of agents, including BCL2 family inhibitors (e.g., ABT-263) and other agents described herein. Regardless of the underlying mechanism, reduced 19S subunit expression (e.g., associated with promoter methylation of a gene that encodes a 19S subunit, e.g., PSMD5), serves as a biomarker useful to identify cancer cells or cancers that have increased sensitivity to such agents and/or to select patients who are suitable candidates to be treated with such agents.

In certain embodiments the present disclosure provides methods as set forth in Claim Set 2 below, wherein an ALDH inhibitor, dithiocarbamate, or a bis(thio-hydrazide amide) is used instead of, or in addition to, a BCL2 family inhibitor. In some embodiments the dithiocarbamate is disulfiram. In some embodiments the bis(thio-hydrazide amide) is elesclomol.

It should be understood that wherever the present disclosure describes a compound or a method of use of a compound, a pharmaceutically acceptable salt, prodrug, analog, or active metabolite of such compound or analog may be provided or used instead or in addition.

EXAMPLES

Example 1: Unbiased Mammalian Screen Identifies 19S Subunits as Key Determinants of Resistance to Proteasome Inhibitors Despite an exquisitely detailed understanding of proteasome function, and of the mechanism of action of proteasome inhibitors, we have a limited understanding of the molecular mechanisms that cells deploy to resist the cytotoxic effects of reduced flux through the proteasome (Kale and Moore, 2012). Such an understanding is of great importance in the dynamics of natural ecosystems in the face of diverse proteotoxic stresses and in the clinic, where pre-existing intrinsic resistance and acquired resistance following drug exposure have limited the effectiveness of bortezomib as a therapeutic.

To gain insights into the mechanisms that allow cells to withstand reduced flux through the proteasome, we took advantage of highly specific chemical inhibitors, namely bortezomib and the peptide aldehyde MG132, which allow dosage-dependent control. These inhibit both 20S and 26S proteasomes by targeting the core proteolytic catalytic activity of the 20S subunits (Goldberg, 2012; Kisselev et al., 2006; Kisselev et al., 2012).

We used these inhibitors at toxic levels in an unbiased, genome-wide screen. We selected for cells that were resistant to the inhibitors from a library of 100 million gene-trap insertions, using a human cell line that is haploid for all chromosomes except chromosome 8 (Carette et al., 2009; Carette et al., 2011a). This approach is analogous to screens so broadly and effectively used in haploid yeast, and identifies loss-of-function events that allow human cells to survive diverse toxic insults (Carette et al., 2011a; Carette et al., 2011b; Guimaraes et al., 2011; Reiling et al., 2011; Winter et al., 2014). The results of our screen led us to the discovery of a surprising and highly conserved strategy by which organisms can protect themselves from the toxic effects of reduced flux through the proteasome.

For our screens, we used a library of near-haploid human chronic myeloid leukemia cells (KBM7) containing approximately 100 million retroviral gene-trap insertions that target over 98% of transcribed genes. To identify genes that increase resistance to proteasome inhibition we exposed cells for four weeks to either MG132 or bortezomib. We then further expanded the pools of resistant cells to enable the amplification and sequencing of the insertion sites (FIG. 1A).

Figure 1B:
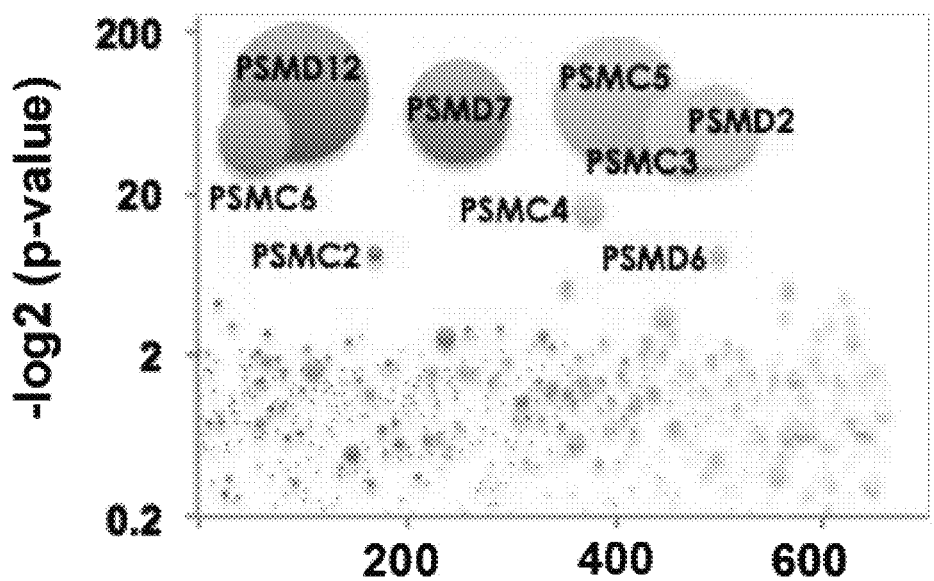

For the MG132 resistance screen, we identified 992 independent insertion sites in the pool of surviving cells. Surprisingly, all insertions that reached a high level of statistical enrichment (p-value <1 $e^{-7}$) lay in genes encoding subunits of the proteasome 19S regulatory complex (FIGS. 1B and 1C). These included both ATPase subunits (PSMC2, PSMC3, PSMC4, PSMC5, and PSMC6) as well as non-ATPase subunits (PSMD2, PSMD6, PSMD7, and PSMD12). No insertions were recovered in genes encoding subunits of the 20S catalytic core (Table 51). For the bortezomib resistance screen, we recovered 538 independent insertions. The results of the two screens were remarkably similar with seven of the ten most highly-enriched genes encoding subunits of the 19S complex. Table 51 shows the top 30 hits for each screen.

Such strikingly similar results from two unbiased screens with chemically distinct proteasome inhibitors strongly indicated that altering the 19S complex can protect cells against compounds that inhibit the 20S catalytic core. From the resistant pools of cells, we then attempted to isolate stable clones that contained 19S subunit gene insertions. We were unable to do so. Next, we attempted to delete PSMD12 in a near-haploid fibroblast cell line (HAP1; (Carette et al., 2010; Essletzbichler et al., 2014). With this targeted approach using CRISPR constructs we were only able to recover diploid cell variants in which just one of the two PSMD12 alleles was disrupted.

Figures 31A, 31B:
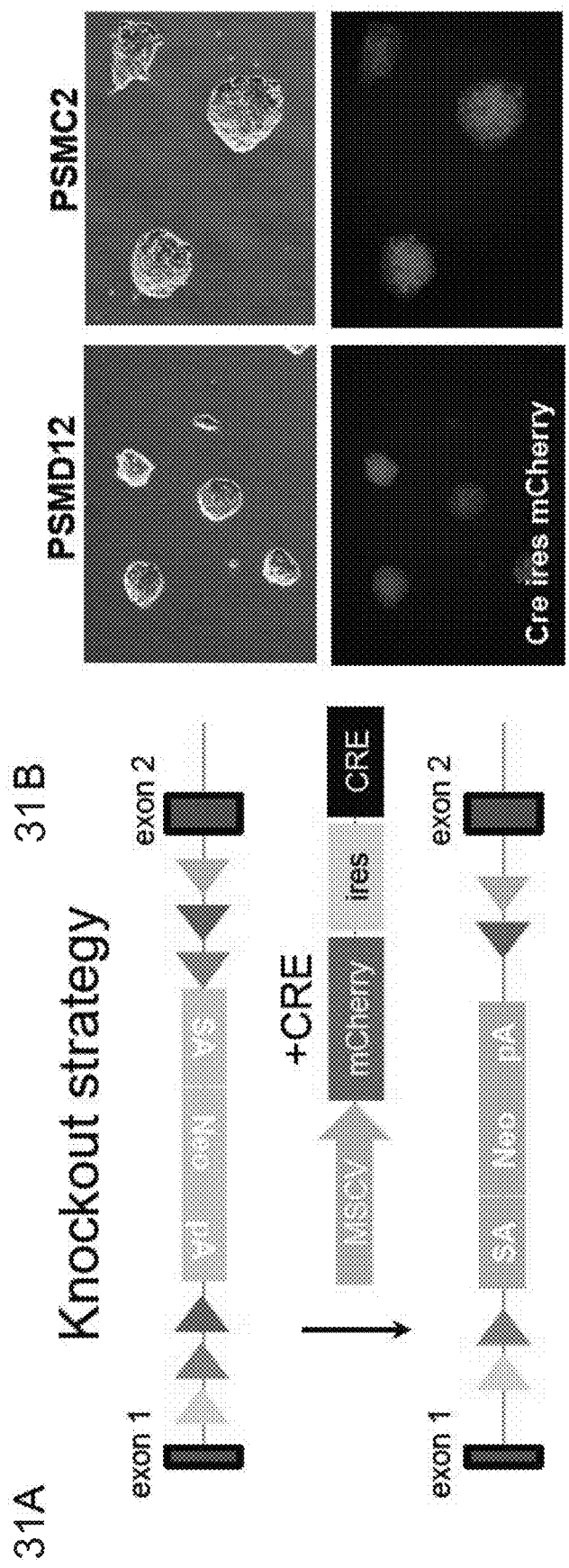
FIGS. 31A-31D.
Figures 31C, 31D:
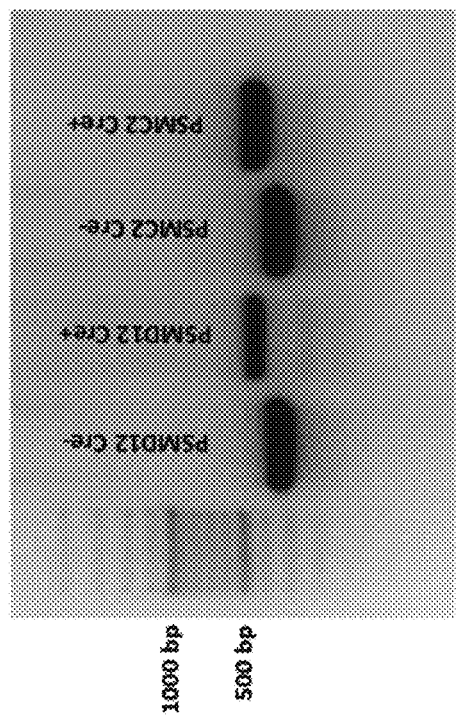

Finally, from a collection of haploid mouse embryonic stem cells that harbor reversible gene-trap cassettes (Elling et al., 2011), we identified two clones with cassettes located in first intron of the PSMC2 or PSMD12 genes. In these cells, inversion of the cassettes would generally be expected to inactivate the targeted gene. We induced Cre-mediated inversion in over 3,000 cells harboring each cassette, but less than 1% of the cells survived. We confirmed that inversion had occurred in the surviving cells. However, all of the stable clones that emerged retained expression of the targeted subunits (FIG. 31).

These findings confirm that, as others have found in yeast and drosophila, the function of the 19S regulatory complex is essential for sustained proliferation of mammalian cells under basal conditions. Presumably, cells carrying 19S mutations had become enriched in our initial MG132 and bortezomib screens because they provided cells with a short-term advantage for growth over several generations.

Example 2: Reducing 19S Subunits Protects Human Cancer Cells from Proteasome Inhibitors Next, we asked if a simple reduction in the expression of 19S subunits could protect against the toxicity of proteasome inhibitors. We assembled a panel of shRNA-expressing lentiviruses targeting seventeen 19S subunits and three 20S subunits (PSMB5, PSMB7 and PSMA3). Each gene was targeted separately using four different shRNAs (FIG. 2, Table S2) and we averaged the effects on viability from these four hairpins.

With or without bortezomib, knockdown of any of the subunits of the 20S catalytic core reduced viability (FIG. 2, FIGS. 32A-32D). In contrast, the effects of knocking down several different 19S subunits had opposing effects, depending on the absence or presence of the inhibitor. In its absence, 19S subunit reduction had a fitness cost and decreased cell viability; in its presence, 19S subunit reduction provided a survival advantage and increased viability (FIG. 2, FIGS. 32A-32D).

Figures 2A, 2B, 2C:
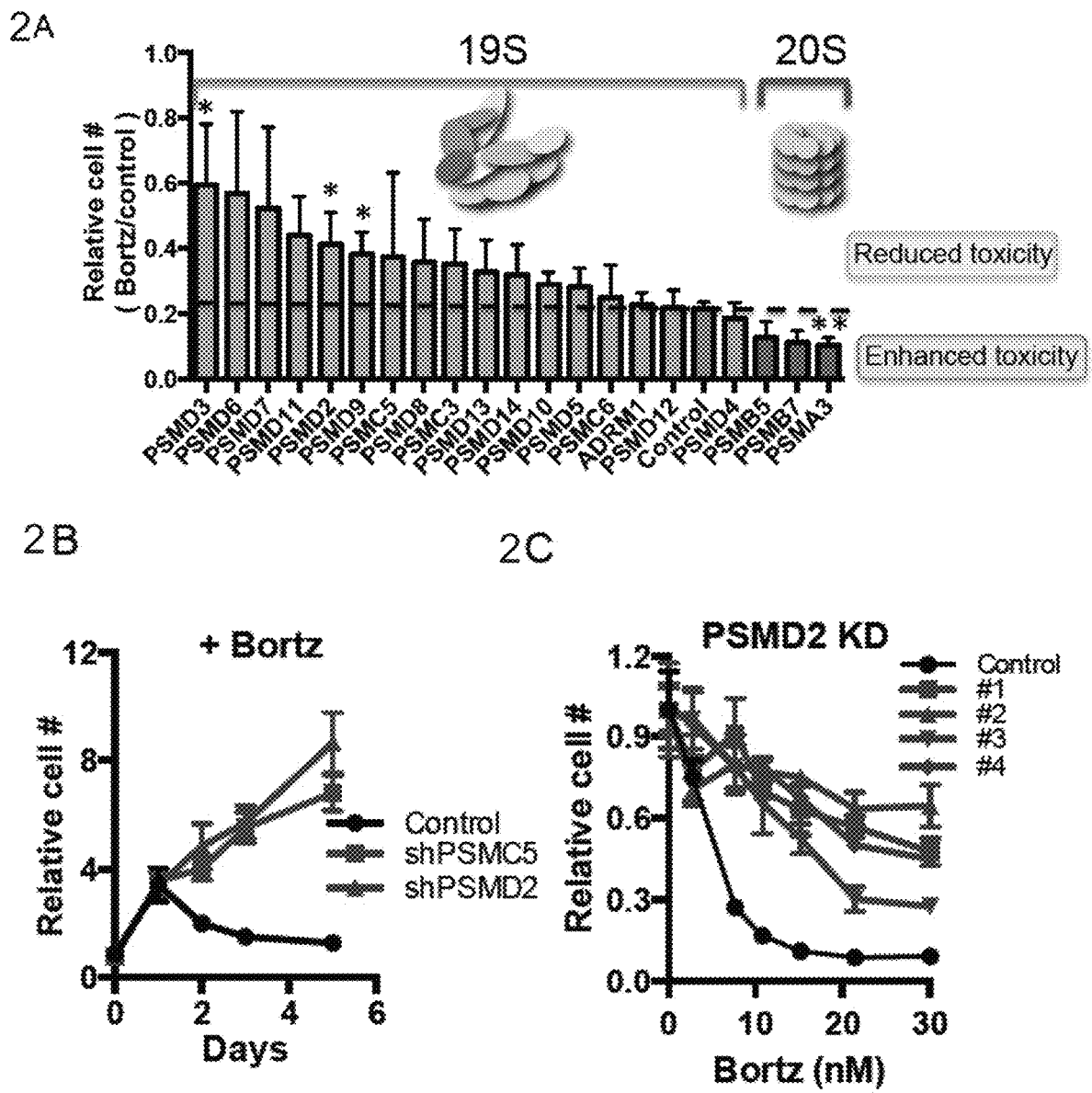
FIGS. 2A-2F: Reducing expression of 19S subunits increases the levels of active 20S proteasomes and protects cancer cells from proteasome inhibition.
Figures 32A, 32B, 32C, 32D:
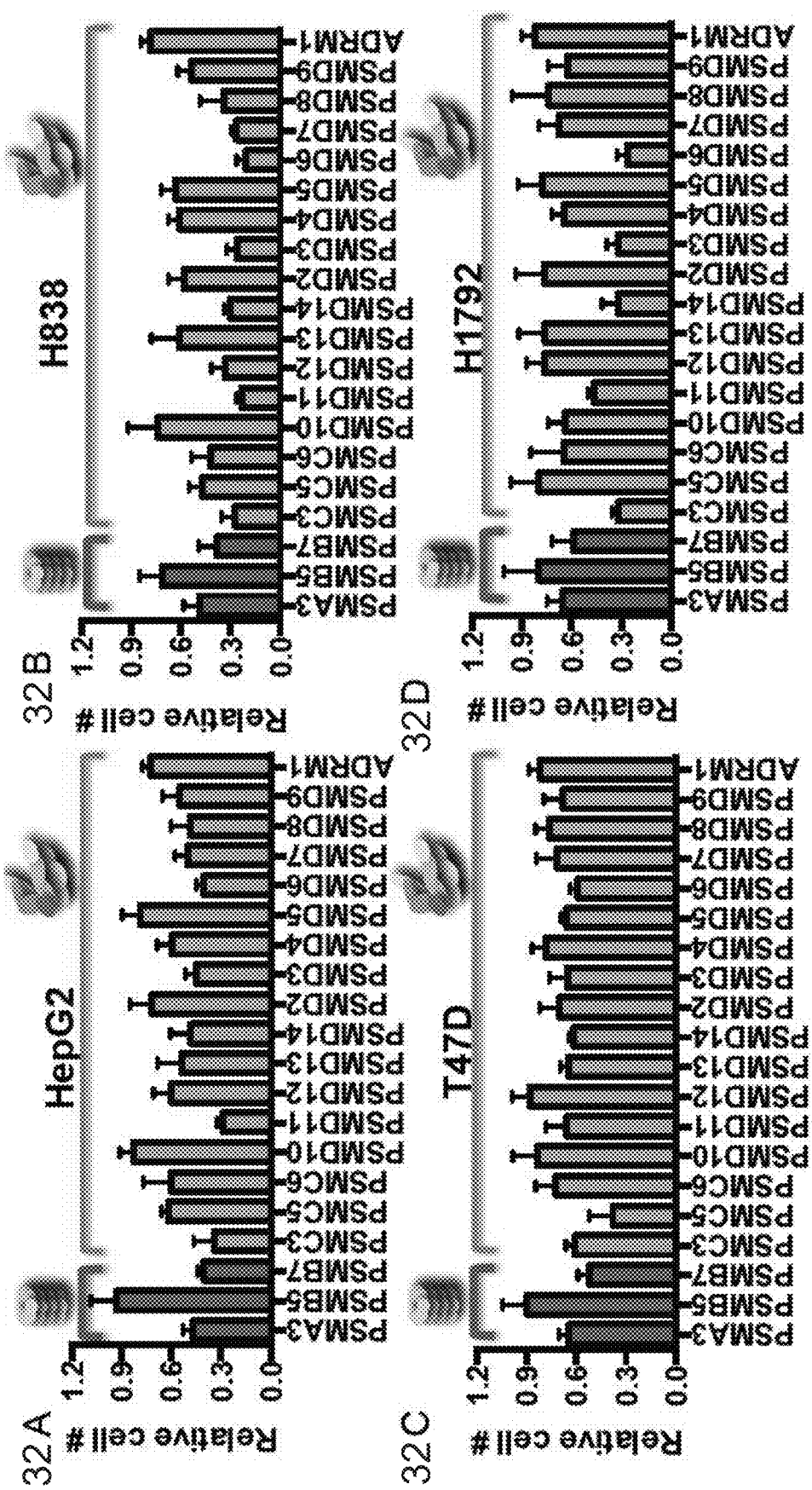
Figures 32E, 32F, 32G, 32H:
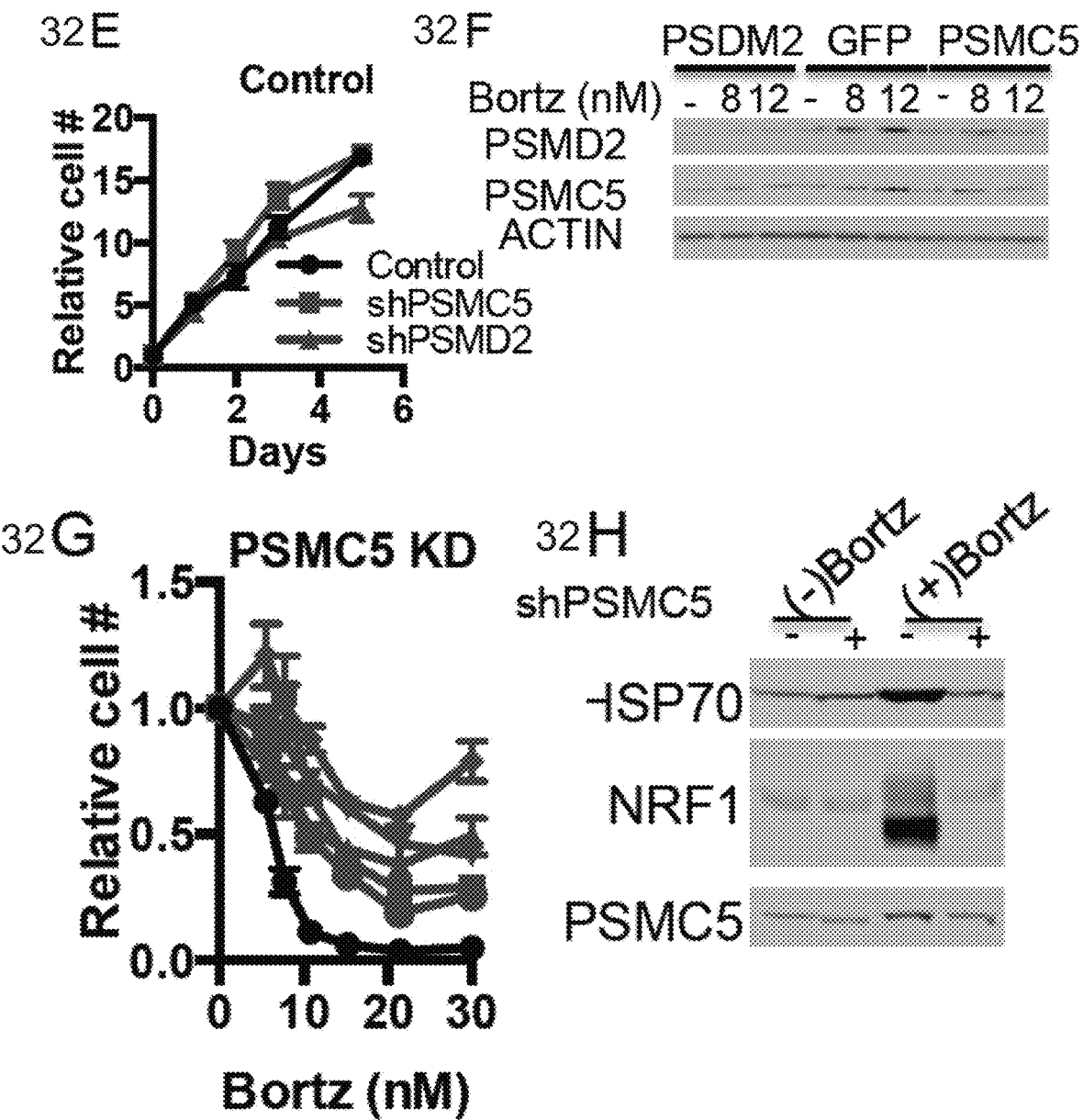
(FIGS. 32E-32F) HepG2 cells with shRNAs targeting PSMC5, PSMD2 and GFP were grown out. Their relative growth was analyzed in the absence of bortezomib (FIG. 32E) and their protein content was analyzed 24 hours after the addition of either 8 or 12 nM of bortezomib (FIG. 32F).
(FIG. 32G) The relative cell number of cells harboring a control shLacZ (black) or each of 5 individual shRNAs targeting shPSMC5 (Cayenne) was analyzed 4 days after addition of the indicated concentrations of bortezomib.
(FIG. 32H) HepG2 cells stably expressing shRNAs targeting the PSMC5 subunit and a control shRNA (lacZ) were analyzed by western blot for the indicated proteins 24 hours with or without bortezomib treatment.
Figures 32I, 32J, 32K, 32L, 32M, 32N:
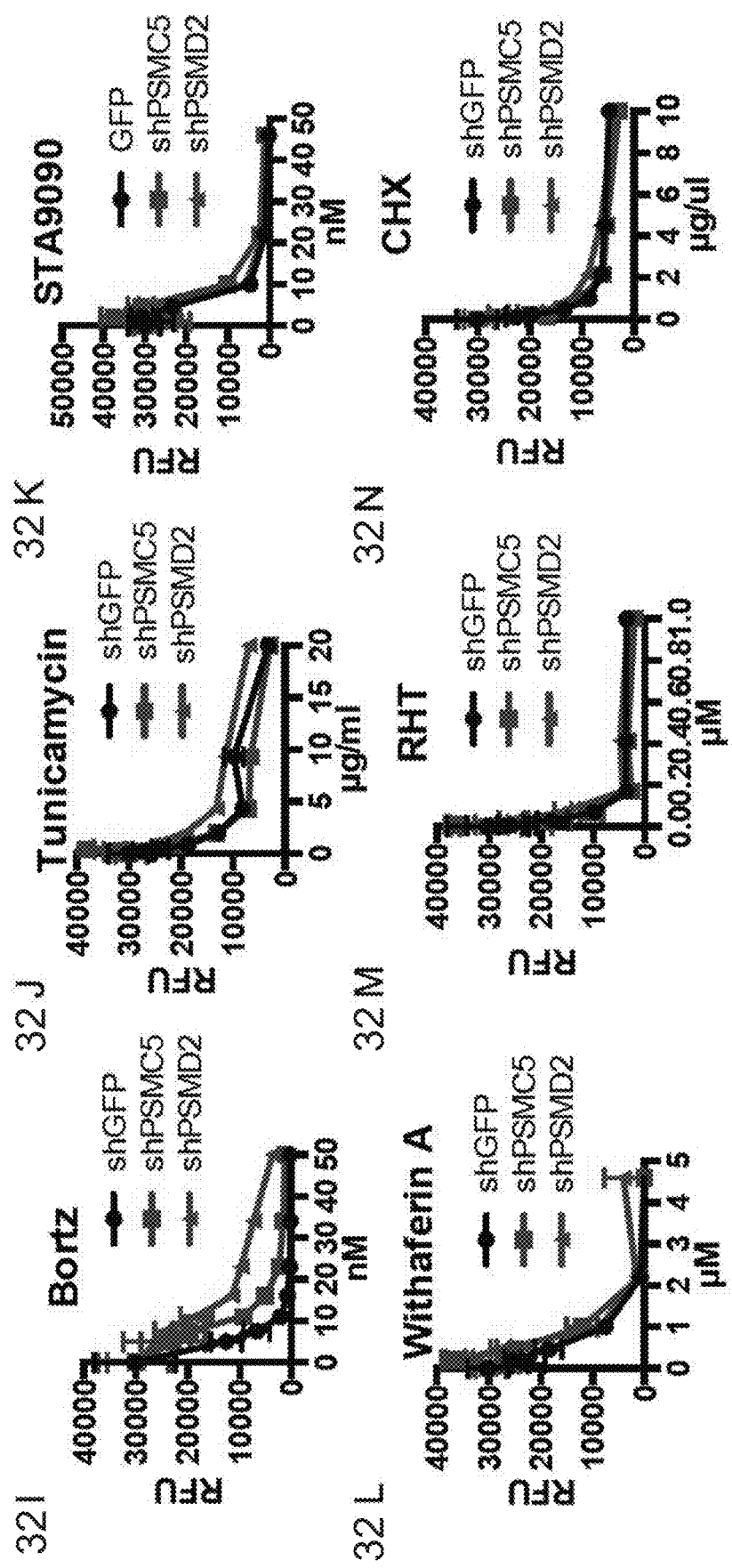

To investigate further, we sought to recover stable clones with reduced levels of 19S subunits. Long-term 19S subunit reduction impeded the growth of most cells, but we were able to propagate two lines that proliferated normally (FIG. 32E). These lines stably expressed shRNA targeting either PSMC5 or PSMD2. In both cases the lines had only a modest reduction in protein levels (FIG. 32F). At a concentration of bortezomib that completely inhibited the proliferation of control cells (12 nM), these cells continued proliferating (FIG. 2B, FIG. 32G).

To validate this finding we selected four additional cell lines each with a different shRNA driving modest reduction in PSMD2 protein levels. Again, all of these lines were significantly more resistant to bortezomib than the parental line (EC50 values increased by three to six-fold, FIG. 2C). These results establish that reducing the expression of a 19S regulatory complex protein increases cellular resistance to proteasome inhibitors.

Example 3: 19S Subunit Reduction does not Activate Classic Cytoprotective Stress Responses and Blunts Bortezomib-Mediated Stress Responses We reasoned that a likely mechanism by which 19S subunit reduction might promote resistance is by induction of the cytoprotective stress responses that allow cells to cope with the increase in proteotoxic stress caused by the proteasome inhibitor. One major response to such inhibition is the activation of NRF1, a transcriptional regulator of proteasome gene expression that increases the expression of proteasome subunits, elevates proteasome content and promotes resistance (Radhakrishnan et al., 2014; Radhakrishnan et al., 2010; Sha and Goldberg, 2014; Steffen et al., 2010). A second major response to proteasome inhibitors is activation of heat-shock factor 1 (HSF1), the master regulator of the heat-shock response, which increases levels of HSP70 and other protein chaperones (Bush et al., 1997).

Figure 2D:
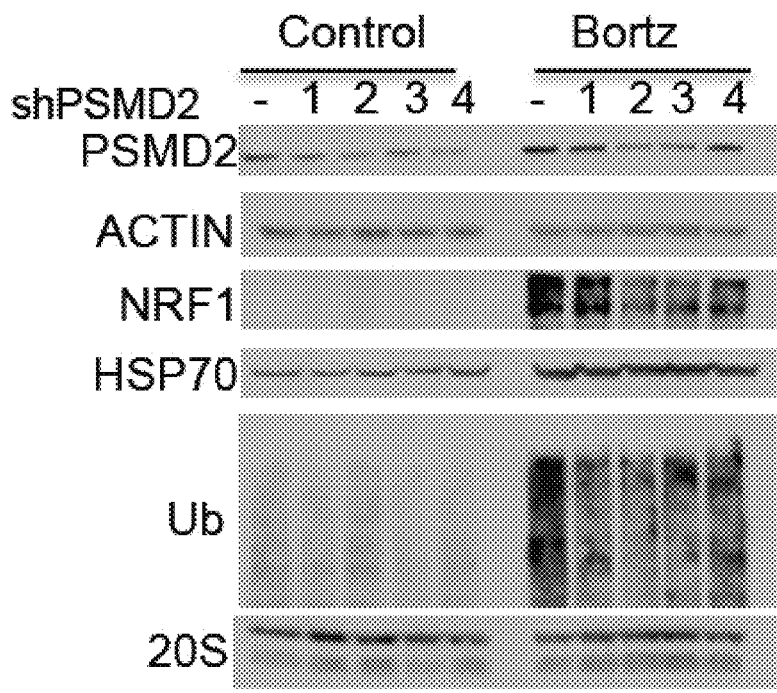

Surprisingly, in the four cell lines with modest reductions of PSMD2 we did not detect constitutive activation of NRF1 and, correspondingly, the expression of 20S subunits was unaltered (FIG. 2D). Moreover, HSF1 was not activated as reflected by the stable expression HSP70, the protein that is most highly responsive to proteotoxic stress (FIG. 2D). Consistent with these findings, polyubiquitinated proteins did not accumulate in the PSMD2 knockdown cells (FIG. 2D), suggesting that modestly reducing 19S subunit levels did not itself induce a cytoprotective stress response.

Not only were stress response pathways not activated, but the response to bortezomib was blunted in cells with reduced PSMD2 levels. The accumulation of polyubiquitinated proteins was reduced relative to control cells treated with the inhibitor. The activation of NRF1 was also reduced (FIG. 2D). We obtained very similar results in cells with PSMC5 knockdown except in this case HSP70 levels were also reduced (FIG. 32H).

Notably, the protective effect of 19S subunit reduction was specific to the toxicity caused by proteasome inhibitors. Cells with reduced PSMD2 levels remained fully sensitive to small molecule mediators of ER stress, HSP90 inhibition, thiol adduct formation or blockade of translation initiation or translation elongation among other stresses (FIGS. 32I-32N). Thus, modest 19S subunit reduction protected cells by selectively lowering the proteotoxic stress that is generated by proteasome inhibition.

Example 4: 19S Subunit Reduction Increases Levels of 20S Proteasome Complexes

Figure 2E:
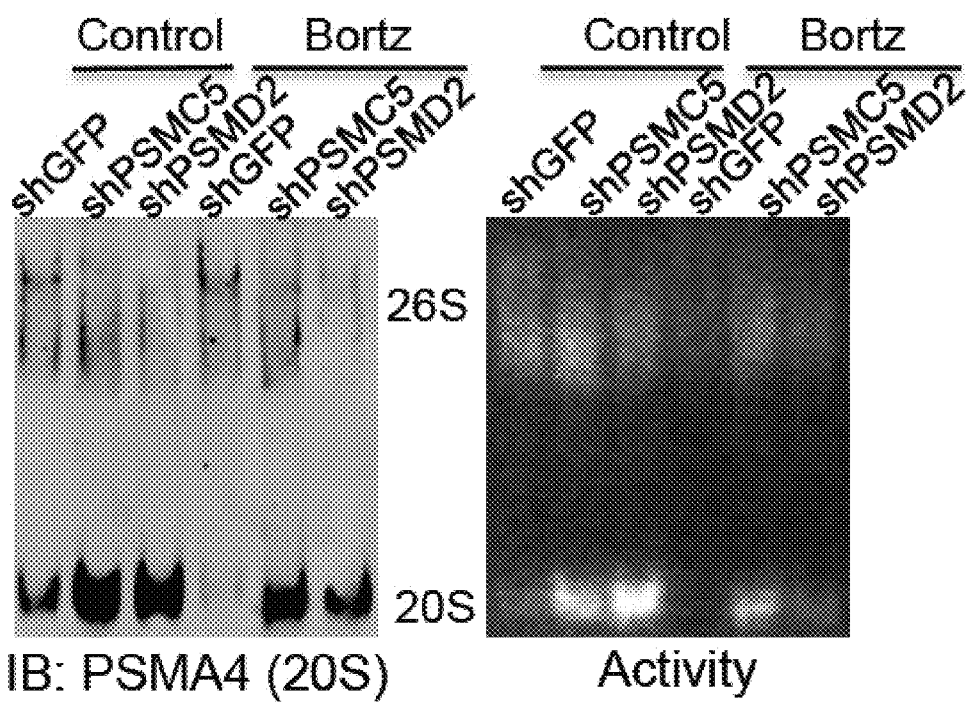
Figure 2F:
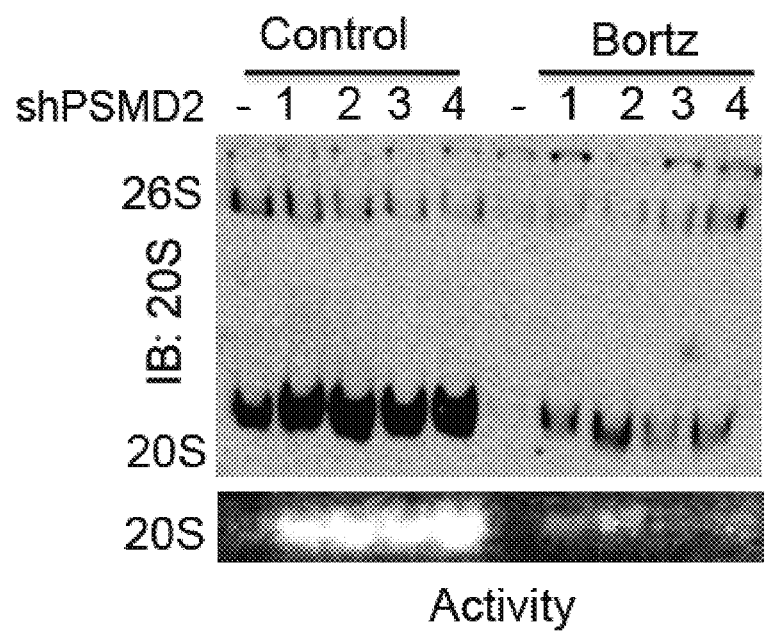

Because classic adaptive responses are not induced by 19S subunit reduction, we sought other explanations for the increased resistance to proteasome inhibition. We first separated 20S and 26S proteasomes on native gels and examined effects on the relative levels of 26S and 20S proteasome complexes. In cells with reduced levels of either PSMC5 or PSMD2, 26S proteasome complexes were reduced and 20S proteasome complexes were increased (FIGS. 2E and 2F). These changes persisted in the presence of bortezomib (FIGS. 2E and 2F). Next, we assayed their activity with a fluorescently labeled substrate. Exposing control cells to 12 nM bortezomib for 24 hours led to a nearly complete inactivation of 20S proteasome function. Cells with reduced levels of either PSMC5 or PSMD2 maintained a significant level of 20S proteasome activity (FIGS. 2E and 2F).

Example 5: Compromising the 19S Regulatory Complex Suppresses Bortezomib-Induced Stress Responses To examine in detail the transcriptional changes that characterize cells with increased resistance to proteasome inhibition, we performed whole genome RNA-sequencing in two lines with modest reductions in PSMD2. Sequence data confirmed that PSMD2 mRNA levels were reduced by ~50% in both lines. We examined basal gene expression and the effects of bortezomib treatment on these cells, comparing them to cells carrying a control lacZ shRNA construct.

Figures 3A, 3B, 3C:
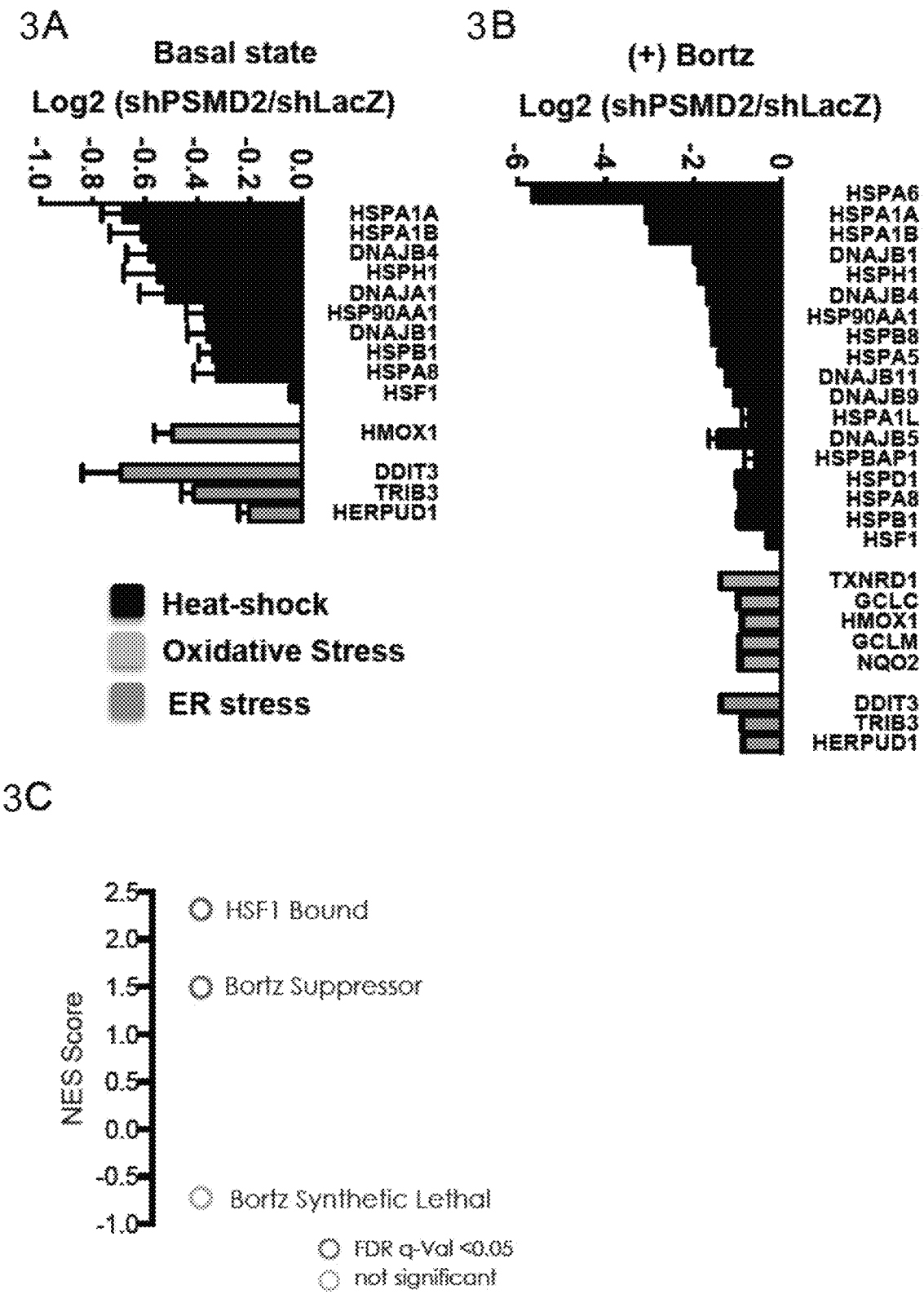
FIGS. 3A-3E: Inhibition of bortezomib-mediated transcriptional responses in PSMD2 knockdown cells. RNA-seq gene expression profiling was conducted on cells that harbor two different shRNAs targeting PSMD2 (PSMD2-1, PSMD2-2) and on control cells (shLacZ). The effects of reducing PSMD2 levels on gene expression were highly correlated in both basal conditions (Pearson's r=0.99) and following bortezomib treatment (Pearson's r=0.94).
Figure 33A:
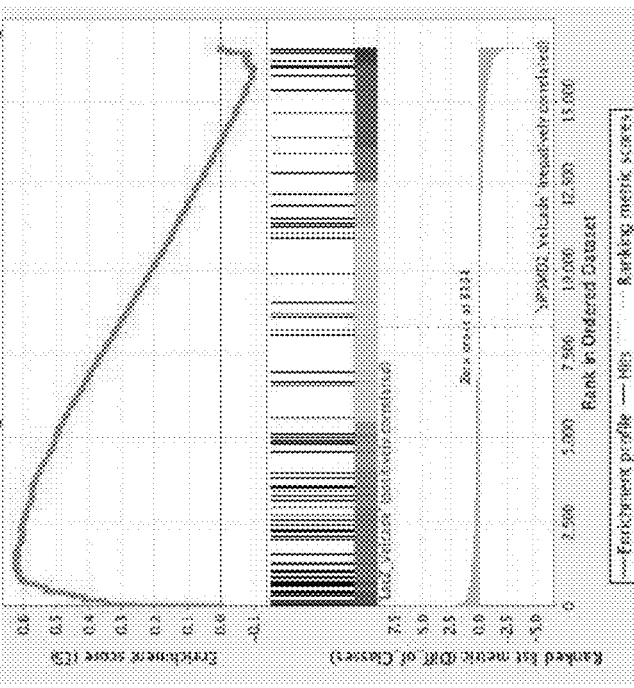
FIGS. 33A-33C.

Under basal conditions (in the absence of bortezomib), cells with reductions in PSMD2 showed a strong induction of components of the ribosome (gene set enrichment analysis FDR q-value=4.0 $e^{-22}$) (Table S3). Genes encoding the 20S subunits of the proteasome were not induced, consistent with our earlier observation that NRF1 is not activated and 20S subunit levels are unchanged (FIG. 2D). The most strongly downregulated gene category involved components of diverse proteotoxic stress responses (FDR q-value=2.31 $e^{-9}$) (Table S3). These included genes for sentinel proteins that respond to heat-shock (e.g. HSPA1A, HSPA1B, HSPA8, HSPB1, and HSP9OAA1), oxidative stress (e.g. HMOX1) and ER stress (e.g. CHOP/DDIT3, TRIB3 and HERPUD1) (FIG. 3A). Genes previously identified as an HSF1-regulated cancer-specific transcriptional program were also downregulated (Mendillo et al., 2012; Santagata et al., 2013) (FDR q-value=0.042; normalized enrichment score 1.57) (FIG. 33A). Therefore, 19S subunit reduction not only fails to induce classic adaptive stress responses, but actually lowers basal levels of proteotoxic stress.

Figure 33B:
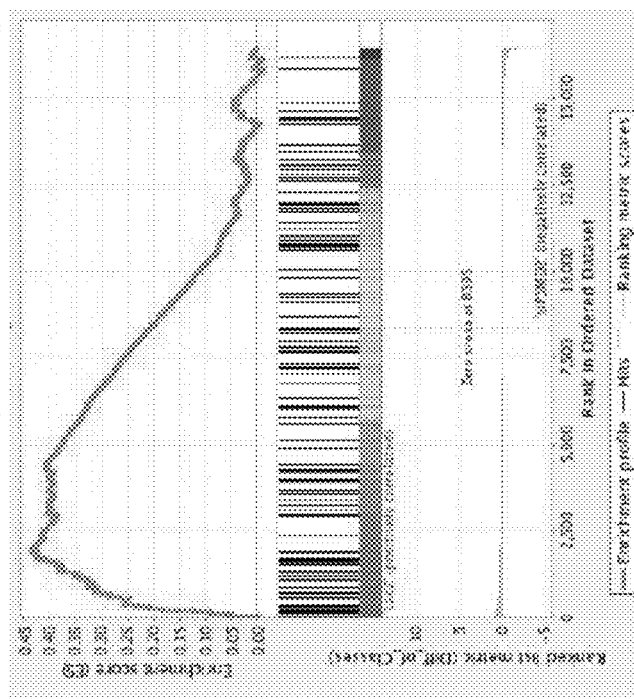

As expected, in control cells, bortezomib treatment unleashed a powerful transcriptional response characterized by a sharp increase in stress-response transcripts (FDR q-value=7.07 $e^{-13}$) (Table S3). This potent bortezomib-induced stress-response was markedly attenuated in cells with reduced PSMD2 levels (FIG. 3B). The suppressed genes include ones involved in oxidative stress and ER stress responses, as well as genes in the HSF1-mediated heat-shock response (FDR q-value <0.01; normalized enrichment score 2.317) (FIGS. 3B and 3C, FIG. 33B). For example, induction of HSP70 family heat-shock genes HSPA1A and HSPA1B was reduced by eight-fold while HSPA6 was entirely suppressed (FIG. 3B).

Figure 3D:
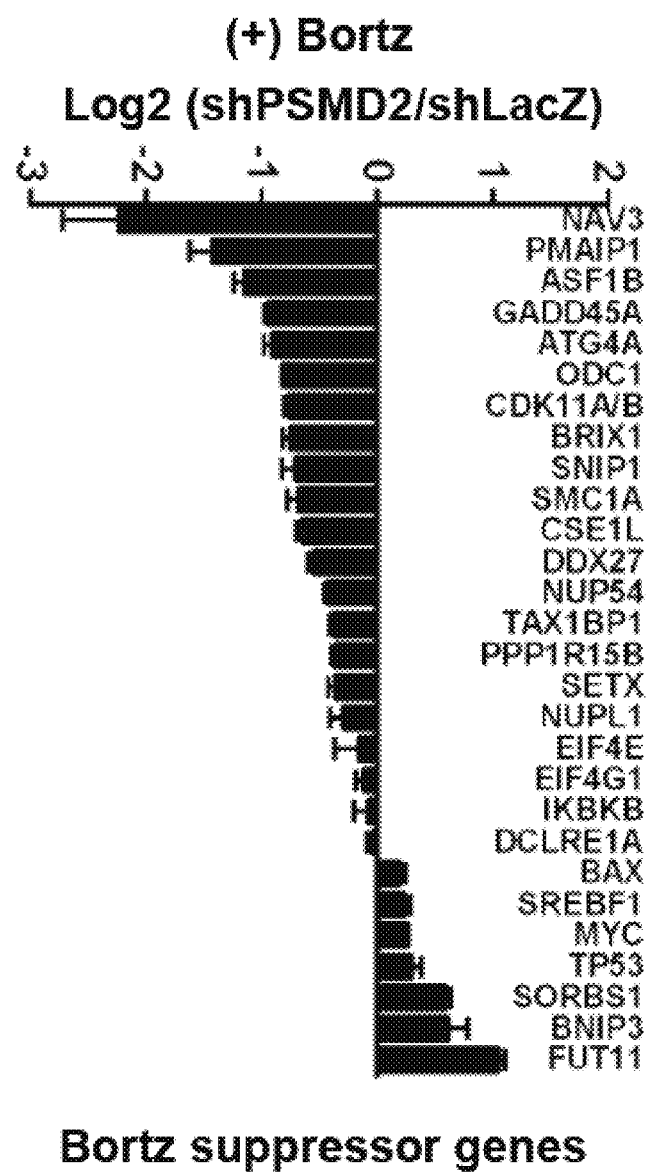
Figure 33C:
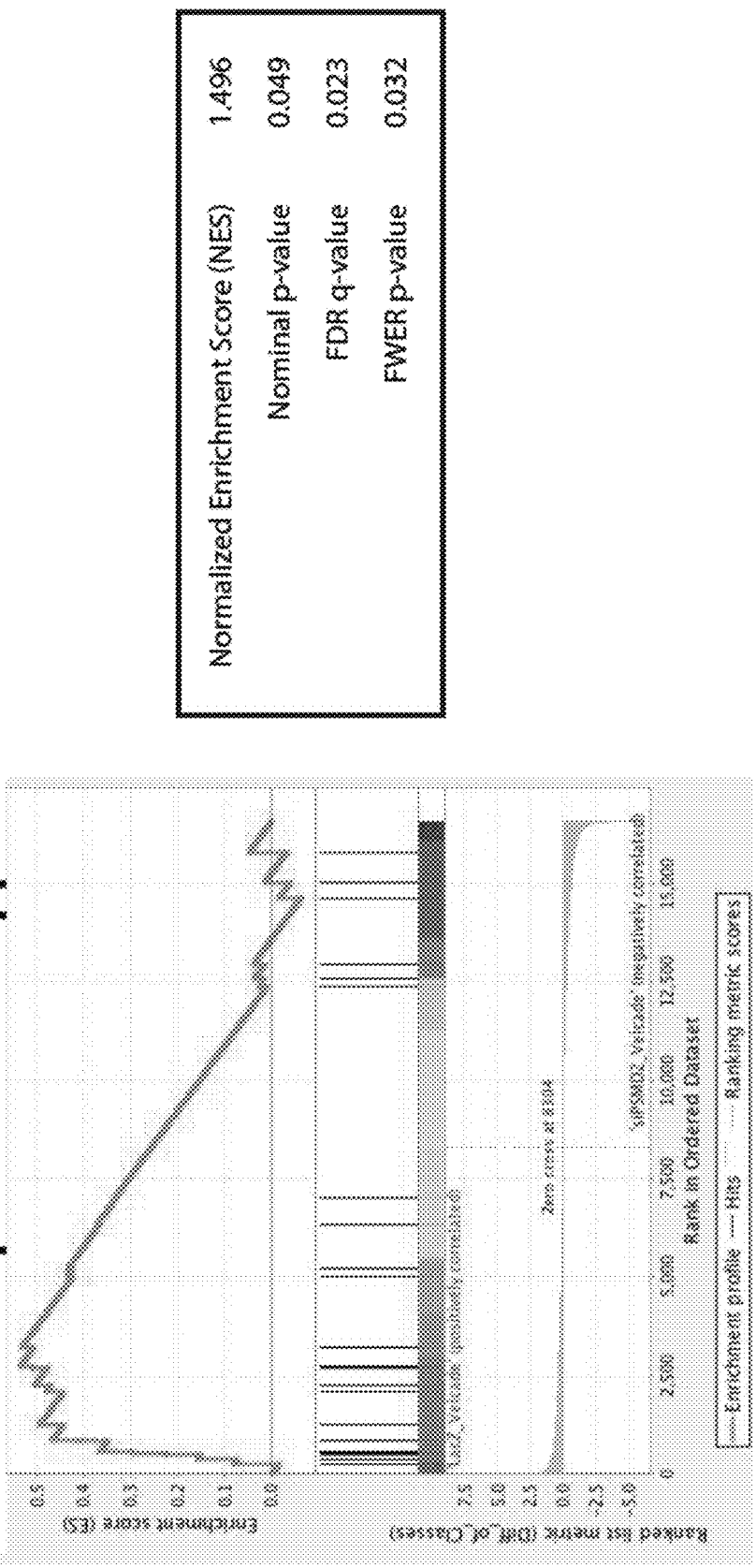

Previous work has identified 28 mediators of bortezomib toxicity, many of which are upregulated upon bortezomib exposure (Chen et al., 2010). When we treated control cells with bortezomib, the mRNA transcripts of many of these genes increased significantly (e.g. ATG4A, DDX27, GADD45A, NUP54, ODC1, PMAIP1/NOXA, SETX, SNIP1, and TAX1BP1) (Table S3). This response was also strongly attenuated in cells with reduced PSMD2 levels (FIGS. 3C and 3D, FIG. 33C). Overall, selectively compromising 19S subunit expression broadly reduces the diverse transcriptional responses that normally ensue when flux through the proteasome is reduced.

Example 6: Compromising 19S Function Primes a Cell Cycle Response to Bortezomib

Figure 3E:
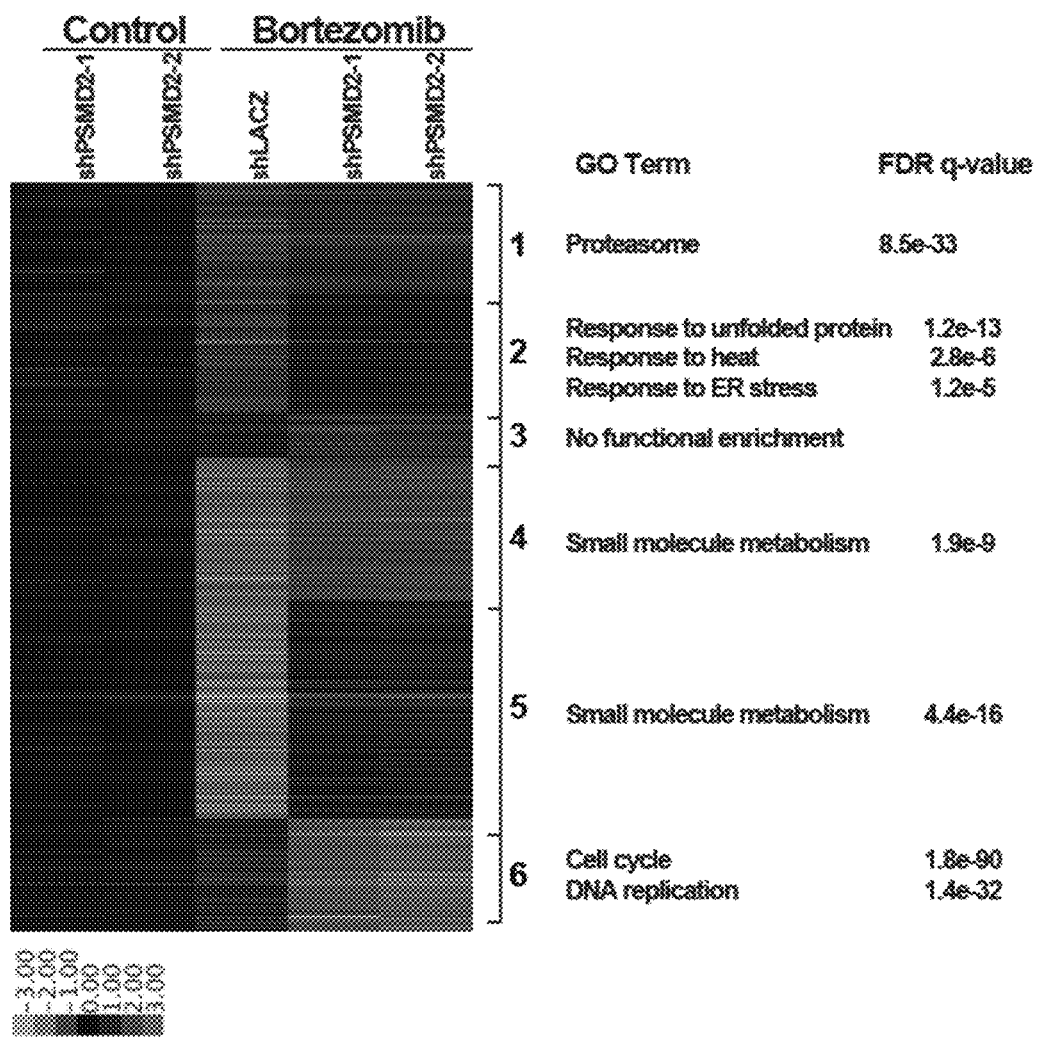

To further characterize the transcriptional effects of 19S subunit reduction we performed a cluster analysis on the genes displaying the highest differential expression in our RNA-seq experiment (FIG. 3E). This analysis confirmed that PSMD2 reduction strongly blunted the bortezomib-mediated induction of stress response genes (FDR q-values 1.2 $e^{-5}$ to 1.2 $e^{-13}$). It also revealed broad changes in genes involved in small molecule metabolism, which remain to be deciphered.

One group of genes highlighted by this analysis revealed a connection between the suppression of the cell cycle and increased resistance to bortezomib. In cells with reduced levels of PSMD2, bortezomib treatment strongly repressed genes involved in DNA replication (FDR q-value=1.4 $e^{-32}$) and cell cycle control (FDR q-value=1.8 $e^{-90}$). These genes include replication factors, polymerases, cyclins and cyclin-dependent kinases. This accentuated anti-proliferation response suggests that cells with reduced 19S subunits are primed to enter a protected, quiescent-like state when flux through the proteasome is compromised.

Figures 4A, 4B:
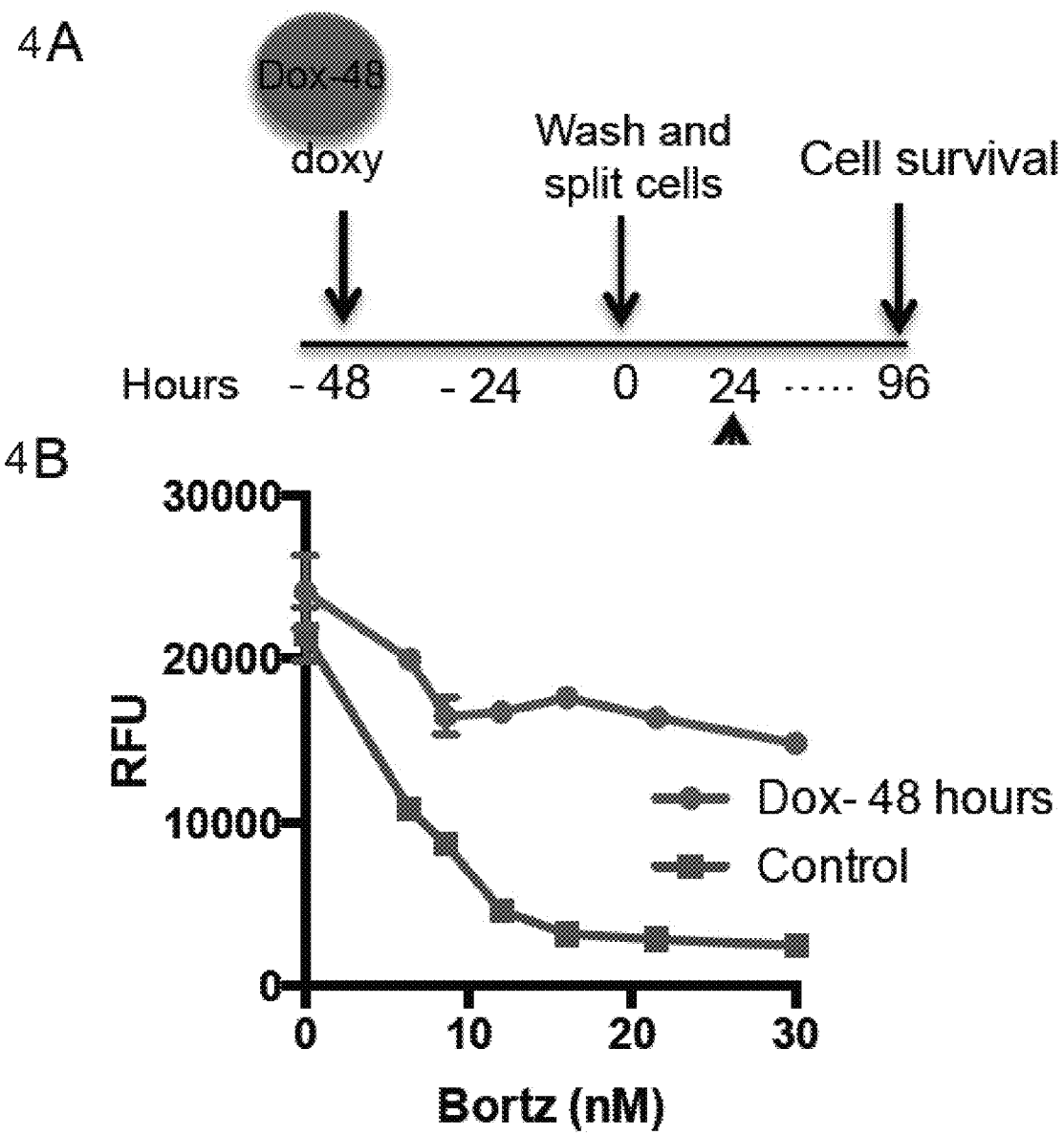
FIGS. 4A-4F: Transient induction of PSMD2 shRNA is sufficient to promote resistance to proteasome inhibition.
Figure 4C:
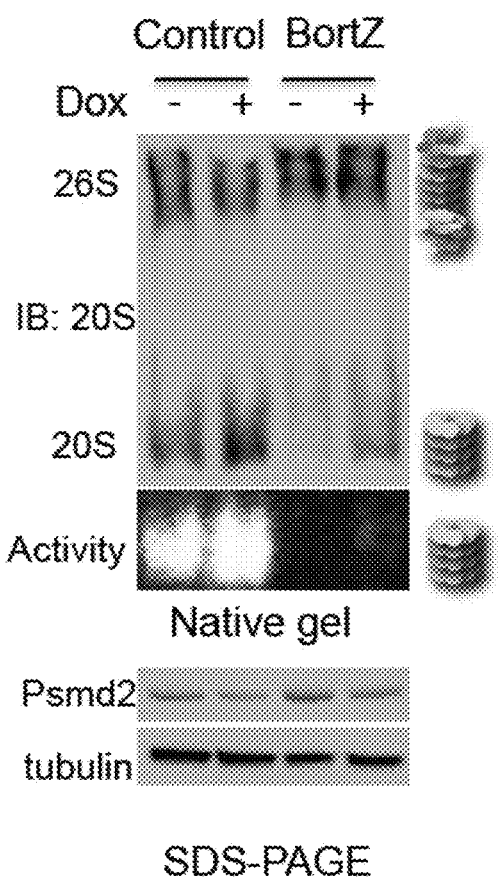
Figure 4D:
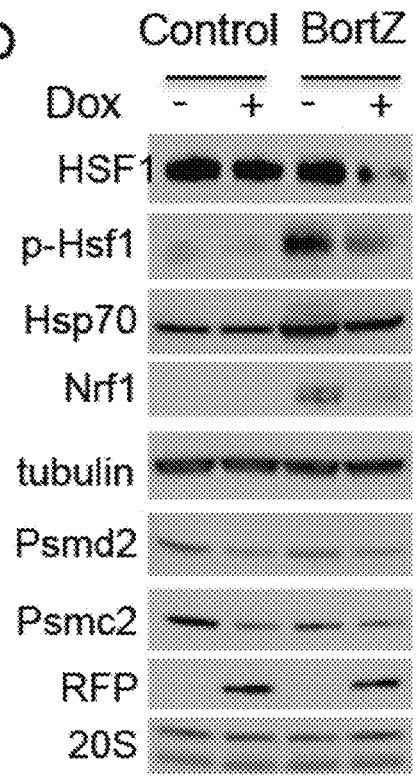
Figures 34A, 34B, 34C, 34D, 34E, 34F:
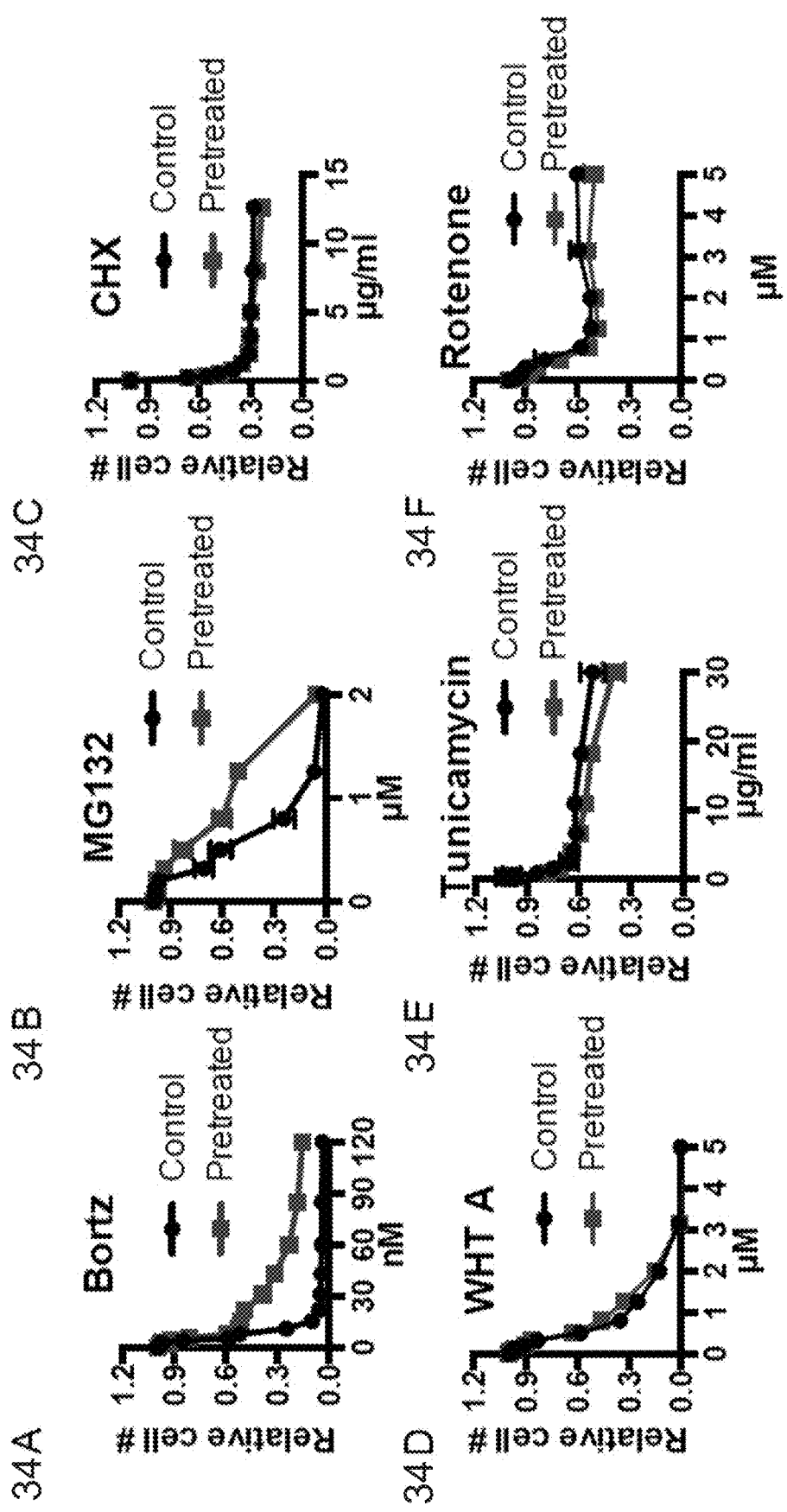
FIGS. 34A-34G.

Example 7: Transiently Reducing 19S Subunits Mirrors the Effects of Stable 19S Subunit Reduction To model the effects of transient reduction of 19S subunits, we developed a cell line in which a PSMD2-targeting shRNA is transiently expressed from a doxycycline-regulated promoter (FIG. 4). The effects of transient reduction of PSMD2 mirrored the effects of stable PSMD2 reduction. Most notably, it significantly increased resistance to both bortezomib (FIG. 4B, FIG. 34A) and MG132 (FIG. 34B). Again, this resistance was selective, and not accompanied by increased resistance to other small molecule stressors (FIGS. 34C-34F). In the absence of bortezomib, transient 19S reduction increased the ratio of 20S/26S proteasomes and total level of 20S proteasome activity (FIG. 4C) without activating NRF1 or increasing total cellular protein levels of 20S subunits (FIG. 4D). Moreover, in the presence of bortezomib, transient 19S reduction strongly reduced the activation of NRF1 and HSF1 that would normally follow bortezomib exposure (FIG. 4D). Thus, transient compromise of the 19S regulatory complex provides a rapid route to accommodating decreased flux through the proteasome.

Figure 4E:
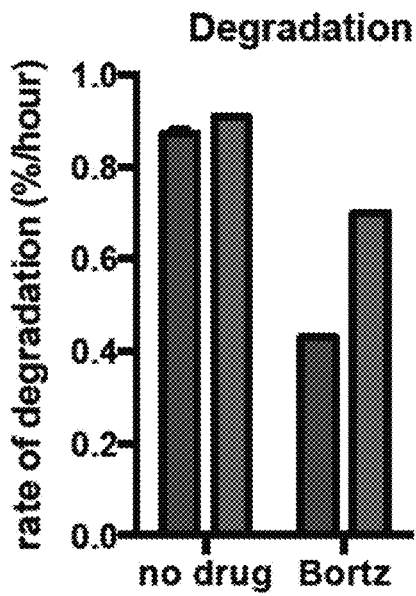
Figure 34G:
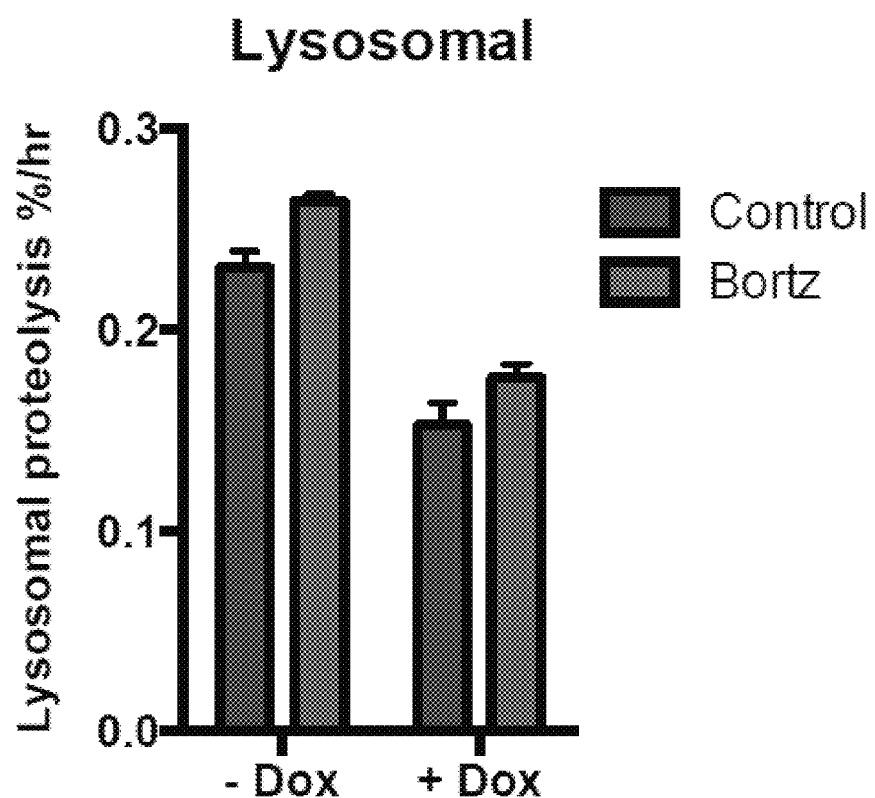

Example 8: 19S Subunit Reduction Counteracts the Effects of Bortezomib on Proteasome Degradation Capacity and Protein Translation Next we examined the impact of reducing PSMD2 levels on protein degradation and protein synthesis. Cells were labeled with tritiated-phenylalanine for 24 hrs. We then separately measured the rates at which labeled proteins were degraded through the proteasome and through the lysosome. In the absence of bortezomib, transiently reducing PSMD2 lowered rates of proteolysis by the lysosome (FIG. 34G), but it did not affect protein degradation by the proteasome (FIG. 4E). This suggests that the 26S proteasome is normally present in excess.

Figure 4F:
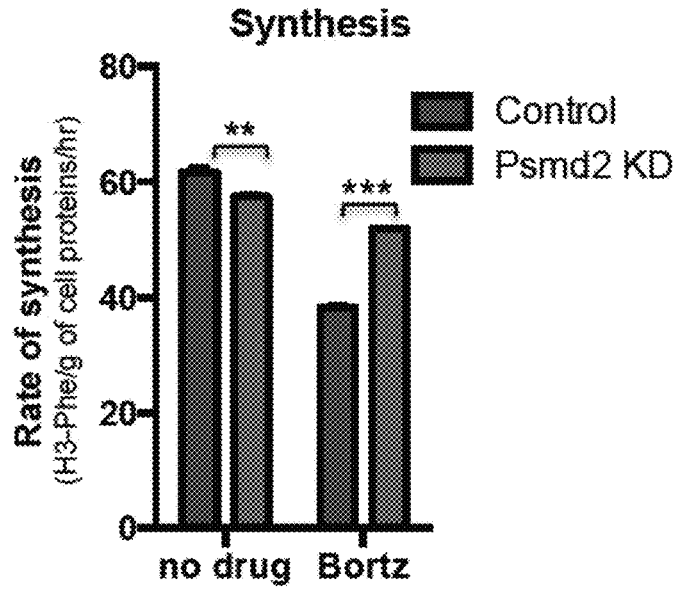

To measure rates of protein synthesis, cells were pulse labeled with tritiated-phenylalanine for 1 hr. Reducing PSMD2 levels resulted in a significant and reproducible 7% decrease in the rate of protein synthesis (FIG. 4F). Thus, even though PSMD2 knockdown did not reduce protein degradation capacity, it did trigger a reduction in protein translation (FIG. 4F), a change that may contribute to lowering basal levels of proteotoxic stress.

Next, we measured protein degradation and synthesis rates after a 20-hour treatment with bortezomib. The rate of protein degradation sharply decreased in control cells (FIG. 4E). While rates of proteolysis by the lysosome remained unchanged (FIG. 34G), transiently reducing PSMD2 strongly counteracted the inhibition of proteasome degradation (FIG. 4E). This finding is consistent with the reduced ability of bortezomib to activate proteotoxic stress responses in cells with reduced levels of PSMD2 (FIGS. 2 and 3).

Following bortezomib treatment, the rate of protein synthesis also sharply decreased in control cells (FIG. 4F). This drop reflects the global repression of protein synthesis that normally follows strong proteotoxic stress (Holcik and Sonenberg, 2005; Shalgi et al., 2013). Transiently reducing PSMD2 protein levels strongly counteracted the bortezomib-mediated suppression of protein synthesis (FIG. 4F). Thus, reducing PSMD2 levels counteracts the effects of bortezomib on both protein degradation and protein synthesis.

Example 9: Lower 19S Subunit Expression Levels Correlate with Increased Resistance to Proteasome Inhibitors Across a Broad Spectrum of Cancer Cells Human cancer cell lines have a broad range of sensitivities to proteasome inhibition. We asked if this might correlate with changes in 19S subunit expression. We analyzed the Genomics of Drug Sensitivity in Cancer (GDSC) database, a public resource of transcriptional data and drug responsiveness collected from a spectrum of human cancer cell lines with diverse tissue origins and diverse oncogenic lesions (Garnett et al., 2012). We ranked the 310 cell lines in the dataset by their half maximal inhibitory concentration (IC50) to either MG132 or to bortezomib (highest to lowest). The cells comprising the top 10% were defined as the "resistant" group and those in the bottom 10% were defined as the "sensitive" group.

Figure 5A:
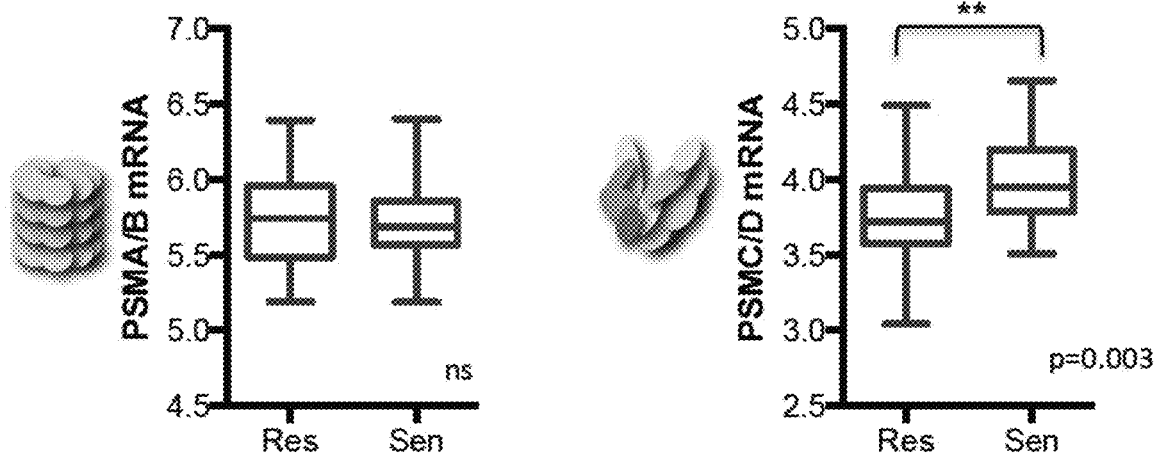
FIGS. 5A-5C: Reduced expression of 19S subunits correlates with resistance to proteasome inhibitors.
Figure 5B:
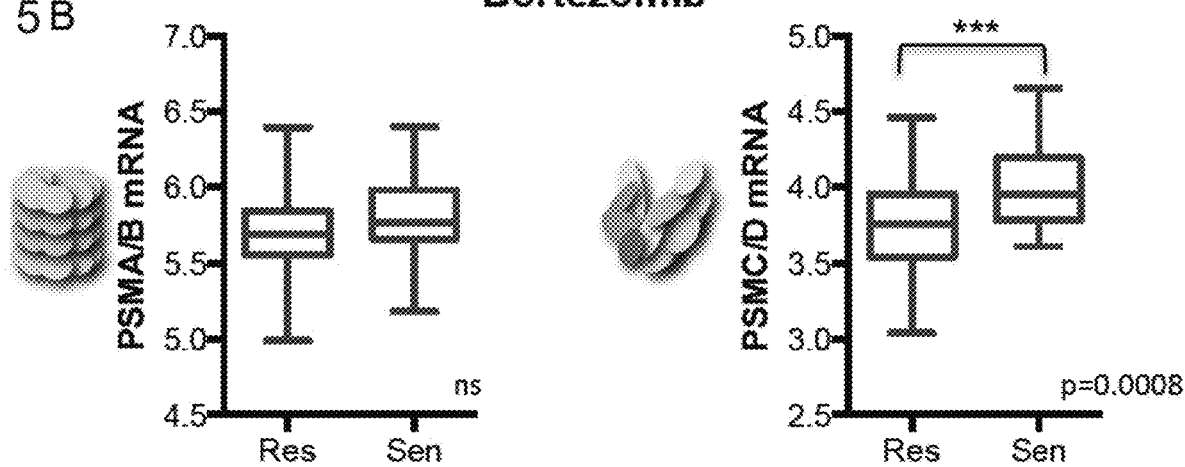

From the 31 cell lines in each group, we averaged the expression levels of all of the 20S subunits (PSMA and PSMB mRNA) and the expression levels of all of the 19S subunits (PSMC and PSMD mRNA). We found no significant difference in the average expression of 20S subunits between the two groups (FIGS. 5A and 5B left panels). However, cells that were the most resistant to either MG132 or to bortezomib had significantly lower levels of 19S transcripts (PSMC and PSMD mRNA) than cells that were sensitive (FIGS. 5A and 5B right panels; p-value=0.003 for MG132; p-value=0.0008 for bortezomib). This observation is striking as the expression levels of all proteasome subunits, both 20S and 19S, are regulated by similar mechanisms and are normally highly correlated (Jansen et al., 2002; Radhakrishnan et al., 2014; Radhakrishnan et al., 2010; Sha and Goldberg, 2014).

Figure 5C:
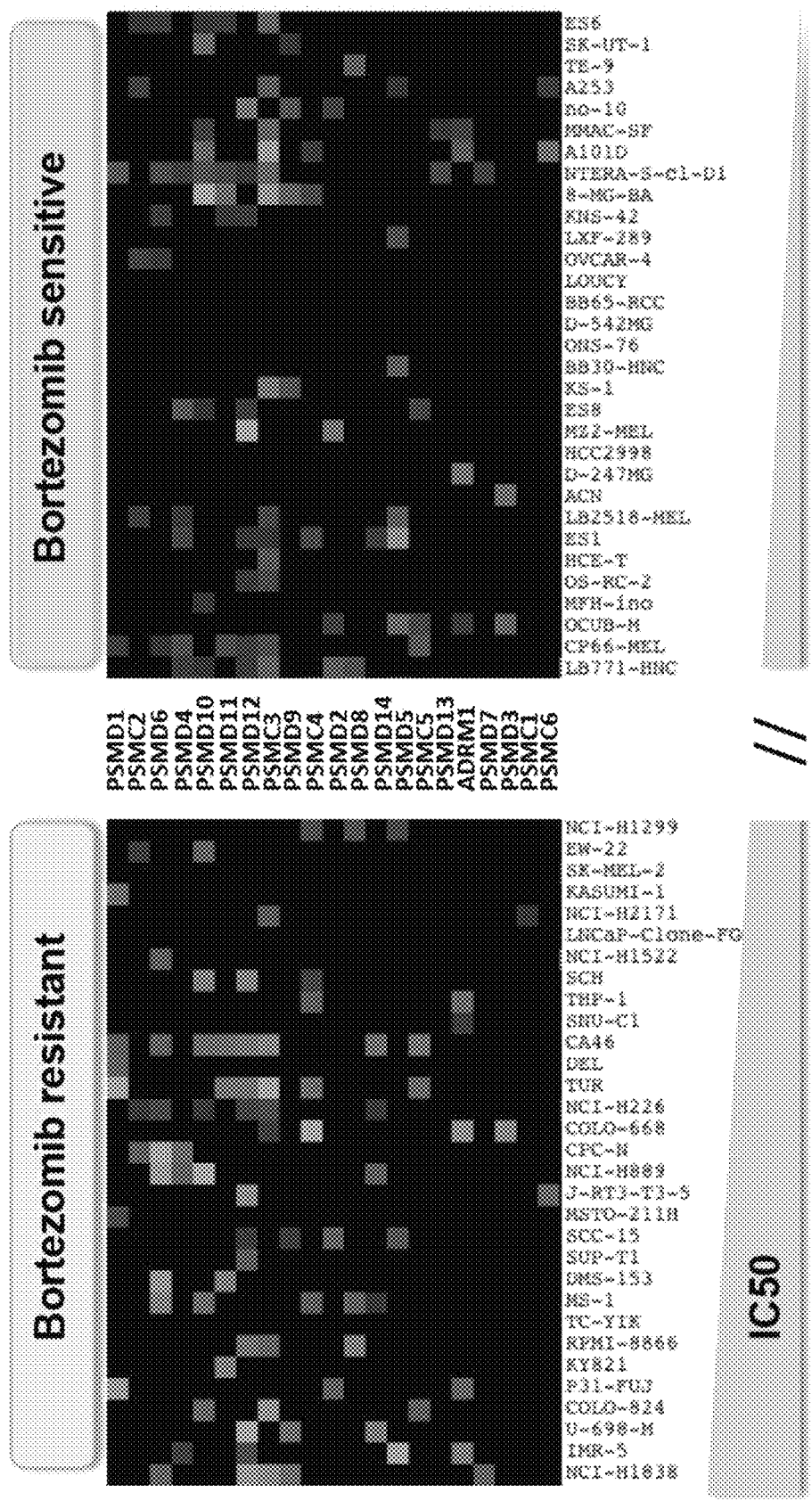

We next assessed the expression of the individual 19S regulatory complex subunits in each of the resistant and sensitive cell lines. A heat map of genes with significantly altered expression (>2-fold deviation from average) revealed that bortezomib sensitive cells commonly showed increased expression of many different 19S subunits (FIG. 5C, right panel-red). Resistant cells generally had at least a two-fold reduction in expression of one or more 19S subunits (FIG. 5C, left panel-green). This was also true in the case of MG132 (FIG. 35). Thus, alterations in 19S subunit expression commonly occur in the evolution of cancer cells.

Example 10: Transiently Reducing a 19S Subunit Confers a Competitive Survival Advantage in the Face of Protein Flux Inhibition Human cancers are increasingly viewed as complex ecosystems comprised of cells harboring enormous genetic, functional and phenotypic heterogeneity (Meacham and Morrison, 2013). We asked if heterogeneity arising from 19S subunit expression can alter population dynamics and confer a fitness advantage in the face of exposure to proteasome inhibitors. To do so, we investigated the effects of transiently reducing PSMD2 expression in only a subpopulation of cells.

Figure 6A:
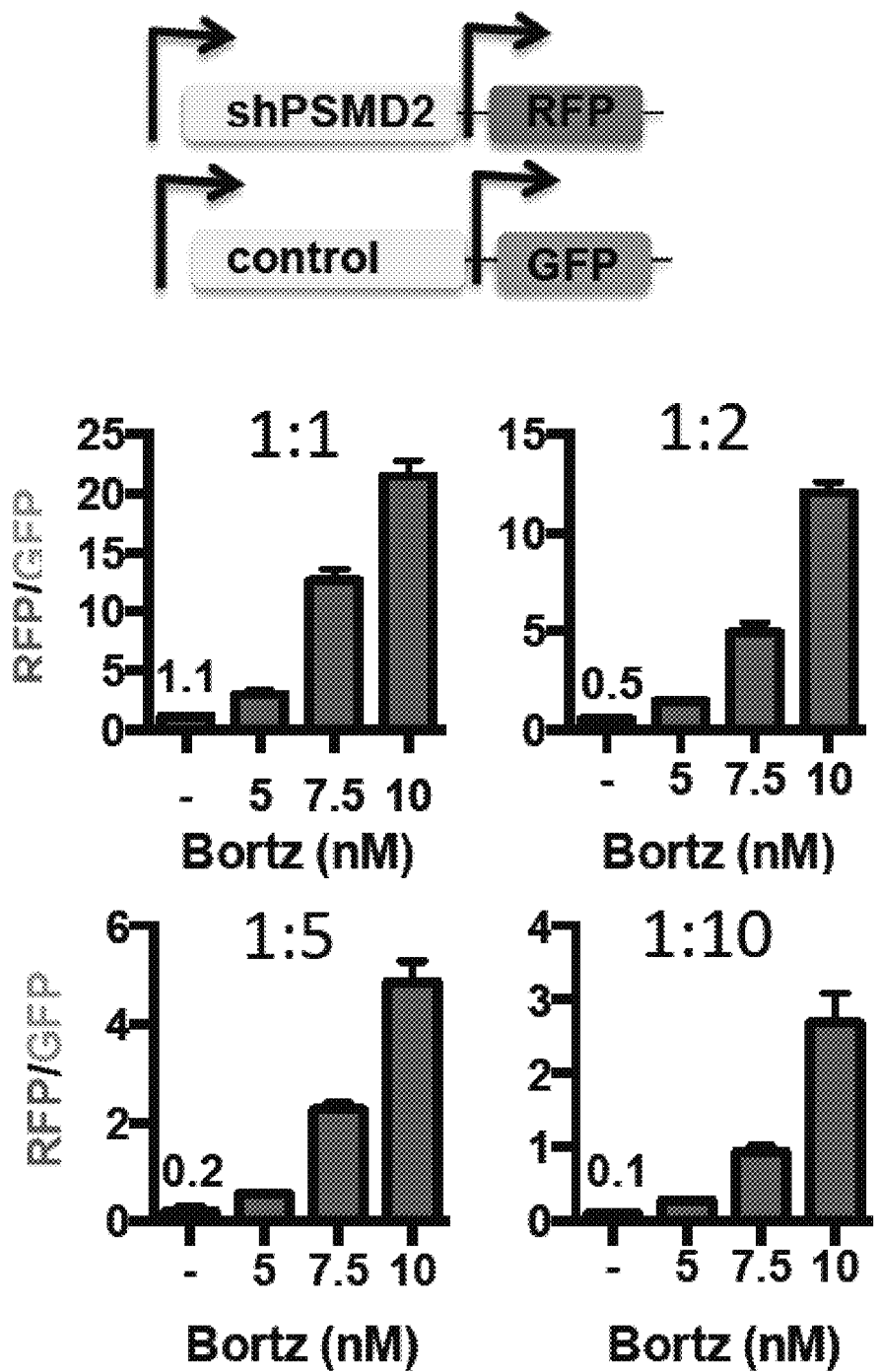
FIGS. 6A-6B: Transient 19S subunit reduction confers a competitive survival advantage in the presence of proteasome inhibitors.
Figure 6B:
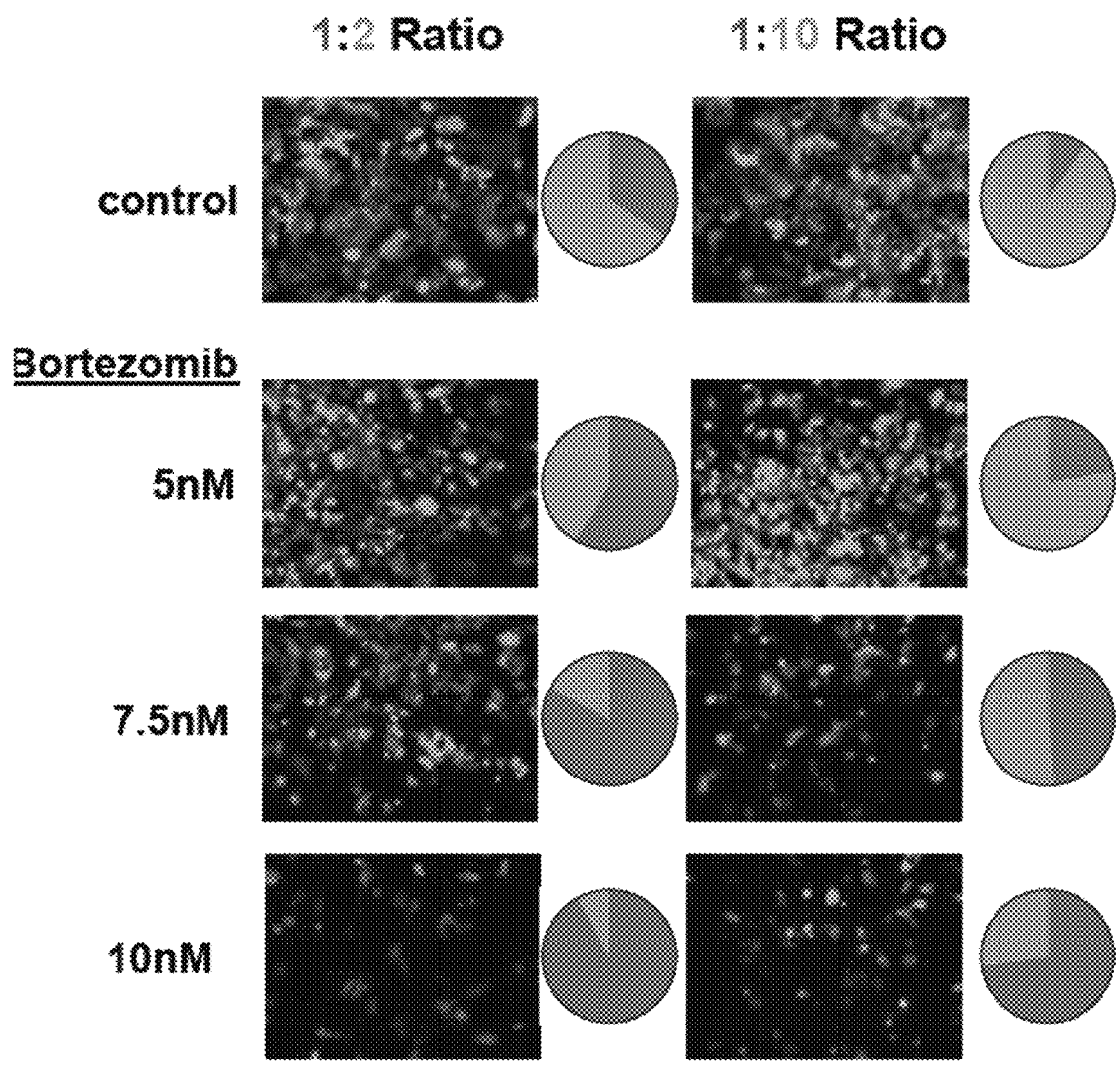

We created two cell lines—one line that expresses red fluorescent protein (turboRFP) and the doxycycline-inducible PSMD2-targeting shRNA and another line that expresses green fluorescent protein (GFP) and a doxycycline-inducible control shRNA (FIG. 6A). First, we induced shRNA expression with doxycycline for 48 hours. After recovery, we mixed shPSMD2-RFP and shControl-GFP cells at different ratios (either 1:1, 1:2, 1:5 or 1:10), adding the cells with reduced PSMD2 as the minority subpopulation. Twenty-four hours after plating, we treated these mixed populations of cells for 48 hours with increasing concentrations of bortezomib (5, 7.5 or 10 nM). We allowed the cells to recover in the absence of bortezomib and then we quantified the red and green cells by FACS analysis (FIG. 6A) and captured representative images by fluorescence microscopy (FIG. 6B).

In the absence of proteasome inhibitors, the initial plating ratios of these cells were maintained for six days (1:1, 1:2, 1:5 and 1:10) (FIG. 6A). In contrast, even low concentrations of bortezomib (5 nM) substantially shifted the populations of surviving cells and higher concentrations (7.5 nM and 10 nM) elicited even more substantial shifts (FIGS. 6A and 6B). In the presence of proteasome inhibitors, cells with modestly reduced levels of PSMD2 have a strong competitive advantage.

Example 11: The Protective Effect of 19S Subunit Reduction is Conserved in Yeast Additionally, because the essential role of the proteasome in maintaining protein homeostasis is conserved across all eukaryotes (Hilt and Wolf, 1995), we asked whether reducing expression of 19S subunits confers resistance to proteasome inhibitors in an evolutionary distant organism—the yeast *Saccharomyces cerevisiae*. As the 19S regulatory complex components are essential for viability in yeast, we utilized a library of hypomorphic (DAmP) alleles for essential yeast genes. In this library, the expression of individual mRNA species is reduced from two to ten-fold by replacing the mRNA's 3' untranslated region (Breslow et al., 2008).

Figure 7:
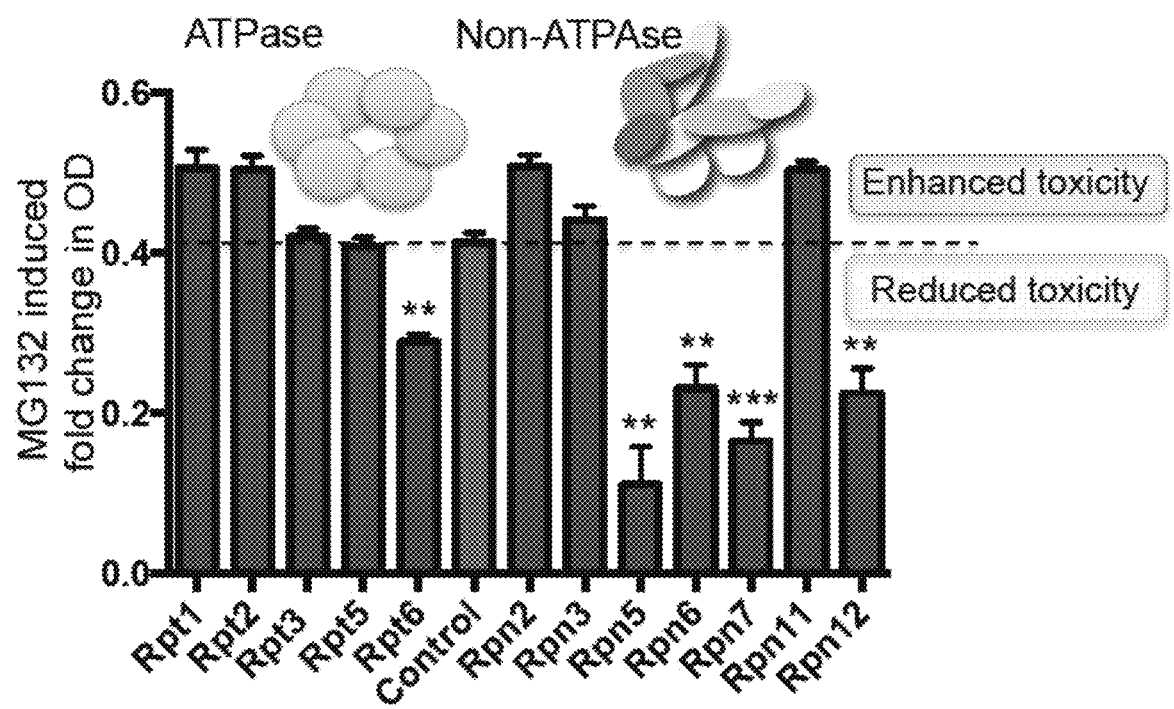
FIG. 7: Reducing the levels of 19S subunits is an evolutionarily conserved mechanism to acquire resistance to proteasome inhibition. Proteasome subunit DAmP strains and the BY4741 control strain were grown in the presence or absence of 50 µM MG132 for 48 hours. The relative change in OD induced by MG132 is plotted. Five proteasome subunit DAmP strains exhibited significantly reduced toxicity in the presence of MG132.  $p<0.01$, * $p<0.001$
Figure 36:
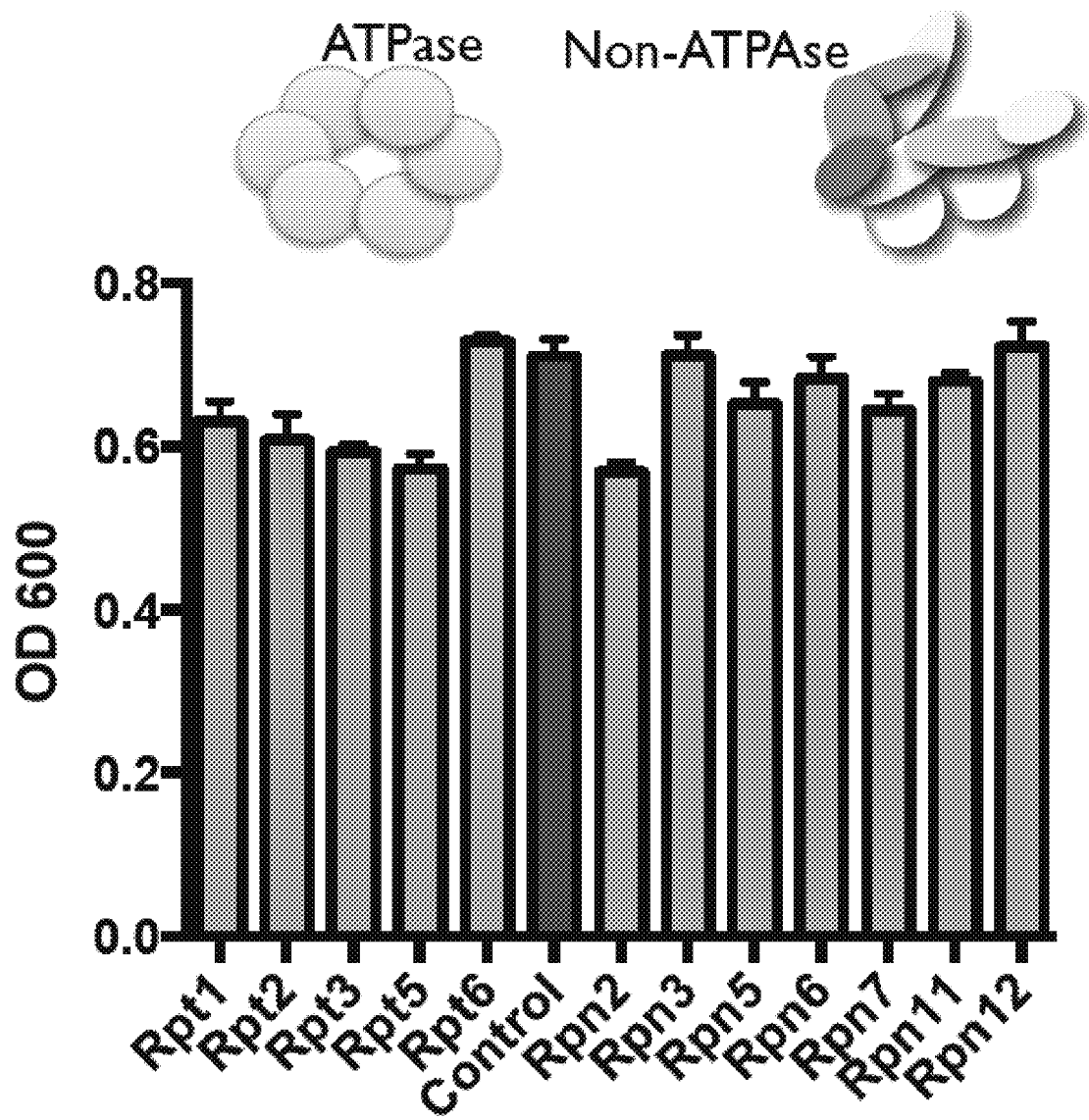
FIG. 36: Proteasome subunit DAmP strains and the BY4741 control strain were grown in YPD media and OD600 was measured after 48 hours.

DAmP-strains were available for 12 genes comprising the 19S regulatory complex. These strains showed no significant growth-impairment under basal conditions (FIG. 36). However, five of these twelve strains had significantly increased resistance to proteasome inhibition by MG132 (FIG. 7). Most notable were Rpn5 and Rpt6, the yeast orthologs of PSMD12 and PSMC5—the two most significantly enriched genes in our MG132 screen in human cells (FIG. 1C).

Figure 8A:
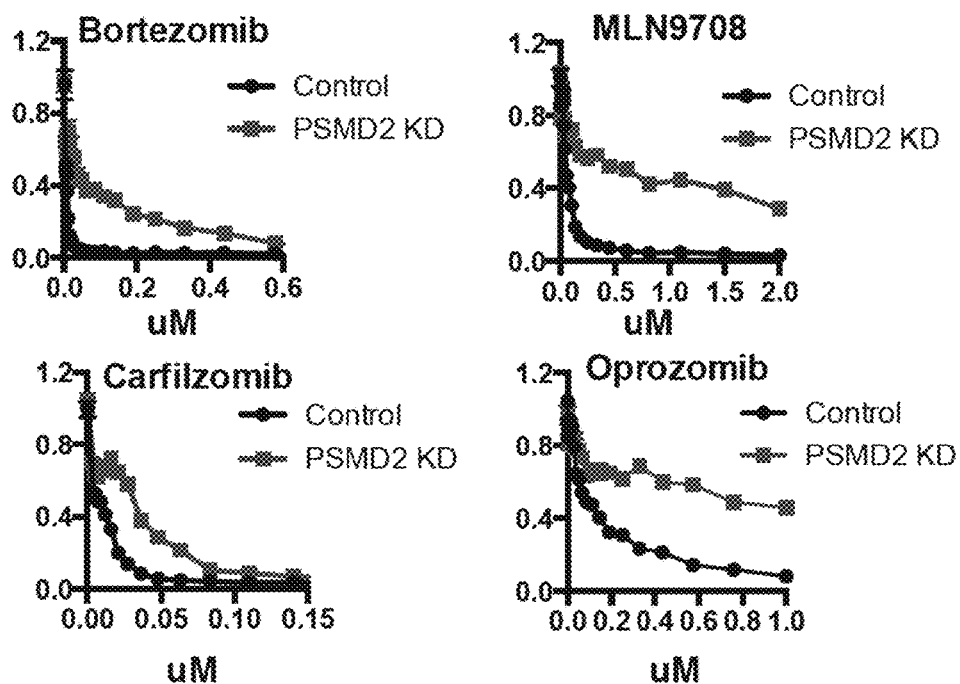
FIGS. 8A-8C: Transient 19S subunit reduction confers resistance to diverse proteasome inhibitors.

Example 12: Transient 19S Subunit Reduction Confers Resistance to Diverse Proteasome Inhibitors The effect of transient PSMD2 reduction on growth of T47D cells in the presence of different proteasome inhibitors (bortezomib, MLN9708, carfilzomib, oprozomib) was tested. T47D cells harboring a doxycycline inducible control shRNA (GFP) or a doxycycline-inducible PSMD2 shRNA (TurboRFP) were incubated with doxycycline for 3 days. Cells were then split and grown in the absence of Dox and proteasome inhibitors were then added at various concentrations. Cells were maintained in culture and then counted. In each case, the cells harboring the PSMD2 shRNA were considerably more resistant to the proteasome inhibitor than the parental line (EC50 values increased considerably as shown in FIG. 8A). These results further confirm that reducing the expression of a 19S regulatory complex protein increases cellular resistance to proteasome inhibitors.

Figure 8B:
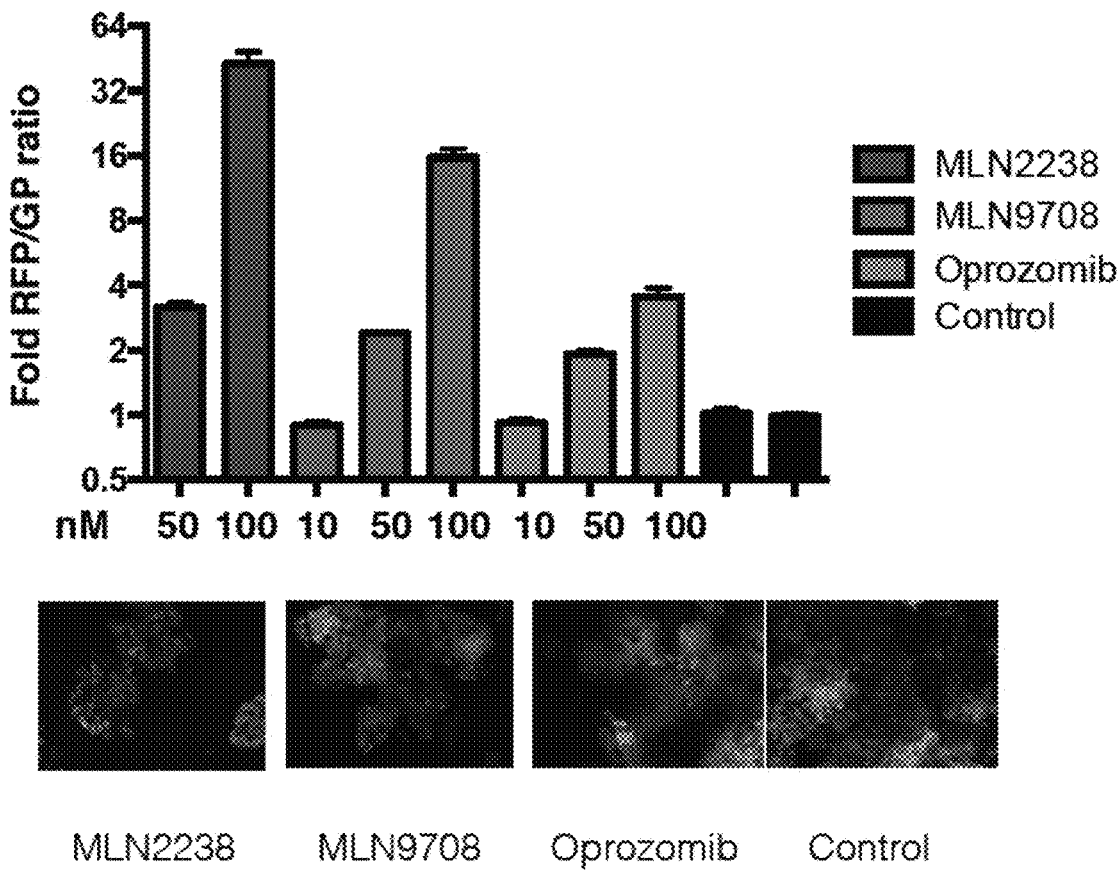
Figure 8C:
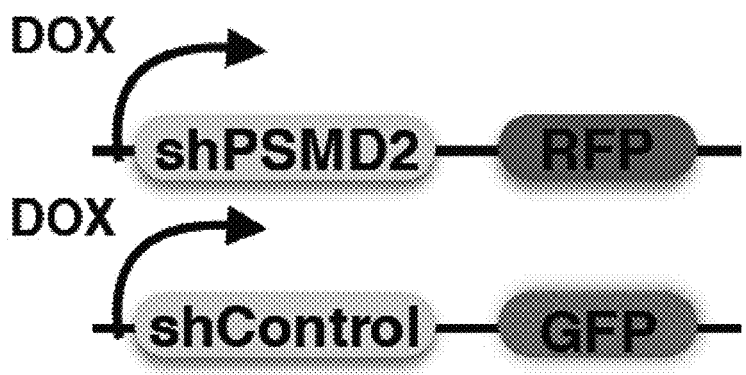

The experiment described in Example 10 was repeated with minor differences using a panel of different proteasome inhibitors: MLN2238, MLN9708, and oprozomib T47D cells harboring a doxycycline inducible control shRNA (GFP) or a doxycycline-inducible PSMD2 shRNA (TurboRFP) were incubated with doxycycline for 3 days. Cells were collected, counted, and plated at a 1:10 ratio of TurboRFP-expressing PSMD2 shRNA cells/GFP expression control shRNA cells in the absence of Dox. Proteasome inhibitors were added at the specified concentrations and cells were maintained in culture. Cells were allowed to recover in the absence of the proteasome inhibitor and then analyzed by FACS (FIG. 8B, top) or visualized by microscopy (FIG. 8B, bottom). In the absence of proteasome inhibitors, the initial plating ratio of these cells (1:10) was maintained over the duration of the experiment (FIG. 8B). In contrast, the presence of proteasome inhibitors substantially shifted the populations of surviving cells, increasing the relative number of cells harboring the PSMD2 shRNA. The effect was concentration-dependent in that higher concentrations elicited more substantial shifts. In the presence of each proteasome inhibitor tested, cells with modestly reduced levels of PSMD2 have a strong competitive advantage.

Example 13: 3-Sigma Cells are Highly Resistant to Proteasome Inhibitors

Figure 9A:
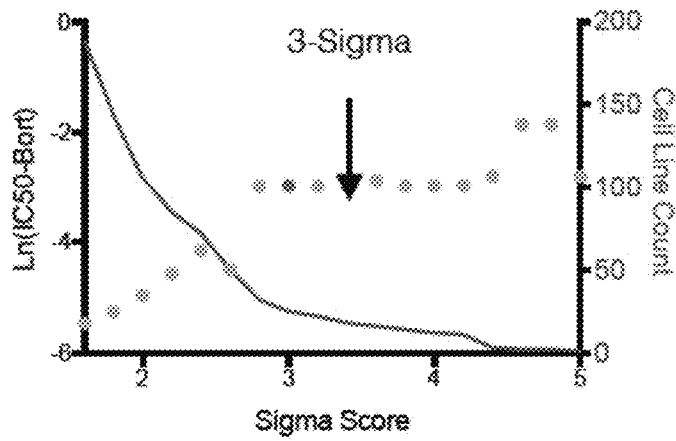
FIGS. 9A-9D: 3-Sigma cells are highly resistant to proteasome inhibitors.
Figure 9B:
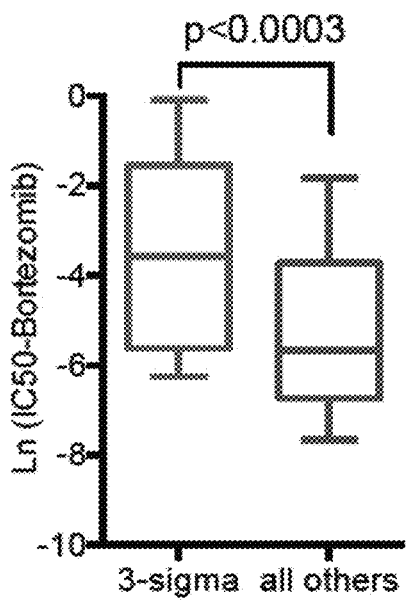
Figure 9C:
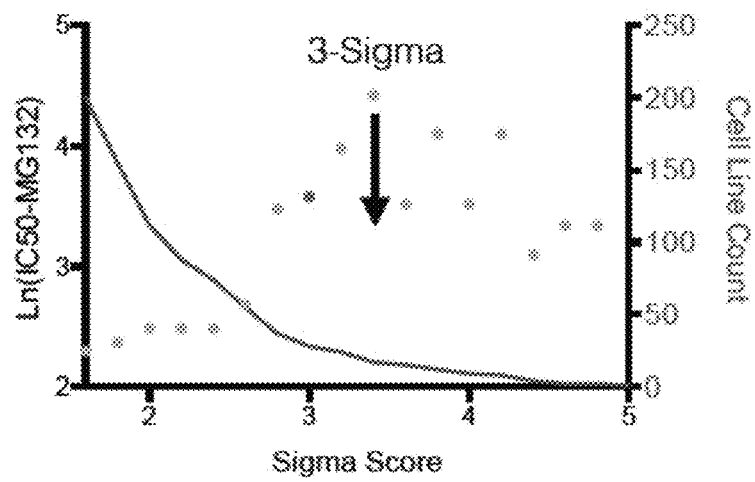
Figure 9D:
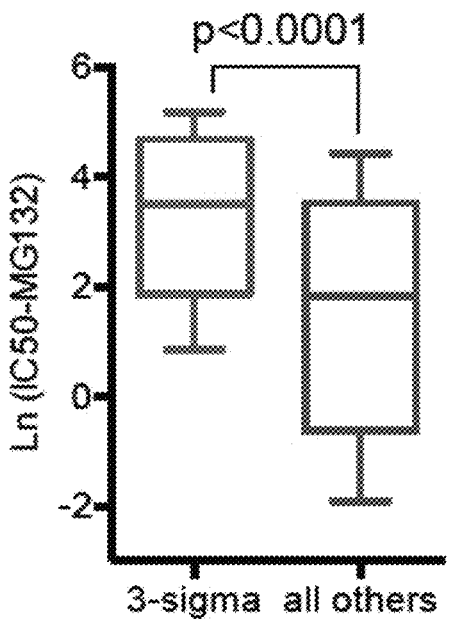

We used data in the Genomics of Drug Sensitivity in Cancer (GDSC) database (Garnett et al., 2012) to further characterize the ability of reduction in 19S subunit expression to confer proteasome inhibitor resistance. We asked how many cell lines in the GDSC database exhibit lower expression of at least one subunit of the 19S proteasome complex relative to the average expression level of all 19S subunits in the same cell line and how such a drop is correlated with the IC50 for MG132 and bortezomib. We defined the "sigma score" for a given cell line as the maximum decrease in expression of any 19S subunit in that cell line compared to the average expression of that 19S subunit in the set of cell lines in the GDSC, expressed as the number of standard deviations (SD). As shown in FIG. 9, sigma scores correlated with resistance both to bortezomib (FIGS. 9A and 9B and to MG132 (FIGS. 9C and 9D). We defined "3-Sigma cells" as cells that have at least a 3 standard deviation (SD) lower expression of at least one subunit of the 19S proteasome complex as compared with its average expression among cell lines in the panel. As shown in FIG. 9B, the average IC50 value for bortezomib in 3-Sigma cell lines was considerably higher than in all other lines (non-3-Sigma) for which data was available. Similarly, as shown in FIG. 9D, the average IC50 value for MG132 in 3-Sigma cell lines was considerably higher than in all other lines (non-3-Sigma) for which data was available.

A similar analysis was performed in which the sigma score for a cell line was defined as the maximum decrease in expression of any 19S subunit in that particular cell line compared to the average expression of all 19S and 20S subunits in that cell line, expressed as the number of standard deviations (SD). In this analysis, sigma scores above about 1.5 correlated with increased resistance to proteasome inhibitors.

Further details of methods used in GDSC dataset analysis: Gene expression and drug sensitivity data was downloaded from the World Wide Web at subdomain cancerrxgene.org. The expression data was RMA normalized, and log transformed. For each gene, expression was collapsed to the highest expressing probe. For each proteasomal subunit gene, a-score was calculated for each cell line. Duplicate cell lines were collapsed to the lowest z-scoring subunit. This was utilized to plot the expression of individual subunits across cells in the dataset. For each cell line, 19S gene scores and 20S gene scores were calculated by adding the expression all genes in each respective list and the values of 19S versus 20S gene scores for each cell line were plotted. The drug sensitivity data were calculated by averaging the natural log EC50 (for all drugs analyzed) for cell lines that are above the denoted z-score cutoff. Cell lines that did not have drug sensitivity data were dropped from the analysis. Mann-Whitney test was used to calculate a p-value. When analyzing all the drug sensitivities in the dataset a volcano plot was generated by calculating the median EC50 for the 3-sigma group versus the control (the non 3-sigma group) and plotting the difference in the natural log of the median EC50 between the 3 sigma lines and the not 3 sigma lines. P-values were calculated by t-test, comparing the logEC5Os between the 3 sigma and not 3 sigma.

Example 14: Reduced Expression of 19S Subunits Occurs in Diverse Cancer Cell Lines and Correlates with Resistance to MG132

Figure 10A:
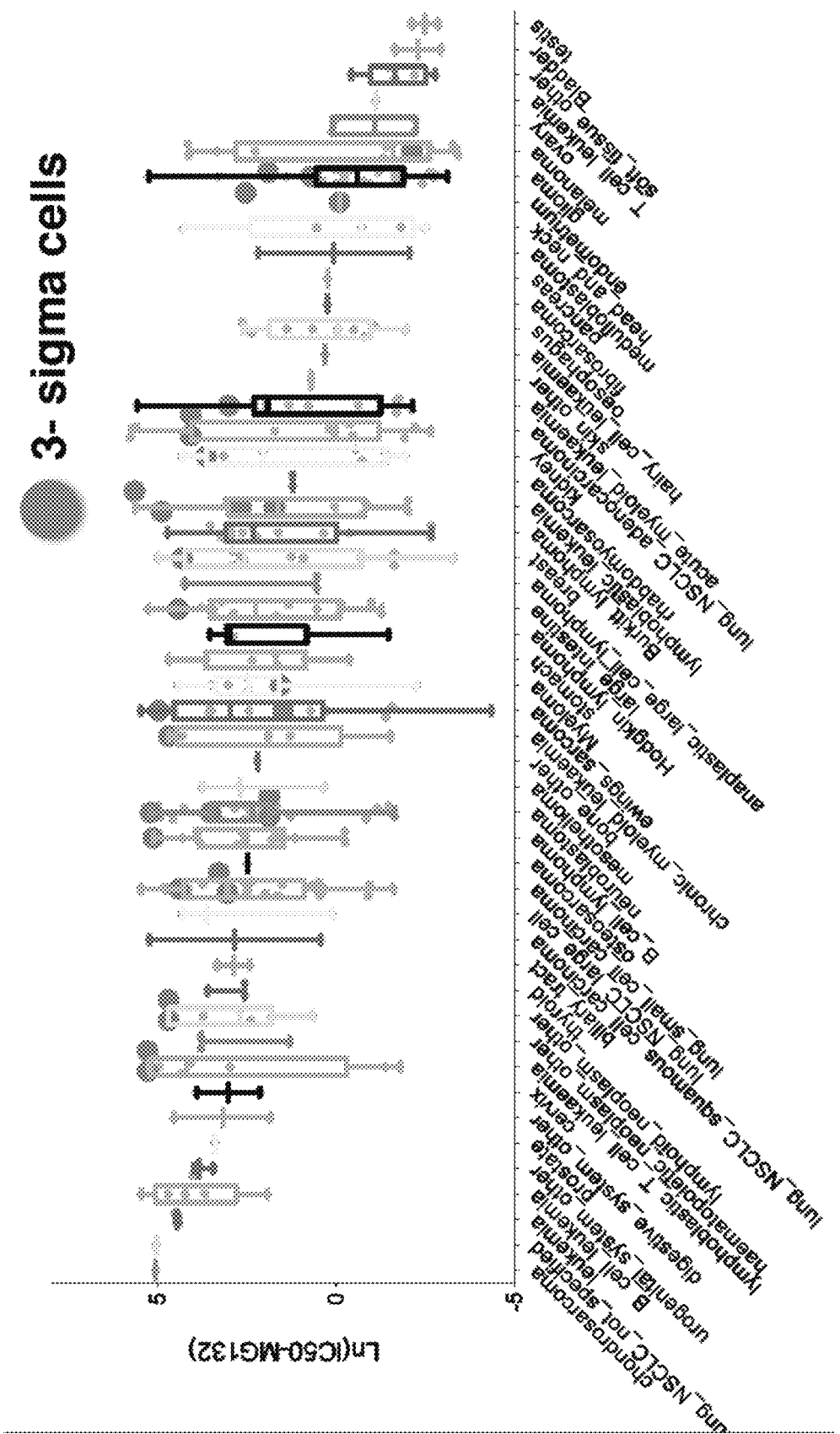
FIGS. 10A-10B.
Figure 10B:
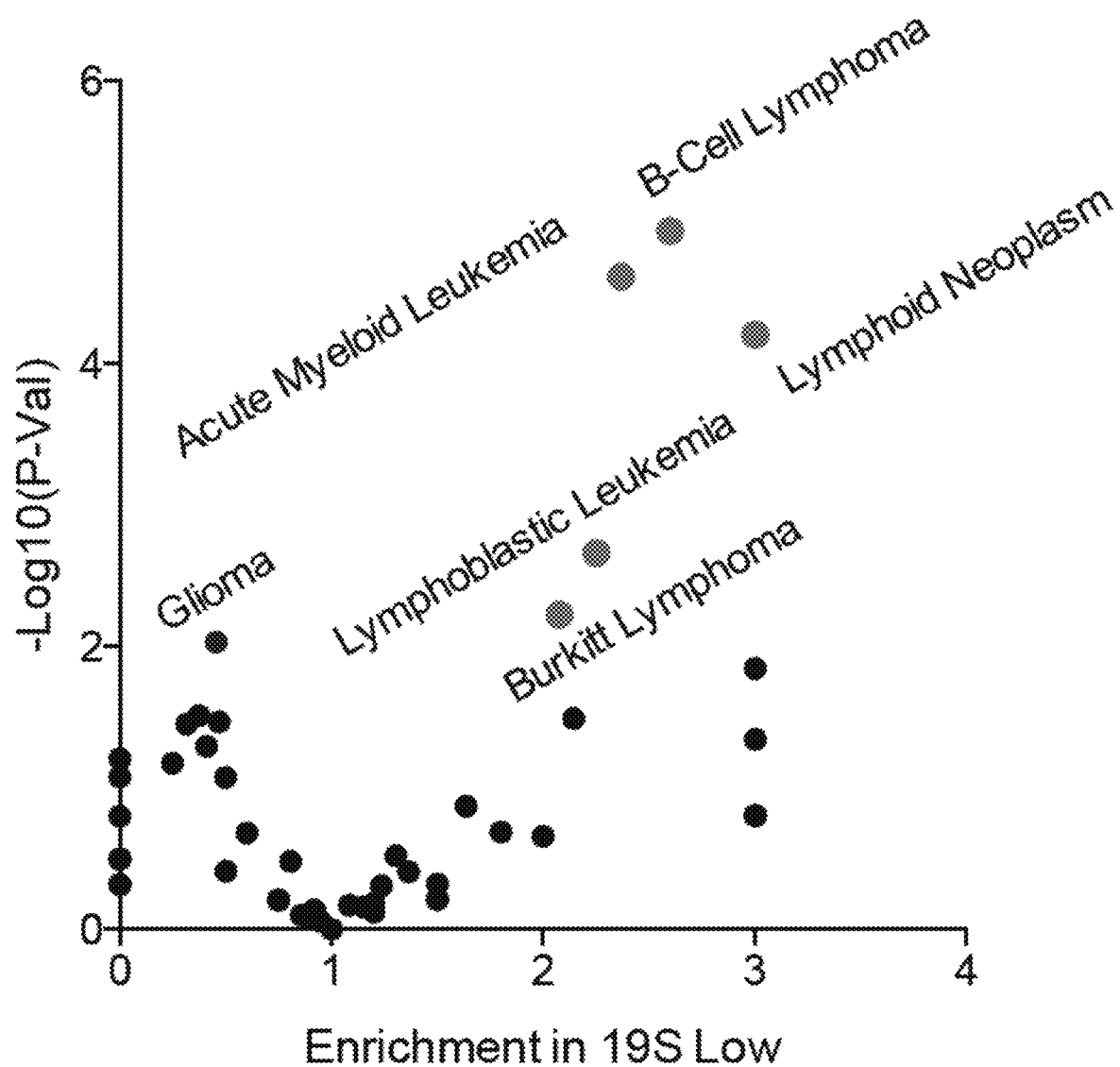

We examined the distribution of IC50 values for MG132 across cancer cell lines of different cancer types using data in the GDSC database and identified the 3-Sigma cell lines. We found that the group of 3-Sigma cell lines include diverse cancer types (FIG. 10A) but is statistically enriched for blood cancers (FIG. 10B).

Example 15: PSMD5 is the 19S Subunit Whose Expression is Most Frequently Reduced in Cancer Cell Lines in the GDSC and CCLE Databases We analyzed the data in the GDSC database to determine the frequency with which expression of each 19S subunit was reduced by at least 3 SD relative to the average expression level of that 19S subunit in all of the cell lines (i.e., the frequency of 3-Sigma cell lines for each subunit) and to determine whether there is a subunit that exhibits reduced expression more frequently than others. In this analysis expression of PSMD5 was found to be the most commonly reduced (FIG. 11A). Reduced expression of PSMD1, PSMC6, PSMD10, PSMD14, and PSMD6 was also observed, though in fewer cell lines.

Figures 11B, 11C:
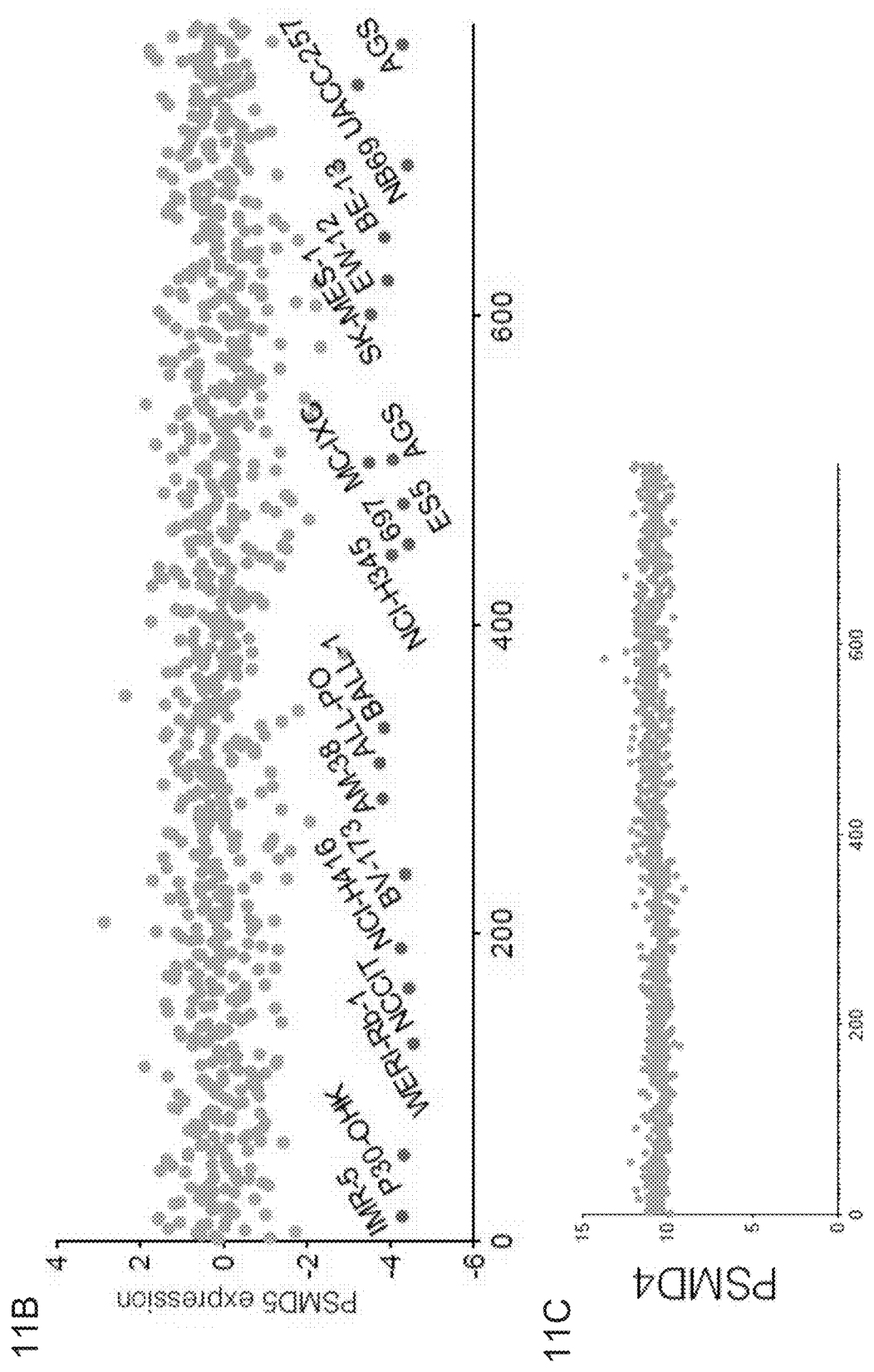
Figures 12A, 12B, 12C:
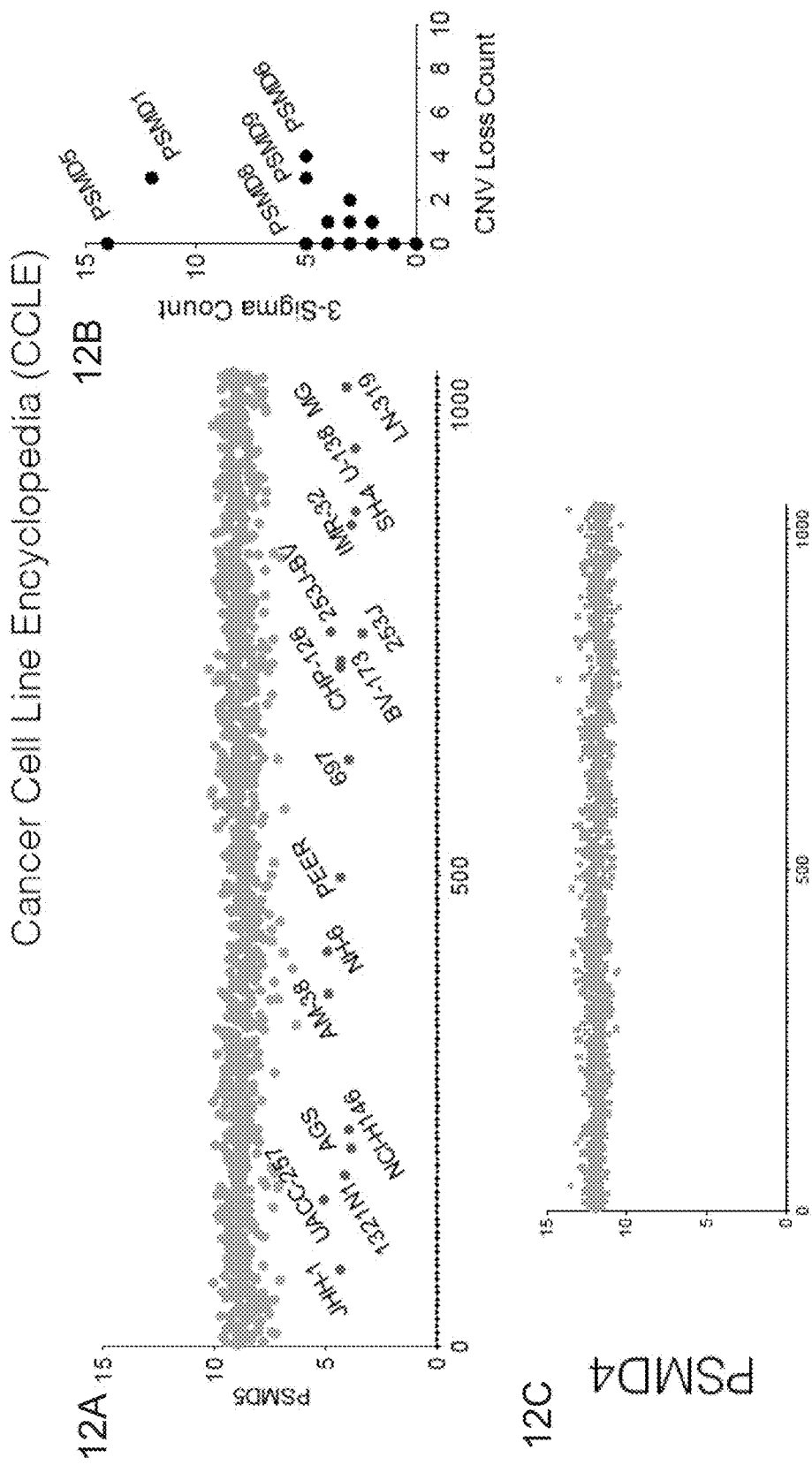
FIGS. 12A-12C.

We also examined data in the Cancer Cell Line Encyclopedia database, a database that provides access to genomic data, analysis and visualization for about 1000 cell lines. (Barretina, et al. The Cancer Cell Line Encyclopedia enables predictive modelling of anticancer drug sensitivity. Nature. 2012; 483(7391):603-7), to determine the frequency with which expression of the various 19S subunits was reduced by at least 3 SD relative to the average expression level of that 19S subunit in all of the cell lines (i.e., the frequency of 3-Sigma cell lines for each subunit). We found that, as in the GDSC database, expression of PSMD5 was the most commonly reduced (FIG. 11B). Reduced expression of PSMD1, PSMD8, PSMD9, and PSMD6 was also observed, though in fewer cell lines (FIG. 12B).

Example 16: Reduction in 19S Subunit Expression May Occur Due to Transcriptional or Post-Transcriptional Regulation In order to investigate potential mechanisms by which 19S subunit expression may be reduced in cancer, we examined copy number variation data in the CCLE database to determine whether there was a correlation between loss of expression of a 19S subunit and copy number loss of the gene. In particular, we asked whether any of the 3-Sigma cell lines for which data was available exhibited copy number loss affecting the 19S subunit gene whose expression was reduced in that cell line. As shown in FIG. 12B, although some genes encoding 19S subunits showed copy number reduction in some of the lines that had reduced expression of that subunit, PSMD5 showed no loss of copy number, suggesting that in the cell lines with reduced PSMD5 expression, the reduction in expression is due to transcriptional and/or post-transcriptional mechanisms. A total of 14 cell lines had mRNA levels of PSMD5 that were reduced by more than 3-standard deviations. None of these cell lines, however, had copy number losses involving the PSMD5 gene.

Further details of methods used in CCLE dataset analysis: Processed CCLE data was downloaded from the World Wide Web at subdomain at broadinstitute.org. For each proteasomal subunit gene, a z-score was calculated for each cell line and that was utilized to plot the expression of individual subunits across all cells in the dataset. For each of these 3-sigma lines we calculated if the particular subunit was lost on a genomic level. We looked at the copy number estimates for each cell line published by CCLE. A cell line was considered to have a copy number loss if the estimated hybridization was 0.5× the baseline hybridization.

Figure 13:
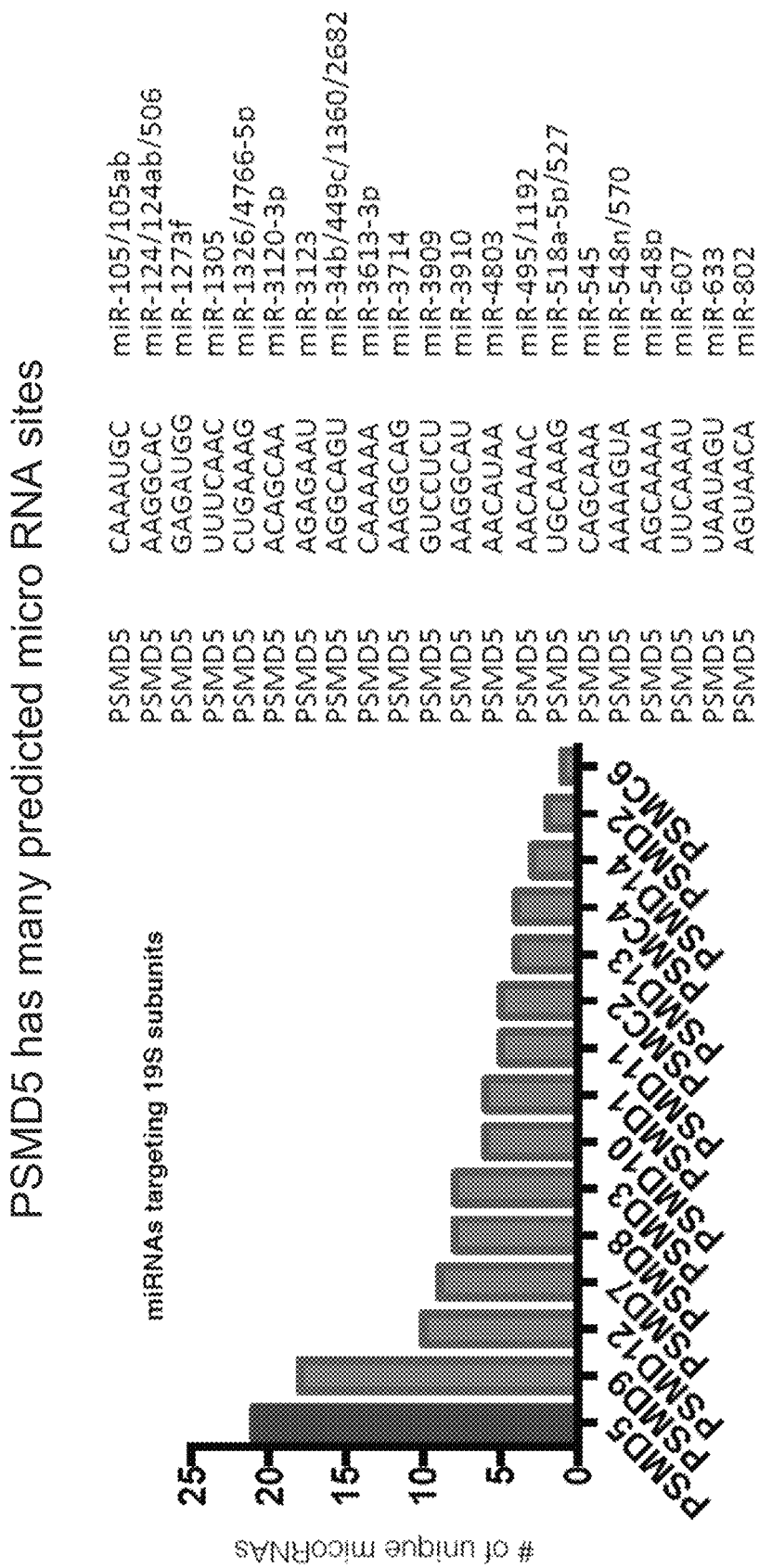
FIG. 13: Plot showing number of unique microRNAs for which predicted binding sites exist in the indicated 19S subunit transcript 3' UTR. PSMD5 3' UTR contains many predicted microRNA binding sites.

We also examined the frequency with which miRNA target sites are found in 19S subunit mRNA transcript 3' UTRs using TargetScan (www.targetscan.org). PSMD5 transcript 3' UTR exhibits more than 20 predicted sites for human microRNAs, followed by PSMD9 (FIG. 13). Other 19S subunit transcripts also exhibit multiple predicted miRNA target sites in their 3' UTRs, including PSMD12, PSMD7, PSMD8, PSMD3, PSMD10, PSMD1, PSMD11, PSMD13, PSMD14, PSMD2, PSMC2, PSMC4, and PSMC6. Table 3 lists microRNA families whose members have predicted target sites in the indicated 19S transcript 3'UTR. The microRNA family ID for each microRNA family is also shown. Additional analyses determined that the following miRNA families are most likely to differentially regulate the CD subunits versus the AB subunits: miR-4282, miR-570, miR-3120-3p, miR-545, miR-30abcdef/30abe-5p/384-5p, miR-2355-5p, miR-763/1207-3p/1655, miR-802, miR-452/4676-3p, miR-4680-3p, and miR-3600/4277.

TABLE 3

| \  miRNA with target sites in 19S transcript |  |  |
|---|---|---|
| PSMD1 | CUUCUUC | miR-1903/4778-3p |
| PSMD1 | AAAACCA | miR-548aaf |
| PSMD1 | GAAAACA | miR-570 |
| PSMD10 | GCCUGGA | miR-1254/3116 |
| PSMD10 | GGGAGGG | miR-2127/4728-5p |
| PSMD10 | CUGGAAA | miR-875-3p |
| PSMD11 | CCCGCCA | miR-4258 |
| PSMD11 | CCCCACU | miR-4286 |
| PSMD11 | CACUCUC | miR-4639-3p |
| PSMD11 | GGGCCAG | miR-4640-5p/4726-5p |
| PSMD11 | AAAAACU | miR-548aeajamx |
| PSMD12 | AUGACAC | miR-425/425-5p/489 |
| PSMD12 | UAUACAC | miR-467f/4789-5p |
| PSMD12 | UAUUAUU | miR-4795-3p |
| PSMD12 | AAAAACC | miR-548d-3p/548acbz |
| PSMD12 | GAAAACA | miR-570 |

TABLE 3-continued

| \  miRNA with target sites in 19S transcript |  |  |
|---|---|---|
| PSMD13 | AGAACAG | miR-4773 |
| PSMD13 | AACAUUC | miR-543 |
| PSMD14 | AUUGCAC | miR-25/32/92abc/363/363-3p/367 |
| PSMD14 | GAUGUAU | miR-3171 |
| PSMD14 | UCAAAUA | miR-3671 |
| PSMD2 | AACAAAC | miR-495/1192 |
| PSMD2 | AGUAACA | miR-802 |
| PSMD3 | GAGAACU | miR-146ac/146b-5p |
| PSMD3 | GCAGGGG | miR-1909 |
| PSMD3 | UCCCCAG | miR-2355-5p |
| PSMD3 | CAAAAAA | miR-3613-3p |
| PSMD3 | GGAGAAG | miR-4434/4516 |
| PSMD3 | UGGAGAA | miR-4531 |
| PSMD3 | GACCCUG | miR-504/4725-5p |
| PSMD3 | AAAAAUC | miR-548c-3p |
| PSMD5 | CAAAUGC | miR-105/105ab |
| PSMD5 | AAGGCAC | miR-124/124ab/506 |
| PSMD5 | GAGAUGG | miR-1273f |
| PSMD5 | UUUCAAC | miR-1305 |
| PSMD5 | CUGAAAG | miR-1326/4766-5p |
| PSMD5 | ACAGCAA | miR-3120-3p |
| PSMD5 | AGAGAAU | miR-3123 |
| PSMD5 | AGGCAGU | miR-34b/449c/1360/2682 |
| PSMD5 | CAAAAAA | miR-3613-3p |
| PSMD5 | AAGGCAG | miR-3714 |
| PSMD5 | GUCCUCU | miR-3909 |
| PSMD5 | AAGGCAU | miR-3910 |
| PSMD5 | AACAUAA | miR-4803 |
| PSMD5 | AACAAAC | miR-495/1192 |
| PSMD5 | UGCAAAG | miR-518a-5p/527 |
| PSMD5 | CAGCAAA | miR-545 |
| PSMD5 | AAAAGUA | miR-548n/570 |
| PSMD5 | AGCAAAA | miR-548p |
| PSMD5 | UUCAAAU | miR-607 |
| PSMD5 | UAAUAGU | miR-633 |
| PSMD5 | AGUAACA | miR-802 |
| PSMD7 | CCCUGAG | miR-125a-5p/125b-5p/351/670/4319 |
| PSMD7 | AGCAGCA | miR-15abc/16/16abc/195/322/424/497/1907 |
| PSMD7 | GUAAACA | miR-30abcdef/30abe-5p/384-5p |

TABLE 3-continued

| miRNA with target sites in 19S transcript | | |
|---|---|---|
| PSMD7 | AAAGAAC | miR-3133 |
| PSMD7 | UAAUUUU | miR-4775 |
| PSMD7 | GAAGGUC | miR-493/493b |
| PSMD7 | UACAAAG | miR-518a-5p/520d-5p/524-5p |
| PSMD7 | AAGGUAA | miR-548agai |
| PSMD7 | AAGAACC | miR-548b-3p |
| PSMD8 | GGGGAGA | miR-3175 |
| PSMD8 | AGGCUGA | miR-3929/4419b/4478 |
| PSMD8 | AGGGCCU | miR-4512 |
| PSMD8 | CUGGGGA | miR-4667-5p/4700-5p |
| PSMD8 | GCCCCAC | miR-4758-3p |
| PSMD8 | GAGGCUG | miR-485-5p/1698/1703/1962 |
| PSMD8 | UGGGGAG | miR-612/3150a-3p |
| PSMD8 | CAGCUGG | miR-763/1207-3p/1655 |
| PSMD9 | CUCUUCC | miR-1236 |
| PSMD9 | UCCCCAG | miR-2355-5p |
| PSMD9 | GGCUGGA | miR-2428/3473b/3652/4430 |
| PSMD9 | GUAAACA | miR-30abcdef/30abe-5p/384-5p |
| PSMD9 | ACAGCAA | miR-3120-3p |
| PSMD9 | UUCCAGA | miR-3180-5p |
| PSMD9 | GGGGUGC | miR-342-5p/4664-5p |
| PSMD9 | CCAGGGC | miR-3594-5p/4685-5p |
| PSMD9 | CUGUAAA | miR-3607-3p |
| PSMD9 | CAGGGAG | miR-4270/4441 |
| PSMD9 | CUGGUGG | miR-4456 |
| PSMD9 | UCCAGAG | miR-520a-5p/525-5p/2464-3p |
| PSMD9 | AUGCCUU | miR-532-5p/511 |
| PSMD9 | CAGCAAA | miR-545 |
| PSMD9 | GAGAACC | miR-589 |
| PSMD9 | GGGGUGG | miR-608/1331/4651 |
| PSMD9 | CAGCUGG | miR-763/1207-3p/1655 |
| PSMD9 | CUUUGGU | miR-9/9ab |
| ADRM1 | GGCAGGU | miR-4736 |
| PSMD10 | GCCUGGA | miR-1254/3116 |
| PSMD12 | AUGACAC | miR-425/425-5p/489 |
| PSMC4 | UGGGACA | miR-1302/1302bd/4298 |
| PSMD10 | GGGAGGG | miR-2127/4728-5p |
| PSMC4 | UUGGGAC | miR-3122/3913-5p |
| PSMD1 | CUUCUUC | miR-1903/4778-3p |
| PSMD12 | UAUACAC | miR-467f/4789-5p |
| PSMD1 | AAAACCA | miR-548aaf |
| PSMD13 | AGAACAG | miR-4773 |
| PSMD13 | AACAUUC | miR-543 |
| PSMD10 | CUGGAAA | miR-875-3p |
| PSMD12 | AAAAACC | miR-548d-3p/548acbz |
| PSMD12 | UAUUAUU | miR-4795-3p |
| PSMD1 | GAAAACA | miR-570 |

Example 17: Reduced 19S Subunit Expression Occurs in Multiple Settings of Acquired and Natural Resistance to Proteasome Inhibitors We analyzed data from bortezomib-resistant HT-29 cells that had been obtained by culture in successively increasing concentrations of bortezomib (Suzuki E et al. (2011) Molecular Mechanisms of Bortezomib Resistant Adenocarcinoma Cells. PLoS ONE 6(12): e27996. Data in GSE29713 in NCBI GEO database). We calculated the ratio of expression level of each 19S subunit (as determined by microarray measurements of RNA) in the bortezomib-resistant cells versus the parental (bortezomib-sensitive) cells (termed "fold change" (FC)). As shown in FIG. 14, we found that PSMD5 and PSMD8 have lower expression in bortezomib resistant cells than in wild type cells ($\log_2 FC$ is less than 0 for PSMD5 and PSMD8). In contrast to the expression levels of the other 19S subunits and the 20S subunits, which were increased in bortezomib resistant cells vs wild type cells, the expression levels of PSMD5 and PSMD8 were reduced in bortezomib resistant cells vs wild type cells. All other subunits were expressed at about the same or greater level in bortezomib-resistant cells as in wild type cells.

We also examined data on proteasome subunit expression levels in mantle cell lymphoma (MCL) cell lines derived from MCL tumors with natural resistance to bortezomib and found that they showed reduced expression of at least one 19S subunit relative to MCL cell lines derived from bortezomib-sensitive MCL tumors (FIG. 14B). We found that expression of PSMD5 in particular is reduced in the bortezomib resistant versus bortezomib sensitive cells.

FIG. 14D shows a comparison between average expression in tumors derived from a bortezomib-resistant cell line (JBR) and average expression in tumors derived from a bortezomib-sensitive cell line (JeKo-1). To perform the analysis, data from GSE51371 was downloaded and log transformed. The expression of each gene was collapsed to the highest expressing probe. For each proteasomal subunit, a log 2 fold change was calculated as the difference between average expression in tumors derived from a bortezomib-resistant cell line (JBR (n=2)) and average expression in tumors derived from a bortezomib-sensitive cell line (JeKo-1 (n=5)). Plotted is the log 2 fold change between sensitive and resistant cells.

We analyzed data obtained from carfilzomib-sensitive multiple myeloma cell lines and carfilzomib-resistant clones of these MM cell lines that had been generated (by others) by exposure to stepwise increasing concentrations of carfilzomib over a period of 18 weeks to generate clones able to survive and proliferate in 12 nM carfilzomib (Riz, I., et al., Oncotarget. 2015; 6(17):14814-31). As shown in FIG. 14C, we found that the multiple myeloma cells with acquired resistance to carfilzomib have reduced fold change in expression of three 19S subunits (PSMC5, PSMD5, and PSMD6) compared to the average fold change in expression of the 19S subunits in these cells. Furthermore, in contrast to the expression levels of most other 19S subunits, which were increased in carfilzomib resistant cells vs wild type cells, the expression levels of PSMD5 and PSMC6 were reduced in carfilzomib resistant cells vs carfilzomib sensitive cells.

Example 18: Multiple Myeloma Patients with 3-Sigma Disease and Treated with Bortezomib have Reduced Progression-Free Survival We analyzed gene expression data from 135 patients with relapsed multiple myeloma who participated in Phase II or III trials of bortezomib (~2007; Mulligan, G., Mitsiades, et al. (2007) Gene expression profiling and correlation with outcome in clinical trials of the proteasome inhibitor bortezomib. *Blood* 109, 3177-3188) and determined the sigma score for each cancer. The sigma score for each cancer (prior to treatment) was computed by comparing the expression of each 19S subunit (except PSMC4, which was not included in the analysis for technical reasons) in each cancer with the average expression of that subunit in the total set of cancers (reference level) and determining the number of standard deviations by which each expression level differed from the reference level. We compared the progression-free survival of patients with 3-Sigma cancer versus patients whose cancer had a sigma score less than 3. Of the 135 patients, 16 had cancers that showed a 3-sigma drop in expression level of at least one 19S subunit. Some patients had cancers that showed a 3-sigma drop in more than one subunit.

Figure 15A:
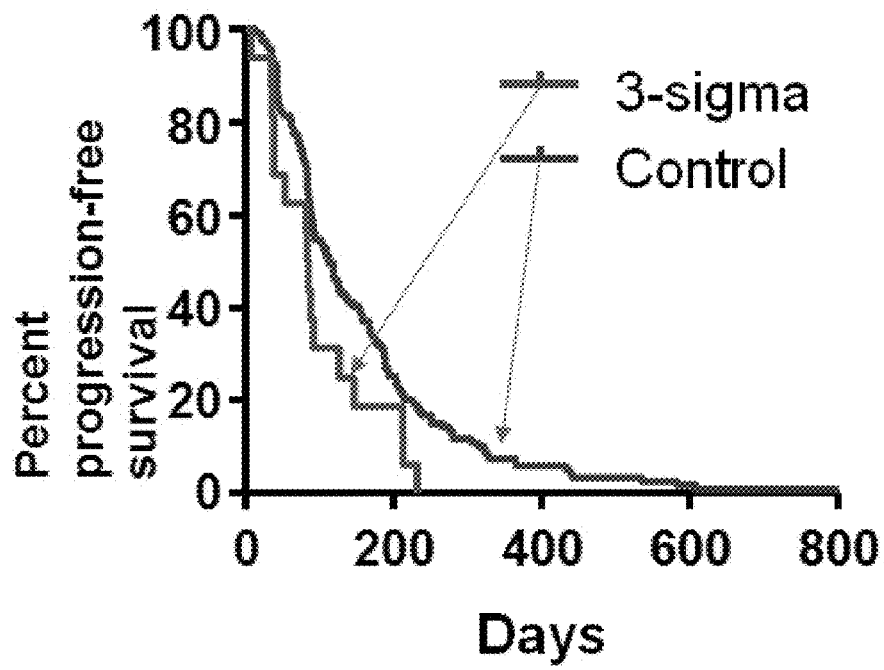
FIGS. 15A-15B.

As shown in FIG. 15A, patients with 3-Sigma disease tended to progress considerably faster than patients with cancers that had a sigma score less than 3. The following table indicates the number of times each listed 19S subunit was found to have an expression level at least 3 SD lower than the reference level.

TABLE 4

| | |
|---|---|
| PSMD5 | 9 |
| PSMC3 | 4 |
| PSMD3 | 3 |
| PSMD4 | 2 |
| PSMD6 | 2 |
| PSMD7 | 2 |
| PSMC5 | 1 |
| PSMD1 | 1 |
| PSMD11 | 1 |
| PSMD13 | 1 |
| PSMD8 | 1 |
| PSMD10 | 1 |
| PSMC2 | 0 |
| PSMC1 | 0 |
| PSMD14 | 0 |
| PSMD2 | 0 |
| ADRM1 | 0 |
| PSMD9 | 0 |
| PSMD12 | 0 |
| PSMC6 | 0 |

Figure 15B:
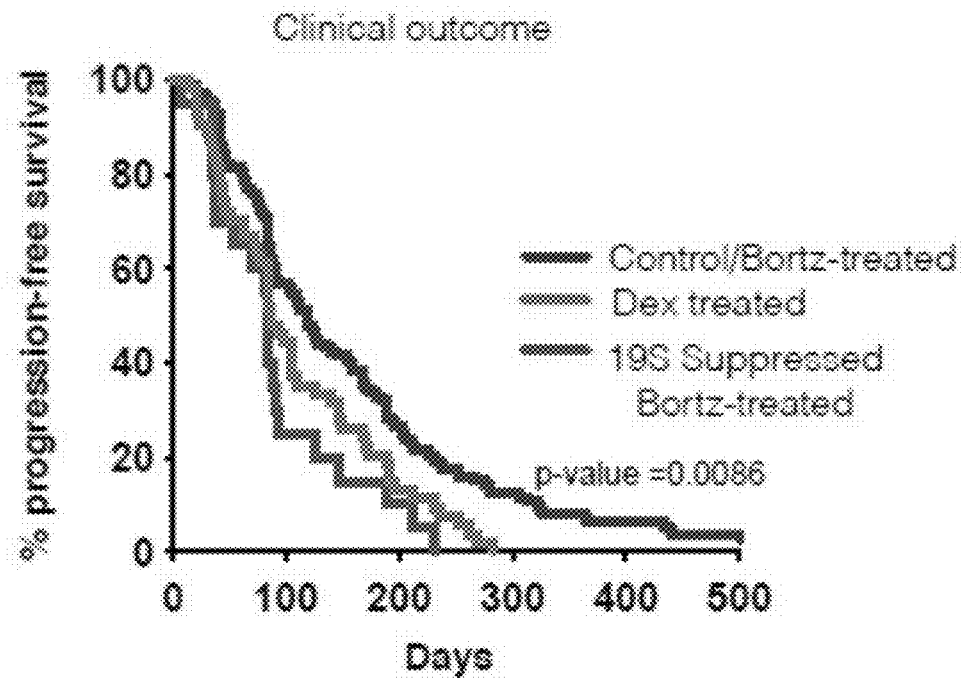

In a more extensive analysis of data from these trials, we found that myeloma samples from 54 of 264 patients exhibited reduced expression of at least one of the 19S proteasome subunits. Of these 54 cases, 34 patients subsequently received bortezomib. These 34 patients exhibited a shortened time to progression compared to patients with myeloma that did not have relative suppression of 19S subunit expression (p-value=0.0086) (FIG. 15B). Notably, bortezomib treatment of patients with reduced expression of 19S proteasome subunit(s) showed no significant effectiveness over the dexamethasone control (FIG. 15B). Suppression of 19S subunit(s) did not induce a significant change in response to dexamethasone treatment.

Methods details: re-treatment gene expression data from relapsed multiple myeloma patients undergoing clinical trials with bortezomib were downloaded from GSE9782 (34). Gene expression data was RMA normalized and log transformed. Sigma scores were calculated from all probes. Patients were binned into two groups: those that had a subunit drop more than 2.8 sigma or those that had not. For each group, the time to relapse from bortezomib treatment was plotted as a Kaplan-Meier plot. P-value was calculated using Wilcoxon test.

DISCUSSION

We have identified a highly conserved mechanism that enables organisms as diverse as yeast and humans—separated in evolution by over one billion years—to withstand inhibition of protein flux through the proteasome. Surprisingly, when the proteasome is inhibited to toxic levels, suppressing individual components of the 19S regulatory complex increases cell survival. While strong reduction of any of these subunits is not tolerated, modest reduction is protective. In this protective state, 26S proteasomes decrease and the levels and activity of 20S proteasomes sharply increase. Furthermore, in the absence of proteasome inhibitors, protein degradation is not reduced, polyubiquitinated substrates are not elevated and the hallmark stress responses are not activated. Moreover, at concentrations of proteasome inhibitors that normally unleash these responses, they are suppressed.

While changes in the ratio of 20S/26S proteasomes have not previously been shown to protect cells from inhibition of flux through the proteasome, it is well documented that they occur. Indeed, a broad range of genetic, metabolic and environmental factors can elicit such changes. In human stem cells, manipulation of just a single subunit of the 19S regulatory complex modified the 20S/26S proteasome ratio (Vilchez et al., 2012). In cancer cells, many chromosomal regions are recurrently lost, and these often harbor genes that encode 19S subunits (Davoli et al., 2013; Nijhawan et al., 2012). Indeed, mining data from a survey of 310 cancer cell lines, we find that those that have increased resistance to proteasome inhibitors have reduced expression of at least one but often of several genes encoding 19S subunits.

The metabolic and environmental factors that can elicit reversible shifts in the 20S/26S proteasome ratio are many and varied. For example, nutrient deprivation in yeast (Bajorek et al., 2003), the activation of glutamate receptor signaling in neurons (Tai et al., 2010), mitochondrial dysfunction in yeast and mammalian cells (Livnat-Levanon et al., 2014) and various states of increased oxidative stress (Livnat-Levanon et al., 2014; Wang et al., 2010) can all increase the levels of 20S proteasome complexes. The ratio of proteasomes can also be regulated by cellular levels of NADH, a co-enzyme that directly binds 19S subunits and influences 26S proteasome stability (Tsvetkov et al., 2014). Further, the ratio is shifted by post-translational modifications mediated by NAD⁺ ADP-ribosyltransferases (Cho-Park and Steller, 2013; Ullrich et al., 1999).

The modest reductions in 19S subunits in our experiments (using shRNAs) did not reduce the overall rates of protein degradation and did not activate proteotoxic stress responses suggesting that these cells normally have a buffer, or excess, of 26S proteasomes. Such a buffer has been recently described in neurons (Asano et al., 2015) and, if true more broadly, might generally allow cells to tolerate reductions in 19S subunit expression without altering basal rates of proteolysis by the proteasome. In our hands, 19S subunit reduction was accompanied by accumulation of active 20S proteasome complexes. These complexes are highly effective in degrading oxidized (Grune et al., 2003; Reinheckel et al., 1998) and intrinsically disordered proteins (Baugh et al., 2009; Ben-Nissan and Sharon, 2014; Tsvetkov et al., 2009a; Wiggins et al., 2011) in an ubiquitin-independent manner. Our results suggest that cells with expanded 20S capacity might be even more broadly positioned to cope with toxic products that accumulate following inhibition of the proteasome.

The increase in 20S proteasomes may also have other, pleiotropic effects that contribute to the protective state. First, these complexes mediate the endoproteolytic cleavage of translation initiating factors eIF4G1, eIF4F, and eIF3a (Baugh and Pilipenko, 2004), which could directly contribute to the inhibition of protein synthesis that occurs following 19S subunit reduction. Second, the 20S proteasomes were shown to preferentially degrade newly synthesized substrates (Adler et al., 2010; Tsvetkov et al., 2009b). In addition, 20S proteasome complexes degrade numerous intrinsically disordered proteins involved in cell cycle regulation, cell cycle control and oncogenesis (Asher et al., 2006; Ben-Nissan and Sharon, 2014; Jariel-Encontre et al., 2008). The degradation of such 20S substrates could underlie the robust anti-proliferation response that follows bortezomib treatment of cells with reduced 19S subunits. Such a shift into a quiescent-like state likely triggers adaptive cytoprotection. This is reminiscent of yeast that transition into stationary phase when nutrients are exhausted. In this setting there is also a reversible reduction in protein translation (Fuge et al., 1994) and levels of 26S proteasomes sharply decrease in favor of active 20S proteasomes which are essential for viability during prolonged periods of nutrient depravation (Bajorek et al., 2003). Thus, the protective mechanism that is generated upon 20S formation is likely conserved from yeast to human and may be part of the natural transitions used to established stress-resistant quiescent states.

In our experiments, this mechanism for increasing resistance was revealed by the use of highly-controllable chemical compounds. However, in nature, mechanisms for rebalancing the 20S/26S proteasome ratio most likely emerged to help cells contend with perturbations that cause protein misfolding. In fact, intracellular and environmental insults that generate large protein aggregates are known to impair the proteolytic function of the proteasome (Ayyadevara et al., 2015; Deriziotis et al., 2011). Such mechanisms may have also helped organisms withstand naturally-occurring 20S proteasome inhibitors that are elaborated by microorganisms cohabiting their niches (Schneekloth and Crews, 2011). Such selective pressures could have shaped the evolution of this ancient survival mechanism, one that emerged long before the advent of the use of proteasome inhibitors as anticancer therapeutics. In agreement with our results indicating that yeast cells are protected from proteasome inhibitors by reducing 19S subunits, Breslow et al. found that reducing 19S subunits can rescue yeast strains that are growth inhibited by reductions in 20S subunits (Breslow et al., 2008).

Suppressing the expression of many different 19S subunits provided resistance to proteasome inhibitors and there are many potential routes for suppressing their expression (e.g., genetic, metabolic, epigenetic, environmental). This raises the intriguing possibility that large populations of cells might harbor functional heterogeneity for surviving altered flux through the proteasome. At one extreme, some cells might be highly proliferative yet highly sensitive to proteasome inhibition while, at the other extreme, some cells could be slowly proliferative yet highly-resistant to proteasome inhibition. Because of their slower proliferation capacity, the latter would have generally reduced relative fitness, analogous to the small populations of drug-tolerant "persister" cells that reside within tumor populations (Glickman and Sawyers, 2012; Knoechel et al., 2014; Sharma et al., 2010). Strategies to address this state of resistance would have significant therapeutic value.

We have demonstrated that reduced 19S subunit expression occurs in proteasome resistant cancer cell lines as well as in naturally occurring and experimentally induced settings of proteasome inhibitor resistance in cancer.

Experimental Procedures

Screening—

The construction of gene-trap viral vectors, generation of mutagenized KBM7 libraries, mapping of insertion sites, and screening approach were performed as described previously (Carette et al., 2009; Carette et al., 2011a; Carette et al., 2011b). We performed pilot experiments to determine the concentrations of MG132 and bortezomib that would allow the emergence of resistant clones from a pilot collection of mutagenized KBM-7 cells following a 10-day incubation. 700 nM MG132 and 18 nM bortezomib were found to be optimal concentrations. 100 million mutagenized cells were exposed to 700 nM MG132 and 18 nM bortezomib and resistant clones were expanded and pooled. Genomic DNA was isolated, and a PCR based approach was followed to amplify the retroviral insertion sites followed by Illumina sequencing. Mutations that were predicted to be disruptive in genes were counted per gene and compared to mutation frequencies in the same gene in a non-selected cell population. Genes significantly enriched for mutations in the selected cell population were identified. Deep sequencing data have been deposited in the NCBI Sequence Read Archive under accession number: PRJNA281714.

Cell Culture Methods—

HEK293T and HepG2 were cultured in Dulbecco's modified Eagle's medium supplemented with 10% fetal bovine serum; H838, H1792, T47D were cultured in RPMI-1640 medium supplemented with 10% fetal bovine serum.

Small Hairpin Knock Down of Proteasome Subunits and Controls—

For the analysis of multiple proteasome subunit knockdown 80 shRNA targeting 20 proteasome subunits (4 different shRNAs) and 13 control shRNAs (Table S2) in pLKO lentiviral vectors from the RNAi consortium shRNA library were utilized. Cells were plated in 96 wells with the volume of 100 μL media at the concentration of 2500 cells/well. 24 hours after plating media was discarded and 50 μl with 7.5-10 μg/μl of polybrene and 7 μl of purified virus was added. After incubation for 24 hours the media was discarded and 200 μl of fresh media with 1 μg/ml puromycin was added. Bortezomib was added where specified. pLKO lentiviral vectors from the RNAi consortium shRNA library targeting the PSMC5 and PSMD2 (Table 2) were further used to create HepG2 and T47D stably overexpressing these shRNAs by selection with puromycin 1 µg/ml for one week.

TABLE 2

(SEQ ID NOS: 1-9, respectively)

| Clone ID | Vector | Gene | shRNA |
|---|---|---|---|
| TRCN0000290022 | pLKO_TRC005 | PSMD2 | CCACATTTGTAGCGAACACTT |
| TRCN0000058089 | pLKO.1 | PSMD2 | GCTGGCTCAAATCGTGAAGAT |
| TRCN0000058090 | pLKO.1 | PSMD2 | CCCTATAACATGGCCCAAT |
| TRCN0000290023 | pLKO_TRC005 | PSMD2 | CGAAACATTATTCTAGGCAAA |
| TRCN0000290093 | pLKO_TRC005 | PSMD2 | GAGGATAAACAGCTTCAAGAT |
| TRCN0000020259 | pLKO.1 | PSMC5 | GCACAGAGGAACGAACTAAAT |
| TRCN0000020261 | pLKO.1 | PSMC5 | GAAGATTCATTCTCGGAAGAT |
| TRCN0000352809 | pLKO_TRC005 | PSMC5 | CAAGGTTATCATGGCTACTAA |
| TRCN0000020263 | pLKO.1 | PSMC5 | TGCTCCATCTATCATCTTCAT |

For the generation of the T47D Tet-inducible PSMD2 knockdown cell line—the TRIPZ vector with an inducible shRNA targeting PSMD2 was purchased from Dharmacon (clone V3THS_403760). It was introduced to the T47D cells according to manufactures protocol and cells were selected with puromycin 1 µg/ml for one week. The cells were exposed to doxycycline for 24 hours and cells were FACS sorted for the top 10% of most RFP expressing cells (highest expression of shRNA). The cells were further cultured in the absence of doxycycline and PSMD2 knockdown was induced as specified in the relevant Examples. The TRIPZ control GFP vector was created by removing the turboRFP from the TRIPZ control vector by digestion with AgeI and ClaI and replacing it with GFP amplified with primers flanking with AgeI and ClaI restriction sites.

Primers:

```
5' Primer for GFP-
                                    (SEQ ID NO: 10)
AAAAAACCGGTCGCCACCatggtgagcaagggcgagga, 3' Primer for GFP-
                                    (SEQ ID NO: 11)
TTTTTATCGATTActtgtacagctcgtccatgccga.
```

Generation of Mutant PSMD12 and PSMC2 ES Cells—

PSMD12 and PSMC2 ES clones were infected with a retro virus carrying cre ires fusion gene under the control of CMV promoter.

72 hours after the infection, Cre+ cells were sorted by FACS and expanded in ES cell medium. After 3-4 weeks, individual subclones were picked, separately plated, further expanded, and finally analyzed for successful inversion event and PSMD12/PSMC2 gene expression.

Primer sequences for genotype analysis (Cre inversion) are (standard PCR conditions):

```
F1:
                                    (SEQ ID NO: 12)
TCGACCTCGAGTACCACCACACT

F2:
                                    (SEQ ID NO: 13)
AAACGACGGGATCCGCCATGTCA

R1:
                                    (SEQ ID NO: 14)
TATCCAGCCCTCACTCCTTCTCT
```

Primer sequences for gene expression analysis are (standard RT PCR conditions):

```
PSMD12 F:
                                    (SEQ ID NO: 15)
CTGTGGATGAGTCAGAGGCT

PSMD12 R:
                                    (SEQ ID NO: 16)
TTGGCTATGAGGTGTGTCGT

PSMC2 F:
                                    (SEQ ID NO: 17)
ACAGCCATTACAGGTGGCAA

PSMC2 R:
                                    (SEQ ID NO: 18)
GTCCACACCGACTCTCATCC
```

Visualization and FACS Analysis of GFP/RFP Levels— cells were trypsinized in 100 µL Accumax® solution and further diluted into 100 µl PBSx1. The number of cells with red or green fluorescent proteins was measured by MACSQuant® VYB according to manufactures protocol. Images of RFP and GFP were created by overlaying images using Fiji software.

Protein Level Expression Analyses—

For the analysis of protein expression, cells were lysed in HENG buffer [50 mM Hepes-KOH pH 7.9, 150 mM NaCl, 2 mM EDTA pH 8.0, 20 mM sodium molybdate, 0.5% Triton X-100, 5% glycerol, 0.2 mM PMSF, 1 mM NaF and protease inhibitor cocktail (Roche Diagnostics, Cat #11836153001)]. Protein concentration was determined by the BCA assay (Thermo Fisher Scientific 23227) and proteins were resolved on SDS-PAGE for immunoblot analysis. The antibodies used are specified below:

| Protein | clone | company | dillution | origin |
|---|---|---|---|---|
| 20S (alphabeta) | PW8195 | Enzo Life Sciences | 1:10,000 | Mouse |
| Nrf1 | D5B10 | Cell signaling | 1:5,000 | Rabbit |
| Hsp70 | c92f3a-5 | Enzo Life Sciences | 1:4,000 | Mouse |
| PSMD2 | H-300 | Santa-cruz | 1:4,000 | Rabbit |
| PSMC5 | SAB2702171 | Sigma | 1:4,000 | Mouse |
| PSMC2 | PW8825 | Enzo Life Sciences | 1:2,000 | Mouse |
| RFP | 10367 | life technologies | 1:2,000 | Rabbit |
| Tubulin | ab80779 | Abcam | 1:4,000 | Mouse |
| Actin | | Cell signaling | 1:2,000 | Rabbit |
| Ubiquitin | PW8810 | Enzo Life Sciences | 1:2,000 | Mouse |
| p-Hsf1 (S326) | EP1713Y | Epitomics | 1:2,000 | Rabbit |
| Hsf1 | AB4 | Thermo | 1:1,000 | Rat |

Compounds Used—

The following compounds were used. MG132 (EMD Millipore), Bortezomib (LC Laboratories # B-1408), Cyclohexamide (Enzo life sciences), withaferin A, tunicamycin (Sigma).

Cell Viability Assay—

Relative cell growth and survival were measured in 96-well microplate format in the shRNA experiments and in 384 well format in the drug toxicity assays, by using the fluorescent detection of resazurin dye reduction as an endpoint (544 nm excitation and 590 nm emission). 2,500 cells in 96 wells format or 1,000 cells in 384 well format were plated 24 hours before compound exposure (for 72 hours or indicated time). Each analysis was performed at least with three replicas.

Gene Expression Analysis—

RNA was extracted from triplicate samples and RNA libraries were prepared for sequencing by NEBNext Ultra RNA Library Prep Kit for Illumina (New England BioLabs, Ipswich, Mass.), including the removal of large and small RNA, synthesis of cDNA, and construction of cDNA libraries. Libraries were barcoded using NEBNext Multiplex Oligos for Illumina (NEB). Libraries were sequenced using Illumina HiSeq 2500, with paired-end 100 bp reads. Paired-end reads were aligned to UCSC human transcriptome 19 (hg19) using TopHat (Bowtie v2.0.9). Alignment quality and read distribute was assessed via SAMtools (v0.1.19) (Li et al., 2009). Transcript assembly was conducted using cufflinks (v2.2.1). Normalized expression data was generated from aligned BAM files using cuffnorm and cuffdiff (Trapnell et al., 2012). Transcripts with zero values for FPKM across all samples were removed. The mean for the triplicate technical replicates was created and, after adding 1 pseudocount count, were log 2-normalized. RNA sequencing data have been deposited in the NCBI Sequence Read Archive under accession number: PRJNA281613.

Genes differentially expressed upon PSMD2 knockdown in either the presence or absence of bortezomib treatment were determined as follows (FIG. 3E): For each gene in the matrix described above, the values were normalized to the average expression in the LacZ control cells. Genes for which the absolute value of any condition versus control was greater than 1 and whose expression was significantly different between any condition (<0.05 p-value in a student's t test) versus control were included. These differentially expressed genes were clustered by k-means clustering.

Selective gene set enrichment analysis (FIG. 3C, FIG. 33) was conducted by using GSEA v2.2.0 software. Genes without detectable levels of expression across all samples within the individual analyses were excluded. The metric used for ranking genes was the difference of classes. The gene-sets "HSF1 bound" and "heat-shock up" were derived from GEO (GSE45851) (Mendillo et al., 2012). The gene-sets "bortezomib suppressor" and "bortezomib synthetic lethal" were obtained from Table 1 in (Chen et al., 2010). Gene ontology (GO) enrichment (FIG. 3E, Table S3 (data not shown)) was calculated using GOrilla software (Eden et al., 2009).

Genomics of Drug Sensitivity in Cancer Data Analysis—

The IC50 values for bortezomib and MG132 across 315 cancer cell lines were obtained from the World Wide Web at subdomain cancerrxgene.org (Garnett et al., 2012). Gene expression data was obtained from the Oncomine Platform. The average gene expression for the genes that comprise the 20S proteasome subunit (PSMAs and PSMBs) and the average gene expression for the genes that comprise the 19S subunit (PSMCs and PSMDs) was analyzed in the cell lines that are the 10% most sensitive or the 10% most resistant to either MG132 or bortezomib. The p-values were obtained by conducting a two-tailed unpaired t-test.

Translation and Degradation Assays—

For measuring overall rate of synthesis, cells were pre-treated with 10 nM Bortezomib for 20 hours, then incorporation of $^3$H-phenylalanine was measured for 1 h. The rate of synthesis was described as counts incorporated into cell proteins per hour and per µg of total cell proteins. When working with T47D cells, knockdown of PSMD2 was induced for 3 days with doxycycline before bortezomib treatment. For measuring overall rates of protein degradation, pulse-labeling with $^3$H-phenylalanine for 24 hours was done before the bortezomib treatment as previously described (Zhao et al., 2007).

Yeast Strains and MG132 Sensitivity Assay—

MG132 sensitivity protocol was conducted as previously described (Liu et al., 2007). Yeast cells were grown over night in media containing L-proline as nitrogen source instead of ammonium sulfate. The overnight cultures were diluted into OD 0.1 and were grown in the L-proline culture with 0.003% SDS with or without 50 µM MG132. OD was measured over the period of 48 hours.

Native Gel Analysis of Proteasomal Complexes—

Proteasomal samples were loaded on a nondenaturing 4% polyacrylamide gel using the protocol described previously (Tsvetkov et al., 2014). Gels were either overlaid with Suc-LLVY-AMC (50 µM) for assessment of proteasomal activity or transferred to nitrocellulose membranes where immunoblotting specific for proteasomal subunits was conducted. Proteasomal activity was assessed by measuring the hydrolysis of Suc-LLVY-AMC by substrate overlay assays in native polyacrylamide gels with 50 mM Tris-HCl, pH 7.8, 5 mM MgCl2, 1 mM DTT, 2 mM ATP, 50 µM Suc-LLVY-AMC peptide, and incubating the gels at 37° C. for 30-60 min. Activity was visualized by transilluminated by a UV light and photographed with BIORAD Chemidoc imaging system.

Example 19: Screen Identifies Compounds that Selectively Inhibit Growth of PSMD2 Knockdown Cells T47D cells harboring a doxycycline inducible PSMD2 KD shRNA construct (760S cells) were incubated in the absence or presence of 1 ug/ml of doxycycline for 48 hours (control versus PSMD2 KD cells respectively). After 48 hours the cells were collected, counted, and plated at 1000 cells/well in 384 well plates in duplicates for each cell line. Compounds from the Selleck Chemicals anti-cancer compound library β49 drugs in 4 concentrations; 25 uM, 250 uM, 2500 uM, 25000 uM) were pinned the next day and viability was measured after 72 hours by the reduction of Resazurin (Ex=530 nm, Em=590 nm).

Figure 16:
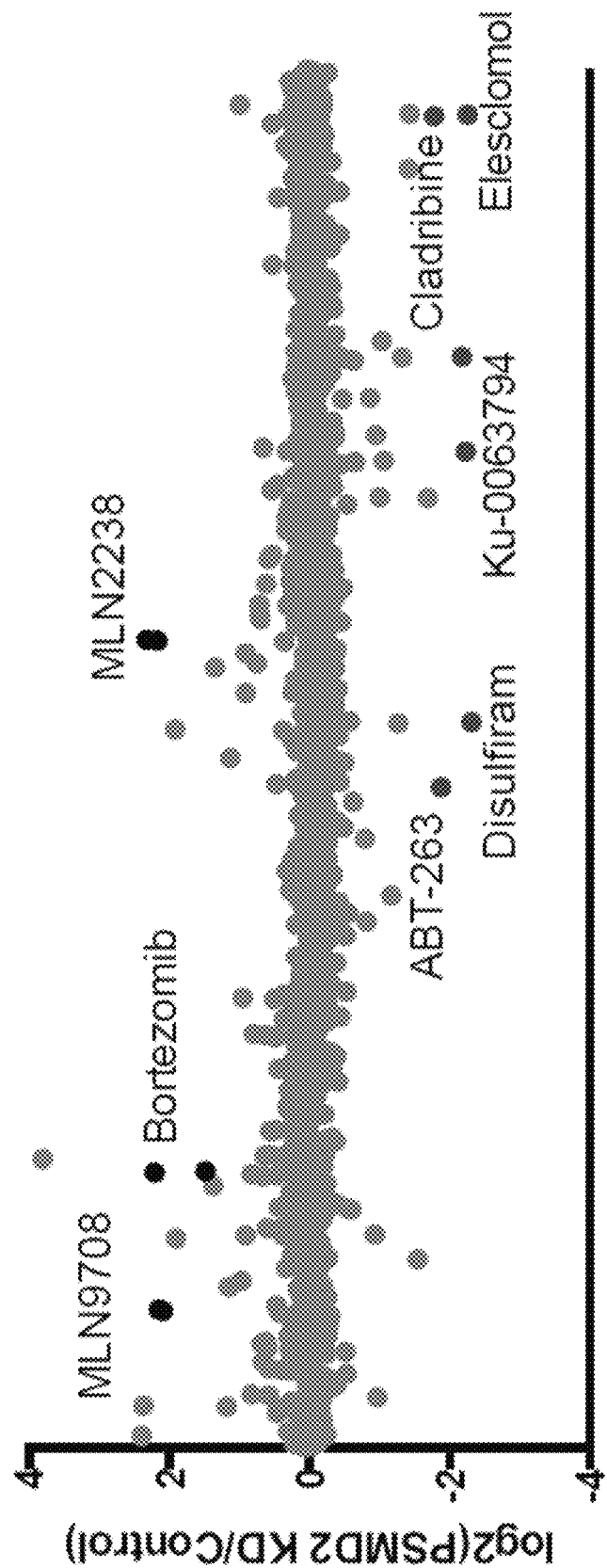
FIG. 16: Results of screen of Selleck anti-cancer drug library to identify compounds that selectively inhibit growth of PSMD2 knockdown cells.

The effect of each drug on viability of cells was calculated by averaging the duplicate experiments. The data is plotted in FIG. 16 as the $log_2$ of the ratio of viability of PSMD2 KD versus control cells ($log_2$ (shPSMD2/Control)). Some hits in the screen are color coded and represented on the graph. Most compounds did not selectively affect the viability of PSMD2 KD cells versus control cells. Several proteasome inhibitors (MLN9708, bortezomib, and MLN2238) present in the library were identified as compounds that selectively reduce viability of control cells versus PSMD2 KD cells, consistent with the findings described herein that decreased expression of 19S subunits renders cells more resistant to proteasome inhibitors. A number of compounds that selectively reduce the viability of PSMD2 KD cells versus control cells were identified, including ABT-263, disulfiram, elesclomol, cladribine, and Ku-0063794.

Figure 17:
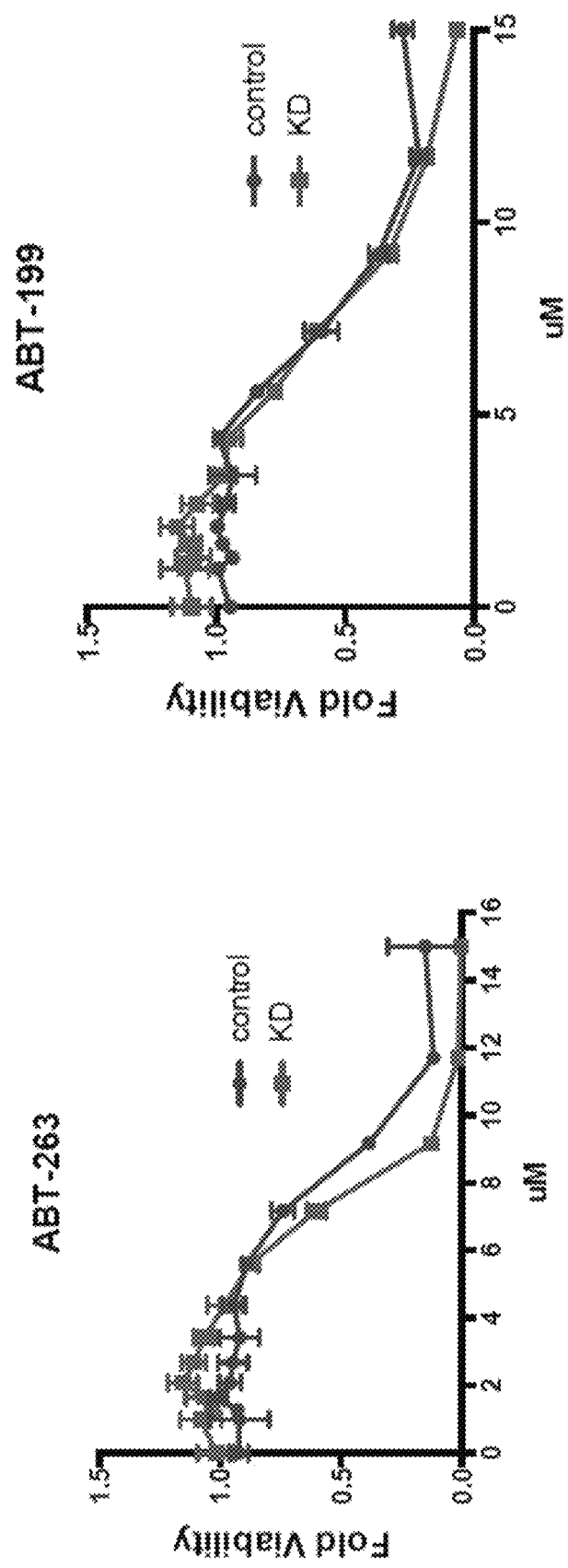
FIG. 17: Plot showing effect of ABT-263 (left) or ABT-199 (right) on viability of T47D cells with reduced expression of PSMD2 (KD) or control cells. Fold viability refers to the number of viable cells of the indicated type (PSMD2 KD or control cells) after culture in the presence of the test compound (ABT-263 or ABT-199) divided by the number of viable cells of that type after culture in the absence of the test compound.

Example 20: Effect of ABT-263 or ABT-199 on Viability of PSMD2 Knockdown Cells Versus Control Cells T47D cells harboring a doxycycline inducible PSMD2 KD shRNA construct were cultured in the absence or presence of 1 ug/ml of doxycycline for 72 hours (control versus PSMD2 KD cells respectively) and then either ABT-263 or ABT-199 was added at various concentrations as indicated in FIG. 17 (x-axis). Cell viability was measured by CellTiter-Glo® Luminescent Cell Viability Assay 72 hours after addition of the compounds to cells. As shown on FIG. 17, PSMD2 KD cells were more sensitive to ABT-263 than were control Cells.

Figure 18:
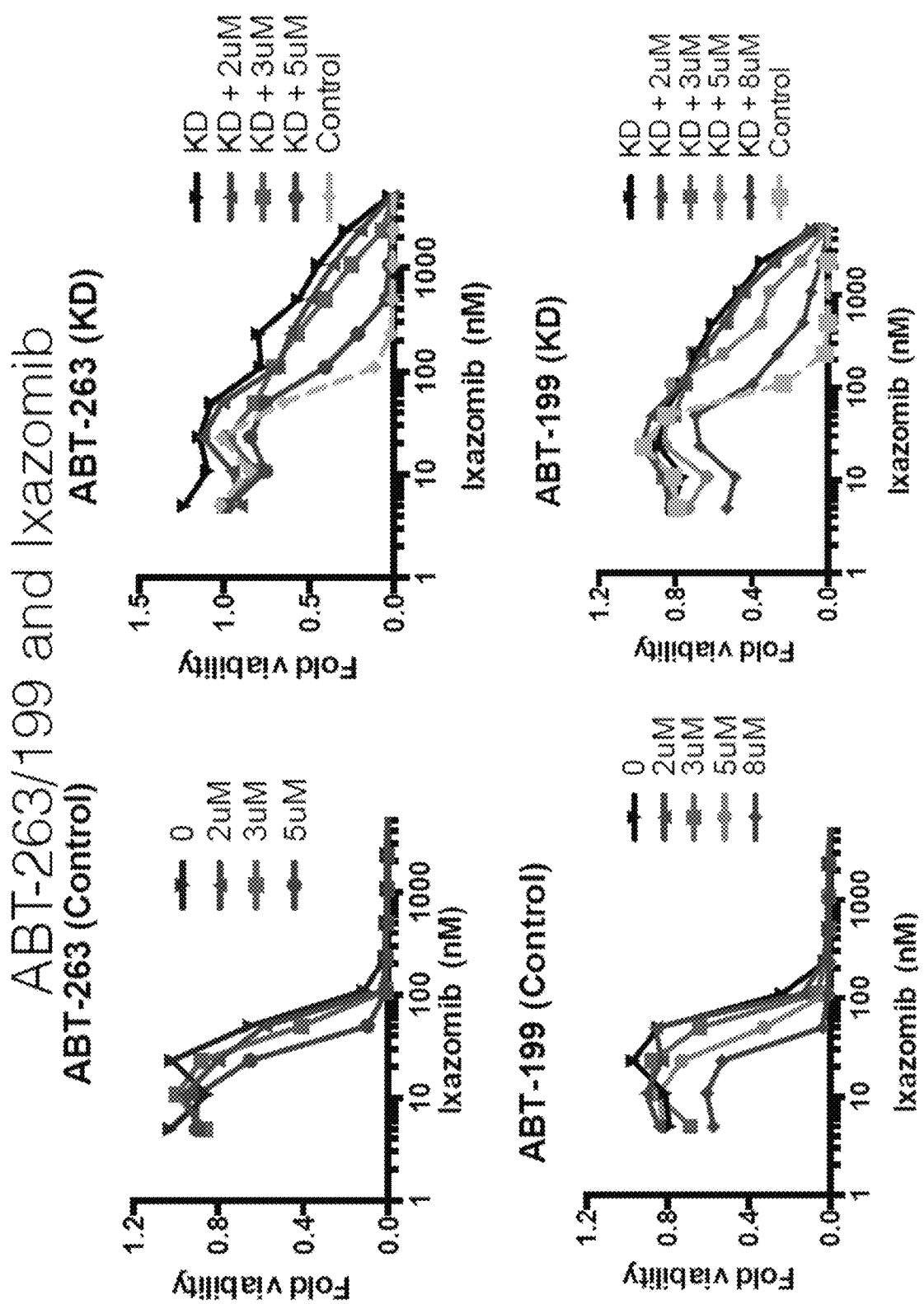
FIG. 18: Plots showing effect of various concentrations of ABT-263 (upper panels) or ABT-199 (lower panels) in combination with various concentrations of ixazomib on viability of T47D cells with reduced expression of PSMD2 (KD) (right panels) or control cells (left panels). Fold viability refers to the number of viable cells of the indicated type (PSMD2 KD or control cells) after culture in the presence of the test compounds (ixazomib+ABT-263 or ixazomib+ABT-199) divided by the number of viable cells of that type after culture in the absence of the test compounds. The concentrations of ABT-263 or ABT-199 tested are shown in the legend on the right side of each panel. If no concentration is listed, the compound was absent. Fold viability of control cells cultured in the presence of ixazomib alone (i.e., in the absence ABT-263 or ABT-199) is also shown in the panels showing effect of ixazomib+ABT-263 or ixazomib+ABT-199 on PSMD2 KD cells.

Example 21: Effect of a Combination of a BCL2 Family Inhibitor and Ixazomib on PSMD2 Knockdown Cells Versus Control Cells T47D cells harboring a doxycycline inducible PSMD2 KD shRNA construct were cultured in the absence or presence of 1 ug/ml of doxycycline for 72 hours (control versus PSMD2 KD cells respectively) and then either ABT-263 and ixazomib or ABT-199 and ixazomib were added at various concentrations as indicated in FIG. 18 (x-axis indicates ixazomib concentrations; concentrations of ixazomib are indicated at the right on each panel). Cell viability was measured by CellTiter-Glo® Luminescent Cell Viability Assay 72 hours after addition of the compounds were added to cells. Results are shown in FIG. 18

Figure 19:
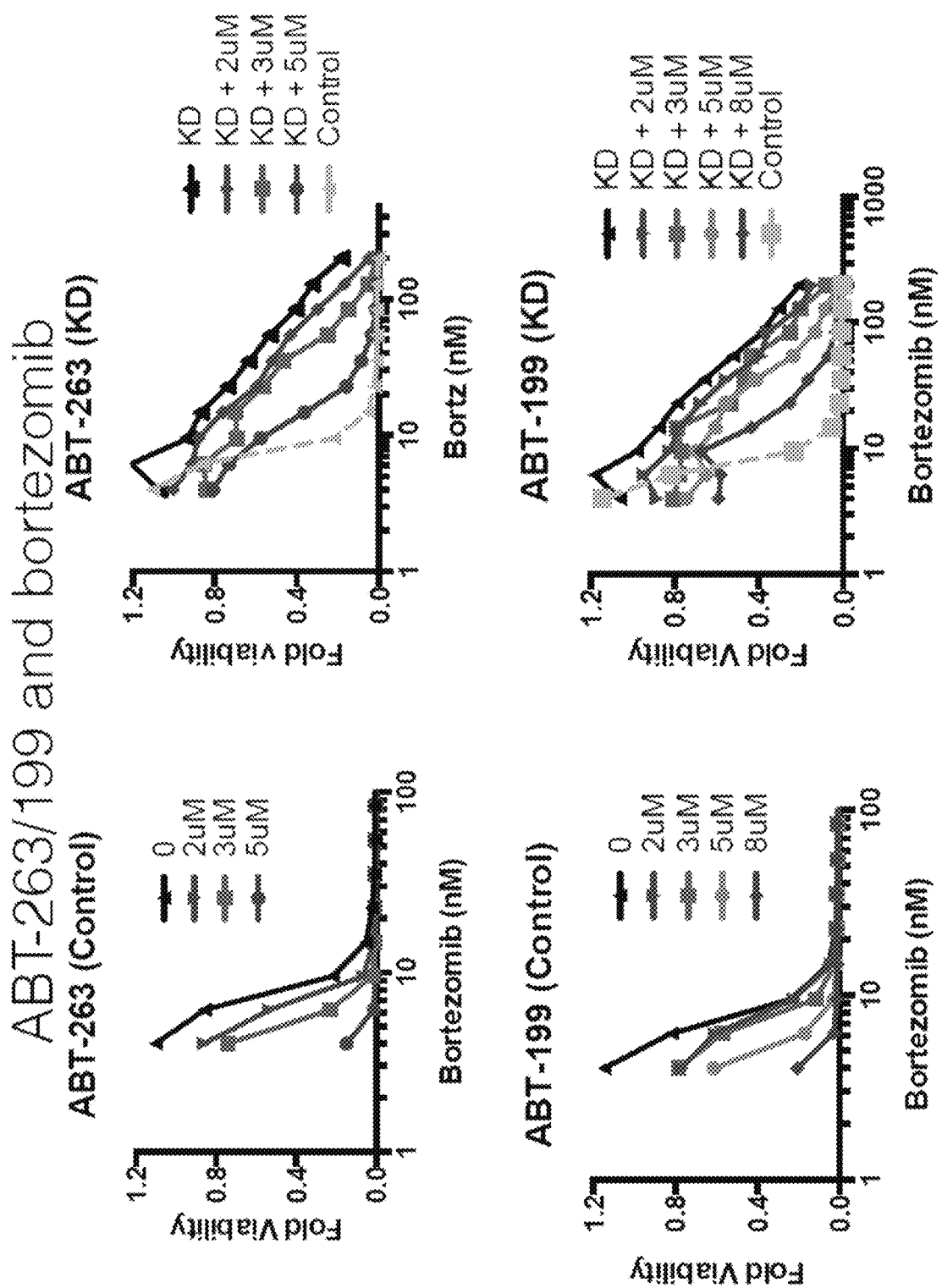
FIG. 19: Plots showing effect of various concentrations of ABT-263 (upper panels) or ABT-199 (lower panels) in combination with various concentrations of bortezomib on viability of T47D cells with reduced expression of PSMD2 (KD) (right panels) or control cells (left panels). Fold viability refers to the number of viable cells of the indicated type (PSMD2 KD or control cells) after culture in the presence of the test compounds divided by the number of viable cells of that type after culture in the absence of the test compounds. The concentrations of ABT-263 or ABT-199 tested are shown in the legend on the right side of each panel. If no concentration is listed, the compound was absent. Fold viability of control cells cultured in the presence of bortezomib alone (i.e., in the absence ABT-263 or ABT-199) is also shown in the panels showing effect of bortezomib+ABT-263 or bortezomib+ABT-199 on PSMD2 KD cells.
Figures 21A, 21B, 21C:
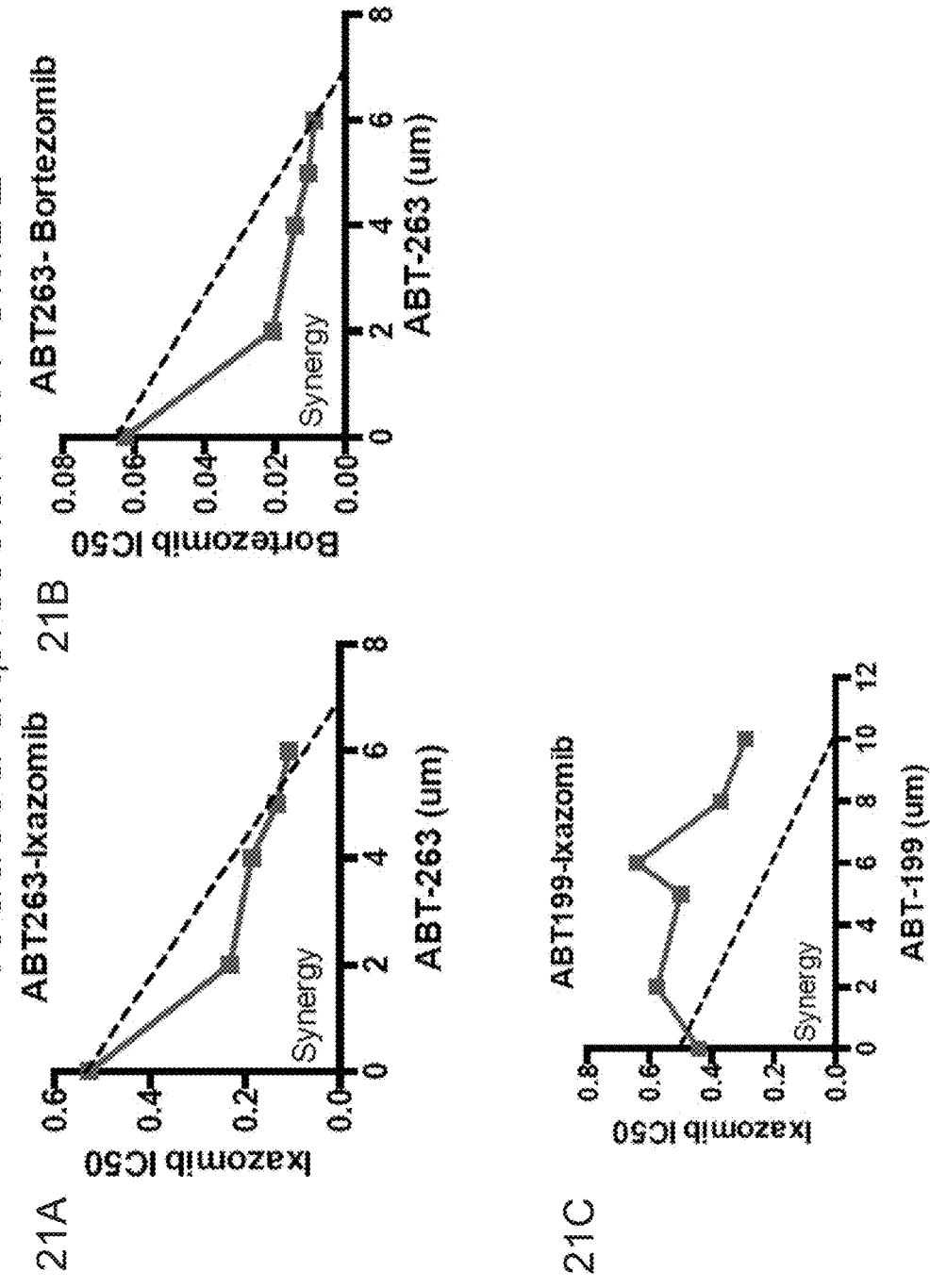
FIGS. 21A-21C.

Example 22: Effect of a Combination of a BCL2 Family Inhibitor and Bortezomib on PSMD2 Knockdown Cells Versus Control Cells T47D cells harboring a doxycycline inducible PSMD2 KD shRNA construct were cultured in the absence or presence of 1 ug/ml of doxycycline for 72 hours (control versus PSMD2 KD cells respectively) and then either ABT-263 and bortezomib or ABT-199 and bortezomib were added at various concentrations as indicated in FIGS. 19 and 20 (x-axis indicates ixazomib concentrations; concentrations of bortezomib are indicated at the right on each panel). Cell viability was measured by CellTiter-Glo® Luminescent Cell Viability Assay 72 hours after addition of the compounds to cells. Results are shown in FIGS. 19 and 20.

Example 23: Reduced PSMD5 Expression in Neuroblastoma

Figure 22A:
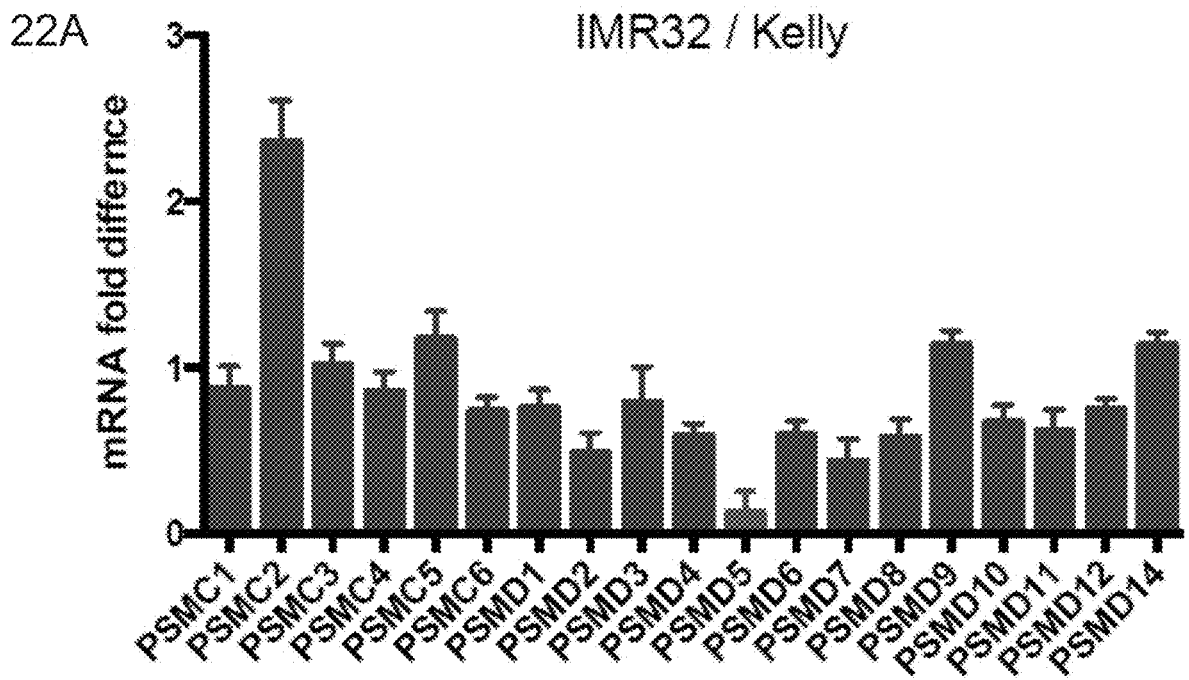
FIGS. 22A-22C.

Levels of mRNA encoding 19 of the 19S subunits were measured in two neuroblastoma cell lines, IMR32 and Kelly. IMR32 cells were found to have reduced expression of PSMD5, as validated by qPCR (FIG. 22A). The rest of the 19S subunits were found to have very similar expression levels (except for PSMC2 where more was detected in the IMR32 cells).

Figure 22B:
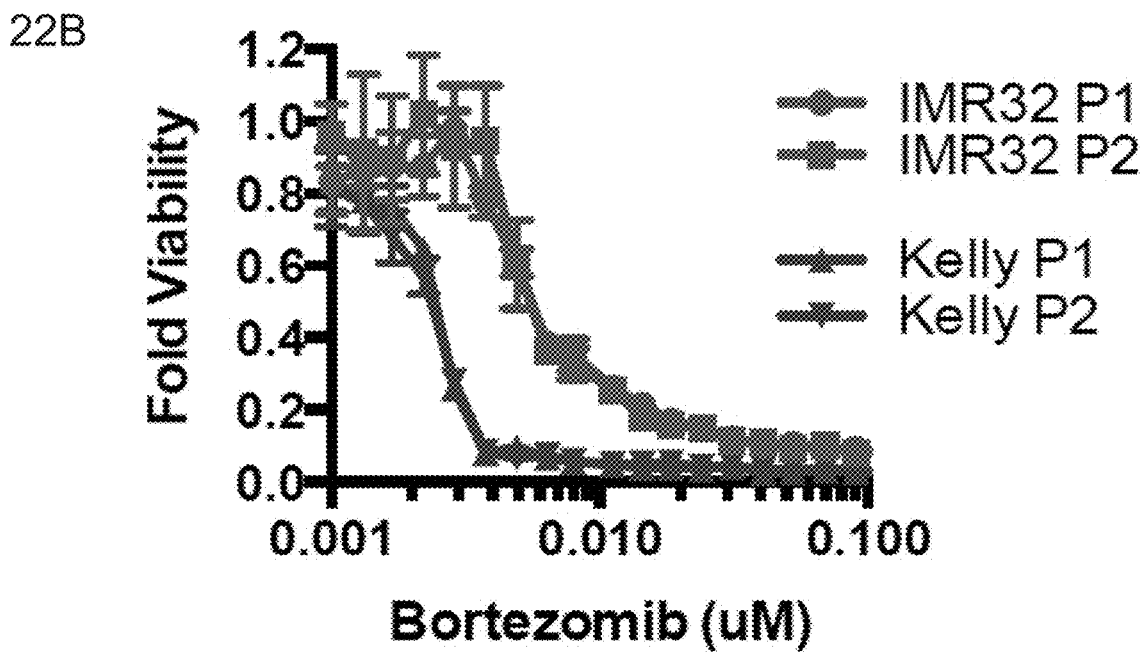
Figure 22C:
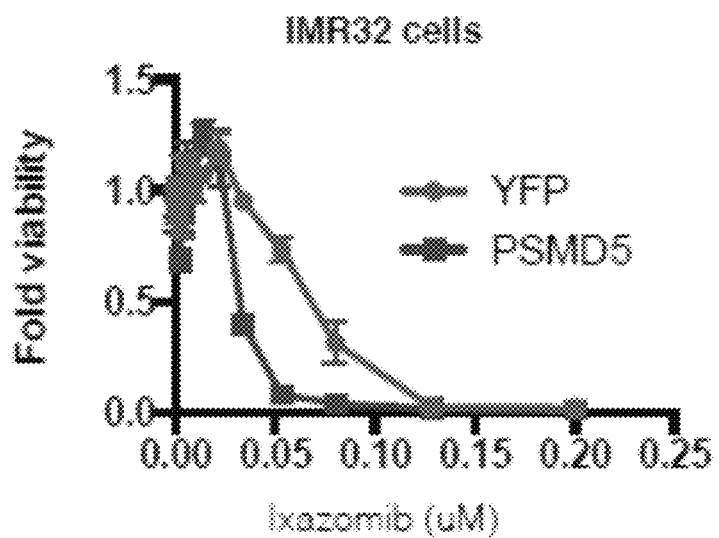

IMR32 and Kelly cells were each cultured in the presence of bortezomib at concentrations ranging from 0.001 um to 0.100 um. Cell viability was measured by CellTiter-Glo® Luminescent Cell Viability Assay 72 hours after addition of the compound to cells. The fold viability relative to culture in the absence of bortezomib was determined for each cell line. As expected based on their reduced expression of PSMD5, dose response testing revealed that IMR32 cells have increased resistance to bortezomib relative to Kelly cells (FIG. 22B). IMR32 cells can be re-sensitized to a proteasome inhibitor by forced transgenic expression of the PSMD5 subunit (FIG. 22C).

Figure 25A:
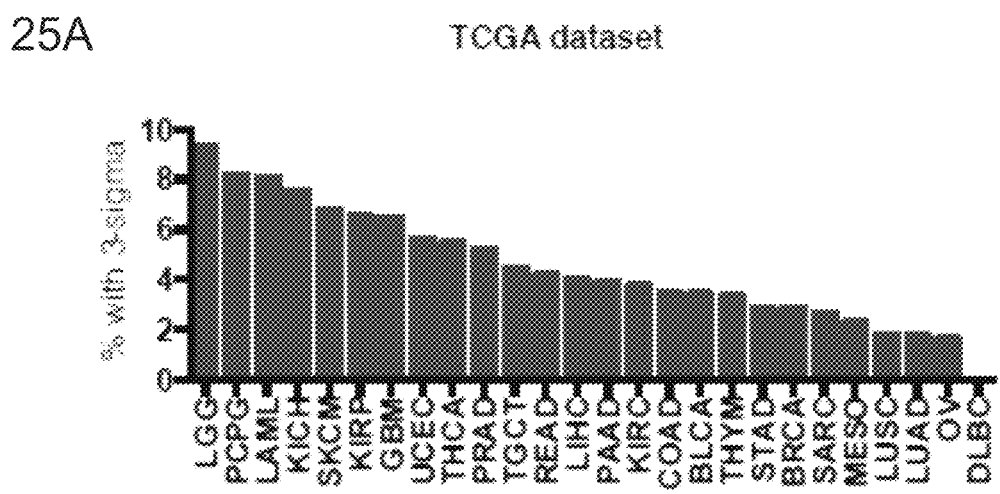
FIGS. 25A-25B.

Example 24A: 3-sigma 19S Subunit Reductions Occur in Tumors of Diverse Histology To investigate the frequency and patterns of 19S subunit mRNA suppression in resection specimens of human primary tumors, we analyzed mRNA expression data from The Cancer Genome Atlas (TCGA). We examined the expression profiles of 9,217 primary tumors from 53 different cancer types. The frequency of tumors with a 3-sigma drop of at least one subunit of the 19S proteasome was 4.2%. Moreover, this analysis of the TCGA data showed that 3-sigma subunit reductions were present in tumors of diverse histology, amounting to 6% to 9% of some tumor types such as low-grade and high-grade gliomas, pheochromocytomas and paragangliomas, acute myeloid leukemias, renal cell carcinomas and cutaneous melanomas (FIG. 25A).

Figure 25B:
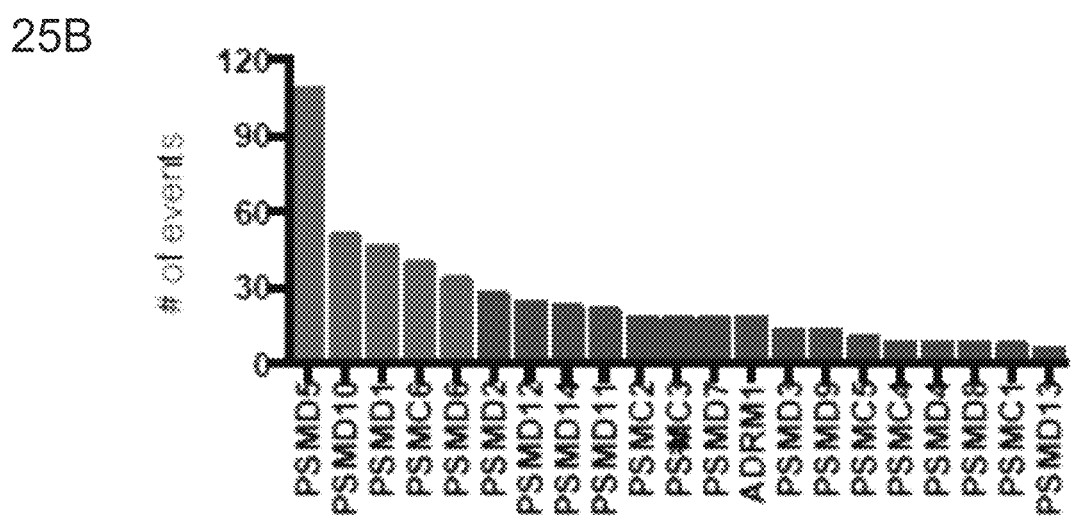
Figure 26A:
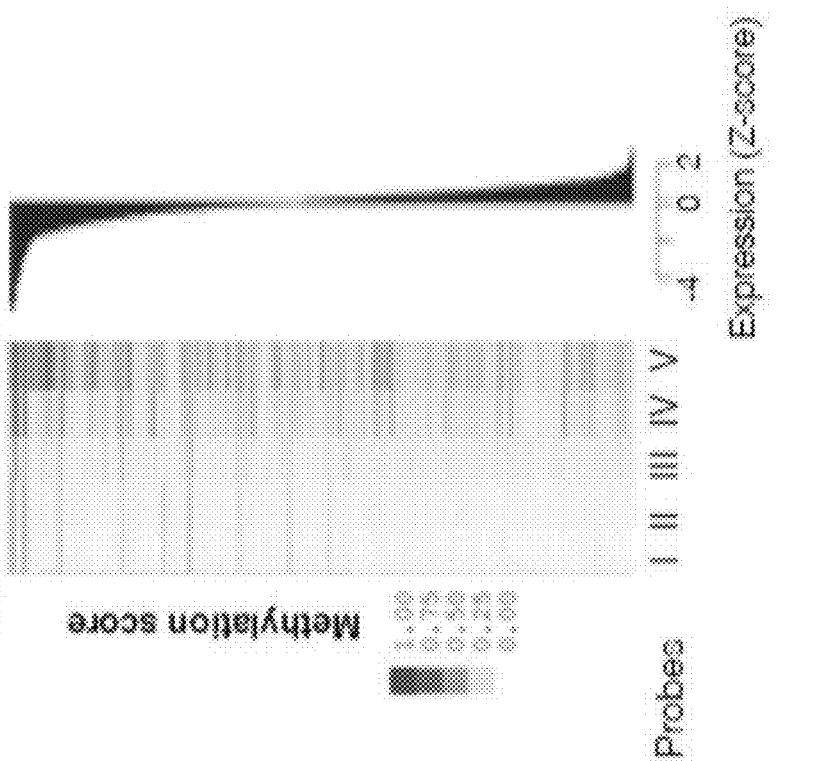
FIGS. 26A-26D.
Figure 26B:
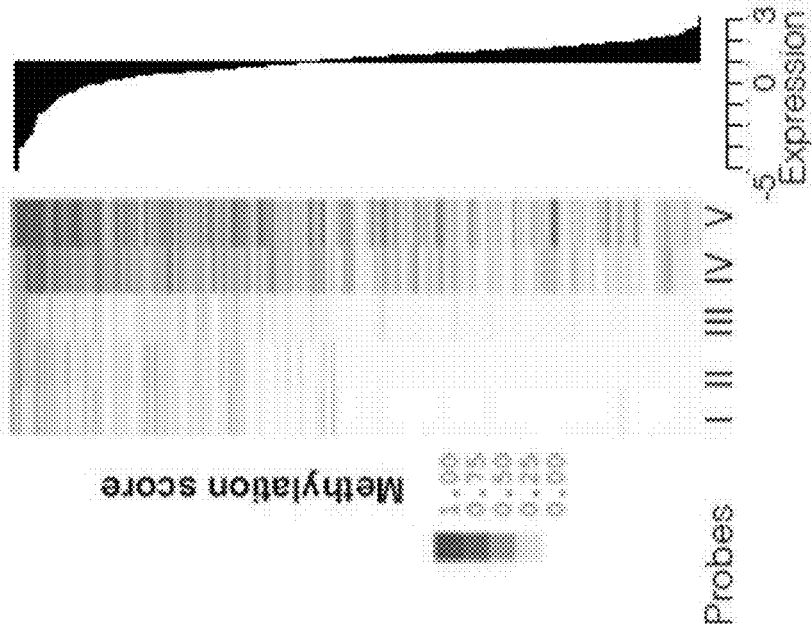
Figure 26C:
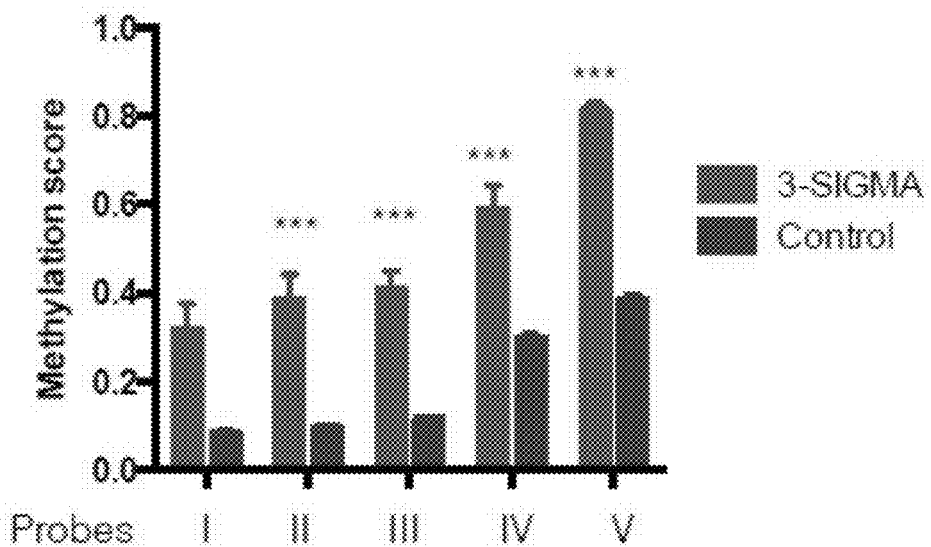
Figure 26D:
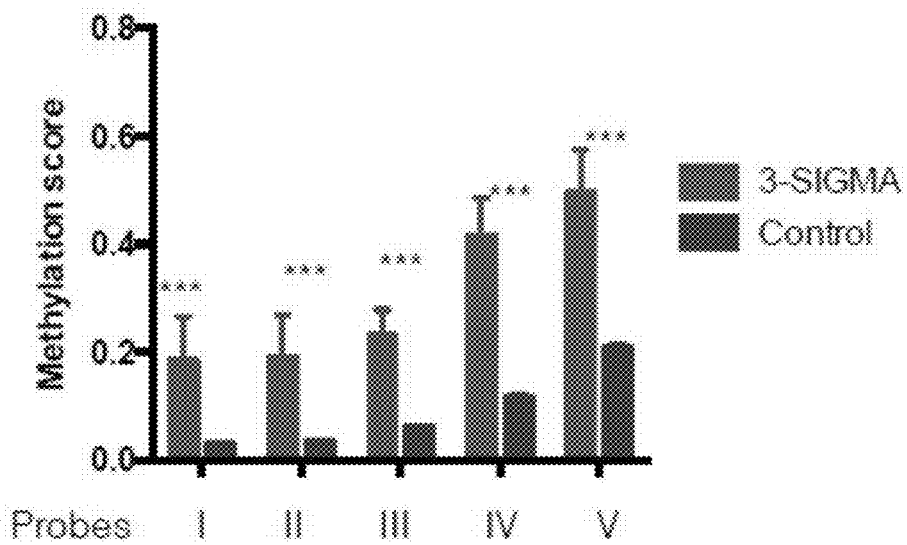
Figure 27:
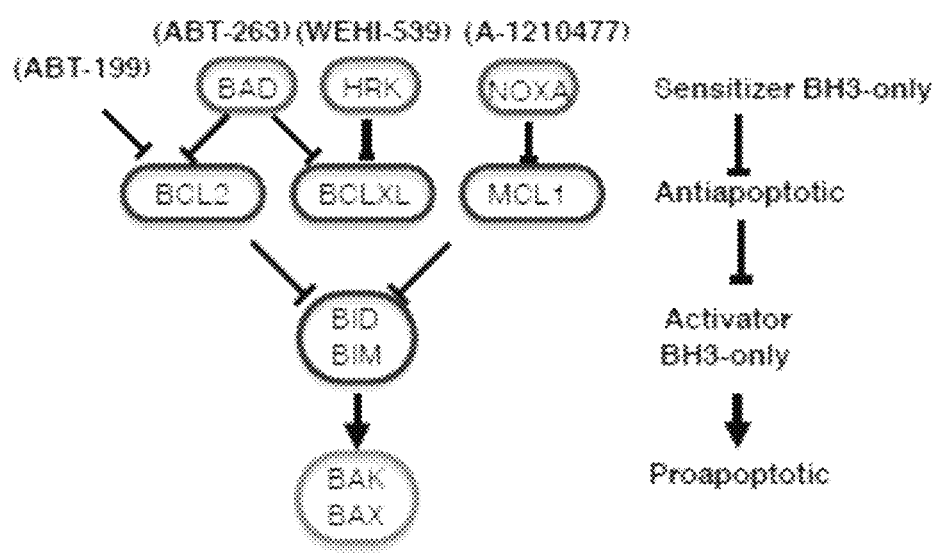
FIG. 27: Schematic representation of the BH3-BCL2 apoptotic program. In green are the BH3 sensitizing peptides that can be mimicked by drugs. BAD (ABT-263), NOXA (A-1210477), HRK (WEHI-539) and ABT-199 specifically targeting BCL2. In red the anti-apoptotic proteins (BCL2, BCLXL and MCL1) are marked that bind and inhibit the BH3 activator proteins BIM and BID (in blue).

Similar to the results from the GDSC and CCLE datasets described above, PSMD5 was the most commonly suppressed 19S subunit gene in human tumor resection samples (FIG. 25B). In addition, other 19S subunit genes that commonly showed 3-sigma changes in the GDSC and CCLE cell line datasets, such as PSMD1, PSMC6, PSMD10, and PSMD6, were suppressed in tumors from the TCGA (FIG. 25B).

Methods used in TCGA data analysis: The Cancer Genome Atlas (TCGA: cancergenome.nih.gov) data for methylation (IIlumina 450k Bead Chip) and expression (RNASeq V2) were downloaded using TCGA-assembler (Zhu, Y., et al. (2014) *Nat Methods* 11, 599-600). Downloaded level 3 data for each gene included a methylation score (0 to 1) for methylation data, and RNASeq data were quantified as RSEM. Sigma score was calculated for each primary tumor category separately by calculating a Z-score for every individual proteasomal subunit gene and categorizing the tumors as 3-sigma or control.

Example 24B: PSMD5 Gene Expression Silencing By Promoter Methylation in Tumors

The profound drop in PSMD5 mRNA expression in the absence of copy number aberrations discussed above suggested a strong epigenetic repressor mechanism. One common mechanism employed for epigenetic silencing is DNA methylation of gene promoters by the addition of a methyl group to cytosine residues within CpG dinucleotides. To assess whether DNA methylation is responsible for suppressed PSMD5 expression, we investigated levels PSMD5 promoter methylation in both low grade gliomas (LGG) and bladder carcinomas (BLCA), tumor types with the highest frequency of PSMD5 3-sigma samples in the TCGA dataset (FIGS. 26A-26D). In both LGG and BLCA, the 19S proteasome 3-sigma tumors had significantly higher methylation of the PSMD5 promoter, suggesting that promoter methylation may be a major mechanism for repressing PSMD5 mRNA expression in tumors.

Example 24C: PSMD5 Gene Expression Silencing By Promoter Methylation in Neuroblastoma Cells To further explore the effect of promoter methylation on PSMD5 gene expression, we selected two neurobalstoma cell lines that had highly divergent expression of PSMD5 based on the CCLE dataset; Kelly cells have normal proteasome subunit expression while IMR32 cells have strongly reduced PSMD5 mRNA expression. We first verified 19S proteasome subunit expression in both cell lines by quantitative PCR. The relative mRNA expression of all the 19S subunits was remarkably similar between the two cell lines with the exception of slightly increased levels of PSMC2 mRNA in the Kelly cells and the 8-fold decrease in PSMD5 mRNA in IMR32 cells expected from the CCLE data. CpG methylation in the PSMD5 promoter region was examined in IMR32 and Kelly cells by bisulfite sequencing. DNA was extracted from IMR32 and Kelly cells with DNeasy Blood & Tissue Kit (Qiagen) according to manufactures protocol. Bisulfite conversion of the DNA was conducted utilizing the EpiTect Bisulfite Kit (Qiagen) according to manufactures protocol. The modified DNA was then used as template for PCR of the PSMD5 promoter using the following primers:

```
Fw
                                        (SEQ ID NO: 19)
5' GGTTGGTTTAGCGGTTTAGTTTTCG,
and Rv
                                        (SEQ ID NO: 20)
3' CATCCAATCTTCCAAAAACATAACGCT.
```

The PCR reaction was conducted using Epimark hot start Taq polymerase (NEB) in a reaction volume of 50 uL with the following PCR program: 95° C. for 30 sec; 95° C. for 15 sec; 55° C. for 20 sec; 68° C. for 45 sec; repeat steps 2-4×45; 68° C. for 5 min; pause at 4° C. The amplified PCR product was gel purified and cloned into pCR2.1-TOPO-TA cloning vector (Life Technologies). Ten separate clones were amplified and sequenced with M13 Fw and M13 Rv primers. The sequence analyzed in the promoter region is 50-382 bps downstream of the PSMD5 gene ATG and contains 29 CpGs. The methylation status of each CpG in each cell line is depicted in FIG. 23 (black circle methylated, empty circle unmethylated). The PSMD5 promoter in the IMR32 cells is highly methylated whereas it is not methylated in the Kelly cells. More specifically, we found strong DNA methylation of this promoter in IMR32 cells with methylation of 98% of the cytosine residues within promoter CpG islands (98%) whereas there was minimal methylation of the PSMD5 promoter in Kelly cells, with only 4% of the cytosines within the CpG islands harboring methyl groups. The methylation of the PSDMS promoter of IMR32 indicates an altered epigenetic state that can explain the highly suppressed levels of PSMD5 mRNA within these cells and the markedly altered sensitivity to bortezomib.

Figures 24A, 24B, 24C:
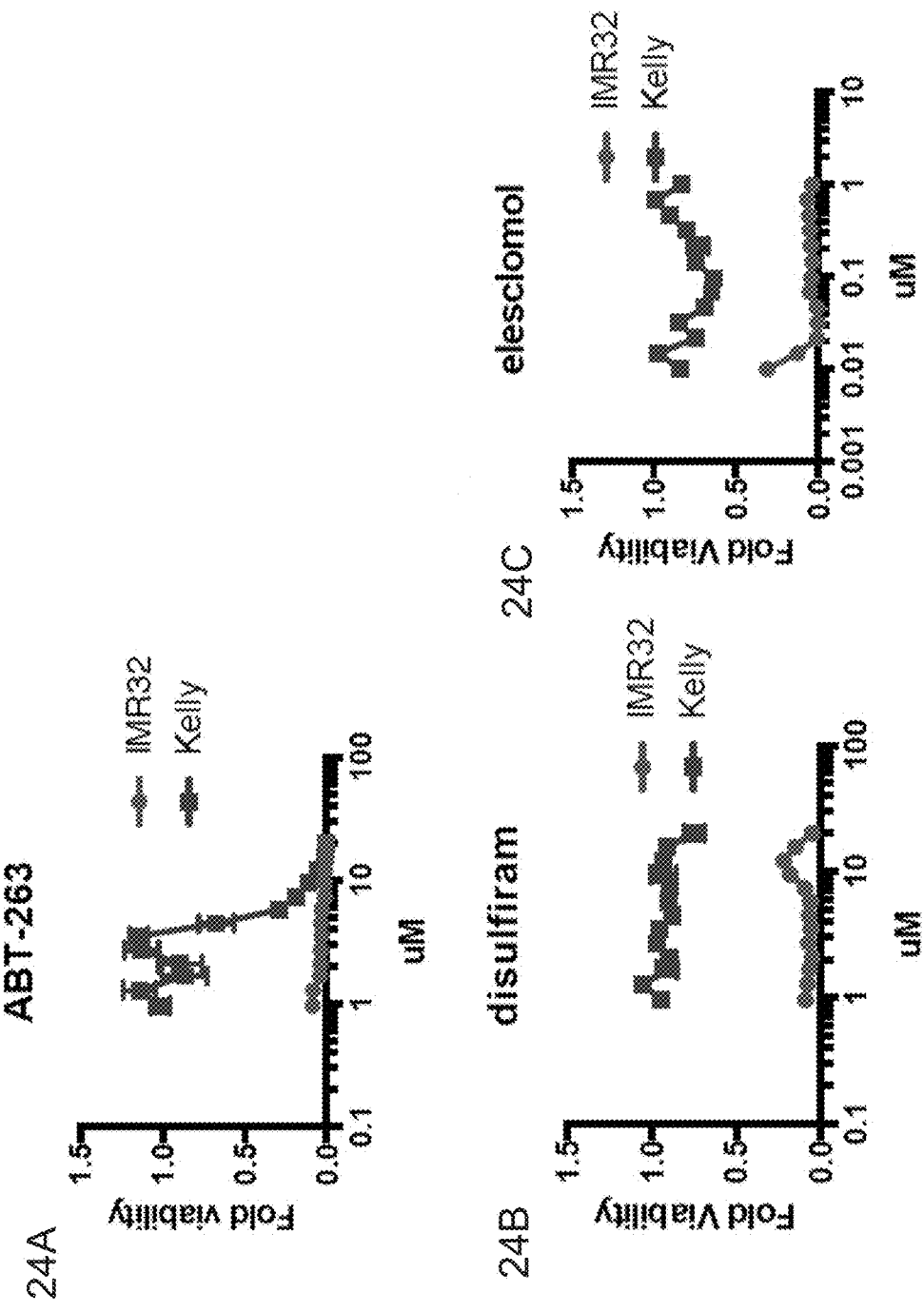
FIGS. 24A-24C.

Example 25: Reduced Expression of PSMD5 in Neuroblastoma Exposes New Vulnerabilities As described in Example 19, ABT-263, disulfiram, and elesclomol were identified in a screen as compounds that selectively inhibit growth of PSMD2 knockdown cells, a model system for proteasome inhibitor resistant cancers. To determine whether these compounds also differentially affect cells with reduced expression of PSDMS, IMR32 and Kelly cells were each cultured in the presence of ABT-263, disulfiram, or elesclomol across a range of concentrations. Cell viability was measured by CellTiter-Glo® Luminescent Cell Viability Assay 72 hours after addition of the compound to cells. The fold viability relative to culture in the absence of the compound was determined for each cell line. IMR32 cells were found to be dramatically more sensitive to each compound than were Kelly cells. (FIG. 24). In the experiment shown in FIG. 24, the lowest lower concentration of ABT-263 and disulfiram tested was 1 uM. In other experiments in which lower concentrations were tested (e.g., 0.1 uM) a similar level of toxicity was observed.

Figure 28:
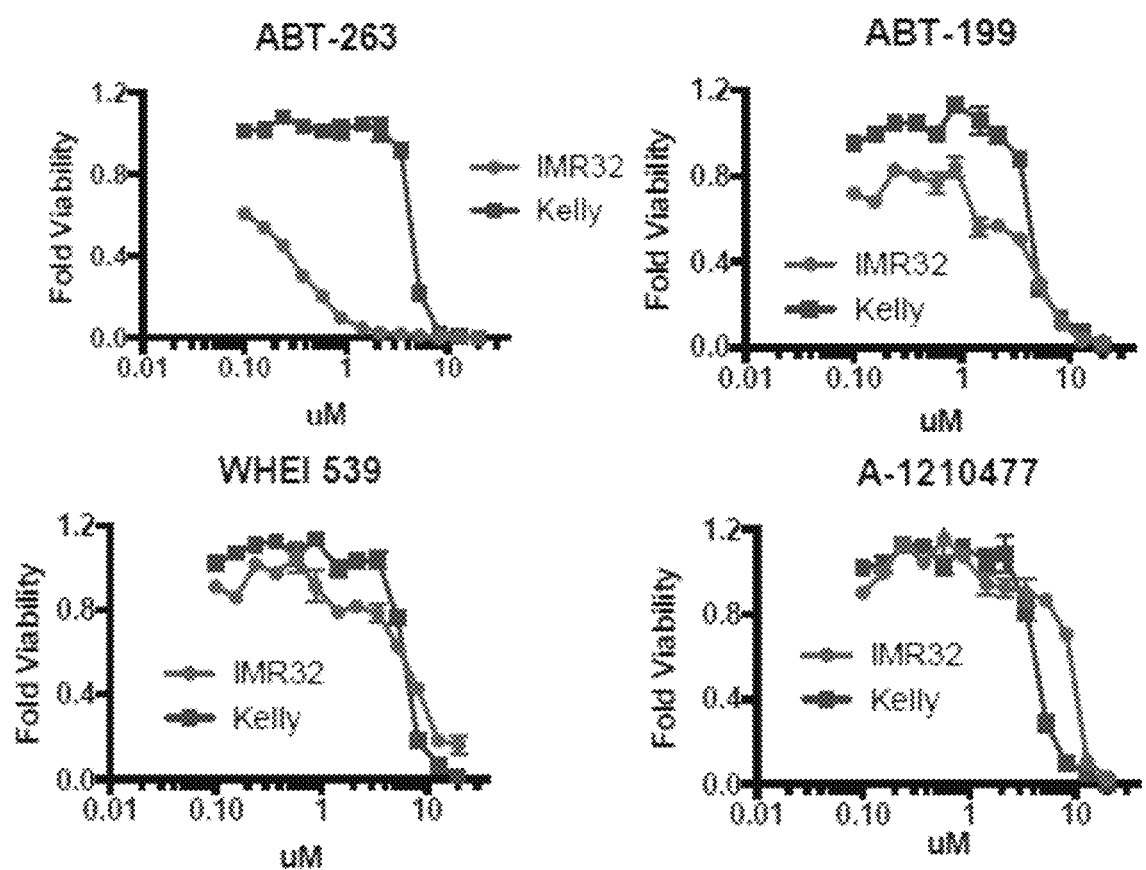
FIG. 28: The relative viability was examined in IMR32 cells and Kelly cells after addition of indicated concentrations of the different BCL2 family inhibitors. ABT-263 (BCL2, BCLXL, MCL1) (upper left panel), ABT-199 (BCL2) (upper right panel), WEHI-539 ($BCLX_L$) (lower left panel), A-1210477 (MCL1) (lower right panel). The relative effect on cell growth was analyzed 72 hours after addition of drugs.

ABT-263 targets several members of the BCL2 family, including BCL2 and BCL-XL. We characterized the sensitivities to more selective BCL2 family member inhibitors of IMR32 cells, that have PSMD5 epigenetically suppressed and the Kelly control cells. As predicted by our large scale chemical genetic analysis, the IMR32 cells were significantly more sensitive to ABT-263 than Kelly cells (FIG. 28, upper left panel). This preferential sensitivity was much greater for ABT-263 as compared with the more specific BCL2 (ABT-199), BCL-XL (WHEI 539) and MCL-1 (A-1210477) inhibitors.

Example 26: Effect of 19S Subunit Loss Alone on Sensitivity to ABT-263

Figures 29A, 29B:
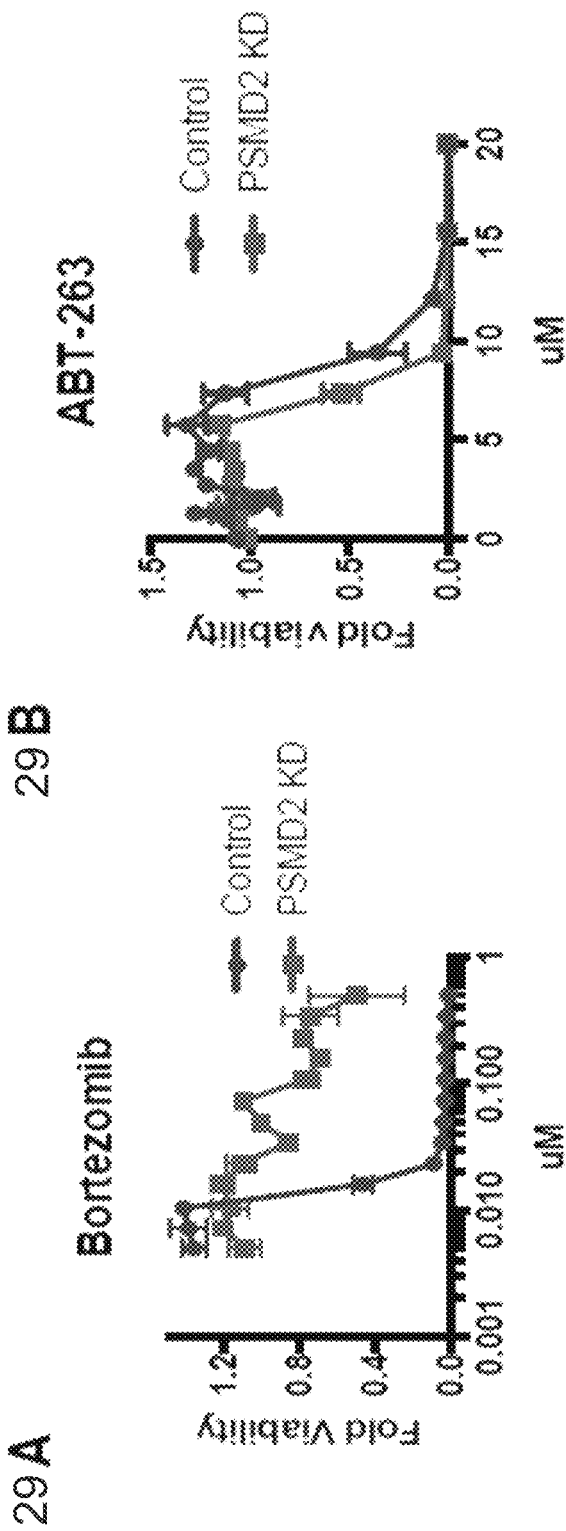
FIGS. 29A-29B: Plotted is the relative viability following bortezomib (FIG. 29A) or ABT-263 (FIG. 29B) treatment of control T47D cells and cells expressing shRNA targeting the PSMD2 subunit of the proteasome.
Figures 30A, 30B, 30C:
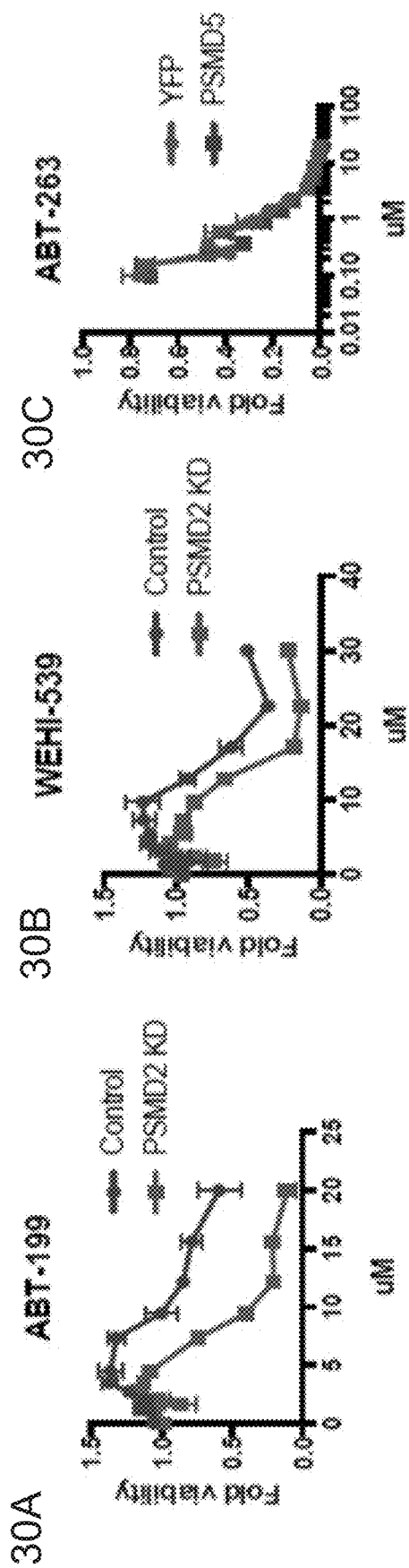
FIGS. 30A-30C.

To investigate whether 19S regulatory subunit loss is the driver of increased sensitivity to ABT-263, we examined the effect of BCL2 inhibitors in an engineered breast cancer cell line model (T47D) where reduced expression of a 19S subunit can be induced by doxycycline with a concomitant increase in resistance to proteasome inhibitors such as bortezomib (described above; also FIG. 29A). The suppression of 19S subunit PSMD2 was not sufficient, however, to induce a profound sensitization to ABT-263 (FIG. 29B) or to the other BCL2 family inhibitors (FIGS. 30A-30C). In IMR32 cells where the PSMD5 subunit is epigenetically suppressed, reintroduction of the PSMD5 subunit did not significantly alter ABT-263 sensitivity (FIG. 22C). These data suggest that the profound sensitivity to ABT-263 observed in the 19S proteasome 3-sigma cells may not be directly driven by the proteasome subunit unit loss.

REFERENCES

Adams, J., Palombella, V. J., and Elliott, P. J. (2000). Proteasome inhibition: a new strategy in cancer treatment. Investigational new drugs 18, 109-121.

Adler, J., Reuven, N., Kahana, C., and Shaul, Y. (2010). c-Fos proteasomal degradation is activated by a default mechanism, and its regulation by NAD(P)H:quinone oxidoreductase 1 determines c-Fos serum response kinetics. Molecular and cellular biology 30, 3767-3778.

Asano, S., Fukuda, Y., Beck, F., Aufderheide, A., Forster, F., Danev, R., and Baumeister, W. (2015). Proteasomes. A molecular census of 26S proteasomes in intact neurons. Science 347, 439-442.

Asher, G., Reuven, N., and Shaul, Y. (2006). 20S proteasomes and protein degradation "by default". BioEssays: news and reviews in molecular, cellular and developmental biology 28, 844-849.

Ayyadevara, S., Balasubramaniam, M., Gao, Y., Yu, L. R., Alla, R., and Shmookler Reis, R. (2015). Proteins in aggregates functionally impact multiple neurodegenerative disease models by forming proteasome-blocking complexes. Aging cell 14, 35-48.

Bajorek, M., Finley, D., and Glickman, M. H. (2003). Proteasome disassembly and downregulation is correlated with viability during stationary phase. Current biology: CB 13, 1140-1144.

Balch, W. E., Morimoto, R. I., Dillin, A., and Kelly, J. W. (2008). Adapting proteostasis for disease intervention. Science 319, 916-919.

Baugh, J. M., and Pilipenko, E. V. (2004). 20S proteasome differentially alters translation of different mRNAs via the cleavage of eIF4F and eIF3. Mol Cell 16, 575-586.

Baugh, J. M., Viktorova, E. G., and Pilipenko, E. V. (2009). Proteasomes can degrade a significant proportion of cellular proteins independent of ubiquitination. Journal of molecular biology 386, 814-827.

Ben-Nissan, G., and Sharon, M. (2014). Regulating the 20S proteasome ubiquitin-independent degradation pathway. Biomolecules 4, 862-884.

Besche, H. C., Peth, A., and Goldberg, A. L. (2009). Getting to first base in proteasome assembly. Cell 138, 25-28.

Breslow, D. K., Cameron, D. M., Collins, S. R., Schuldiner, M., Stewart-Ornstein, J., Newman, H. W., Braun, S., Madhani, H. D., Krogan, N. J., and Weissman, J. S. (2008). A comprehensive strategy enabling high-resolution functional analysis of the yeast genome. Nature methods 5, 711-718.

Carette, J. E., Guimaraes, C. P., Varadarajan, M., Park, A. S., Wuethrich, I., Godarova, A., Kotecki, M., Cochran, B. H., Spooner, E., Ploegh, H. L., et al. (2009). Haploid genetic screens in human cells identify host factors used by pathogens. Science 326, 1231-1235.

Carette, J. E., Guimaraes, C. P., Wuethrich, I., Blomen, V. A., Varadarajan, M., Sun, C., Bell, G., Yuan, B., Muellner, M. K., Nijman, S. M., et al. (2011a). Global gene disruption in human cells to assign genes to phenotypes by deep sequencing. Nature biotechnology 29, 542-546.

Carette, J. E., Pruszak, J., Varadarajan, M., Blomen, V. A., Gokhale, S., Camargo, F. D., Wernig, M., Jaenisch, R., and Brummelkamp, T. R. (2010). Generation of iPSCs from cultured human malignant cells. Blood 115, 4039-4042.

Carette, J. E., Raaben, M., Wong, A. C., Herbert, A. S., Obernosterer, G., Mulherkar, N., Kuehne, A. I., Kranzusch, P. J., Griffin, A. M., Ruthel, G., et al. (2011b). Ebola virus entry requires the cholesterol transporter Niemann-Pick C1. Nature 477, 340-343.

Chen, D., Frezza, M., Schmitt, S., Kanwar, J., and Dou, Q. P. (2011). Bortezomib as the first proteasome inhibitor anticancer drug: current status and future perspectives. Current cancer drug targets 11, 239-253.

Chen, S., Blank, J. L., Peters, T., Liu, X. J., Rappoli, D. M., Pickard, M. D., Menon, S., Yu, J., Driscoll, D. L., Lingaraj, T., et al. (2010). Genome-wide siRNA screen for modulators of cell death induced by proteasome inhibitor bortezomib. Cancer Res 70, 4318-4326.

Cho-Park, P. F., and Steller, H. (2013). Proteasome regulation by ADP-ribosylation. Cell 153, 614-627.

Crawford, L. J., and Irvine, A. E. (2013). Targeting the ubiquitin proteasome system in haematological malignancies. Blood reviews 27, 297-304.

Davoli, T., Xu, A. W., Mengwasser, K. E., Sack, L. M., Yoon, J. C., Park, P. J., and Elledge, S. J. (2013). Cumulative haploinsufficiency and triplosensitivity drive aneuploidy patterns and shape the cancer genome. Cell 155, 948-962.

Deriziotis, P., Andre, R., Smith, D. M., Goold, R., Kinghorn, K. J., Kristiansen, M., Nathan, J. A., Rosenzweig, R., Krutauz, D., Glickman, M. H., et al. (2011). Misfolded PrP impairs the UPS by interaction with the 20S proteasome and inhibition of substrate entry. The EMBO journal 30, 3065-3077.

Deshaies, R. J. (2014). Proteotoxic crisis, the ubiquitin-proteasome system, and cancer therapy. BMC biology 12, 94.

Eden, E., Navon, R., Steinfeld, I., Lipson, D., and Yakhini, Z. (2009). GOrilla: a tool for discovery and visualization of enriched GO terms in ranked gene lists. BMC bioinformatics 10, 48.

Elling, U., Taubenschmid, J., Wirnsberger, G., O'Malley, R., Demers, S. P., Vanhaelen, Q., Shukalyuk, A. I., Schmauss, G., Schramek, D., Schnuetgen, F., et al. (2011). Forward and reverse genetics through derivation of haploid mouse embryonic stem cells. Cell stem cell 9, 563-574.

Essletzbichler, P., Konopka, T., Santoro, F., Chen, D., Gapp, B. V., Kralovics, R., Brummelkamp, T. R., Nijman, S. M., and Burckstummer, T. (2014). Megabase-scale deletion using CRISPR/Cas9 to generate a fully haploid human cell line. Genome research 24, 2059-2065.

Finley, D. (2009). Recognition and processing of ubiquitin-protein conjugates by the proteasome. Annual review of biochemistry 78, 477-513.

Fuge, E. K., Braun, E. L., and Werner-Washburne, M. (1994). Protein synthesis in long-term stationary-phase cultures of Saccharomyces cerevisiae. Journal of bacteriology 176, 5802-5813.

Garnett, M. J., Edelman, E. J., Heidorn, S. J., Greenman, C. D., Dastur, A., Lau, K. W., Greninger, P., Thompson, I. R., Luo, X., Soares, J., et al. (2012). Systematic identification of genomic markers of drug sensitivity in cancer cells. Nature 483, 570-575.

Gidalevitz, T., Prahlad, V., and Morimoto, R. I. (2011). The stress of protein misfolding: from single cells to multicellular organisms. Cold Spring Harbor perspectives in biology 3.

Glickman, M. S., and Sawyers, C. L. (2012). Converting cancer therapies into cures: lessons from infectious diseases. Cell 148, 1089-1098.

Goldberg, A. L. (2012). Development of proteasome inhibitors as research tools and cancer drugs. The Journal of cell biology 199, 583-588.

Grune, T., Merker, K., Sandig, G., and Davies, K. J. (2003). Selective degradation of oxidatively modified protein substrates by the proteasome. Biochemical and biophysical research communications 305, 709-718.

Guimaraes, C. P., Carette, J. E., Varadarajan, M., Antos, J., Popp, M. W., Spooner, E., Brummelkamp, T. R., and Ploegh, H. L. (2011). Identification of host cell factors required for intoxication through use of modified cholera toxin. The Journal of cell biology 195, 751-764.

Hilt, W., and Wolf, D. H. (1995). Proteasomes of the yeast *S. cerevisiae*: genes, structure and functions. Molecular biology reports 21, 3-10.

Hochstrasser, M. (1996). Ubiquitin-dependent protein degradation. Annu Rev Genet 30, 405-439.

Holcik, M., and Sonenberg, N. (2005). Translational control in stress and apoptosis. Nature reviews Molecular cell biology 6, 318-327.

Jansen, R., Greenbaum, D., and Gerstein, M. (2002). Relating whole-genome expression data with protein-protein interactions. Genome research 12, 37-46.

Jariel-Encontre, I., Bossis, G., and Piechaczyk, M. (2008). Ubiquitin-independent degradation of proteins by the proteasome. Biochimica et biophysica acta 1786, 153-177.

Kale, A. J., and Moore, B. S. (2012). Molecular mechanisms of acquired proteasome inhibitor resistance. Journal of medicinal chemistry 55, 10317-10327.

Kisselev, A. F., Callard, A., and Goldberg, A. L. (2006). Importance of the different proteolytic sites of the proteasome and the efficacy of inhibitors varies with the protein substrate. J Biol Chem 281, 8582-8590.

Kisselev, A. F., van der Linden, W. A., and Overkleeft, H. S. (2012). Proteasome inhibitors: an expanding army attacking a unique target. Chemistry & biology 19, 99-115.

Knoechel, B., Roderick, J. E., Williamson, K. E., Zhu, J., Lohr, J. G., Cotton, M. J., Gillespie, S. M., Fernandez, D., Ku, M., Wang, H., et al. (2014). An epigenetic mechanism of resistance to targeted therapy in T cell acute lymphoblastic leukemia. Nature genetics 46, 364-370.

Labbadia, J., and Morimoto, R. I. (2015). The Biology of Proteostasis in Aging and Disease. Annual review of biochemistry.

Li, H., Handsaker, B., Wysoker, A., Fennell, T., Ruan, J., Homer, N., Marth, G., Abecasis, G., Durbin, R., and Genome Project Data Processing, S. (2009). The Sequence Alignment/Map format and SAMtools. Bioinformatics 25, 2078-2079.

Liu, C., Apodaca, J., Davis, L. E., and Rao, H. (2007). Proteasome inhibition in wild-type yeast *Saccharomyces cerevisiae* cells. BioTechniques 42, 158, 160, 162.

Livnat-Levanon, N., Kevei, E., Kleifeld, O., Krutauz, D., Segref, A., Rinaldi, T., Erpapazoglou, Z., Cohen, M., Reis, N., Hoppe, T., et al. (2014). Reversible 26S proteasome disassembly upon mitochondrial stress. Cell reports 7, 1371-1380.

Matyskiela, M. E., Lander, G. C., and Martin, A. (2013). Conformational switching of the 26S proteasome enables substrate degradation. Nature structural & *molecular biology* 20, 781-788.

Meacham, C. E., and Morrison, S. J. (2013). Tumour heterogeneity and cancer cell plasticity. Nature 501, 328-337.

Mendillo, M. L., Santagata, S., Koeva, M., Bell, G. W., Hu, R., Tamimi, R. M., Fraenkel, E., Ince, T. A., Whitesell, L., and Lindquist, S. (2012). HSF1 drives a transcriptional program distinct from heat shock to support highly malignant human cancers. Cell 150, 549-562.

Nijhawan, D., Zack, T. I., Ren, Y., Strickland, M. R., Lamothe, R., Schumacher, S. E., Tsherniak, A., Besche, H. C., Rosenbluh, J., Shehata, S., et al. (2012). Cancer vulnerabilities unveiled by genomic loss. Cell 150, 842-854.

Parsell, D. A., Kowal, A. S., Singer, M. A., and Lindquist, S. (1994). Protein disaggregation mediated by heat-shock protein Hsp104. Nature 372, 475-478.

Petrocca, F., Altschuler, G., Tan, S. M., Mendillo, M. L., Yan, H., Jerry, D. J., Kung, A. L., Hide, W., Ince, T. A., and Lieberman, J. (2013). A genome-wide siRNA screen identifies proteasome addiction as a vulnerability of basal-like triple-negative breast cancer cells. Cancer Cell 24, 182-196.

Radhakrishnan, S. K., den Besten, W., and Deshaies, R. J. (2014). p 97-dependent retrotranslocation and proteolytic processing govern formation of active Nrf1 upon proteasome inhibition. eLife 3, e01856.

Radhakrishnan, S. K., Lee, C. S., Young, P., Beskow, A., Chan, J. Y., and Deshaies, R. J. (2010). Transcription factor Nrf1 mediates the proteasome recovery pathway after proteasome inhibition in mammalian cells. Mol Cell 38, 17-28.

Reiling, J. H., Clish, C. B., Carette, J. E., Varadaraj an, M., Brummelkamp, T. R., and Sabatini, D. M. (2011). A haploid genetic screen identifies the major facilitator domain containing 2A (MFSD2A) transporter as a key mediator in the response to tunicamycin. Proceedings of the National Academy of Sciences of the United States of America 108, 11756-11765.

Reinheckel, T., Sitte, N., Ullrich, O., Kuckelkorn, U., Davies, K. J., and Grune, T. (1998). Comparative resistance of the 20S and 26S proteasome to oxidative stress. The Biochemical journal 335 (Pt 3), 637-642.

Santagata, S., Mendillo, M. L., Tang, Y. C., Subramanian, A., Perley, C. C., Roche, S. P., Wong, B., Narayan, R., Kwon, H., Koeva, M., et al. (2013). Tight coordination of protein translation and HSF1 activation supports the anabolic malignant state. Science 341, 1238303.

Scherz-Shouval, R., Santagata, S., Mendillo, M. L., Sholl, L. M., Ben-Aharon, I., Beck, A. H., Dias-Santagata, D., Koeva, M., Stemmer, S. M., Whitesell, L., et al. (2014). The reprogramming of tumor stroma by HSF1 is a potent enabler of malignancy. Cell 158, 564-578.

Schneekloth, J. S., Jr., and Crews, C. M. (2011). Natural product inhibitors of the ubiquitin-proteasome pathway. Current drug targets 12, 1581-1594.

Sha, Z., and Goldberg, A. L. (2014). Proteasome-mediated processing of Nrf1 is essential for coordinate induction of all proteasome subunits and p 97. Current biology: CB 24, 1573-1583.

Shalgi, R., Hurt, J. A., Krykbaeva, I., Taipale, M., Lindquist, S., and Burge, C. B. (2013).

Widespread regulation of translation by elongation pausing in heat shock. Molecular cell 49, 439-452.

Sharma, S. V., Lee, D. Y., Li, B., Quinlan, M. P., Takahashi, F., Maheswaran, S., McDermott, U., Azizian, N., Zou, L., Fischbach, M. A., et al. (2010). A chromatin-mediated reversible drug-tolerant state in cancer cell subpopulations. Cell 141, 69-80.

Steffen, J., Seeger, M., Koch, A., and Kruger, E. (2010). Proteasomal degradation is transcriptionally controlled by TCF11 via an ERAD-dependent feedback loop. Mol Cell 40, 147-158.

Tai, H. C., Besche, H., Goldberg, A. L., and Schuman, E. M. (2010). Characterization of the Brain 26S Proteasome and its Interacting Proteins. Frontiers in molecular neuroscience 3.

Tomko, R. J., Jr., and Hochstrasser, M. (2013). Molecular architecture and assembly of the eukaryotic proteasome. Annual review of biochemistry 82, 415-445.

Trapnell, C., Roberts, A., Goff, L., Pertea, G., Kim, D., Kelley, D. R., Pimentel, H., Salzberg, S. L., Rinn, J. L., and Pachter, L. (2012). Differential gene and transcript expression analysis of RNA-seq experiments with TopHat and Cufflinks. Nature protocols 7, 562-578.

Tsvetkov, P., Myers, N., Eliav, R., Adamovich, Y., Hagai, T., Adler, J., Navon, A., and Shaul, Y. (2014). NADH binds and stabilizes the 26S proteasomes independent of ATP. J Biol Chem 289, 11272-11281.

Tsvetkov, P., Reuven, N., Prives, C., and Shaul, Y. (2009a). Susceptibility of p53 unstructured N terminus to 20 S proteasomal degradation programs the stress response. J Biol Chem 284, 26234-26242.

Tsvetkov, P., Reuven, N., and Shaul, Y. (2009b). The nanny model for IDPs. Nature chemical biology 5, 778-781.

Ullrich, O., Reinheckel, T., Sitte, N., Hass, R., Grune, T., and Davies, K. J. (1999). Poly-ADP ribose polymerase activates nuclear proteasome to degrade oxidatively damaged histones. Proceedings of the National Academy of Sciences of the United States of America 96, 6223-6228.

Varshaysky, A. (2012). Three decades of studies to understand the functions of the ubiquitin family. Methods in molecular biology 832, 1-11.

Vilchez, D., Boyer, L., Morantte, I., Lutz, M., Merkwirth, C., Joyce, D., Spencer, B., Page, L., Masliah, E., Berggren, W. T., et al. (2012). Increased proteasome activity in human embryonic stem cells is regulated by PSMD11. Nature 489, 304-308.

Wang, X., Yen, J., Kaiser, P., and Huang, L. (2010). Regulation of the 26S proteasome complex during oxidative stress. Science signaling 3, ra88.

Wiggins, C. M., Tsvetkov, P., Johnson, M., Joyce, C. L., Lamb, C. A., Bryant, N. J., Komander, D., Shaul, Y., and Cook, S. J. (2011). BIM(EL), an intrinsically disordered protein, is degraded by 20S proteasomes in the absence of poly-ubiquitylation. Journal of cell science 124, 969-977.

Winter, G. E., Radic, B., Mayor-Ruiz, C., Blomen, V. A., Trefzer, C., Kandasamy, R. K., Huber, K. V., Gridling, M., Chen, D., Klampfl, T., et al. (2014). The solute carrier SLC35F2 enables YM155-mediated DNA damage toxicity. *Nature chemical biology* 10, 768-773.

Zhao, J., Brault, J. J., Schild, A., Cao, P., Sandri, M., Schiaffino, S., Lecker, S. H., and Goldberg, A. L. (2007). Fox03 coordinately activates protein degradation by the autophagic/lysosomal and proteasomal pathways in atrophying muscle cells. Cell metabolism 6, 472-483.

Those skilled in the art will recognize, or be able to ascertain using no more than routine experimentation, many equivalents to the specific embodiments described herein. The scope of the present invention is not intended to be limited to the Description or the details set forth therein. Articles such as "a", "an" and "the" may mean one or more than one unless indicated to the contrary or otherwise evident from the context. Claims or descriptions that include "or" or "and/or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims (whether original or subsequently added claims) is introduced into another claim (whether original or subsequently added). For example, any claim that is dependent on another claim can be modified to include one or more element(s), feature(s), or limitation(s) found in any other claim, e.g., any other claim that is dependent on the same base claim. Any one or more claims can be modified to explicitly exclude any one or more embodiment(s), element(s), feature(s), etc. For example, any particular proteasome inhibitor, cancer type, 19S subunit, etc., can be excluded from any one or more claims.

It should be understood that (i) any method of classification, prediction, treatment selection, treatment, etc., can include a step of providing a sample, e.g., a sample obtained from a subject in need of classification, prediction, treatment selection, treatment, for cancer, e.g., a cancer sample obtained from the subject; (ii) any method of classification, prediction, treatment selection, treatment, etc., can include a step of providing a subject in need of such classification, prediction, treatment selection, treatment, or treatment for cancer.

Where the claims recite a method, certain aspects of the invention provide a product, e.g., a kit, agent, or composition, suitable for performing the method.

Where elements are presented as lists, e.g., in Markush group format, each subgroup of the elements is also disclosed, and any element(s) can be removed from the group. For purposes of conciseness only some of these embodiments have been specifically recited herein, but the present disclosure encompasses all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where phrases such as "less than X", "greater than X", or "at least X" is used (where X is a number or percentage), it should be understood that any reasonable value can be selected as the lower or upper limit of the range. It is also understood that where a list of numerical values is stated herein (whether or not prefaced by "at least"), the invention includes embodiments that relate to any intervening value or range defined by any two values in the list, and that the lowest value may be taken as a minimum and the greatest value may be taken as a maximum. Furthermore, where a list of numbers, e.g., percentages, is prefaced by "at least", the term applies to each number in the list. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments 5% or in some embodiments 10% of a number in either direction (greater than or less than the number) unless otherwise stated or otherwise evident from the context (e.g., where such number would impermissibly exceed 100% of a possible value).

It should be understood that, unless clearly indicated to the contrary, in any methods claimed herein that include more than one act, the order of the acts of the method is not necessarily limited to the order in which the acts of the method are recited, but the disclosure encompasses embodiments in which the order is so limited. In some embodiments a method may be performed by an individual or entity. In some embodiments steps of a method may be performed by two or more individuals or entities such that a method is collectively performed. In some embodiments a method may be performed at least in part by requesting or authorizing another individual or entity to perform one, more than one, or all steps of a method. In some embodiments a method comprises requesting two or more entities or individuals to each perform at least one step of a method. In some embodiments performance of two or more steps is coordinated so that a method is collectively performed. It should also be understood that unless otherwise indicated or evident from the context, any product or composition described herein may be considered "isolated". It should also be understood that, where applicable, unless otherwise indicated or evident from the context, any method or step of a method that may be amenable to being performed mentally or as a mental step or using a writing implement such as a pen or pencil, and a surface suitable for writing on, such as paper, may be expressly indicated as being performed at least in part, substantially, or entirely, by a machine, e.g., a computer, device (apparatus), or system, which may, in some embodiments, be specially adapted or designed to be capable of performing such method or step or a portion thereof.

Section headings used herein are not to be construed as limiting in any way. It is expressly contemplated that subject matter presented under any section heading may be applicable to any aspect or embodiment described herein.

Embodiments or aspects herein may be directed to any agent, composition, article, kit, and/or method described herein. It is contemplated that any one or more embodiments or aspects can be freely combined with any one or more other embodiments or aspects whenever appropriate. For example, any combination of two or more agents, compositions, articles, kits, and/or methods that are not mutually inconsistent, is provided. It will be understood that any description or exemplification of a term anywhere herein may be applied wherever such term appears herein (e.g., in any aspect or embodiment in which such term is relevant) unless indicated or clearly evident otherwise.

TABLE S1

| screen name | gene | inactivating insertions in this gene in this screen | inactivating insertions in other genes in this screen | insertions in control dataset in this gene | insertions in control dataset in all other genes | p-value Fischer exact test | p-value Fischer exact test corrected for FDR |
|---|---|---|---|---|---|---|---|
| mg132 | PSMD12 | 35 | 957 | 6 | 413488 | 4.46E-86 | 2.94E-83 |
| mg132 | PSMC5 | 31 | 961 | 3 | 413491 | 2.08E-78 | 6.86E-76 |
| mg132 | PSMD7 | 26 | 966 | 3 | 413491 | 1.87E-65 | 4.10E-63 |
| mg132 | PSMD2 | 21 | 971 | 3 | 413491 | 1.48E-52 | 2.44E-50 |
| mg132 | PSMC3 | 21 | 971 | 8 | 413486 | 3.10E-49 | 4.09E-47 |
| mg132 | PSMC6 | 18 | 974 | 3 | 413491 | 7.51E-45 | 8.26E-43 |
| mg132 | PSMC4 | 7 | 985 | 2 | 413492 | 1.58E-17 | 1.49E-15 |
| mg132 | PSMC2 | 4 | 988 | 4 | 413490 | 2.27E-09 | 1.66E-07 |
| mg132 | PSMD6 | 4 | 988 | 4 | 413490 | 2.27E-09 | 1.66E-07 |
| mg132 | ZNF366 | 3 | 989 | 10 | 413484 | 3.84E-06 | 0.000253413 |
| mg132 | EXOSC10 | 3 | 989 | 11 | 413483 | 4.88E-06 | 0.000292681 |
| mg132 | TPH1 | 2 | 990 | 1 | 413493 | 1.71E-05 | 0.000942667 |
| mg132 | ESAM | 2 | 990 | 3 | 413491 | 5.69E-05 | 0.002891288 |
| mg132 | NR6A1 | 5 | 987 | 218 | 413276 | 0.000222055 | 0.010468304 |
| mg132 | C11orf83 | 2 | 990 | 8 | 413486 | 0.000254241 | 0.01118662 |
| mg132 | CDH8 | 2 | 990 | 10 | 413484 | 0.000371703 | 0.015332739 |
| mg132 | PSMD1 | 2 | 990 | 13 | 413481 | 0.000588531 | 0.022848852 |
| mg132 | PAQR5 | 2 | 990 | 16 | 413478 | 0.000853495 | 0.031294816 |
| mg132 | USP12 | 2 | 990 | 19 | 413475 | 0.001165895 | 0.040499521 |
| mg132 | ENOPH1 | 2 | 990 | 20 | 413474 | 0.00128045 | 0.042254862 |
| mg132 | TM9SF2 | 2 | 990 | 23 | 413471 | 0.001655024 | 0.05201505 |
| mg132 | BHLHE40 | 2 | 990 | 24 | 413470 | 0.001790101 | 0.053703032 |
| mg132 | C14orf156 | 2 | 990 | 25 | 413469 | 0.001930245 | 0.055389648 |
| mg132 | C9orf24 | 1 | 991 | 0 | 413494 | 0.002393326 | 0.056321144 |
| mg132 | IL16 | 5 | 987 | 378 | 413116 | 0.002474717 | 0.056321144 |
| mg132 | HS3ST4 | 1 | 991 | 0 | 413494 | 0.002393326 | 0.056321144 |
| mg132 | MIR886 | 1 | 991 | 0 | 413494 | 0.002393326 | 0.056321144 |
| mg132 | FLNB | 3 | 989 | 103 | 413391 | 0.002195004 | 0.056321144 |
| mg132 | MIRLET7I | 1 | 991 | 0 | 413494 | 0.002393326 | 0.056321144 |
| mg132 | MYB | 3 | 989 | 109 | 413385 | 0.002565856 | 0.056448824 |
| velcade | PSMC6 | 12 | 526 | 3 | 413491 | 9.29E-33 | 3.78E-30 |
| velcade | PSMD2 | 9 | 529 | 3 | 413491 | 2.17E-24 | 4.41E-22 |
| velcade | PSMD7 | 6 | 532 | 3 | 413491 | 3.92E-16 | 5.32E-14 |
| velcade | PSMC5 | 3 | 535 | 3 | 413491 | 4.35E-08 | 4.43E-06 |
| velcade | ATIC | 3 | 535 | 11 | 413483 | 7.86E-07 | 5.74E-05 |
| velcade | NPRL3 | 4 | 534 | 50 | 413444 | 8.47E-07 | 5.74E-05 |
| velcade | DHRS4L1 | 2 | 536 | 0 | 413494 | 1.69E-06 | 9.80E-05 |
| velcade | PSMC4 | 2 | 536 | 2 | 413492 | 1.01E-05 | 0.00051357 |
| velcade | PSMD12 | 2 | 536 | 6 | 413488 | 4.69E-05 | 0.002123 |
| velcade | PSMC3 | 2 | 536 | 8 | 413486 | 7.53E-05 | 0.00306548 |
| velcade | LTB4R | 2 | 536 | 14 | 413480 | 0.00019981 | 0.00715838 |
| velcade | SFRS2B | 2 | 536 | 15 | 413479 | 0.00022626 | 0.00715838 |
| velcade | WT1 | 6 | 532 | 644 | 412850 | 0.00023682 | 0.00715838 |
| velcade | ETV6 | 7 | 531 | 920 | 412574 | 0.00024623 | 0.00715838 |
| velcade | WIPF1 | 5 | 533 | 423 | 413071 | 0.00027074 | 0.00734619 |
| velcade | NBN | 3 | 535 | 94 | 413400 | 0.00029375 | 0.00747216 |
| velcade | CCDC140 | 2 | 536 | 19 | 413475 | 0.00034817 | 0.00787251 |
| velcade | TYMP | 2 | 536 | 19 | 413475 | 0.00034817 | 0.00787251 |
| velcade | C2orf42 | 2 | 536 | 20 | 413474 | 0.00038266 | 0.00819692 |
| velcade | PTPRO | 2 | 536 | 21 | 413473 | 0.00041874 | 0.00852135 |
| velcade | TM9SF2 | 2 | 536 | 23 | 413471 | 0.00049567 | 0.00960664 |
| velcade | CCNB1IP1 | 2 | 536 | 30 | 413464 | 0.00081459 | 0.01469268 |
| velcade | INTS6 | 2 | 536 | 31 | 413463 | 0.0008664 | 0.01469268 |
| velcade | OSBPL8 | 2 | 536 | 31 | 413463 | 0.0008664 | 0.01469268 |

TABLE S1-continued

| screen name | gene | inactivating insertions in this gene in this screen | inactivating insertions in other genes in this screen | insertions in control dataset in this gene | insertions in control dataset in all other genes | p-value Fischer exact test | p-value Fischer exact test corrected for FDR |
|---|---|---|---|---|---|---|---|
| velcade | CAMSAP1 | 2 | 536 | 33 | 413461 | 0.00097466 | 0.01586747 |
| velcade | PRTG | 2 | 536 | 37 | 413457 | 0.00120965 | 0.01599648 |
| velcade | ZNF114 | 2 | 536 | 38 | 413456 | 0.00127222 | 0.01599648 |
| velcade | C1orf226 | 1 | 537 | 0 | 413494 | 0.00129942 | 0.01599648 |
| velcade | DDX41 | 1 | 537 | 0 | 413494 | 0.00129942 | 0.01599648 |
| velcade | MMP24 | 1 | 537 | 0 | 413494 | 0.00129942 | 0.01599648 |

TABLE S2

| Clone ID | Vector | RefSeq (or transcript name) | Symbol | Region | Target Seq |
|---|---|---|---|---|---|
| TRCN0000298162 | pLKO_TRC005 | NM_002809.2 | PSMD3 | CDS | CCATGAGGTTTCCTCCCAAAT (SEQ ID NO. 21) |
| TRCN0000231782 | pLKO_TRC021 | | | | |
| TRCN0000058118 | pLKO.1 | NM_002809.2 | PSMD3 | CDS | GCAGGGCTTCTTCACTTCAAA (SEQ ID NO. 22) |
| TRCN0000293570 | pLKO_TRC005 | NM_002809.2 | PSMD3 | 3UTR | TTTCCCACACACAGCTCATAT (SEQ ID NO. 23) |
| TRCN0000058121 | pLKO.1 | NM_002809.2 | PSMD3 | CDS | GCCGCAAAGTGTTACTATTAT (SEQ ID NO. 24) |
| TRCN0000072256 | pLKO.1 | promegaLuc.1 | LUCIFERASE | CDS | ACGCTGAGTACTTCGAAATGT (SEQ ID NO. 25) |
| TRCN0000330282 | pLKO_TRC005 | NM_002817.3 | PSMD13 | CDS | CTATGATCTCTCCAGTAAATA (SEQ ID NO. 26) |
| TRCN0000330284 | pLKO_TRC005 | NM_002817.3 | PSMD13 | CDS | GACACTTCAGGTGCTTGATTT (SEQ ID NO. 27) |
| TRCN0000330283 | pLKO_TRC005 | NM_002817.3 | PSMD13 | CDS | AGATGGTCTCATTAAGCTTTA (SEQ ID NO. 28) |
| TRCN0000330217 | pLKO_TRC005 | NM_002817.3 | PSMD13 | 3UTR | CAGACGGTCGACATTGAATTT (SEQ ID NO. 29) |
| TRCN0000208001 | pLKO.1 | | | | |
| TRCN0000072250 | pLKO.1 | promegaLuc.1 | LUCIFERASE | CDS | AGAATCGTCGTATGCAGTGAA (SEQ ID NO. 30) |
| TRCN0000072199 | pLKO.1 | clonetechGfp.1 | GFP | CDS | TGACCCTGAAGTTCATCTGCA (SEQ ID NO. 31) |
| TRCN0000296469 | pLKO_TRC005 | NM_002811.3 | PSMD7 | CDS | GCTCAGTGTGGTGGATCATTT (SEQ ID NO. 32) |
| TRCN0000290012 | pLKO_TRC005 | NM_002811.3 | PSMD7 | CDS | GCCATCAACGAACTCATGAAA (SEQ ID NO. 33) |
| TRCN0000307155 | pLKO_TRC005 | NM_002811.3 | PSMD7 | CDS | GCTGAGGAAGTTGGAGTTGAA (SEQ ID NO. 34) |
| TRCN0000072242 | pLKO.1 | lacZ.1 | lacZ | CDS | GTCGGCTTACGGCGGTGATTT (SEQ ID NO. 35) |
| TRCN0000296468 | pLKO_TRC005 | NM_002811.3 | PSMD7 | CDS | ATTCCGTATTGGTCATCATTG (SEQ ID NO. 36) |
| TRCN0000003950 | pLKO.1 | NM_002815.2 | PSMD11 | CDS | CCGACGTGGAAAGGAAATTAT (SEQ ID NO. 37) |
| TRCN0000272509 | pLKO_TRC005 | NM_002815.2 | PSMD11 | CDS | GGACATGCAGTCGGGTATTAT (SEQ ID NO. 38) |
| TRCN0000272450 | pLKO_TRC005 | NM_002815.2 | PSMD11 | CDS | CTGGTGTCTTTGTACTTTGAT (SEQ ID NO. 39) |
| TRCN0000272451 | pLKO_TRC005 | NM_002815.2 | PSMD11 | 3UTR | CCTCATTTGGTGCATCTGTAT (SEQ ID NO. 40) |
| TRCN0000286432 | pLKO_TRC005 | NM_007002.2 | ADRM1 | CDS | AGTCAACGAGTATCTGAACAA (SEQ ID NO. 41) |
| TRCN0000293817 | pLKO_TRC005 | NM_007002.2 | ADRM1 | CDS | CAGACGGACGACTCGCTTATT (SEQ ID NO. 42) |
| TRCN0000298206 | pLKO_TRC005 | NM_007002.2 | ADRM1 | CDS | CCCTGACGACTGTGAGTTCAA (SEQ ID NO. 43) |
| TRCN0000115942 | pLKO.1 | NM_007002.2 | ADRM1 | CDS | TGCCGGAAAGTCAACGAGTAT (SEQ ID NO. 44) |
| TRCN0000297976 | pLKO_TRC005 | NM_014814.1 | PSMD6 | CDS | GACAGCCTTTCGCAAGACATA (SEQ ID NO. 45) |
| TRCN0000143904 | pLKO.1 | NM_014814.1 | PSMD6 | CDS | CAGGAACTGTCCAGGTTTATT (SEQ ID NO. 46) |
| TRCN0000142957 | pLKO.1 | NM_014814.1 | PSMD6 | CDS | CTTGAAGTGTTGCACAGTCTT (SEQ ID NO. 47) |
| TRCN0000144555 | pLKO.1 | NM_014814.1 | PSMD6 | CDS | GCAGTACCAAGAAACTATCAA (SEQ ID NO. 48) |

TABLE S2-continued

| Clone ID | Vector | RefSeq (or transcript name) | Symbol | Region | Target Seq |
|---|---|---|---|---|---|
| TRCN0000293628 | pLKO_TRC005 | NM_174871.2 | PSMD12 | CDS | TATCGACATCCCGTATCTTAG (SEQ ID NO. 49) |
| TRCN0000286174 | pLKO_TRC005 | NM_174871.2 | PSMD12 | CDS | GTAGACAGATTAGCAGGAATT (SEQ ID NO. 50) |
| TRCN0000293629 | pLKO_TRC005 | NM_174871.2 | PSMD12 | 3UTR | GACTGTTATAATGGTGTATAT (SEQ ID NO. 51) |
| TRCN0000058059 | pLKO.1 | NM_174871.1 | PSMD12 | CDS | CCTTCCTATCAAACTTCGATT (SEQ ID NO. 52) |
| TRCN0000058100 | pLKO.1 | NM_002812.3 | PSMD8 | CDS | GCCAAACAGGTCATCGAGTAT (SEQ ID NO. 53) |
| TRCN0000058099 | pLKO.1 | NM_002812.3 | PSMD8 | CDS | GCTGACCAAACAGCAGCTAAT (SEQ ID NO. 54) |
| TRCN0000058102 | pLKO.1 | NM_002812.3 | PSMD8 | CDS | GATGACAGACTACGCCAAGAA (SEQ ID NO. 55) |
| TRCN0000058101 | pLKO.1 | NM_002812.3 | PSMD8 | CDS | CCCAGCTCAAATGCTACTACT (SEQ ID NO. 56) |
| TRCN0000050601 | pLKO.1 | NM_002806.2 | PSMC6 | CDS | GCTGGAGTCTAAATTGGACTA (SEQ ID NO. 57) |
| TRCN0000299493 | pLKO_TRC005 | NM_002806.3 | PSMC6 | CDS | CATTGGTGAAAGTGCTCGTTT (SEQ ID NO. 58) |
| TRCN0000299492 | pLKO_TRC005 | NM_002806.3 | PSMC6 | CDS | CCTCTTACAAACCCAGAGTTA (SEQ ID NO. 59) |
| TRCN0000050599 | pLKO.1 | NM_002806.2 | PSMC6 | CDS | CCCATTACAAAGCATGGTGAA (SEQ ID NO. 60) |
| TRCN0000352618 | pLKO_TRC005 | NM_002797.3 | PSMB5 | CDS | CCAGACGGTGAAGAAGGTGAT (SEQ ID NO. 61) |
| TRCN0000003916 | pLKO.1 | NM_002797.2 | PSMB5 | CDS | TCTGGCTCTGTGTATGCATAT (SEQ ID NO. 62) |
| TRCN0000003917 | pLKO.1 | NM_002797.2 | PSMB5 | CDS | CGAAATAAGGAACGCATCTCT (SEQ ID NO. 63) |
| TRCN0000003919 | pLKO.1 | NM_002797.2 | PSMB5 | CDS | CAATGTCGAATCTATGAGCTT (SEQ ID NO. 64) |
| TRCN0000279799 | pLKO_TRC005 | NM_002788.2 | PSMA3 | CDS | CAAGCTGCAAAGACGGAAATA (SEQ ID NO. 65) |
| TRCN0000003882 | pLKO.1 | NM_002788.2 | PSMA3 | CDS | AGAAATGACCTGCCGTGATAT (SEQ ID NO. 66) |
| TRCN0000279800 | pLKO_TRC005 | NM_002788.2 | PSMA3 | CDS | CATCAGGTGTTTCATACGGTT (SEQ ID NO. 67) |
| TRCN0000003883 | pLKO.1 | NM_002788.2 | PSMA3 | CDS | GTACATGACGAAGTTAAGGAT (SEQ ID NO. 68) |
| TRCN0000072194 | pLKO.1 | clonetechGfp.1 | GFP | CDS | CCACATGAAGCAGCACGACTT (SEQ ID NO. 69) |
| TRCN0000058116 | pLKO.1 | NM_005047.2 | PSMD5 | CDS | GCTGTCATGGATAGTCCTCAA (SEQ ID NO. 70) |
| TRCN0000290086 | pLKO_TRC005 | NM_005047.2 | PSMD5 | CDS | CCATACTATGTGAAACCTGTT (SEQ ID NO. 71) |
| TRCN0000290087 | pLKO_TRC005 | NM_005047.2 | PSMD5 | CDS | CCCTGCTTAACGAGAACCATA (SEQ ID NO. 72) |
| TRCN0000058113 | pLKO.1 | NM_005047.2 | PSMD5 | CDS | CCCTGTCAAGAATATCACTAA (SEQ ID NO. 73) |
| TRCN0000072181 | pLKO.1 | clonetechGfp.1 | GFP | CDS | ACAACAGCCACAACGTCTATA (SEQ ID NO. 74) |
| TRCN0000273124 | pLKO_TRC005 | NM_005805.3 | PSMD14 | CDS | CAGATTGATCAATGCTAATAT (SEQ ID NO. 75) |
| TRCN0000273126 | pLKO_TRC005 | NM_005805.3 | PSMD14 | CDS | ACAGCAGAACAAGTCTATATC (SEQ ID NO. 76) |
| TRCN0000006457 | pLKO.1 | NM_005805.1 | PSMD14 | CDS | CATGGACTAAACAGACATTAT (SEQ ID NO. 77) |
| TRCN0000006456 | pLKO.1 | NM_005805.1 | PSMD14 | CDS | CAAGCCATCTATCCAGGCATT (SEQ ID NO. 78) |
| TRCN0000003945 | pLKO.1 | NM_002813.4 | PSMD9 | CDS | GCGGGTCTGCAAGTGGATGAT (SEQ ID NO. 79) |
| TRCN0000003942 | pLKO.1 | NM_002813.4 | PSMD9 | CDS | GCGCAGATCAAGGCCAACTAT (SEQ ID NO. 80) |
| TRCN0000369096 | pLKO_TRC005 | NM_002813.4 | PSMD9 | 3UTR | AGGTACTGGTGTGATTATTAT (SEQ ID NO. 81) |
| TRCN0000003941 | pLKO.1 | NM_002813.4 | PSMD9 | CDS | ACCAGCTTAGACTTGTTCCAA (SEQ ID NO. 82) |
| TRCN0000290093 | pLKO_TRC005 | NM_002808.3 | PSMD2 | CDS | GAGGATAAACAGCTTCAAGAT (SEQ ID NO. 83) |
| TRCN0000290022 | pLKO_TRC005 | NM_002808.3 | PSMD2 | CDS | CCACATTTGTAGCGAACACTT (SEQ ID NO. 84) |
| TRCN0000058089 | pLKO.1 | NM_002808.3 | PSMD2 | CDS | GCTGGCTCAAATCGTGAAGAT (SEQ ID NO. 85) |
| TRCN0000290023 | pLKO_TRC005 | NM_002808.3 | PSMD2 | CDS | CGAAACATTATTCTAGGCAAA (SEQ ID NO. 86) |
| TRCN0000020232 | pLKO.1 | NM_002804.3 | PSMC3 | CDS | CACGGAGCAATACAGTGACAT (SEQ ID NO. 87) |

TABLE S2-continued

| Clone ID | Vector | RefSeq (or transcript name) | Symbol | Region | Target Seq |
|---|---|---|---|---|---|
| TRCN0000278219 | pLKO_TRC005 | NM_002804.4 | PSMC3 | CDS | GTGCAGATGTTCATTGGAGAT (SEQ ID NO. 88) |
| TRCN0000020231 | pLKO.1 | NM_002804.3 | PSMC3 | CDS | CCAGCCCAACACCCAAGTTAA (SEQ ID NO. 89) |
| TRCN0000072209 | pLKO.1 | rfp.1 | RFP | CDS | CTCAGTTCCAGTACGGCTCCA (SEQ ID NO. 90) |
| TRCN0000020233 | pLKO.1 | NM_002804.3 | PSMC3 | CDS | GCTCCTGGATGTTGATCCTAA (SEQ ID NO. 91) |
| TRCN0000020259 | pLKO.1 | NM_002805.4 | PSMC5 | CDS | GCACAGAGGAACGAACTAAAT (SEQ ID NO. 92) |
| TRCN0000072240 | pLKO.1 | lacZ.1 | lacZ | CDS | TCGTATTACAACGTCGTGACT (SEQ ID NO. 93) |
| TRCN0000020261 | pLKO.1 | NM_002805.4 | PSMC5 | CDS | GAAGATTCATTCTCGGAAGAT (SEQ ID NO. 94) |
| TRCN0000352809 | pLKO_TRC005 | NM_002805.4 | PSMC5 | CDS | CAAGGTTATCATGGCTACTAA (SEQ ID NO. 95) |
| TRCN0000072236 | pLKO.1 | lacZ.1 | lacZ | CDS | CCAACGTGACCTATCCCATTA (SEQ ID NO. 96) |
| TRCN0000020263 | pLKO.1 | NM_002805.4 | PSMC5 | CDS | TGCTCCATCTATCATCTTCAT (SEQ ID NO. 97) |
| TRCN0000003928 | pLKO.1 | NM_002799.2 | PSMB7 | 3UTR | GAGCATTGAGGCCCAGTAAGA (SEQ ID NO. 98) |
| TRCN0000003927 | pLKO.1 | NM_002799.2 | PSMB7 | CDS | ACATTGGTGCAGCCCTAGTTT (SEQ ID NO. 99) |
| TRCN0000010831 | pLKO.1 | NM_002799.2 | PSMB7 | CDS | GAGATTGAGGTGCTGGAAGAA (SEQ ID NO. 100) |
| TRCN0000315140 | pLKO_TRC005 | NM_002799.2 | PSMB7 | CDS | TGCCGTCTTGGAAGCCGATTT (SEQ ID NO. 101) |
| TRCN0000003940 | pLKO.1 | NM_002810.1 | PSMD4 | 3UTR | GCACGGAATATAGGGTTAGAT (SEQ ID NO. 102) |
| TRCN0000273213 | pLKO_TRC005 | NM_002810.2 | PSMD4 | CDS | ACAATGAAGCCATTCGAAATG (SEQ ID NO. 103) |
| TRCN0000273214 | pLKO_TRC005 | NM_002810.2 | PSMD4 | CDS | CTCTCATCAGTTCTCCGATTT (SEQ ID NO. 104) |
| TRCN0000273215 | pLKO_TRC005 | NM_002810.2 | PSMD4 | CDS | GTGGACAACAGTGAGTATATG (SEQ ID NO. 105) |
| TRCN0000296520 | pLKO_TRC005 | NM_002814.2 | PSMD10 | 3UTR | GTTCTACTGTTGTCGTATATT (SEQ ID NO. 106) |
| TRCN0000058077 | pLKO.1 | NM_002814.2 | PSMD10 | CDS | GAAGAGTTGAAGGAGAGTATT (SEQ ID NO. 107) |
| TRCN0000072261 | pLKO.1 | promegaLuc.1 | LUCIFERASE | CDS | CACTCGGATATTTGATATGTG (SEQ ID NO. 108) |
| TRCN0000058074 | pLKO.1 | NM_002814.2 | PSMD10 | CDS | GCTCAAGTGAATGCTGTCAAT (SEQ ID NO. 109) |
| TRCN0000058075 | pLKO.1 | NM_002814.2 | PSMD10 | CDS | CAAGGGTAACTTGAAGATGAT (SEQ ID NO. 110) |
| TRCN0000231782 | pLKO_TRC021 | | | | |
| TRCN0000231782 | pLKO_TRC021 | | | | |

TABLE S4

| Cell Line | BORT_IC 50 (Garnett data) | MG132_IC 50 (Garnett Data) | PSMC/D AVG | PSMA/B AVG |
|---|---|---|---|---|
| NCI-H1838 | 1.4318 | 5.6038 | 3.585384762 | 5.768514615 |
| IMR-5 | 1.2266 | 5.2016 | 3.577392381 | 5.572021538 |
| U-698-M | 0.81632 | 4.2278 | 3.826039524 | 5.908106154 |
| COLO-824 | 0.23253 | 2.6946 | 3.393027619 | 5.089173077 |
| P31-FUJ | 0.10683 | 3.0192 | 3.695917143 | 5.714136923 |
| KY821 | 0.035408 | 4.518 | 3.665073333 | 5.792536154 |
| RPMI-8866 | 0.006257 | 4.3142 | 3.54315381 | 5.672605385 |
| TC-YIK | −0.24716 | 3.9127 | 3.865313333 | 5.913443846 |
| MS-1 | −0.2752 | 5.477 | 3.59844381 | 5.554299231 |
| DMS-153 | −0.29191 | 4.8019 | 3.285638095 | 5.384613846 |
| SUP-T1 | −0.37682 | 4.9678 | 3.785947143 | 5.674859231 |
| SCC-15 | −0.40426 | 4.2814 | 4.357602381 | 6.186963846 |
| MSTO-211H | −0.55467 | 2.6909 | 4.192721429 | 5.843266923 |
| J-RT3-T3-5 | −0.63004 | 2.9656 | 3.52385381 | 5.588938462 |
| NCI-H889 | −0.77237 | 4.6467 | 3.307012381 | 5.215093077 |
| CPC-N | −0.9069 | 3.1789 | 3.392865714 | 5.269090769 |
| COLO-668 | −0.90741 | 4.4017 | 3.645751905 | 5.558027692 |
| NCI-H226 | −0.90824 | 5.241 | 4.456798571 | 6.39164 |

TABLE S4-continued

| Cell Line | BORT_IC 50 (Garnett data) | MG132_IC 50 (Garnett Data) | PSMC/D AVG | PSMA/B AVG |
|---|---|---|---|---|
| TUR | −0.9248 | 5.1232 | 3.04122381 | 5.188872308 |
| DEL | −0.93835 | 3.7243 | 3.55218619 | 5.691087692 |
| CA46 | −0.9845 | 2.338 | 3.126622857 | 4.992403077 |
| SNU-C1 | −1.0159 | 3.444 | 3.814097619 | 5.815003846 |
| THP-1 | −1.1314 | 5.5787 | 3.770859048 | 5.709926154 |
| SCH | −1.1325 | 4.1103 | 3.909285238 | 5.685806923 |
| NCI-H1522 | −1.1807 | 4.2342 | 3.769159048 | 5.437724615 |
| LNCaP-Clone-FGC | −1.2199 | 3.3988 | 3.954359048 | 5.771975385 |
| NCI-H2171 | −1.2416 | 4.3747 | 3.973940952 | 5.914876154 |
| KASUMI-1 | −1.2621 | 1.9239 | 3.961387143 | 5.797707692 |
| SK-MEL-2 | −1.2662 | 4.1587 | 3.761859524 | 5.668816923 |
| EW-22 | −1.3327 | 4.6652 | 4.161209524 | 5.981153077 |
| NCI-H1299 | −1.3405 | 3.6418 | 4.26101 | 5.875363846 |
| COR-L279 | −1.3776 | 3.2881 | 3.114462381 | 5.229934615 |
| NCI-H1155 | −1.4683 | 4.3166 | 3.682140952 | 5.054480769 |
| NCI-H1395 | −1.56 | 4.0744 | 3.62057619 | 5.170580769 |
| KM-H2 | −1.6243 | 0.82874 | 4.456760952 | 5.952124615 |
| NCI-H209 | −1.627 | 1.6474 | 4.280030952 | 6.191534615 |
| NCI-H510A | −1.6854 | 4.8467 | 4.21071381 | 6.296447692 |
| NCI-H1304 | −1.7766 | 3.046 | 3.741696667 | 5.618576154 |
| SCLC-21H | −1.8383 | 2.3665 | 3.700446667 | 5.560358154 |
| NCI-H524 | −1.8382 | 2.4834 | 3.63852381 | 5.448 |
| BV-173 | −2.0979 | 4.6888 | 3.455068095 | 5.485470769 |
| MHH-CALL-2 | −2.1568 | 4.2494 | 3.357189524 | 5.506493846 |
| NCI-H1650 | −2.1603 | 1.425 | 3.650091429 | 5.572180789 |
| ST486 | −2.171 | 3.2233 | 3.826802381 | 5.78391 |
| GR-ST | −2.1773 | 3.0642 | 4.157695238 | 6.066624615 |
| NCI-H1770 | −2.278 | 5.0516 | 3.80213 | 5.765399231 |
| RH-1 | −2.3041 | 1.2201 | 4.374424286 | 6.143686154 |
| AM-38 | −2.4295 | 2.5308 | 3.329042381 | 5.240718462 |
| RL | −2.4524 | 1.6818 | 3.656712857 | 5.534503077 |
| CAL-148 | −2.503 | 2.8892 | 3.862200952 | 5.914302308 |
| SK-N-FI | −2.5232 | 1.8654 | 4.348760952 | 6.130502308 |
| EW-11 | −2.5443 | 2.444 | 3.974292857 | 6.020826923 |
| EW-13 | −2.5541 | 3.5233 | 3.900047619 | 5.800952308 |
| ALL-PO | −2.5555 | 1.7295 | 3.083301429 | 5.222425385 |
| KP-N-YS | −2.5674 | 4.9398 | 4.487379524 | 6.209120769 |
| KMS-12-PE | −2.5739 | 1.3022 | 4.266792857 | 6.206619231 |
| MRK-nu-1 | −2.7836 | 2.5798 | 3.82256381 | 5.64105 |
| LP-1 | −2.7923 | 1.5526 | 3.387176667 | 5.223850769 |
| P30-OHK | −2.9075 | 5.6484 | 3.574733333 | 5.766488462 |
| NCI-N87 | −2.9154 | 2.62 | 3.799187143 | 5.581886923 |
| TALL-1 | −2.9204 | 5.2898 | 3.061459048 | 5.452065385 |
| RS4-11 | −2.9783 | 4.4098 | 3.31227 | 5.247100769 |
| DMS-79 | −2.9817 | 4.7654 | 3.71792 | 5.764875385 |
| NCI-H716 | −3.0199 | 4.4177 | 3.221242857 | 5.305054615 |
| RPMI-6666 | −3.0815 | 3.0615 | 3.467673333 | 5.567496923 |
| L-428 | −3.1267 | 3.5483 | 3.583834762 | 5.522019231 |
| SKM-1 | −3.1552 | 1.312 | 3.699895714 | 5.641794615 |
| NCI-H2227 | −3.2067 | 0.47971 | 4.10041381 | 5.599801538 |
| SHP-77 | −3.2694 | 1.9775 | 4.290960476 | 6.034506154 |
| D-283MED | −3.2757 | 2.188 | 4.29968381 | 6.057217692 |
| MDA-MB-134-VI | −3.328 | 4.999 | 3.797712381 | 5.505993077 |
| C8168 | −3.3326 | 5.8445 | 3.830169524 | 5.935043077 |
| UACC-812 | −3.34 | 4.2416 | 4.02911381 | 5.868118462 |
| ES3 | −3.347 | 1.4652 | 4.018614286 | 5.863663077 |
| KARPAS-422 | −3.3512 | 2.5455 | 3.476628571 | 5.658146923 |
| NCI-H526 | −3.4252 | 4.3642 | 3.795959048 | 5.657221538 |
| EW-3 | −3.487 | 4.5529 | 3.631177143 | 5.46264 |
| OCI-AML2 | −3.5169 | 1.9464 | 3.368397619 | 5.522092308 |
| ECC4 | −3.5476 | 4.5415 | 3.679715238 | 5.403135385 |
| WSU-NHL | −3.5617 | 4.6975 | 3.759794762 | 5.634903846 |
| NH-12 | −3.5873 | 2.3266 | 4.009971429 | 5.799731538 |
| REH | −3.6339 | 5.4665 | 3.421957143 | 5.508315385 |
| LS-1034 | −3.6591 | 2.8725 | 4.110978571 | 5.872059231 |
| HDLM-2 | −3.7075 | 3.0389 | 4.022105714 | 6.104297692 |
| EC-GI-10 | −3.72 | 2.3705 | 4.034911905 | 5.826078462 |
| IM-9 | −3.7491 | 3.0264 | 3.575272857 | 5.701122308 |
| DOHH-2 | −3.753 | 4.3168 | 3.63861619 | 5.743780769 |
| SIMA | −3.7561 | 1.6691 | 4.53974 | 5.589893077 |
| EW-12 | −3.7647 | 4.9747 | 3.693472381 | 6.1089 |
| HCC2157 | −3.7666 | 2.8608 | 3.680522381 | 5.185336154 |
| NCI-H82 | −3.7715 | 4.276 | 3.897623333 | 5.677163077 |
| IST-MES1 | −3.7824 | 0.33796 | 3.924012381 | 5.579883077 |
| NCI-H446 | −3.8545 | 4.6028 | 4.114207143 | 5.941769231 |
| SF539 | −3.879 | 5.2613 | 4.216301905 | 5.954722308 |

TABLE S4-continued

| Cell Line | BORT_IC 50 (Garnett data) | MG132_IC 50 (Garnett Data) | PSMC/D AVG | PSMA/B AVG |
|---|---|---|---|---|
| TE-6 | −3.9078 | 1.3726 | 3.961593333 | 5.842203077 |
| HCC2218 | −3.9374 | 1.244 | 3.826401905 | 5.263144615 |
| DG-75 | −3.984 | 4.7305 | 3.461169048 | 5.375751538 |
| NCCIT | −3.9978 | −1.1462 | 3.944238571 | 5.780080769 |
| EoL-1-cell | −4.0003 | 3.7877 | 3.632757143 | 5.625169231 |
| EB2 | −4.013 | 2.6283 | 3.780256667 | 5.768702308 |
| NB14 | −4.0183 | 4.991 | 3.928900476 | 5.742509231 |
| EW-18 | −4.0195 | 0.70476 | 4.131820476 | 6.077347692 |
| MEM-223 | −4.0224 | 0.91977 | 3.982096667 | 5.947623846 |
| COLO-800 | −4.0378 | 3.3427 | 3.890820952 | 5.812662308 |
| GOTO | −4.0711 | 2.831 | 4.251069048 | 6.096994615 |
| NCI-H1436 | −4.0741 | 4.287 | 4.443802381 | 6.246788462 |
| U-87-MG | −4.0886 | 3.2871 | 4.111931429 | 6.162878462 |
| TGW | −4.1054 | 1.865 | 3.655883333 | 5.342129231 |
| JAR | −4.1269 | 3.4462 | 4.533889524 | 6.257889231 |
| NB7 | −4.1405 | 4.562 | 4.345544286 | 6.154495385 |
| JVM-3 | −4.3432 | 0.66219 | 3.576547619 | 5.752813077 |
| NCI-H23 | −4.4127 | 0.18573 | 4.23949 | 6.157162308 |
| HCC1599 | −4.4301 | 4.3158 | 3.486869524 | 5.147491538 |
| ES5 | −4.5681 | 1.4822 | 3.691360952 | 5.759412308 |
| NCI-H2081 | −4.5959 | 0.43952 | 4.082162381 | 5.973807692 |
| CT8-1 | −4.6384 | −0.24904 | 3.618254762 | 5.693388462 |
| DMS-114 | −4.6436 | 0.36838 | 4.03632 | 5.511384615 |
| SK-NEP-1 | −4.709 | 4.3185 | 4.23280619 | 6.007035385 |
| ATN-1 | −4.7232 | 4.3109 | 3.853511429 | 5.663386154 |
| NB6 | −4.7705 | 3.4324 | 4.032172381 | 5.712730769 |
| MN-60 | −4.8106 | 4.6977 | 3.940452381 | 5.976453846 |
| L-363 | −4.8664 | 3.4724 | 4.164225714 | 5.940574615 |
| LU-134-A | −4.9083 | 4.4205 | 3.816166667 | 5.941112308 |
| JVM-2 | −4.9224 | 2.6928 | 3.69203 | 5.837930769 |
| SU-DHL-1 | −4.9284 | 0.53814 | 3.702820952 | 5.597218462 |
| NCI-H345 | −4.9339 | 3.0476 | 4.111905714 | 5.790782308 |
| NB1 | −4.9797 | 3.2066 | 4.108811905 | 5.837062308 |
| NCI-H2196 | −4.9902 | 4.1147 | 4.177609048 | 6.114455385 |
| GDM-1 | −4.9953 | −1.0469 | 3.464329524 | 5.547791538 |
| BC-3 | −5.0189 | 2.7342 | 3.638811905 | 5.390283077 |
| D-502MG | −5.0554 | 0.51408 | 3.873387619 | 5.731855385 |
| LU-65 | −5.1429 | 0.12003 | 3.203562857 | 5.084485385 |
| EW-1 | −5.2376 | −1.5584 | 4.003145714 | 5.98798 |
| SW962 | −5.2576 | 4.0043 | 3.635898095 | 5.500336923 |
| LU-139 | −5.2734 | 2.5574 | 3.750425238 | 5.415499231 |
| CHP-126 | −5.2857 | 3.0735 | 3.156255238 | 5.069239231 |
| SBC-1 | −5.2969 | 3.742 | 4.090877619 | 6.044010769 |
| JiyoyeP-2003 | −5.2985 | 2.2293 | 3.795845238 | 5.685217692 |
| MHH-NB-11 | −5.3157 | 2.587 | 3.749236667 | 5.526131538 |
| MHH-PREB-1 | −5.3266 | 3.6823 | 3.752256667 | 5.513874615 |
| IST-SL1 | −5.3648 | −1.6047 | 4.175644286 | 6.04317 |
| HL-60 | −5.3672 | 3.0055 | 3.663970952 | 5.799801538 |
| NALM-6 | −5.405 | 1.9268 | 3.563376667 | 5.606204615 |
| Raji | −5.4115 | 0.3496 | 3.959429048 | 5.972307692 |
| NOMO-1 | −5.4425 | 1.98 | 3.533997619 | 5.639075385 |
| TE-12 | −5.4609 | 2.6174 | 3.52772381 | 5.509899231 |
| LB647-SCLC | −5.4675 | 1.518 | 4.161758095 | 5.979045385 |
| OMC-1 | −5.4767 | 2.1426 | 4.061661429 | 5.893918462 |
| NCI-H2141 | −5.51 | 0.51472 | 4.15754619 | 6.008944615 |
| HD-MY-Z | −5.5381 | −1.4566 | 4.405179524 | 5.826626154 |
| RCC10RGB | −5.5387 | 3.6431 | 3.405320952 | 4.971710769 |
| COLO-320-HSR | −5.5428 | 1.3234 | 3.431329524 | 5.351205385 |
| RL95-2 | −5.5746 | 2.0929 | 4.278335238 | 6.119276154 |
| LC-1F | −5.5898 | 0.43953 | 4.499325238 | 6.270469231 |
| NMC-G1 | −5.6059 | 1.9049 | 3.266408095 | 5.094186154 |
| COLO 684 | −5.6095 | −0.098071 | 3.14528 | 4.684832308 |
| DJM-1 | −5.619 | 0.70583 | 3.92056381 | 5.574507692 |
| EVSA-T | −5.6271 | −0.69493 | 3.947548571 | 5.682714615 |
| no-11 | −5.641 | 0.70855 | 3.36409 | 5.153248154 |
| KARPAS-45 | −5.6431 | 0.039378 | 3.805107619 | 5.786056923 |
| HCC1187 | −5.6449 | 4.3517 | 3.814325238 | 6.002700769 |
| LOXIMVI | −5.655 | 4.1243 | 4.191568571 | 6.008031538 |
| RPMI-8402 | −5.6561 | 4.0767 | 3.620498571 | 5.518894615 |
| MEG-01 | −5.6582 | 1.28 | 3.889700476 | 5.841916923 |
| LAMA-84 | −5.6582 | −1.5209 | 3.375151905 | 5.192519231 |
| COR-L88 | −5.6622 | 2.5602 | 3.446709524 | 5.202552308 |
| TE-15 | −5.6747 | 0.65427 | 3.510888095 | 5.7391 |
| DB | −5.6815 | 2.6382 | 3.621047619 | 5.372282308 |
| LB996-RCC | −5.6836 | 3.7104 | 4.387653333 | 6.231590769 |
| NEC8 | −5.6988 | −2.1207 | 4.40831619 | 6.241992308 |
| SK-N-DZ | −5.7282 | 2.0426 | 4.131262381 | 5.908875385 |

TABLE S4-continued

| Cell Line | BORT_IC 50 (Garnett data) | MG132_IC 50 (Garnett Data) | PSMC/D AVG | PSMA/B AVG |
|---|---|---|---|---|
| CW-2 | −5.7416 | 3.803 | 3.44023619 | 5.372063077 |
| MONO-MAC-6 | −5.7751 | −0.62342 | 3.801725714 | 5.692285385 |
| CGTH-W-1 | −5.7762 | 3.6083 | 3.641939524 | 5.46346 |
| KARPAS-299 | −5.7889 | 4.2548 | 4.091480476 | 5.925382308 |
| HT | −5.801 | 3.8221 | 3.671765238 | 5.512396154 |
| SW954 | −5.8439 | 3.8589 | 4.200022381 | 6.051847692 |
| MOLT-16 | −5.8454 | −1.22 | 3.920900952 | 5.775147692 |
| C2BBe1 | −5.847 | −1.2763 | 3.472707619 | 5.244023846 |
| ETK-1 | −5.8629 | 3.3444 | 3.611389048 | 5.54945 |
| CTV-1 | −5.8784 | 2.3123 | 3.33902381 | 5.383580769 |
| EW-16 | −5.8956 | 0.27268 | 4.304735238 | 5.899025385 |
| EB-3 | −5.9305 | 1.6155 | 3.42267619 | 5.393243846 |
| LB1047-RCC | −5.9656 | 2.0441 | 4.245431429 | 6.069628462 |
| KNS-81-FD | −5.9982 | −1.1933 | 4.359543333 | 6.135378462 |
| NB69 | −6.0075 | 3.5159 | 3.770651429 | 6.005910769 |
| NCI-H64 | −6.0166 | 3.6912 | 3.68011381 | 5.307430769 |
| ARH-77 | −6.0386 | 1.7353 | 3.901545238 | 6.11572 |
| SCC-3 | −6.0446 | 1.1341 | 3.367121905 | 5.355604615 |
| RPMI-8226 | −6.0552 | 4.4333 | 4.250943333 | 6.313756923 |
| NB10 | −6.0647 | 2.0789 | 3.283645238 | 4.930338462 |
| BC-1 | −6.0692 | 1.6103 | 3.615429048 | 5.646158462 |
| NB5 | −6.0859 | 4.2534 | 4.099092381 | 5.858416154 |
| KMOE-2 | −6.1042 | 2.978 | 3.926784762 | 5.723759231 |
| SJSA-1 | −6.1132 | 2.2073 | 3.651149048 | 5.491716923 |
| KGN | −6.1411 | 0.049218 | 3.904282857 | 5.634883846 |
| EKVX | −6.1488 | 0.033842 | 3.702783333 | 5.581557692 |
| MOLT-4 | −6.1505 | 2.935 | 3.646050952 | 5.850466154 |
| HH | −6.1531 | −1.1118 | 3.75739381 | 5.673180769 |
| KE-37 | −8.1537 | −2.0191 | 3.722783333 | 5.761544615 |
| BL-70 | −6.155 | −0.36546 | 3.346525238 | 5.37302 |
| GT3TKB | −6.1584 | 1.6442 | 3.774890952 | 5.953323846 |
| NOS-1 | −8.1602 | 2.4878 | 4.354617143 | 6.191785385 |
| EW-24 | −6.1776 | 3.4765 | 3.823317143 | 5.717133077 |
| LAN-6 | −6.1879 | −1.1615 | 4.134174762 | 5.470376154 |
| NB17 | −6.1968 | −0.84468 | 4.308761905 | 5.894384615 |
| LS-123 | −6.2048 | 3.2149 | 4.014325238 | 5.893505385 |
| NB13 | −6.2136 | 2.5633 | 4.123889048 | 6.350344615 |
| NKM-1 | −6.2152 | 1.3281 | 3.90216381 | 5.763344615 |
| 697 | −6.2208 | 2.6708 | 3.281882857 | 5.607869231 |
| BE-13 | −6.2502 | 4.8982 | 3.613201905 | 5.852069231 |
| MPP-89 | −6.2715 | 3.7516 | 3.704239048 | 5.791050769 |
| Becker | −6.301 | −0.2279 | 3.970865238 | 5.912653846 |
| NCI-H1092 | −6.3183 | −0.94562 | 3.523838095 | 5.322579231 |
| NCI-H2126 | −6.3209 | −0.46731 | 4.057901429 | 5.873797692 |
| LC4-1 | −6.3243 | −0.82995 | 3.532768571 | 5.629502308 |
| U-266 | −6.3425 | 1.8748 | 3.991229524 | 5.747112308 |
| KURAMOCHI | −6.3633 | 0.11666 | 3.371590952 | 5.396242308 |
| TGBC1TKB | −6.3741 | 2.4345 | 3.893339048 | 5.911469231 |
| GCIY | −6.4223 | 1.6997 | 4.032908095 | 5.926213077 |
| HEL | −6.4312 | −1.6865 | 3.554488095 | 5.447223846 |
| NB12 | −6.4628 | 1.2806 | 3.95712 | 5.535869231 |
| LS-411N | −6.4848 | 0.52949 | 3.41667381 | 5.322451538 |
| PF-382 | −6.5223 | −1.7894 | 3.810567143 | 5.788646154 |
| ECC12 | −6.5907 | 0.86685 | 4.157279048 | 6.011377692 |
| CAS-1 | −6.5957 | −1.8655 | 3.935299524 | 5.666785385 |
| L-540 | −6.5961 | 0.11189 | 3.91889 | 5.875477692 |
| DU-4475 | −6.5979 | −1.6267 | 3.520582381 | 5.525267692 |
| OPM-2 | −6.6256 | −2.2562 | 4.072527619 | 5.734721538 |
| IST-SL2 | −6.6382 | 0.69939 | 4.154011429 | 5.954528462 |
| CMK | −6.6513 | −1.1673 | 3.506827619 | 5.46972 |
| Calu-6 | −6.6562 | 1.7267 | 3.83553619 | 5.522682308 |
| A3-KAW | −6.6582 | 3.9081 | 3.581778095 | 5.61063 |
| K5 | −6.6614 | 2.5608 | 3.95172619 | 5.798305385 |
| KM12 | −6.6675 | −0.15706 | 3.691361429 | 5.561003077 |
| SR | −6.8606 | 2.3996 | 3.571444286 | 5.842276154 |
| BL-41 | −6.6846 | −2.6668 | 3.925382381 | 5.49297 |
| Daudi | −6.7062 | 2.9404 | 3.03441381 | 5.343100769 |
| TE-8 | −6.7342 | −1.0706 | 4.184471905 | 6.059838462 |
| HAL-01 | −6.7409 | 1.5196 | 3.381078095 | 5.455631538 |
| EM-2 | −8.7588 | 1.8978 | 3.819633333 | 5.260289231 |
| CCRF-CEM | −6.7885 | −0.74078 | 3.747131429 | 5.831786923 |
| D-392MG | −6.8099 | −1.6547 | 4.382395714 | 5.906465385 |
| MZ7-mel | −6.8184 | −1.3328 | 3.878062857 | 5.793696923 |
| SK-MM-2 | −6.8199 | 2.4686 | 4.143788095 | 5.861202308 |
| VA-ES-BJ | −6.8241 | −1.5025 | 3.869769524 | 5.620255385 |
| RKO | −6.8488 | 1.6552 | 4.164981429 | 5.703593846 |
| TE-1 | −6.8746 | −0.79587 | 4.258749524 | 6.31882 |

TABLE S4-continued

| Cell Line | BORT_IC 50 (Garnett data) | MG132_IC 50 (Garnett Data) | PSMC/D AVG | PSMA/B AVG |
|---|---|---|---|---|
| TE-10 | −6.8783 | −0.036349 | 4.069070476 | 5.96053 |
| PSN1 | −6.897 | 0.23914 | 3.786431905 | 5.560446923 |
| SW872 | −6.9114 | −0.41963 | 3.730848095 | 5.614424615 |
| HC-1 | −6.9333 | 0.32331 | 3.768790952 | 6.150068462 |
| KALS-1 | −6.9857 | −0.76392 | 3.784002857 | 5.519255385 |
| SF268 | −6.9883 | −0.42097 | 4.305961905 | 6.08246 |
| IST-MEL1 | −6.9943 | 2.2764 | 3.29624619 | 5.101909231 |
| RXF393 | −6.9979 | −1.3857 | 3.541454286 | 5.557748462 |
| NCI-H1355 | −7.0184 | −0.3766 | 4.057908095 | 5.967126923 |
| QIMR-WIL | −7.0257 | 0.77363 | 3.811513333 | 5.744345385 |
| TE-5 | −7.0531 | −1.9464 | 4.211308571 | 5.909478462 |
| SK-LMS-1 | −7.0656 | −1.6449 | 3.858407143 | 5.519185385 |
| SW684 | −7.1055 | 0.25199 | 4.328438095 | 5.878803077 |
| ML-2 | −7.1055 | −2.1366 | 3.510734286 | 5.285043846 |
| D-263MG | −7.1223 | −1.8322 | 4.188909524 | 5.722415385 |
| LB2241-RCC | −7.1254 | −1.9486 | 3.785672381 | 5.607869231 |
| ES7 | −7.174 | −0.10925 | 4.168585714 | 5.985749231 |
| GI-1 | −7.1765 | 0.38616 | 3.743220476 | 5.567630769 |
| LS-513 | −7.2098 | −0.4042 | 3.566774286 | 5.397970769 |
| KINGS-1 | −7.2342 | −1.9112 | 3.820299048 | 5.426349231 |
| UACC-257 | −7.2499 | −2.1264 | 3.813885714 | 5.589092308 |
| SF128 | −7.2625 | −0.010339 | 3.870263333 | 5.723674615 |
| LB373-MEL-D | −7.2645 | −1.4189 | 4.312940476 | 5.930983846 |
| Ramos-2G6-4C10 | −7.2745 | 3.5351 | 3.627364762 | 5.563618462 |
| TK10 | −7.2949 | −1.369 | 4.130835714 | 5.881851538 |
| D-336MG | −7.3278 | 1.3892 | 3.952452857 | 5.850026154 |
| BB49-HNC | −7.3362 | −0.71139 | 4.133217143 | 6.039170769 |
| HOP-62 | −7.3425 | −2.2119 | 4.070115238 | 5.651443077 |
| LB831-BLC | −7.3533 | −1.643 | 3.985187143 | 5.984907692 |
| GI-ME-N | −7.363 | −1.6448 | 4.048671905 | 5.766935385 |
| A4-Fuk | −7.3812 | 1.8052 | 3.697810476 | 5.545538462 |
| HT-144 | −7.4597 | −1.9736 | 3.578508571 | 5.391721538 |
| NCI-H747 | −7.5255 | −0.99147 | 4.172431905 | 6.114126154 |
| CESS | −7.5271 | −1.7684 | 3.564739048 | 5.602737692 |
| HUTU-80 | −7.537 | 1.8514 | 4.010089524 | 5.841605385 |
| DSH1 | −7.6407 | −2.9395 | 3.668174762 | 5.338664615 |
| LB771-HNC | −7.6534 | −2.5212 | 4.317231429 | 5.680959231 |
| CP66-MEL | −7.6559 | −2.5902 | 4.485437619 | 6.117112308 |
| OCUB-M | −7.7132 | −3.2868 | 4.447644286 | 5.688454615 |
| MFH-ino | −7.7216 | −2.1973 | 4.16760619 | 5.824051538 |
| OS-RC-2 | −7.7282 | −0.73455 | 4.093806667 | 5.834937692 |
| HCE-T | −7.7302 | 0.89561 | 3.945041429 | 5.983603077 |
| ES1 | −7.7523 | 0.076226 | 4.224381905 | 6.070619231 |
| LB2518-MEL | −7.7638 | −3.2807 | 4.197835238 | 5.756520769 |
| ACN | −7.7821 | −1.4855 | 3.777898095 | 5.661068462 |
| D-247MG | −7.7911 | −2.6298 | 3.785271905 | 5.568978462 |
| HCC2998 | −7.7942 | −0.063435 | 3.85381381 | 5.765304615 |
| MZ2-MEL | −7.8072 | −1.7396 | 3.664014762 | 5.612263846 |
| ES8 | −7.8244 | −1.3958 | 4.00661619 | 5.922496923 |
| KS-1 | −7.986 | −2.7398 | 3.690825714 | 5.184153077 |
| BB30-HNC | −8.0005 | 0.5463 | 4.07779 | 6.381387692 |
| ONS-76 | −8.0164 | −2.0452 | 3.782659524 | 5.681386923 |
| D-542MG | −8.02 | −2.8207 | 3.951817619 | 5.856451538 |
| BB65-RCC | −8.098 | −0.56545 | 3.786649524 | 5.80022 |
| LOUCY | −8.1354 | −1.3682 | 3.611266667 | 5.592386923 |
| OVCAR-4 | −8.1479 | −2.2129 | 3.847044286 | 5.898593077 |
| LXF-289 | −8.2214 | −2.6499 | 3.950582857 | 5.715936923 |
| KNS-42 | −8.2629 | −3.1143 | 4.155200952 | 5.669698462 |
| 8-MG-SA | −8.2949 | −0.92038 | 3.742072381 | 5.40336 |
| NTERA-S-cl-D1 | −8.3207 | −2.8521 | 4.653015714 | 6.398818462 |
| A101D | −8.3978 | −3.4177 | 3.775330952 | 5.503757692 |
| MMAC-SF | −8.439 | −2.6216 | 4.291899048 | 6.075171538 |
| no-10 | −8.4691 | −2.4181 | 4.010771429 | 5.829523077 |
| A253 | −8.4758 | −1.8246 | 4.353081429 | 6.195746154 |
| TE-9 | −8.6099 | −0.49375 | 3.6961 | 5.71848 |
| SK-UT-1 | −8.722 | −1.5119 | 3.842938571 | 5.280020769 |
| ES6 | −13.073 | −4.3382 | 4.055194762 | 6.152741538 |

What is claimed is:

1. A method of killing or inhibiting proliferation of a cancer cell comprising: contacting the cancer cell with (a) a BCL2 family inhibitor and (b) a proteasome inhibitor; wherein the method comprises determining that the cancer cell has reduced expression of at least one 19S proteasome subunit prior to contacting the cancer cell with the BCL2 family inhibitor and the proteasome inhibitor.

2. The method of claim 1, wherein the proteasome inhibitor is bortezomib, carfilzomib, oprozomib, ixazomib, or an analog of any of these.

3. The method of claim 1, wherein the cancer cell is a proteasome inhibitor resistant cancer cell.

4. The method of claim 1, wherein the cancer cell is a proteasome inhibitor resistant cancer cell that has reduced expression of at least one 19S proteasome subunit.

5. The method of claim 1, wherein the method comprises determining that the cancer cell has reduced expression of PSMD5, PSMD1, PSMC6, PSMD10, PSMD14, or PSMD6.

6. The method of claim 1, wherein the cancer cell is a blood cancer cell.

7. A method of treating a subject in need of treatment for cancer comprising: administering a BCL2 family inhibitor to the subject, wherein the cancer has reduced expression of at least one 19S proteasome subunit; and wherein the method comprises determining that the cancer has reduced expression of at least one 19S proteasome subunit prior to administering the BCL2 family inhibitor to the subject.

8. The method of claim 7, wherein the method further comprises administering a proteasome inhibitor to the subject.

9. The method of claim 8, wherein the proteasome inhibitor is bortezomib, carfilzomib, oprozomib, ixazomib, or an analog of any of these.

10. The method of claim 7, wherein the cancer has reduced expression of at least one 19S proteasome subunit.

11. The method of claim 7, wherein the method comprises determining that the cancer has reduced expression of PSMD5, PSMD1, PSMC6, PSMD10, PSMD14, or PSMD6.

12. The method of claim 7, wherein the cancer is a blood cancer.

* * * * *